United States Patent
Koseki et al.

(10) Patent No.: US 10,563,208 B2
(45) Date of Patent: Feb. 18, 2020

(54) CO-EXPRESSION PLASMID

(71) Applicant: Anaeropharma Science, Inc., Tokyo (JP)

(72) Inventors: Koichi Koseki, Tokyo (JP); Koichiro Shioya, Tokyo (JP); Satoshi Kobayashi, Nagano (JP); Yuko Shimatani, Nagano (JP); Takeshi Masaki, Nagano (JP); Hitomi Shimizu, Nagano (JP); Tomio Matsumura, Nagano (JP); Masami Okabe, Tokyo (JP); Kengo Inoue, Tokyo (JP)

(73) Assignee: Anaeropharma Science, Inc., Tokyo (JP)

( * ) Notice: Subject to any disclaimer, the term of this patent is extended or adjusted under 35 U.S.C. 154(b) by 380 days.

(21) Appl. No.: 15/529,312

(22) PCT Filed: Dec. 2, 2015

(86) PCT No.: PCT/JP2015/006000
§ 371 (c)(1),
(2) Date: May 24, 2017

(87) PCT Pub. No.: WO2016/088376
PCT Pub. Date: Jun. 9, 2016

(65) Prior Publication Data
US 2017/0260534 A1   Sep. 14, 2017

(30) Foreign Application Priority Data
Dec. 3, 2014 (JP) .................. 2014-245424

(51) Int. Cl.
| | | |
|---|---|---|
| *C12N 15/74* | (2006.01) | |
| *A61K 35/74* | (2015.01) | |
| *A61K 38/19* | (2006.01) | |
| *C07K 14/525* | (2006.01) | |
| *C07K 14/57* | (2006.01) | |
| *C12N 15/09* | (2006.01) | |
| *A61K 38/21* | (2006.01) | |
| *C07K 16/28* | (2006.01) | |
| *C07K 16/32* | (2006.01) | |
| *C07K 14/52* | (2006.01) | |

(52) U.S. Cl.
CPC ............ *C12N 15/746* (2013.01); *A61K 35/74* (2013.01); *A61K 38/191* (2013.01); *A61K 38/217* (2013.01); *C07K 14/525* (2013.01); *C07K 14/57* (2013.01); *C07K 16/2803* (2013.01); *C07K 16/2863* (2013.01); *C07K 16/32* (2013.01); *C12N 15/09* (2013.01); *C07K 14/52* (2013.01); *C07K 16/28* (2013.01); *C07K 2317/622* (2013.01)

(58) Field of Classification Search
CPC .... A61K 35/74; A61K 38/191; A61K 38/217; C07K 14/525; C07K 14/57; C07K 16/32; C12N 15/09; C12N 15/746
See application file for complete search history.

(56) References Cited

U.S. PATENT DOCUMENTS

| | | | |
|---|---|---|---|
| 5,677,171 A | 10/1997 | Hudziak et al. | |
| 2005/0025745 A1* | 2/2005 | Fujimori | A61K 48/00 424/93.2 |
| 2011/0189757 A1 | 8/2011 | Shimatani-Shibata et al. | |
| 2014/0105863 A1 | 4/2014 | Vanden-Broucke et al. | |
| 2017/0218072 A1* | 8/2017 | Taniguchi | A61K 39/395 |

FOREIGN PATENT DOCUMENTS

| | | |
|---|---|---|
| EP | 1227152 | 7/2002 |
| WO | WO 2009/128272 | 10/2009 |
| WO | WO 2010/042189 | 4/2010 |
| WO | WO 2010/126073 | 4/2010 |
| WO | WO 2014/010758 | 1/2014 |
| WO | WO 2015/166640 | 11/2015 |
| WO | WO 2015/166641 | 11/2015 |

OTHER PUBLICATIONS

Supplementary European Search Report for European Application No. 15 86 5570 issued by the European Patent Office dated Apr. 18, 2018, 3 pages.

Scheich et al., "Vectors for co-expression of an unrestricted number of proteins," Nuclec Acids Research, Feb. 20, 207, vol. 35, No. 6, e43, 7 pages.

Sun et al., "Accessing the Inaccessible: Molecular Tools for Bifidobacteria," Applied and Environmental Microbiology, Aug. 2012, vol. 78, No. 15, pp. 5035-5042.

Li et al., "Delivery of the co-expression plasmid pEndo-Si=Stat3 by attenuated *Salmonella serovar* typhimurium for prostate cancer treatment," J Cancer Res Cln Oncol, 2013, 139:971-980.

Callahan, Margaret K., and Jedd D. Wolchok. "At the bedside: CTLA-4- and PD-1-blocking antibodies in cancer immunotherapy." *Journal of leukocyte biology* 94, No. 1 (2013): 41-53, 14 pages.

(Continued)

*Primary Examiner* — Antonio Galisteo Gonzalez
(74) *Attorney, Agent, or Firm* — Occhiuti & Rohlicek LLP

(57) ABSTRACT

The object of the invention is to provide an anaerobic enterobacterium having a higher therapeutic effect on an anaerobic site such as a solid tumor tissue and an ischemic disease site. A bacterium of the genus *Bifidobacterium*, which is transformed with a plasmid co-expressing two types of heterologous polypeptides and comprising two types of secretory expression cassettes each sequentially comprising a promoter DNA functioning in the bacterium of the genus *Bifidobacterium*; a DNA encoding a secretory signal peptide; a DNA encoding a heterologous polypeptide; and a terminator DNA functioning in the bacterium of the genus *Bifidobacterium*, efficiently secretes the two types of heterologous peptides, i.e., two types of antibodies having anticancer effects, outside the bacterial cell.

19 Claims, 26 Drawing Sheets
Specification includes a Sequence Listing.

(56) References Cited

OTHER PUBLICATIONS

Collins, Sara A., Alexandra Buhles, Martina F. Scallan, Patrick T. Harrison, Deirdre M. O'Hanlon, Gerald C. O'Sullivan, and Mark Tangney. "AAV2-mediated in vivo immune gene therapy of solid tumours." *Genetic Vaccines and Therapy* 8, No. 1 (2010): 8, 13 pages.
GenBank: AAN24005.1, possible arabinosidase [Bifidobacterium longum NCC2705], Jan. 31, 2014, 2 pages.
GenBank: AAN24257.1, probable extracellular protein possibly involved in xylan or arabinian degradation, Jan. 31, 2014, 2 pages.
GenBank: AAN24291.1, widely conserved hypothetical membrane protein [Bifidobacterium longum NCC2705], Jan. 31, 2014, 2 pages.
GenBank: AAN24480.1, narrowly conserved hypothetical protein [Bifidobacterium longum NCC2705], Jan. 31, 2014, 2 pages.
GenBank: AAN25334.1, endo-1,4-beta-xylanase D [Bifidobacterium longum NCC2705], Jan. 31, 2014, 2 pages.
GenBank: AAN25335.1, possible extracellular exo-xylanase [Bifidobacterium longum NCC2705], Jan. 31, 2014, 2 pages.
GenBank: BAJ72090.1, putative cell surface protein [*Bifidobacterium longum* subsp. *Infantis* 157F], Oct. 7, 2016, 1 page.
GenBank: BAP82898.1, hypothetical protein BL105A_0241 [Bifidobacterium longum], Feb. 3, 2015, 1 page.
GenBank: EFV36416.1, S-layer protein [*Bifidobacterium* sp. 12_1_47BFAA], Jan. 4, 2011, 2 pages.
GenBank: ESV34135, putative secreted protein with N1pC/P60 domain [Bifidobacterium longum E18], Mar. 23, 2015, 1 page.
GenBank: KHD94729.1, hypothetical protein NL89-07580 [*Bifidobacterium longum* subsp. *Longum*], Nov. 21, 2014, 2 pages.
Notification of Transmittal of Translation of the International Preliminary Report on Patentability and English Translation of the International Preliminary Report on Patentability for International Application No. PCT/JP2015/006000 issued by the International Bureau of WIPO dated Jun. 15, 2017.
Suk, Kyoungho, Inik Chang, Yun-Hee Kim, Sunshin Kim, Ja Young Kim, Hocheol Kim, and Myung-Shik Lee. "Interferon γ (IENγ) and Tumor Necrosis Factor α Synergism in ME-180 Cervical Cancer Cell Apoptosis and Necrosis—IFNγ Inhibits Cytoprotective NF-kB Through STAT1/IRF-1 Pathways." *Journal of Biological Chemistry*, 2001, vol. 276, p. 13153-13159.

* cited by examiner

[Figure 1]
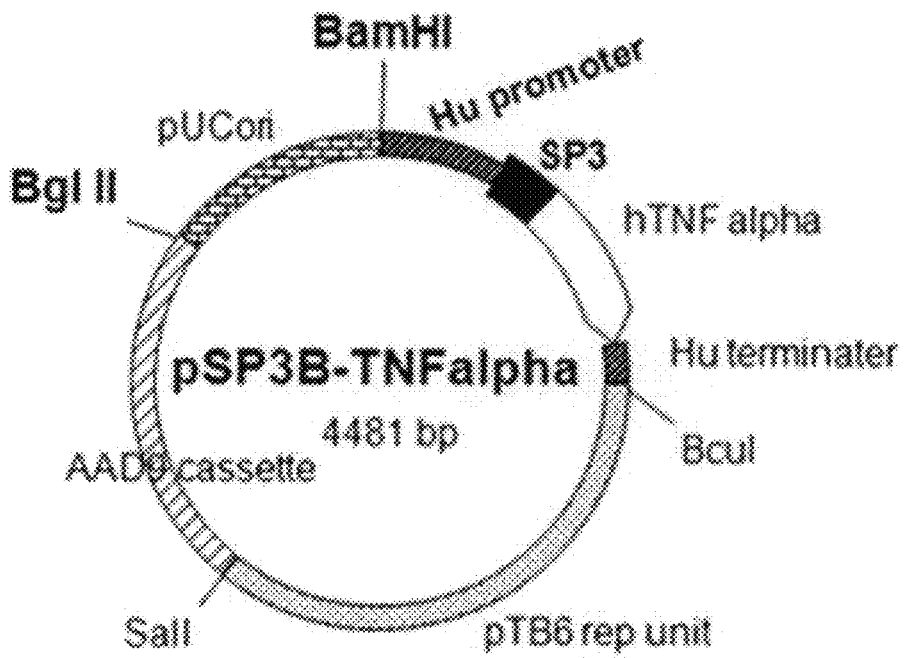
[Figure 2]
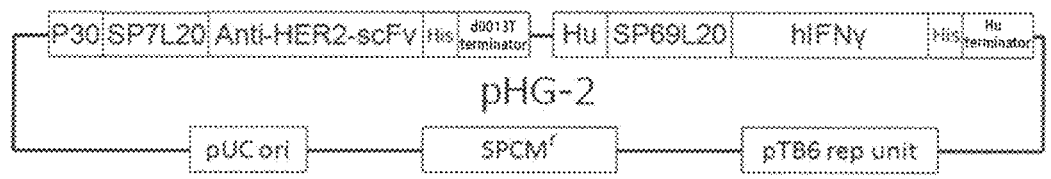
[Figure 3]
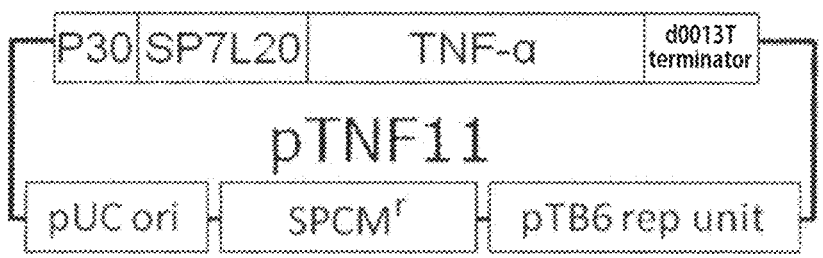

[Figure 4]
(a)
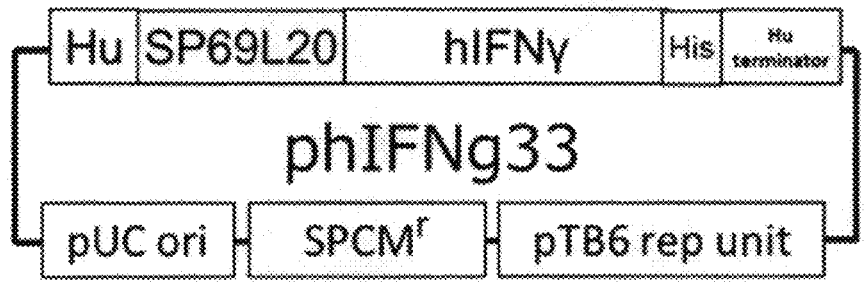
(b)
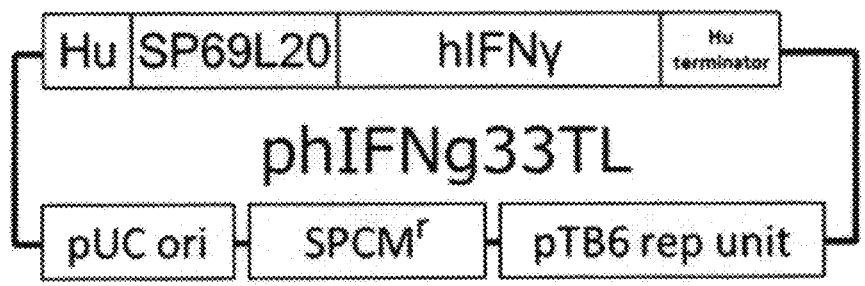
[Figure 5]
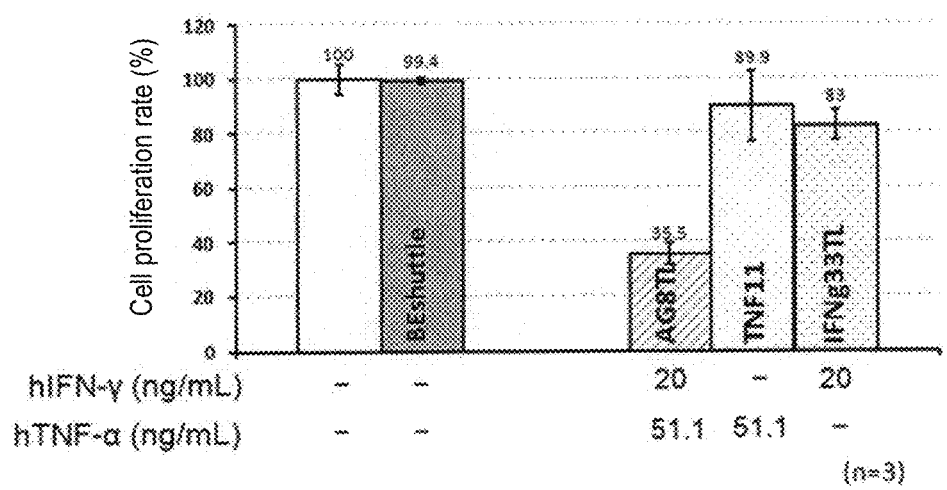

[Figure 6]
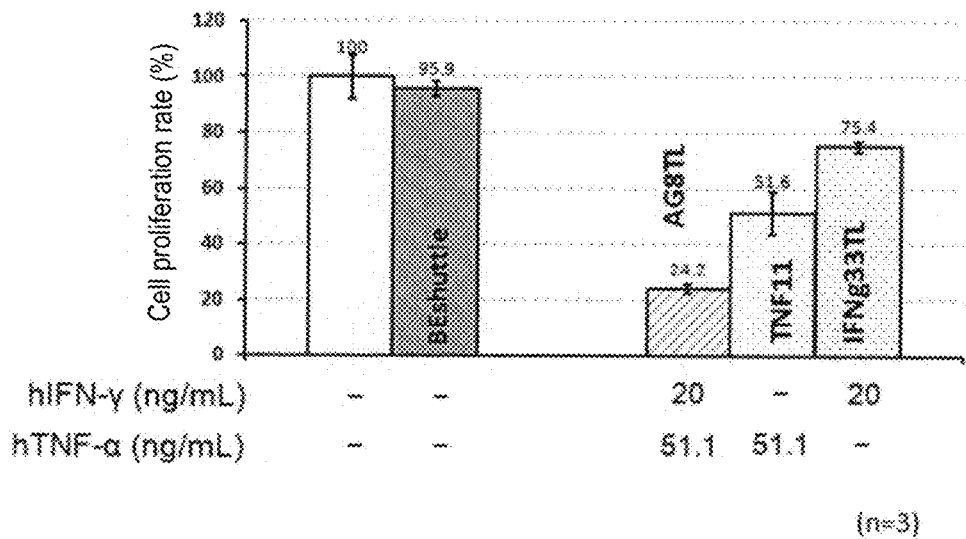
[Figure 7]
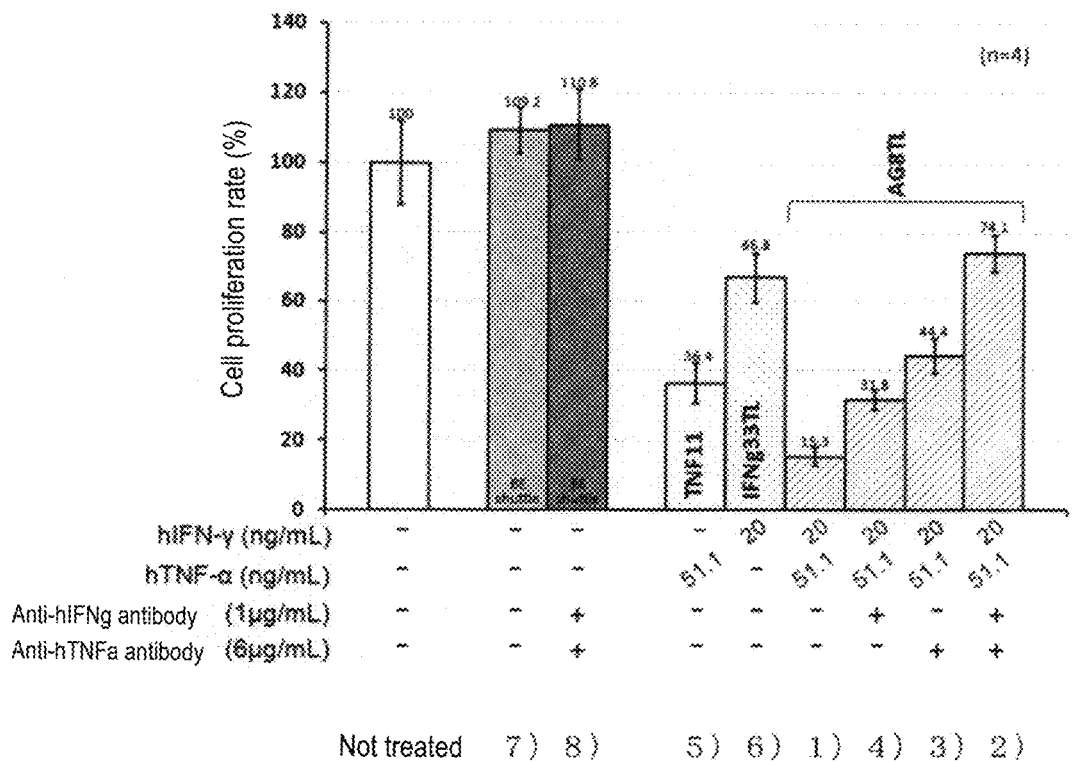

[Figure 8]
(A)
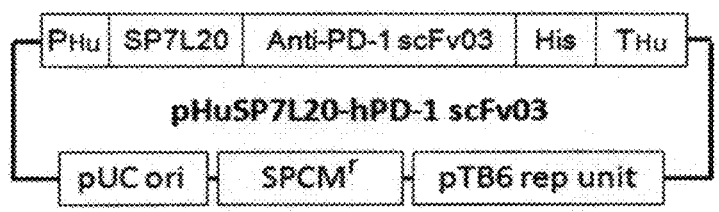
(B)
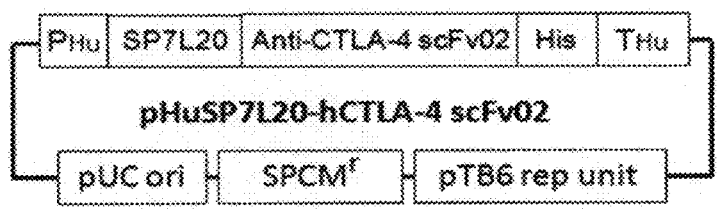
(C)
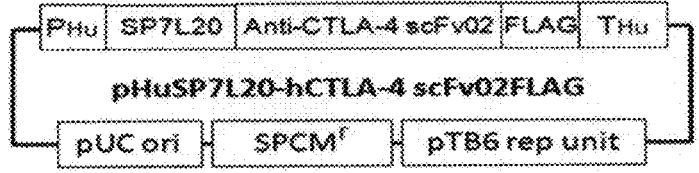

[Figure 9]
(a)
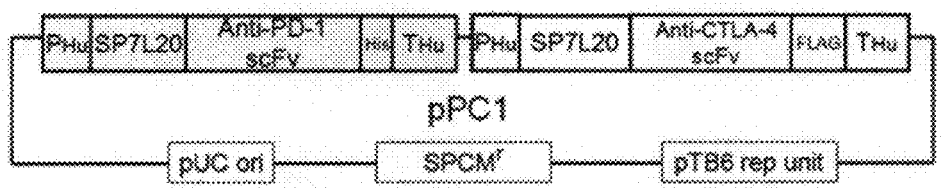
(b)
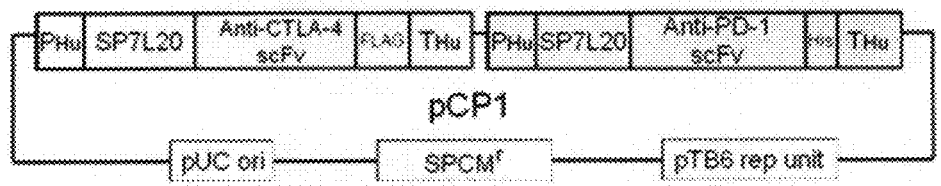

[Figure 10]

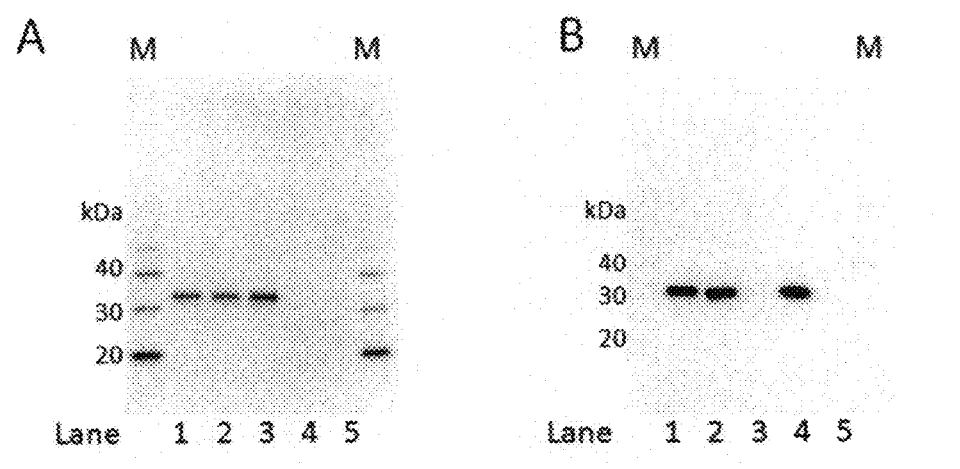

A: Detection of anti-hPD-1scFv03 by anti-His tag antibody

B: Detection of anti-hCTLA-4scFv02 FLAG by anti-FLAG tag antibody

Lane 1: Co-expression strain PC1 (anti-hPD-1scFv03 fused with His-tag at the C terminus, anti-hCTLA-4scFv02 fused with FLAG-tag at the C terminus)

Lane 2: Co-expression strain CP1 (anti-hPD-1scFv03 fused with His-tag at the C terminus, anti-hCTLA-4scFv02 fused with FLAG-tag at the C terminus)

Lane 3: Anti-hPD-1scFv03 single expression strain (anti-hPD-1scFv03 fused with His-tag at the C terminus)

Lane 4: Anti-hCTLA-4scFv02 single expression strain (anti-hCTLA-4scFv02 fused with FLAG-tag at the C terminus)

Lane 5: Negative control strain, BEshuttle

M: Molecular-weight marker

[Figure 11]
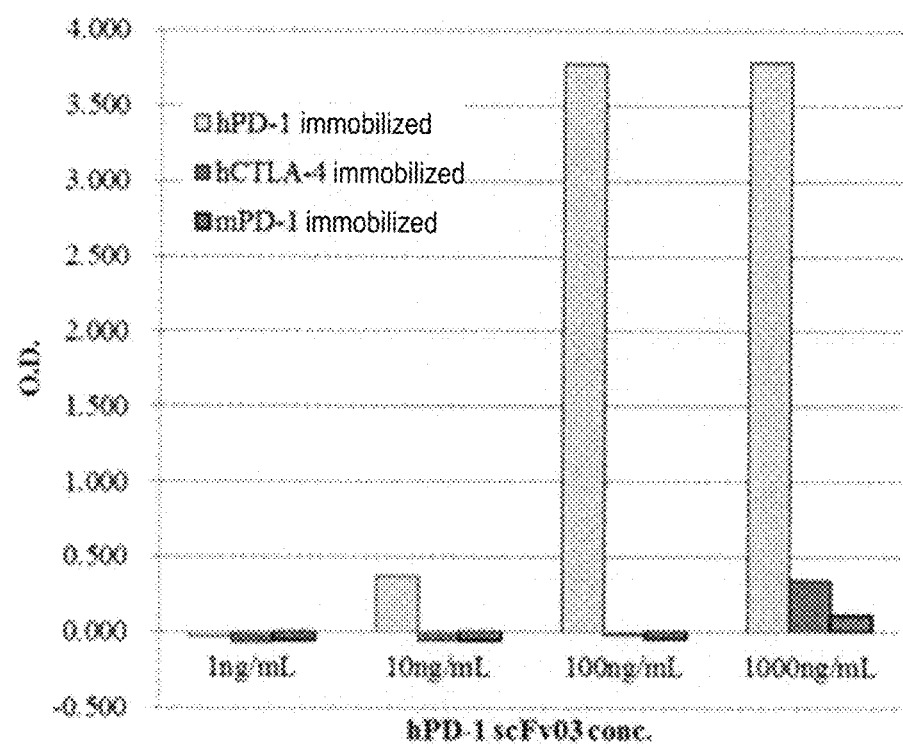

[Figure 12]
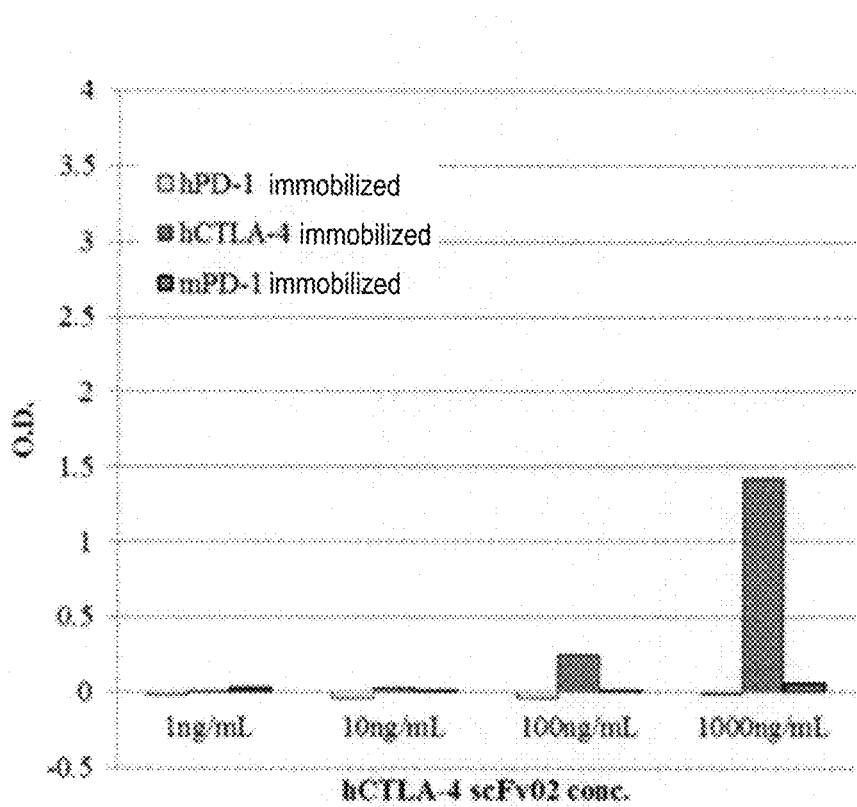

[Figure 13]
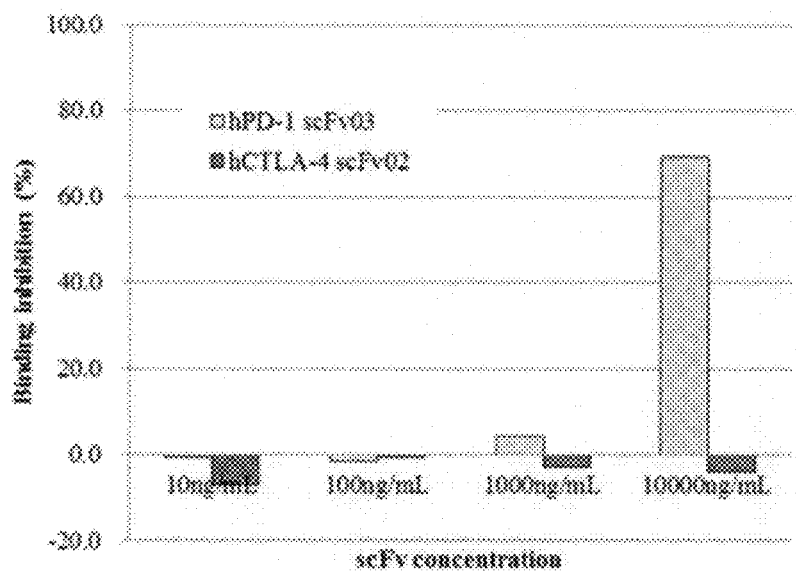
[Figure 14]
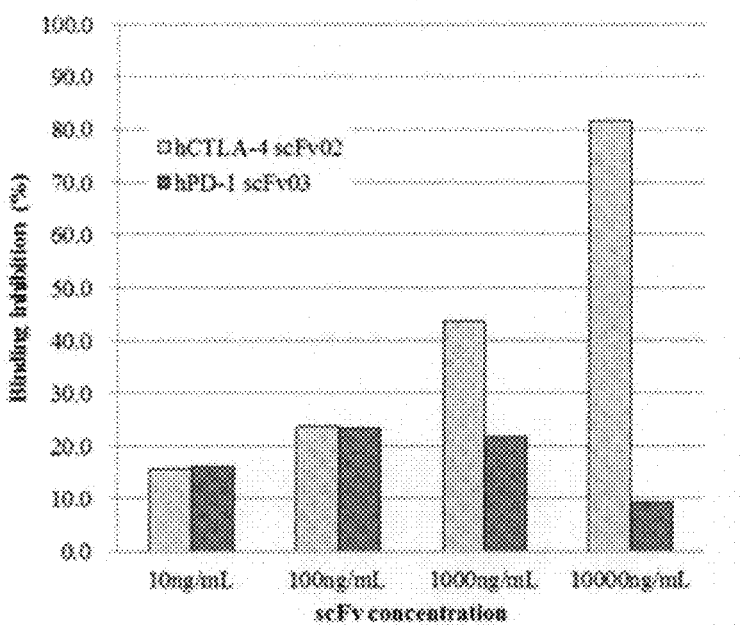

[Figure 15]
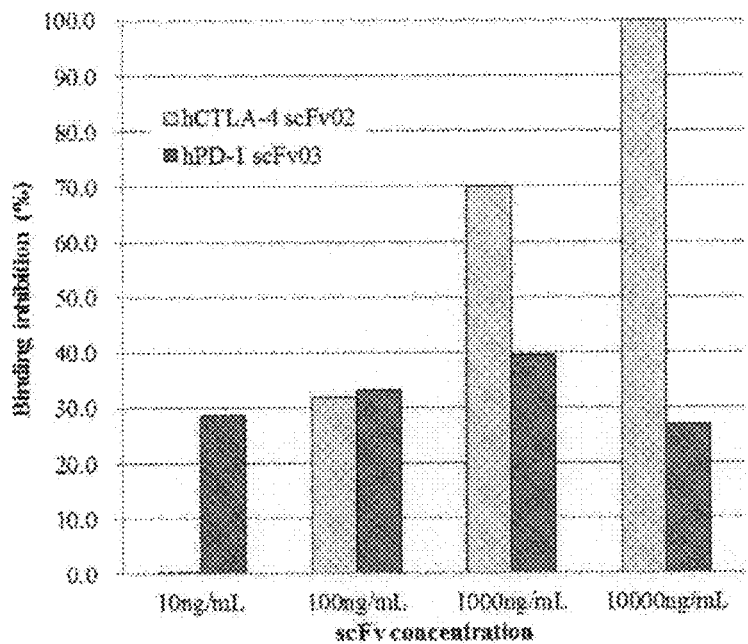
[Figure 16]
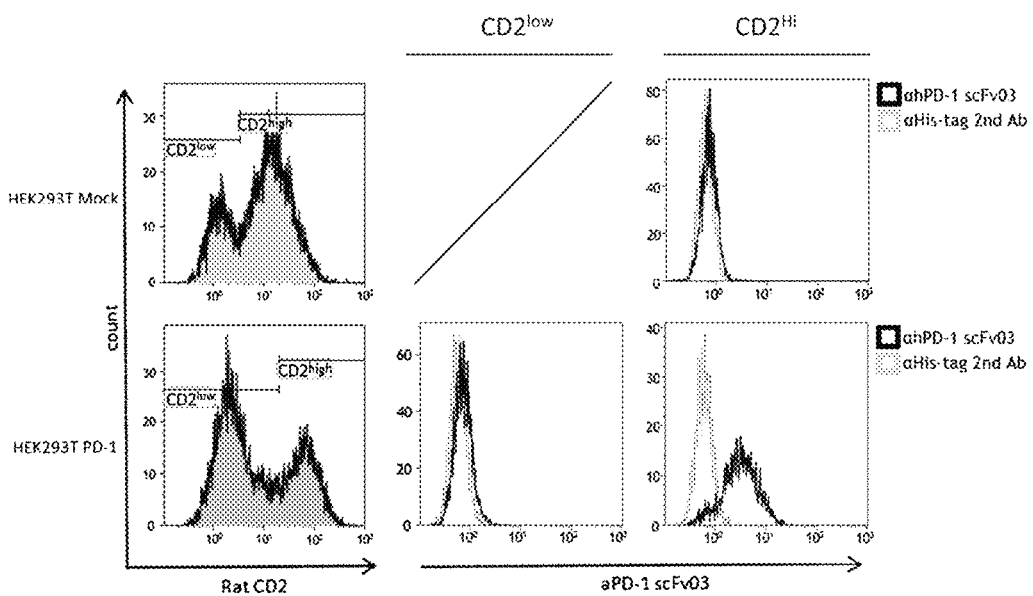

[Figure 17]
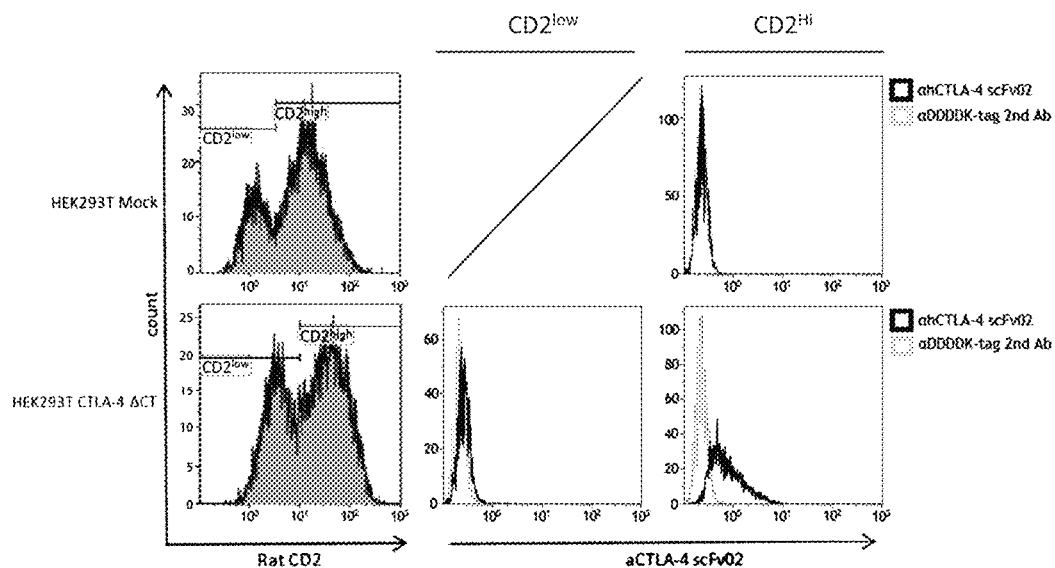
[Figure 18]
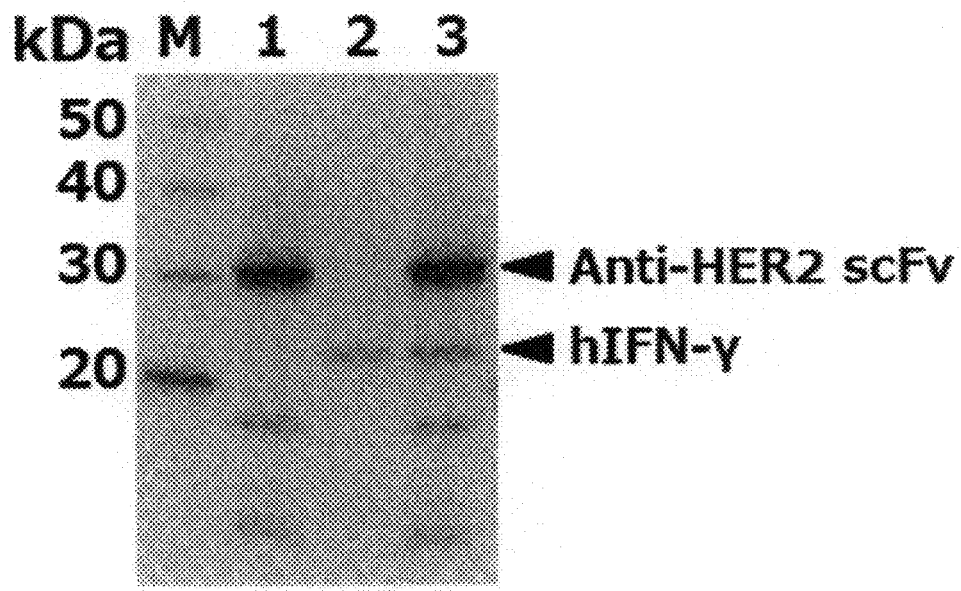
Lane 1: P30SP7L20-bHER2 strain (anti-HER2 scFv single expression)
Lane 2: hIFNg33 strain (IFN-γ single expression)
Lane 3: HG-2 strain (co-expression)

[Figure 19]
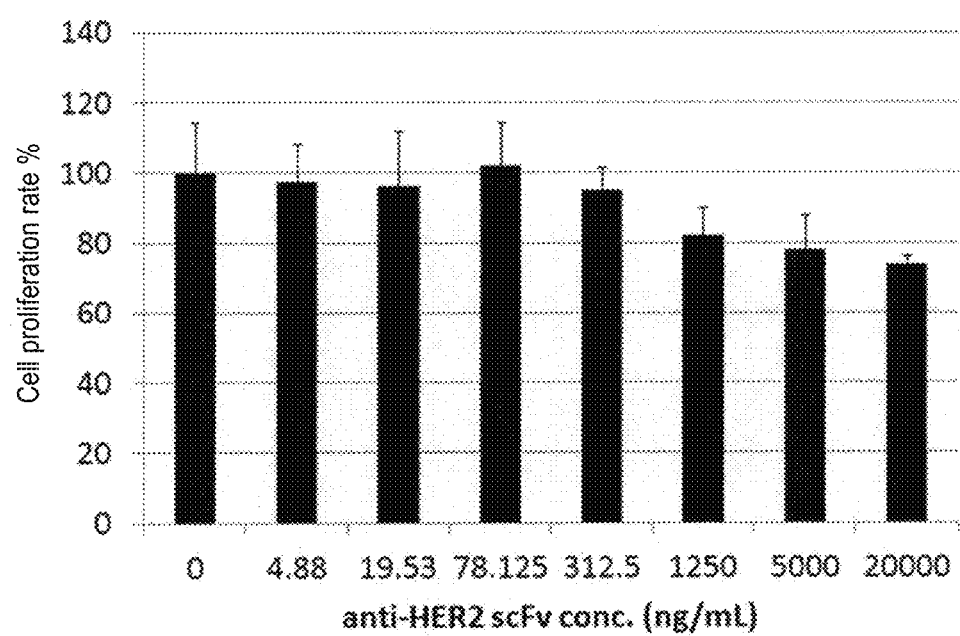

[Figure 20]
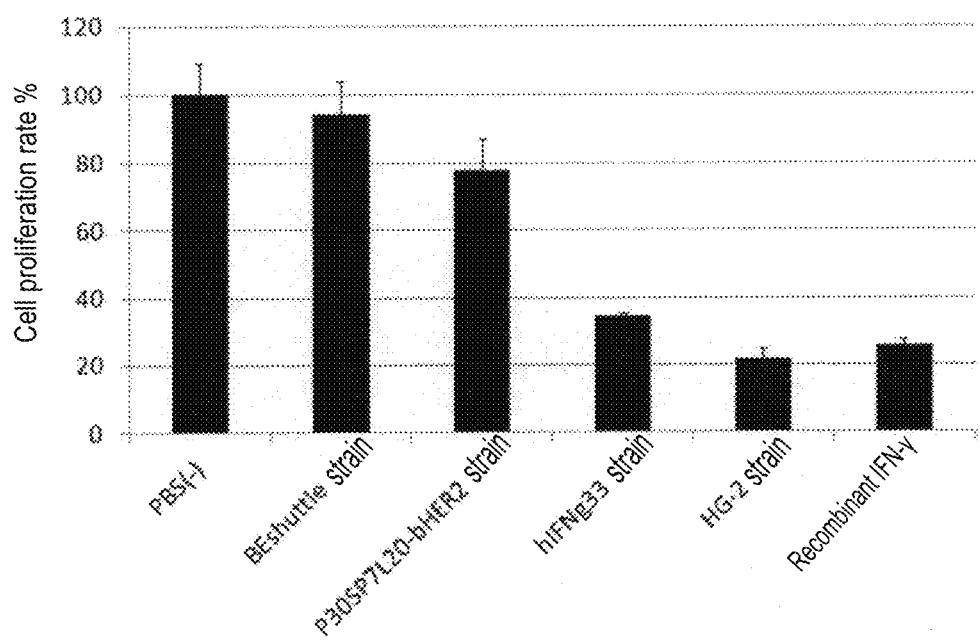

[Figure 21]
(A)
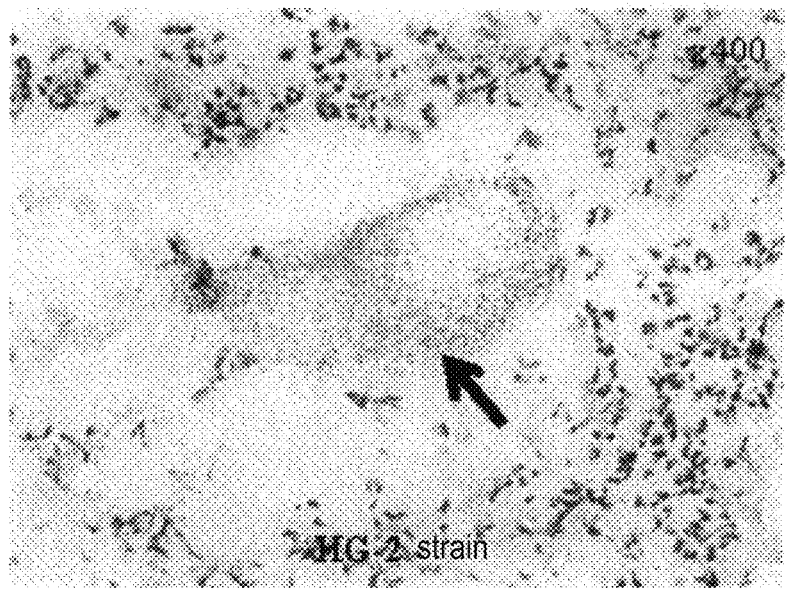
(B)
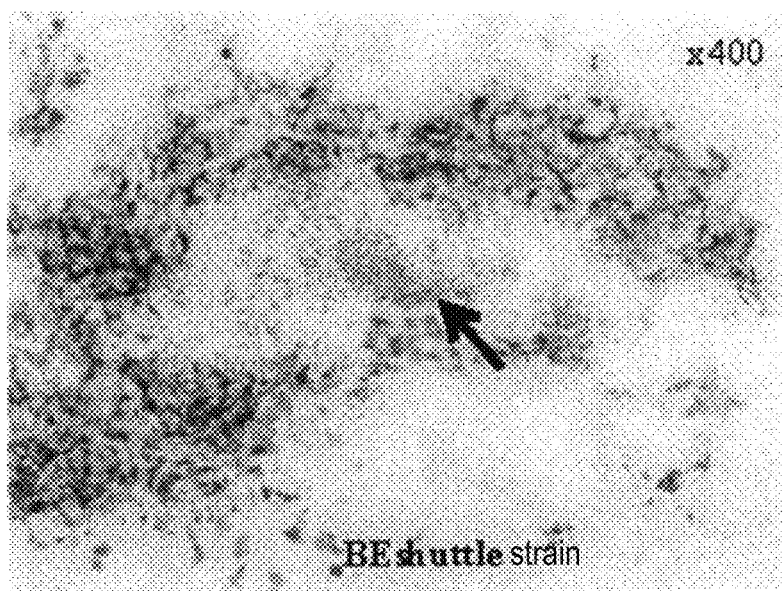

[Figure 22]
Staining with anti-hIFN-γ antibody (↑ hIFN-γ: green)
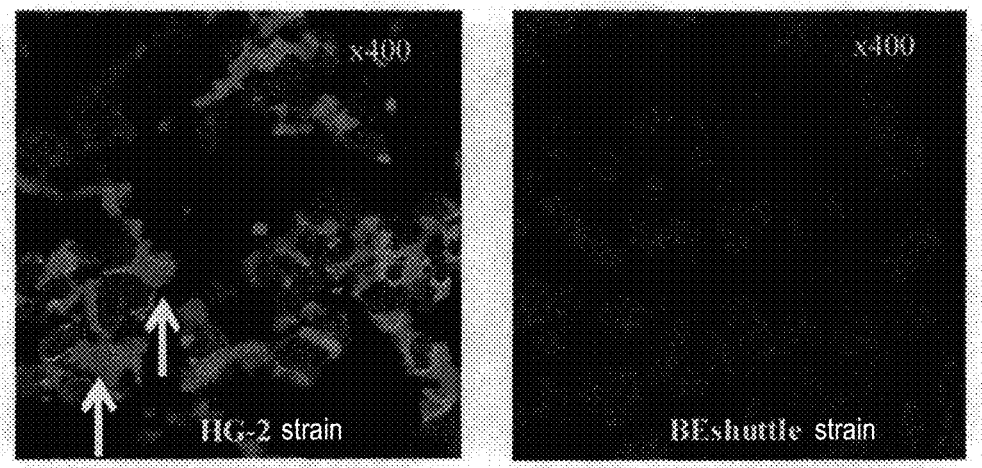
(A)  (B)
[Figure 23]
Staining with anti-histidine tag antibody (↑ histidine tag: red)
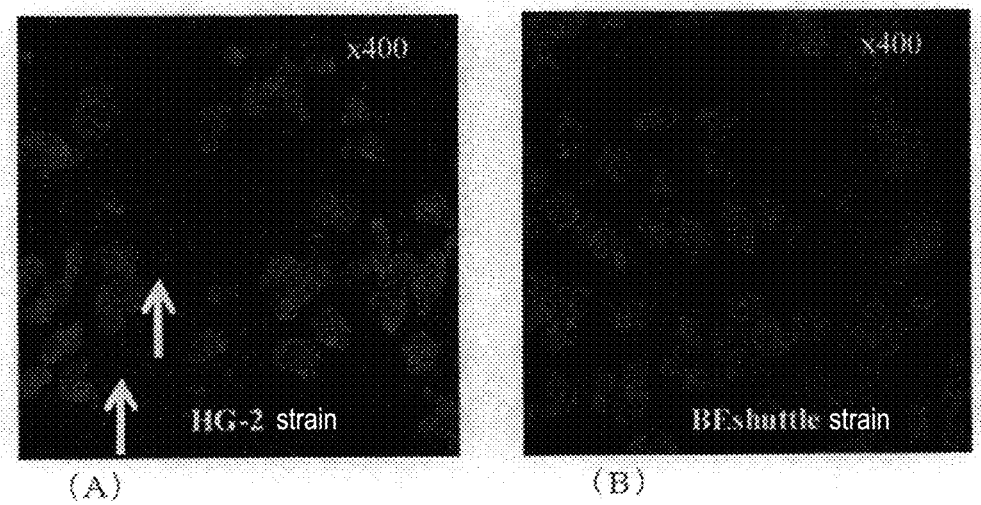
(A)  (B)

[Figure 24]
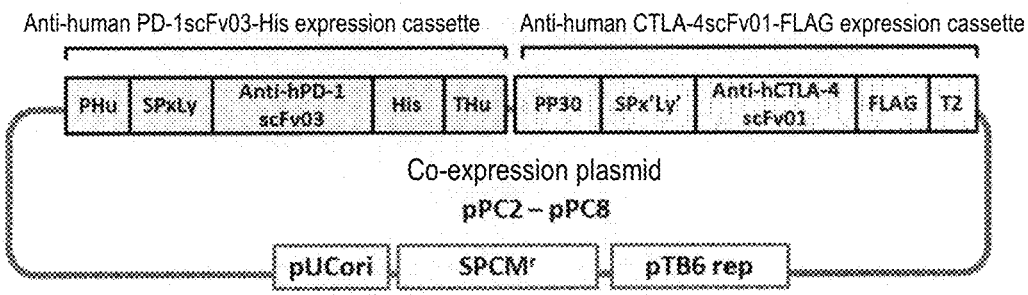
[Figure 25]
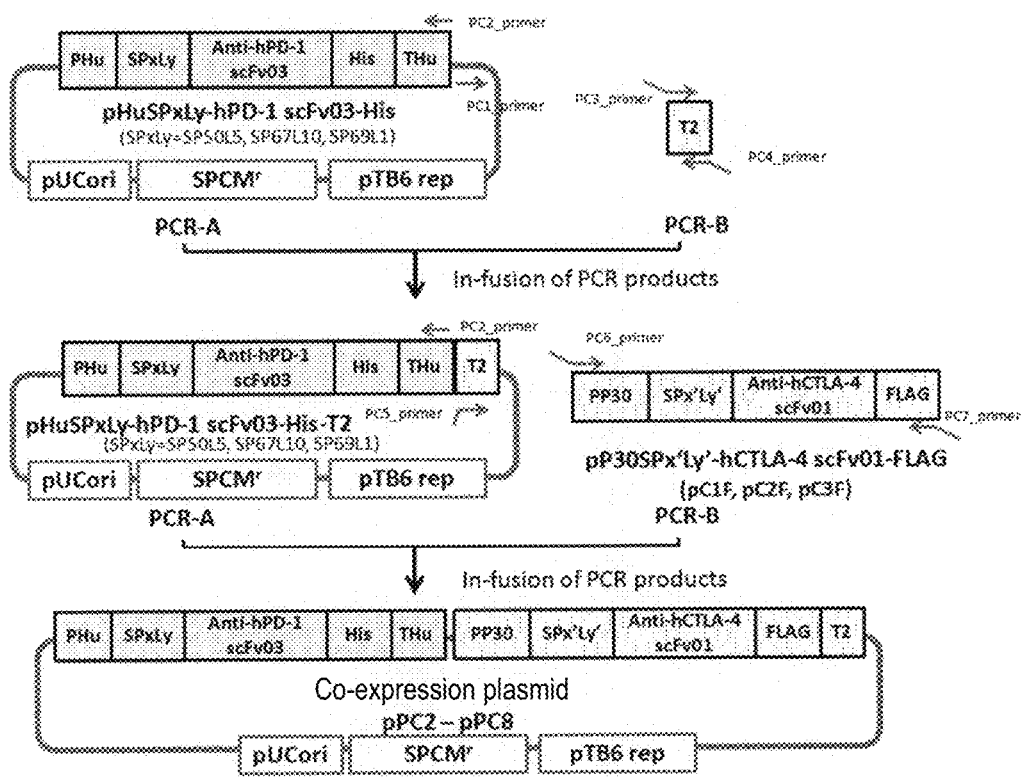

[Figure 26]
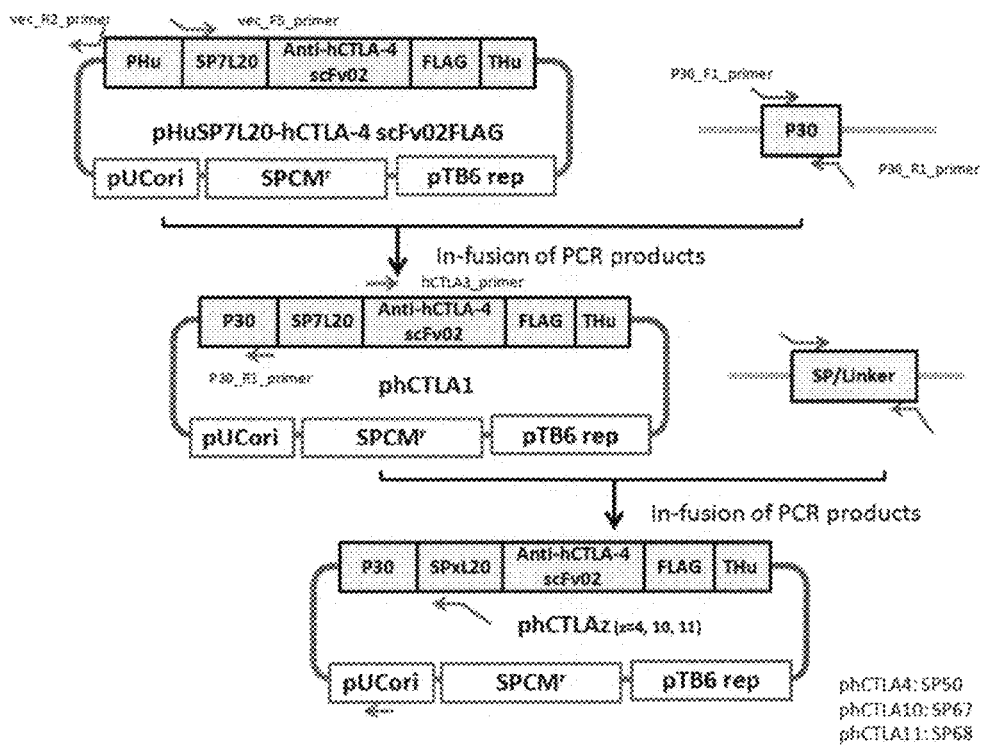
[Figure 27]
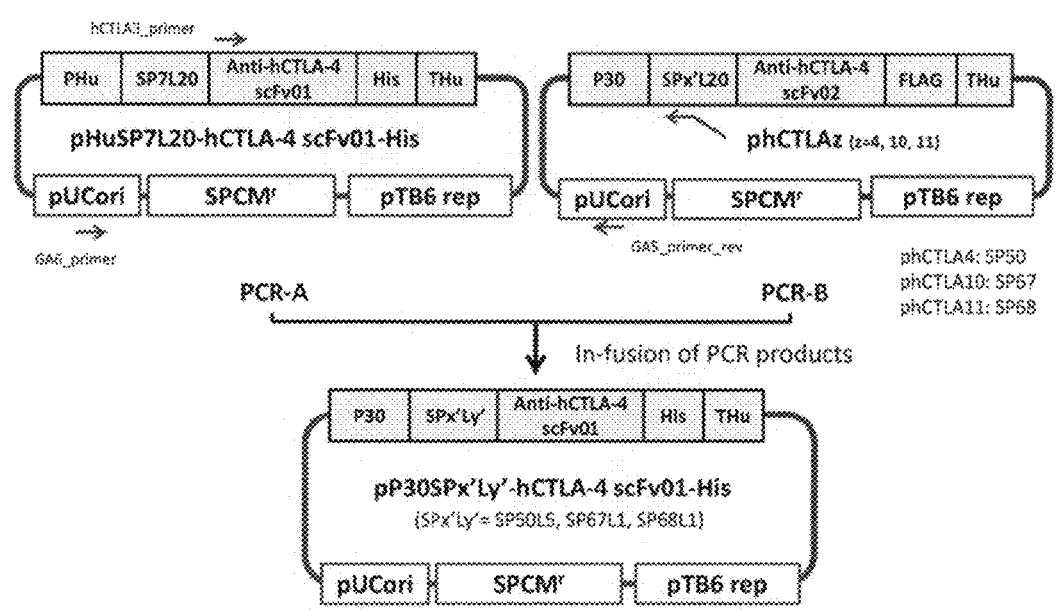

[Figure 28]
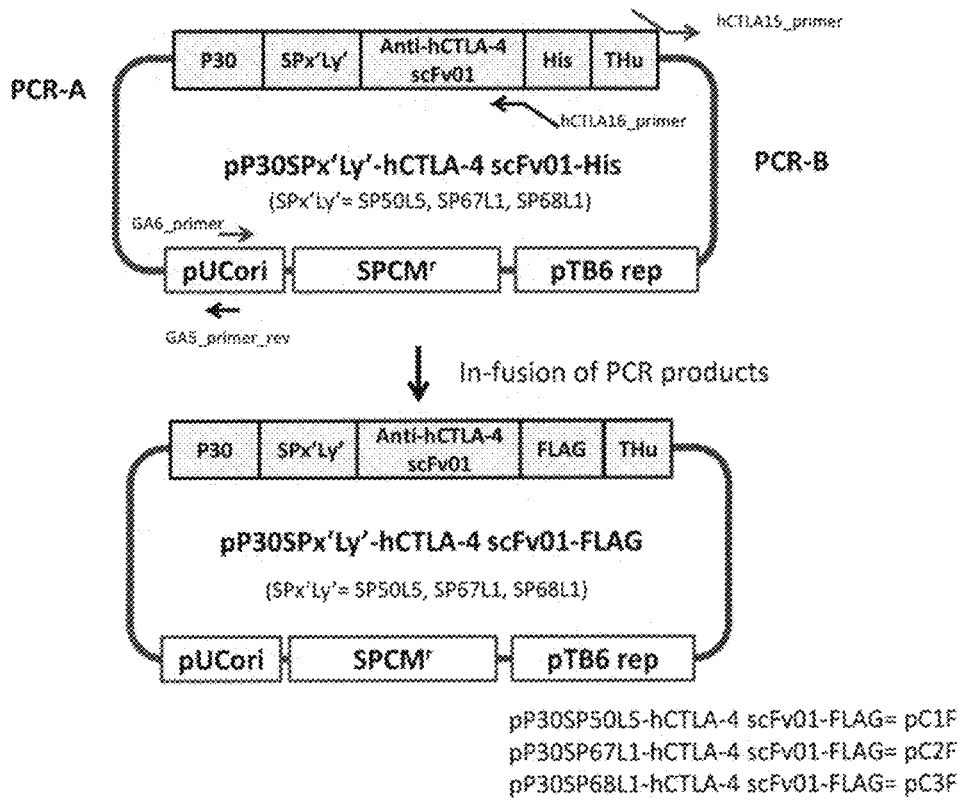
[Figure 29]
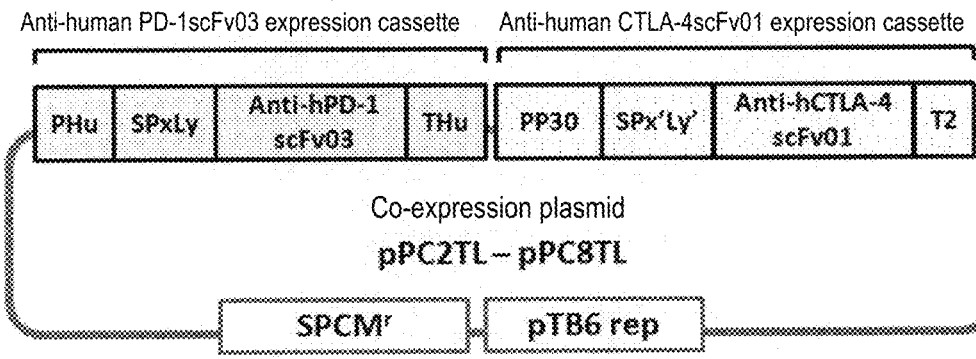

[Figure 30]
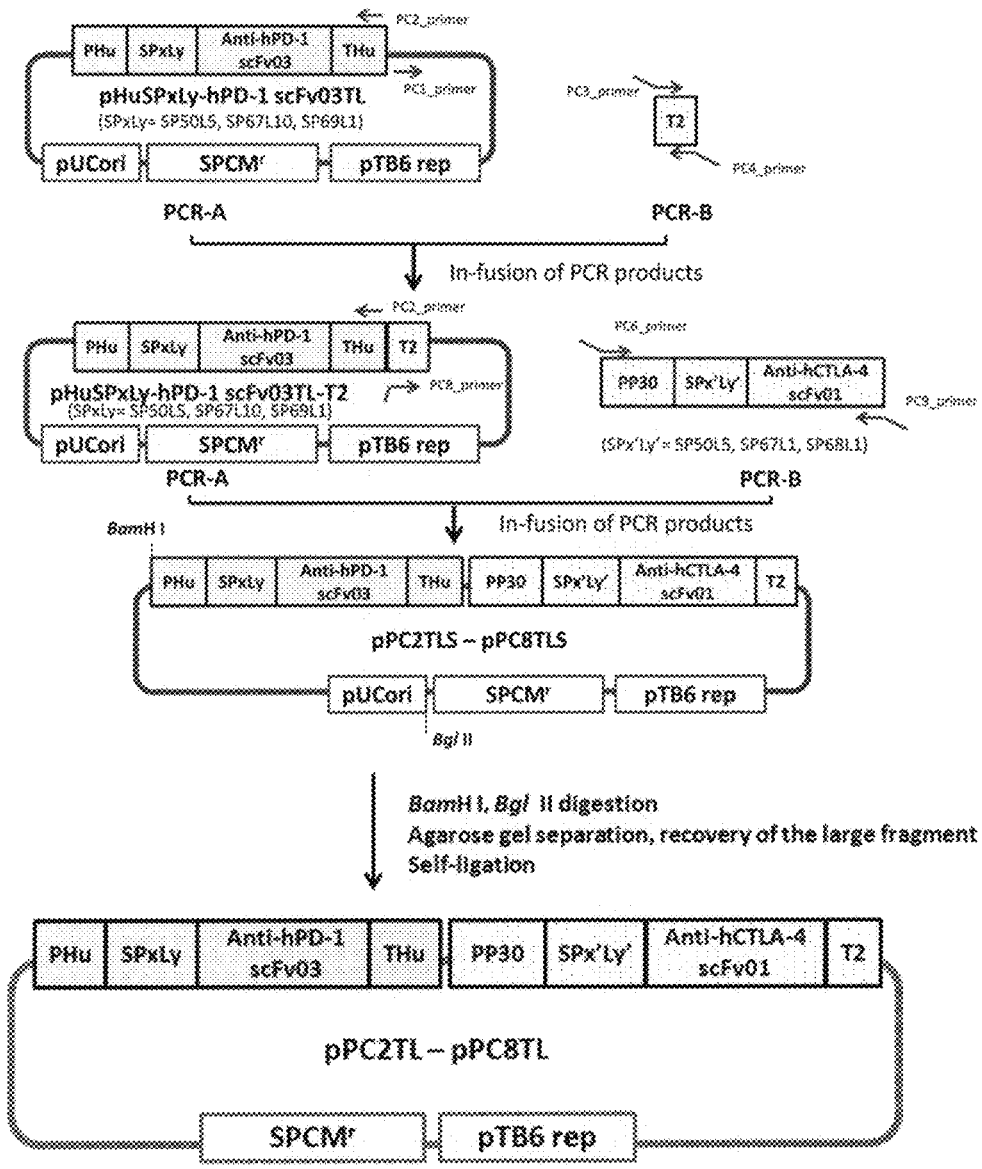

[Figure 31]
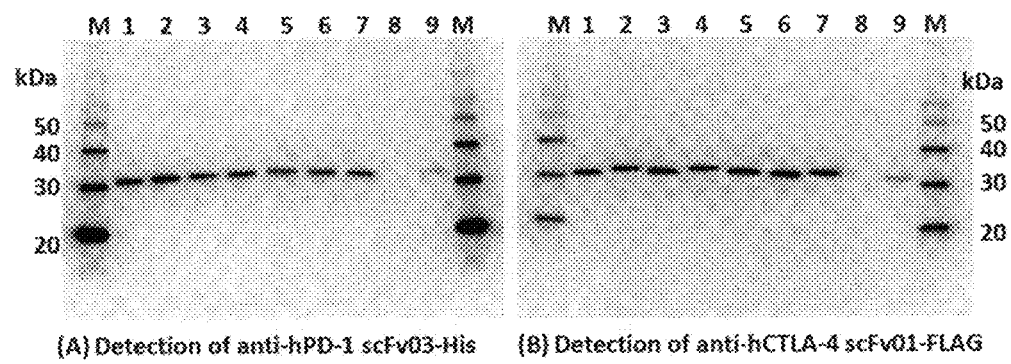
(A) Detection of anti-hPD-1 scFv03-His    (B) Detection of anti-hCTLA-4 scFv01-FLAG
1. PC2 (SP50LS-hPD-1 scFv03-His, SP67L1-hCTLA4-scFv01-FLAG)
2. PC3 (SP50LS-hPD-1 scFv03-His, SP68L1-hCTLA4-scFv01-FLAG)
3. PC4 (SP67L10-hPD-1 scFv03-His, SPSP50LS-hCTLA4-scFv01-FLAG)
4. PC5 (SP67L10-hPD-1 scFv03-His, SP68L1-hCTLA4-scFv01-FLAG)
5. PC6 (SP69L1-hPD-1 scFv03-His, SP50LS-hCTLA4-scFv01-FLAG)
6. PC7 (SP69L1-hPD-1 scFv03-His, SP67L1-hCTLA4-scFv01-FLAG)
7. PC8 (SP69L1-hPD-1 scFv03-His, SP68L1-hCTLA4-scFv01-FLAG)
8. BEshuttle (N.C.)
9. PC1

[Figure 32]
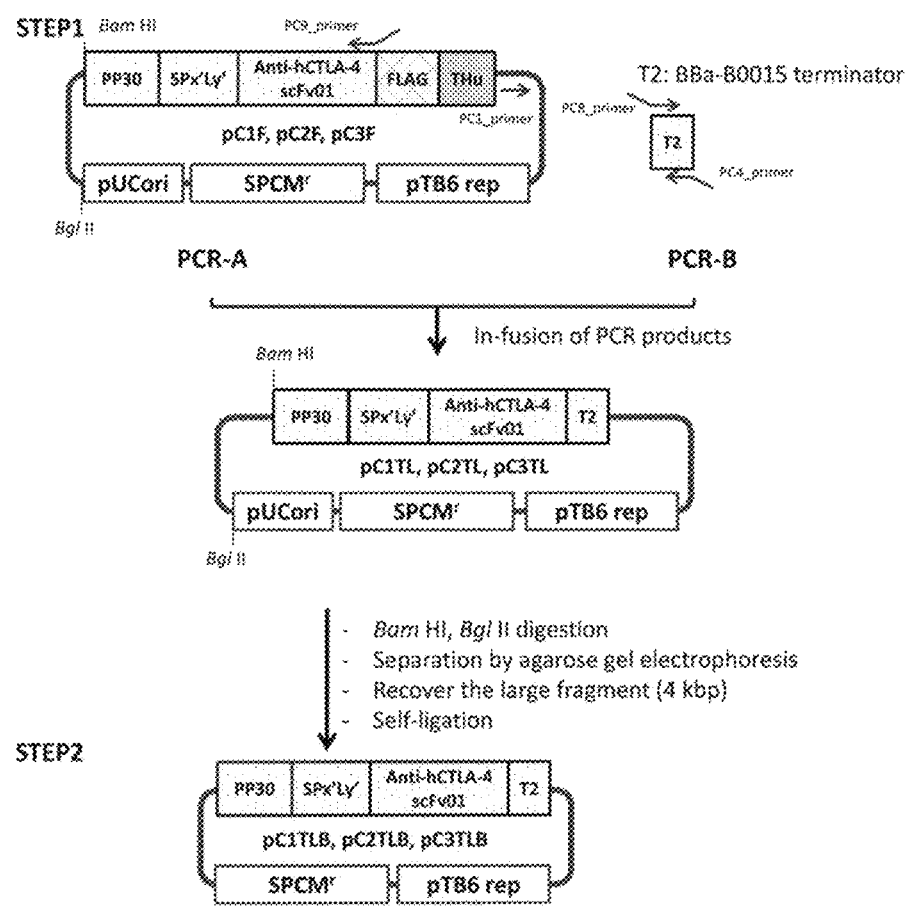

[Figure 33]
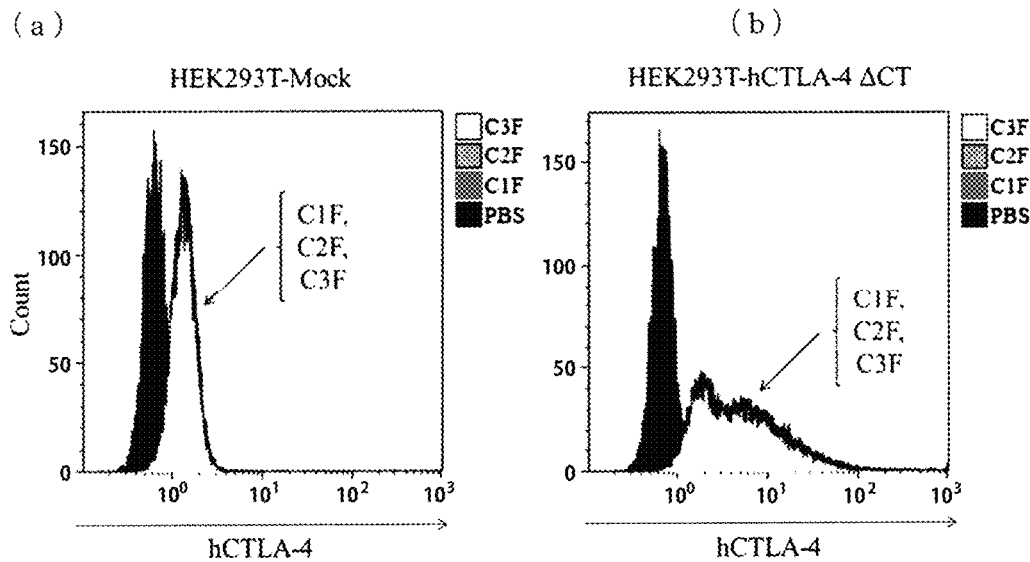
[Figure 34]
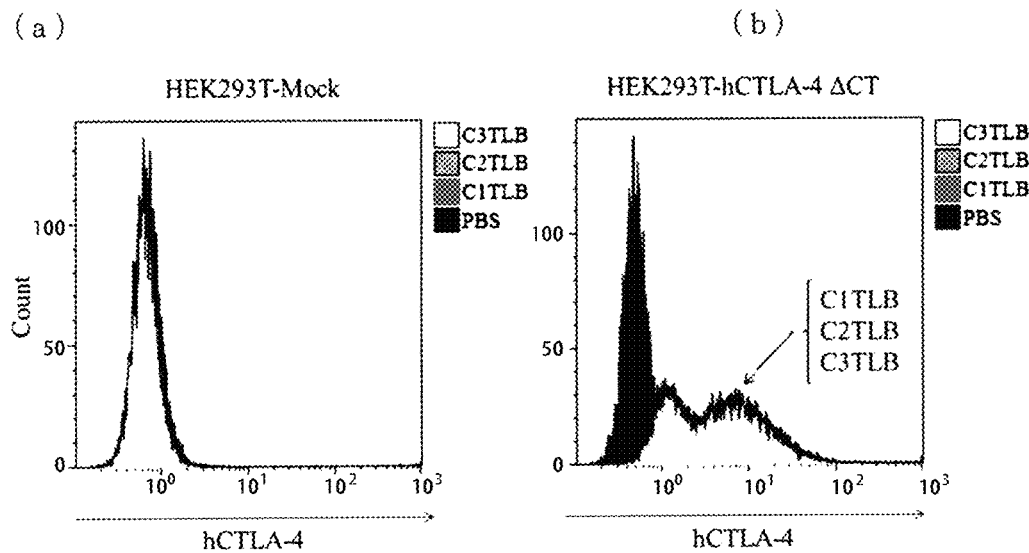

[Figure 35]
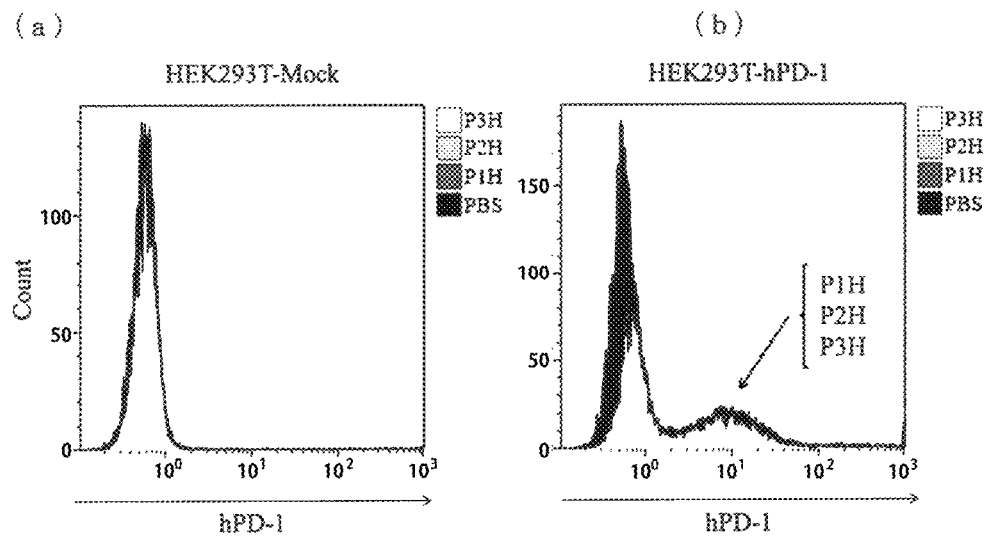
[Figure 36]
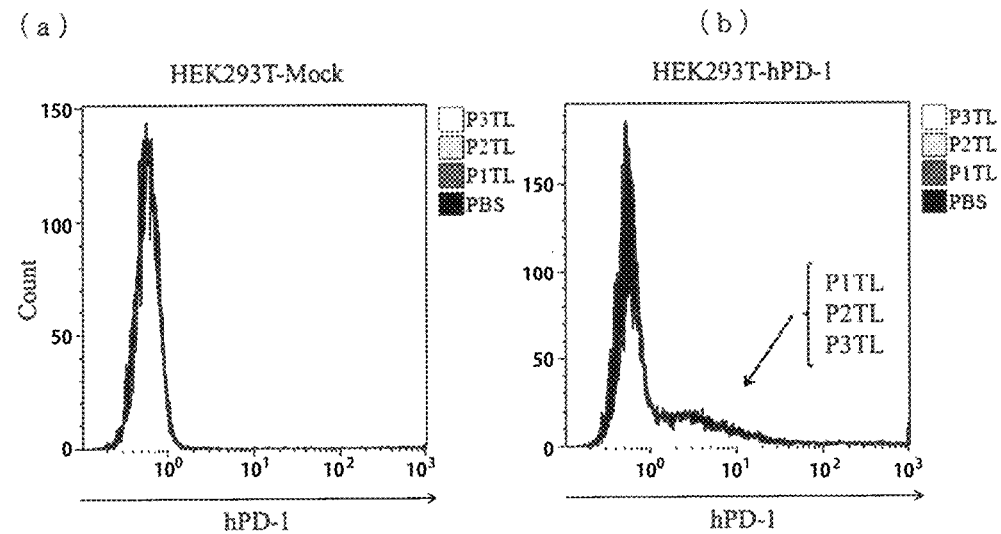

[Figure 37]
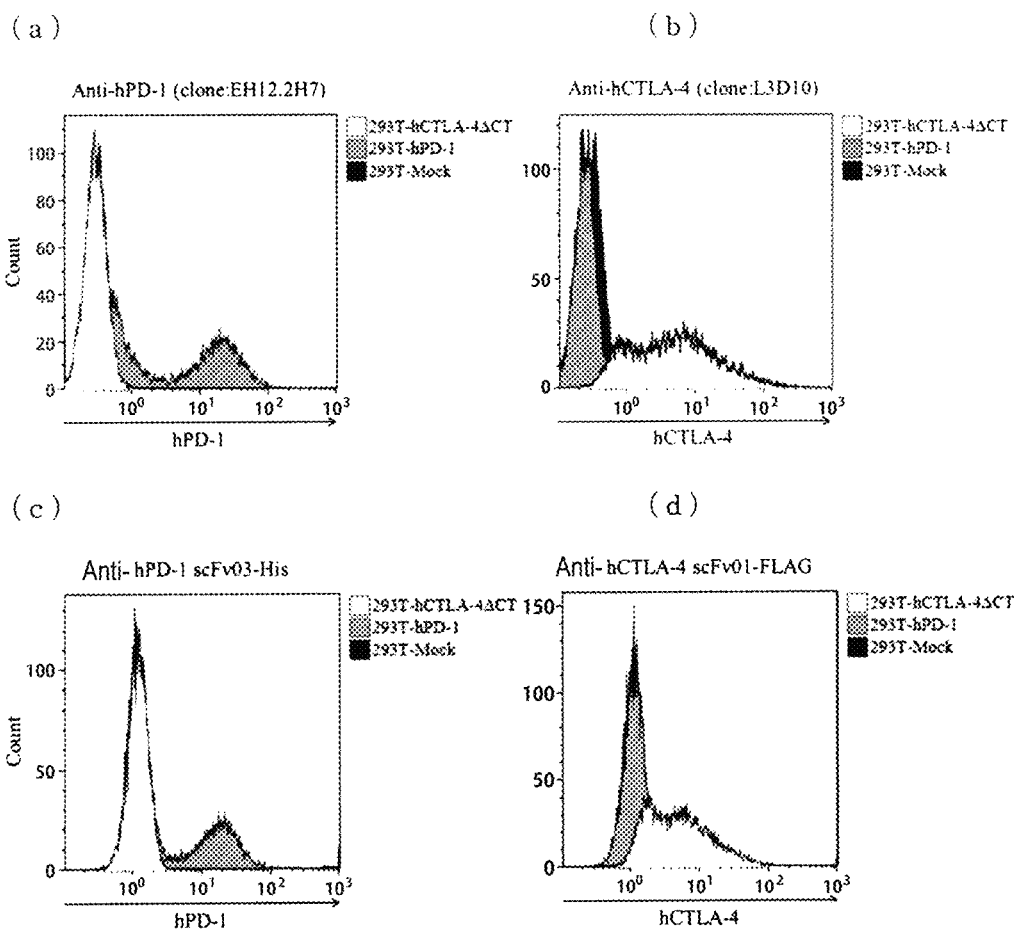

[Figure 38]
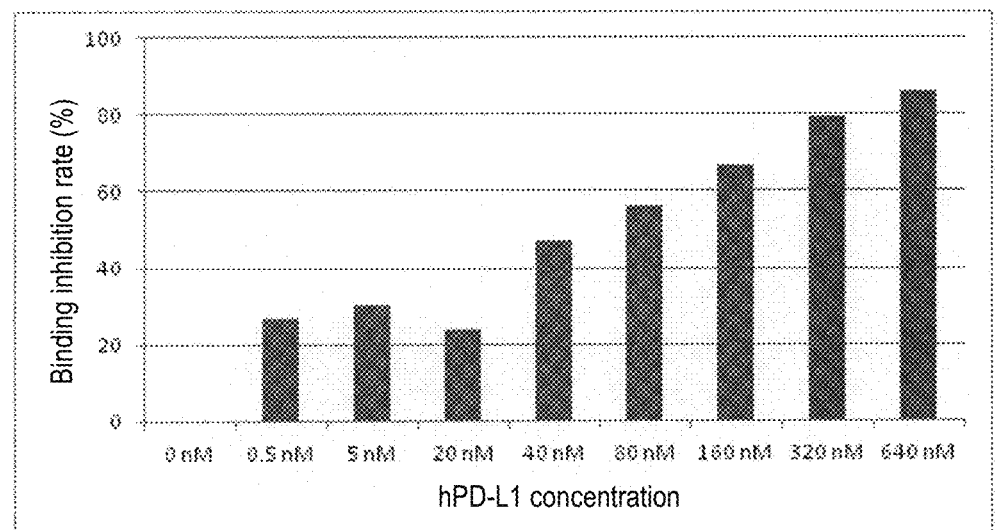
[Figure 39]
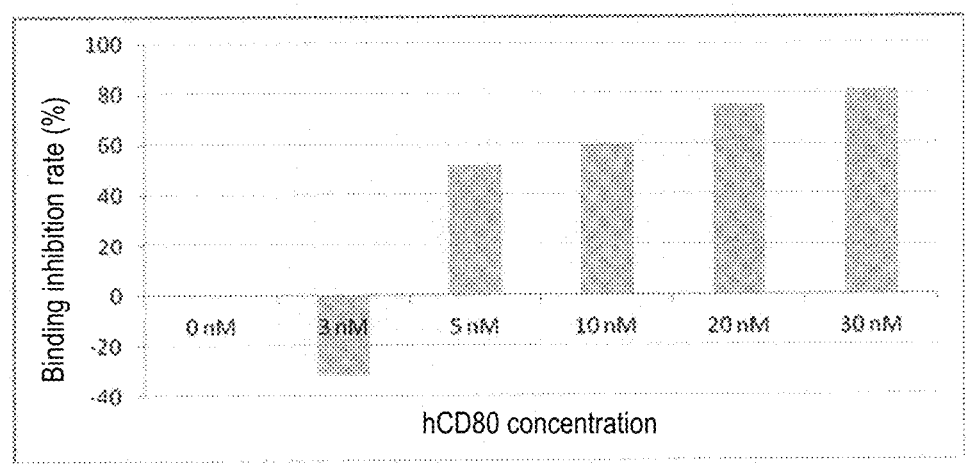

[Figure 40]
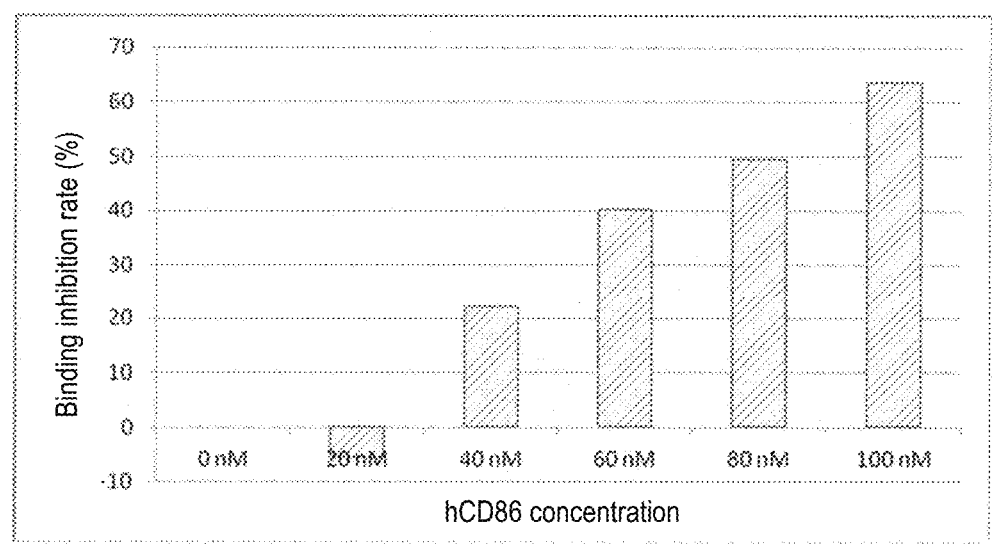

CO-EXPRESSION PLASMID

CROSS REFERENCE TO RELATED APPLICATIONS

This application is a National Phase under 35 USC 371 of International Application No. PCT/JP2015/006000 filed on Dec. 2, 2015, which claims priority to Japanese Application No. 2014-245424 filed Dec. 3, 2014, the contents of which are hereby incorporated by reference in their entirety.

TECHNICAL FIELD

The present invention relates to a co-expression plasmid characterized by comprising two types of secretory expression cassettes each sequentially comprising a promoter DNA functioning in a bacterium of the genus *Bifidobacterium*; a DNA encoding a secretory signal peptide; a DNA encoding a heterologous polypeptide; and a terminator DNA functioning in the bacterium of the genus *Bifidobacterium*. The present invention also relates to a bacterium of the genus *Bifidobacterium* transformed with the co-expression plasmid; a pharmaceutical composition comprising the bacterium; and the like.

SEQUENCE LISTING

The present application contains a Sequence Listing that has been submitted in ASCII format via EFS-Web and is hereby incorporated by reference into the present specification in its entirety. The .txt file was created on May 24, 2017; is named 5F001-003_SL-txt; and is 167 KB in size.

BACKGROUND ART

A great many therapeutic agents have been proposed up to present for treating diseases such as cancer; however the therapeutic agents are all have a limit in effect as pointed out by researchers. Thus, it has been desired to develop therapeutic agents and therapies having higher effects. Recently, development of a therapy using a gene transporting carrier has advanced. For example, a transformed microorganism is proposed (see for example, Patent Document 1), which uses an anaerobic enterobacterium having a nature of being accumulated in a hypoxic solid tumor when it is systemically administered and the transformant thereof expresses a gene encoding a protein having an antitumor activity or a protein having an activity to convert an antitumor substance precursor to an antitumor substance, in a target diseased site. Further development of this is expected as a new technology for delivering a drug which inevitably produces a side effect when it is systemically administered, to a tumor site effectively in a high concentration.

In the meantime, a promoter, a DNA encoding a signal sequence, a DNA encoding a polypeptide or an expression cassette comprising cloning sites for inserting these DNAs (see, for example, Patent Document 2) is proposed.

PRIOR ART DOCUMENTS

Patent Documents

Patent Document 1: International Publication No. WO2009/128272
Patent Document 2: International Publication No. WO2010/126073

SUMMARY OF THE INVENTION

Object to be Solved by the Invention

The DNA encoding a signal sequence and proposed in the aforementioned documents is DNA of a signal sequence found in a membrane protein and a secretory protein. Identification of a signal sequence having more excellent secretion efficiency is expected; at the same time, development of a plasmid expressing a secretory heterologous protein having a higher therapeutic effect and an anaerobic enterobacterium transformed with such a secretory expression plasmid has been desired.

An object of the present invention is to provide an anaerobic enterobacterium having a higher therapeutic effect at an anaerobic site such as a solid tumor tissue and an ischemic disease site.

Means to Solve the Object

The present inventors found that a bacterium of the genus *Bifidobacterium* transformed with a plasmid, which co-expresses two types of heterologous polypeptides, characterized by comprising two types of secretory expression cassettes each sequentially comprising a promoter DNA functioning in the bacterium of the genus *Bifidobacterium*; a DNA encoding a secretory signal peptide; a DNA encoding a heterologous polypeptide; and a terminator DNA functioning in the bacterium of the genus *Bifidobacterium*, has a significantly high cancer cell proliferation inhibitory activity, compared to single-expression strains of the heterologous polypeptides. Based on the finding, the present invention was accomplished.

More specifically, the present invention is as follows.

[1] A co-expression plasmid comprising two types of secretory expression cassettes each sequentially comprising the following DNA (1) to (4) and expressed within a bacterium of the genus *Bifidobacterium*:

(1) a promoter DNA functioning in the bacterium of the genus *Bifidobacterium*;
(2) a DNA encoding a secretory signal peptide;
(3) a DNA encoding a heterologous polypeptide; and
(4) a terminator DNA functioning in the bacterium of the genus *Bifidobacterium*.

[2] The co-expression plasmid according to [1], wherein a DNA encoding a linker peptide is ligated downstream of the DNA encoding a secretory signal peptide.

[3] The co-expression plasmid according to [1] or [2], wherein the promoter functioning in the bacterium of the genus *Bifidobacterium* is one or two promoters selected from P30 promoter, P54 promoter and Hu promoter.

[4] The co-expression plasmid according to any one of [1] to [3], wherein the terminator functioning in the bacterium of the genus *Bifidobacterium* is one or two terminators selected from Hu terminator and T2 terminator.

[5] The co-expression plasmid according to any one of [1] to [4], wherein the secretory signal peptide has the following amino acid sequence a) or b):

a) an amino acid sequence represented by any one of SEQ ID Nos: 57, 59, 61, 63, 65, 67, 69, 71, 73, 75 and 77,
b) an amino acid sequence obtained by deleting, substituting or adding one or several amino acids in the amino acid sequence represented by any one of SEQ ID Nos. 57, 59, 61, 63, 65, 67, 69, 71, 73, 75 and 77, and wherein a peptide consisting of the amino acid sequence serves as a secretory signal peptide in the bacterium of the genus *Bifidobacterium*.

[6] The co-expression plasmid according to any one of [1] to [5], wherein the heterologous polypeptide is a single-chain antibody.

[7] The co-expression plasmid according to [6], wherein the single-chain antibody is an anti-PD-1 antibody.

[8] The co-expression plasmid according to [6], wherein the single-chain antibody is an anti-CTLA-4 antibody.

[9] The co-expression plasmid according to [6], wherein the single-chain antibody is an anti-HER2 antibody.

[10] The co-expression plasmid according to any one of [1] to [5], wherein the heterologous polypeptide is a cytokine.

[11] The co-expression plasmid according to [10], wherein the cytokine is TNF-α.

[12] The co-expression plasmid according to [10], wherein the cytokine is IFN-γ.

[13] The co-expression plasmid according to any one of [1] to [5], wherein the heterologous polypeptide is a combination of the anti-PD-1 antibody and the anti-CTLA-4 antibody.

[14] The co-expression plasmid according to any one of [1] to [5], wherein the heterologous polypeptide is a combination of TNF-α and IFN-γ.

[15] The co-expression plasmid according to any one of [1] to [5], wherein the heterologous polypeptide is a combination of an anti-HER2 antibody and IFN-γ.

[16] A bacterium of the genus *Bifidobacterium* transformed with the co-expression plasmid according to any one of [1] to [15].

[17] The bacterium of the genus *Bifidobacterium* according to [16], wherein the bacterium is *Bifidobacterium longum*.

[18] A pharmaceutical composition comprising the bacterium of the genus *Bifidobacterium* according to [16] or [17].

Effect of the Invention

According to the present invention, it is possible to provide a bacterium of the genus *Bifidobacterium* capable of efficiently secreting two types of heterologous polypeptides outside the bacterial cell by using two types of expression cassettes enabling excellent secretion of a heterologous polypeptide in combination in the same plasmid. If the two types of heterologous polypeptides are e.g., antibodies having an anticancer effect, such as an anti-PD-1 antibody and an anti-CTLA-4 antibody, a synergetic effect of the two types of heterologous polypeptides are obtained. Due to this, such a bacterium of the genus *Bifidobacterium* is extremely useful as an anticancer drug.

BRIEF DESCRIPTION OF DRAWINGS

FIG. 1 The figure is a diagram showing the constitution of plasmid pSP3B-TNFα.

FIG. 2 The figure is a diagram showing the constitution of plasmid pHG-2.

FIG. 3 The figure is a diagram showing the constitution of plasmid pTNF11.

FIG. 4 The figure (a) is a diagram showing the constitution of plasmid phIFNg33; and the figure (b) is a diagram showing the constitution of plasmid phIFNg33TL.

FIG. 5 The figure is a graph showing cell proliferation inhibitory activity of a culture-supernatant crude purified product of an AG8TL strain to KPL-1 cell.

FIG. 6 The figure is a graph showing cell proliferation inhibitory activity of a culture-supernatant crude purified product of an AG8TL strain to MIA PaCa-2 cell.

FIG. 7 The figure is a graph showing an effect of the neutralization antibody added for neutralizing the cell proliferation inhibitory activity of the culture-supernatant crude purified product of an AG8TL strain.

FIG. 8 The figure (A) is a diagram showing the constitution of plasmid pHuSP7L20-hPD-1scFv03; (B) the constitution of pHuSP7L20-hCTLA-4scFv02; and (C) the constitution of pHuSP7L20-hCTLA-4scFv02FLAG.

FIG. 9 The figure (a) is a diagram showing the constitution of plasmid pPC1; and (b) the constitution of plasmid pCP1.

FIG. 10 The figure (A) is an electrophoretogram for checking the expression of anti-hPD-1scFv; and (B) is an electrophoretogram for checking the expression of anti-hCTLA-4scFv.

FIG. 11 The figure is a graph showing the specific binding of anti-hPD-1scFv03 to a human PD-1 immobilized plate.

FIG. 12 The figure is a graph showing the specific binding of anti-hCTLA-4scFv02 to a human CTLA-4 immobilized plate.

FIG. 13 The figure is a graph showing competitive (binding) inhibition of the binding reaction between human PD-1 and human PD-L1 by anti-hPD-1scFv03.

FIG. 14 The figure is a graph showing competitive (binding) inhibition of the binding reaction between human CTLA-4 and human CD80 by anti-hCTLA-4scFv02.

FIG. 15 The figure is a graph showing competitive (binding) inhibition of the binding reaction between human CTLA-4 and human CD86 by anti-hCTLA-4scFv02.

FIG. 16 The figure is a graph showing binding of anti-hPD-1scFv03 purified from PC1 strain to a human PD-1 overexpressing cell.

FIG. 17 The figure is a graph showing binding of anti-hCTLA-4scFv02 purified from PC1 strain to a human CTLA-4 overexpressing cell.

FIG. 18 The figure is an electrophoretogram of western analysis for checking secretion of anti-HER2scFv and hIFN-γ by HG-2 strain.

FIG. 19 The figure is a graph showing proliferation inhibitory activity to HER2 positive cell by anti-HER2scFv in a concentrate of HG-2 strain culture supernatant.

FIG. 20 The figure is a graph showing cell proliferation inhibitory activity to HER2 positive cells by a concentrate of HG-2 strain culture supernatant.

FIG. 21 The figure (A) is a picture showing gram staining of HG-2 strain; and (B) is a picture showing gram staining of BEshuttle strain.

FIG. 22 The figure (A) is a picture showing immunohistochemical staining of HG-2 strain with an anti-hIFN-γ antibody; and (B) is a picture showing immunohistochemical staining of BEshuttle strain with anti-hIFN-γ antibody.

FIG. 23 The figure (A) is a picture showing immunohistochemical staining of HG-2 strain with an anti-histidine tag antibody; and (B) is a picture showing immunohistochemical staining of BEshuttle strain with an anti-histidine tag antibody.

FIG. 24 The figure is a schematic diagram showing the constitution of a co-expression plasmid (pPC2-pPC8).

FIG. 25 The figure is a diagram schematically showing a method for constructing a co-expression plasmid (pPC2-pPC8).

FIG. 26 The figure is a diagram schematically showing a method for constructing anti-human CTLA-4scFv02 expression plasmid.

FIG. 27 The figure is a diagram schematically showing a method for constructing pP30SPxLy-hCTLA-4scFv01-His.

FIG. 28 The figure is a diagram schematically showing a method for constructing pP30SPxLy-hCTLA-4scFv01-FLAG (pC1F-pC3F).

FIG. 29 The figure is a schematic diagram showing the constitution of a co-expression plasmid (pPC2TL-pPC8TL).

FIG. 30 The figure is a diagram schematically showing a method for constructing a co-expression plasmid (pPC2TL-pPC8TL).

FIG. 31 The figure is an electrophoretogram of western analysis for checking secretion of anti-hPD-1scFv03-His (a) and anti-hCTLA-4scFv01-FLAG (b) in individual strains.

FIG. 32 The figure is a diagram schematically showing a method for constructing an anti-hCTLA-4scFv01 single-expression strain (pC1TLB, pC2TLB, pC3TLB).

FIG. 33 The figure is a flow-cytometric analysis chart showing the binding of scFv derived from C1F strain, C2F strain and C3F strain to a human CTLA-4 expressing cell.

FIG. 34 The figure is a flow-cytometric analysis chart showing the binding of scFv derived from C1TLB strain, C2TLB strain and C3TLB strain to a human CTLA-4 expressing cell.

FIG. 35 The figure is a flow-cytometric analysis chart showing the binding of scFv derived from P1H strain, P2H strain and P3H strain to a human PD-1 expressing cell.

FIG. 36 The figure is a flow-cytometric analysis chart showing the binding of scFv derived from P1TL strain, P2TL strain and P3TL strain to a human PD-1 expressing cell.

FIG. 37 The figure (a) is a flow-cytometric analysis chart showing the binding of an anti-human PD-1 antibody (EH12.2H7) to a human PD-1 expressing cell, (b) binding of an anti-human CTLA-4 antibody (L3D10) to a human CTLA-4 expressing cell; (c) binding of PC4-derived scFv to a human PD-1 expressing cell; and (d) binding of PC4-derived scFv to a human CTLA-4 expressing cell.

FIG. 38 The figure is a graph showing (binding) inhibitory activity of hPD-L1 to the binding between hPD-1scFv03-His purified from PC4 strain and hPD-1.

FIG. 39 The figure is a graph showing (binding) inhibitory activity of hCD80 to the binding between hCTLA-4scFv01-FLAG purified from PC4 strain and hCTLA-4.

FIG. 40 The figure is a graph showing (binding) inhibitory activity of hCD86 to the binding between hCTLA-4scFv01-FLAG purified from PC4 strain and hCTLA-4.

MODE OF CARRYING OUT THE INVENTION

The co-expression plasmid of the present invention is not particularly limited as long as it is a plasmid comprising two types of secretory expression cassettes each sequentially comprising (1) a promoter DNA functioning in a bacterium of the genus *Bifidobacterium*; (2) a DNA encoding a secretory signal peptide; (3) a DNA encoding a heterologous polypeptide; and (4) a terminator DNA functioning in the bacterium of the genus *Bifidobacterium*, and capable of co-expressing two types of heterologous polypeptides in the bacterium of the genus *Bifidobacterium* transformed with the plasmid. The 3' end of each of the above DNA fragments and the 5' end of the DNA fragment present immediately downstream may not be directly connected as long as the advantageous effect of the present invention can be obtained; however, the two ends are preferably directly connected.

The promoter DNA of the present invention is not particularly limited as long as it is promoter DNA functioning in a bacterium of the genus *Bifidobacterium*. Examples thereof may include Hu promoter DNA, which is a promoter relating to expression of a gene encoding histone-like DNA binding protein derived from *Bifidobacterium longum*; P30 promoter DNA (J. Microbiology, 2012, 638-643); P54 promoter DNA, which is a promoter relating to expression of a gene encoding Elongation Factor Tu protein (J. Bacteriology, 2005, 5799-5808, J. Microbiology, 2012, 638-643); promoter DNA of Gap gene derived from *Bifidobacterium breve* (Biotechnol. Lett. 2008 30: 1983-1988); promoter DNA of AmyB gene derived from *Bifidobacterium longum* (Biotechnol. Lett. 2006 28: 163-168); 16SrRNA promoter DNA (Biotechnol. Lett. 2008 30: 165-172); promoter DNA of GAPDH (pr-BL1363) gene (Appl Environ Microbiol. 2006 72 (11): 7401-7405); $P_R P_L$ promoter DNA (Cancer Gene Ther. 2007 14: 151-157); promoter DNA of p572 (β-glycosidase from *B. animalis* subsp *lactis*) gene (J. Microbiol Biotechnol. 2012 December; 22 (12): 1714-23); promoter (rplM promoter) DNA of p919 gene (J. Microbiol. 2012 August; 50 (4): 638-43); and promoter (rplR promoter) DNA of p895 gene (J. Microbiology, 2012, 638-643). The promoters of individual expression cassettes excellent in secretion of the heterologous polypeptides are preferably different from each other. More specifically, a combination of Hu promoter DNA and P30 promoter DNA, a combination of Hu promoter DNA and P54 promoter DNA and a combination of P54 promoter DNA and P30 promoter DNA can be preferably mentioned.

As the secretory signal peptide of the present invention, a) a peptide consisting of the amino acid sequence represented by any one of SEQ ID Nos. 57, 59, 61, 63, 65, 67, 69, 71, 73, 75 and 77 more specifically, any one of SP7, SP45, SP50, SP52, SP55, SP58, SP64, SP66, SP67, SP68 and SP69 can be mentioned. Of them, SP7 represented by SEQ ID No. 56 and SP69 represented by SEQ ID No. 66 can be preferably mentioned. Furthermore, b) a peptide consisting of an amino acid sequence obtained by deleting, substituting or adding one or several amino acids in the amino acid sequence represented by any one of SEQ ID Nos. 57, 59, 61, 63, 65, 67, 69, 71, 73, 75 and 77, and functioning as a secretory signal peptide in a bacterium of the genus *Bifidobacterium* (mutated secretory signal peptide) can be mentioned. The "amino acid sequence obtained by deleting, substituting or adding one or several amino acids" refers to an amino acid sequence obtained by deleting, substituting or adding, for example 1 to 5, preferably 1 to 3, more preferably 1 to 2 and further preferably one amino acid. The amino acid sequence of the mutated secretory signal peptide has a sequence identity of preferably 90% or more, more preferably 95% or more and further preferably 98% or more, with the amino acid sequence represented by any one of SEQ ID Nos. 57, 59, 61, 63, 65, 67, 69, 71, 73, 75 and 77.

The DNA encoding a secretory signal peptide consisting of the amino acid sequence as specified in a) is not particularly limited as long as it is DNA having a nucleotide sequence corresponding to the amino acid sequence specified in a). Accordingly, examples thereof, although different DNA due to degeneracy of codon may be included, may include DNA consisting of a nucleotide sequence (sequence listing, upper stage) represented by any one of SEQ ID Nos. 56, 58, 60, 62, 64, 66, 68, 70, 72, 74 and 76. These DNAs can be prepared by a method known to those skilled in the art, such as chemical synthesis and genetic engineering technique.

The DNA encoding a secretory signal peptide consisting of the amino acid sequence as specified in b) is not particularly limited as long as it is a DNA having a nucleotide sequence corresponding to the amino acid sequence specified in b). Accordingly, although different DNAs due to degeneracy of codon are included, these DNAs can be prepared in accordance with a method known to those skilled in the art, such as chemical synthesis, genetic engineering technique and mutagenesis. Mutated DNA can be obtained, for example, by introducing a mutation into DNA in accordance with a method of bringing a drug serving as a mutagen into contact with DNA consisting of the nucleotide sequence represented by any one of SEQ ID Nos. 56, 58, 60, 62, 64, 66, 68, 70, 72, 74 and 76; a method of irradiating the DNA with ultraviolet rays; or a method of applying a genetic engineering technique to the DNA. A genetic engineering technique, i.e., site-specific mutagenesis, is useful since it is a technique of introducing a predetermined mutation into a predetermined site, and is carried out in accordance with the method described in, e.g., Molecular Cloning: A laboratory Manual, 2nd Ed., Cold Spring Harbor Laboratory, Cold Spring Harbor, N.Y., 1989, Current Protocols in Molecular Biology, Supplement 1 to 38, John Wiley & Sons (1987-1997).

The secretory signal peptide is preferably ligated to a linker peptide and used as a signal peptide-linker conjugate in view of expression/secretion efficiency of a heterologous polypeptide. Such a linker peptide is not particularly limited as long as it can be connected to the C terminal of the secretory signal peptide of the present invention and enhance expression/secretion efficiency of a heterologous polypeptide. A peptide consisting of an amino acid sequence having 0 to 30 amino acid residues is preferably mentioned as an example. More specifically, of the following 11 types of amino acid sequences, which follow the aforementioned individual secretory signal peptides identified from *Bifidobacterium longum* 105-A strain, amino acid sequences consisting of any number of amino acids within the range from 0 to 30th amino acid can be mentioned as the linker peptides.

1) Linker peptide sequence represented by SEQ ID No. 79 (downstream of SP7);
2) Linker peptide sequence represented by SEQ ID No. 81 (downstream of SP45);
3) Linker peptide sequence represented by SEQ ID No. 83 (downstream of SP50);
4) Linker peptide sequence represented by SEQ ID No. 85 (downstream of SP52);
5) Linker peptide sequence represented by SEQ ID No. 87 (downstream of SP55);
6) Linker peptide sequence represented by SEQ ID No. 89 (downstream of SP58);
7) Linker peptide sequence represented by SEQ ID No. 91 (downstream of SP64);
8) Linker peptide sequence represented by SEQ ID No. 93 (downstream of SP66);
9) Linker peptide sequence represented by SEQ ID No. 95 (downstream of SP67);
10) Linker peptide sequence represented by SEQ ID No. 97 (downstream of SP68);
11) Linker peptide sequence represented by SEQ ID No. 99 (downstream of SP69)

The number of amino acid residues in the linker peptides mentioned above can be 0 to 30 residues, preferably, 0 to 25 residues, more preferably 0 to 20 residues, further preferably 0 to 15 residues, further more preferably 0 to 10 residues, and particularly preferably 1 to 10 residues.

As the DNA sequences encoding linker peptides consisting of amino acid sequences consisting of any number of amino acids within the range from 0 to 30th amino acid of the above individual sequences, the following sequences can be mentioned:

1) DNA sequence represented by SEQ ID No. 78 (downstream of SP7);
2) DNA sequence represented by SEQ ID No. 80 (downstream of SP45);
3) DNA sequence represented by SEQ ID No. 82 (downstream of SP50);
4) DNA sequence represented by SEQ ID No. 84 (downstream of SP52);
5) DNA sequence represented by SEQ ID No. 86 (downstream of SP55);
6) DNA sequence represented by SEQ ID No. 88 (downstream of SP58);
7) DNA sequence represented by SEQ ID No. 90 (downstream of SP64);
8) DNA sequence represented by SEQ ID No. 92 (downstream of SP66);
9) DNA sequence represented by SEQ ID No. 94 (downstream of SP67);
10) DNA sequence represented by SEQ ID No. 96 (downstream of SP68);
11) DNA sequence represented by SEQ ID No. 98 (downstream of SP69).

The DNA region encoding the secretory signal peptide-linker peptide conjugate of the present invention refers to a DNA region from the 5' end of the DNA encoding each of the secretory signal peptides to the 3' end of the DNA encoding the linker peptide downstream of the secretory signal peptide (including both ends). Since the 3' end of the DNA encoding the secretory signal peptide and the 5' end of the DNA encoding the linker peptide are connected, the secretory signal peptide-linker peptide conjugate of the present invention is sometimes represented by SPxLy (where x is the number of a secretory signal peptide assigned in the specification and y is the number of amino acid residues of the linker peptide). Examples of the secretory signal peptide-linker peptide conjugate may include SP7L20, SP45L20, SP50L20, SP52L20, SP55L20, SP58L20, SP64L20, SP66L20, SP67L20, SP68L20 and SP69L20. For example, SP67L20 represents the secretory signal peptide-linker peptide conjugate obtained by connecting the first 20 amino acids of the sequence represented by SEQ ID No. 95 to the amino acid sequence represented by SEQ ID No. 73. Of the secretory signal peptide-linker peptide connected bodies, SP50L1 to L15, SP67L1 to L15, SP68L1 to L15 and SP69L1 to L15 are preferable; SP50L1 to L10, SP67L1 to L10, SP68L1 to L10 and SP69L1 to L10 are preferable; and SP50L5, SP67L1, SP67L10, SP68L1 and SP69L1 are particularly preferable. Note that, L1 to L15 represent L1, L2, L3, L4, L5, L6, L7, L8, L9, L10, L11, L12, L13, L14 and L15 and L1 to L10 represent L1, L2, L3, L4, L5, L6, L7, L8, L9 and L10.

DNA encoding a heterologous polypeptide as mentioned above is not particularly limited as long as it is DNA which encodes a polypeptide not derived from a bacterium of the genus *Bifidobacterium* and can be expressed by the secretory expression cassette of the present invention. Examples thereof may include DNA encoding a cytokine such as interferon (IFN)-α, β, γ, a granulocyte macrophage colony stimulating factor (GM-CSF), interleukin (IL)-1α, IL-1β, IL-2, IL-3, IL-4, IL-6, IL-7, IL-10, IL-12, IL-13, IL-15, IL-18, IL-21, IL-22, IL-27, a tumor necrosis factor (TNF)-α, lymphotoxin (LT)-β, a granulocyte colony stimulating factor (G-CSF), a macrophage colony stimulating factor (M-CSF) and a macrophage migration inhibitory factor (MIF); and DNA encoding an angiogenesis inhibitor such as endostatin, angiostatin and kringle (NH4). Besides these, DNA encoding cytosine deaminase, which is an enzyme of converting of 5-fluorocytosine (a prodrug of 5-fluorouracil) into 5-fluorouracil; and DNA encoding nitroreductase, which is an enzyme of reducing a nitro group of a prodrug of an anticancer agent having a nitroaromatic skeleton to activate it, can be preferably mentioned. In addition, DNA encoding an antibody polypeptide can be advantageously used. To such DNA encoding a heterologous polypeptide, DNA encoding an affinity tag such as histidine (His) tag and FLAG tag can be appropriately attached in order to facilitate an isolation treatment of the polypeptide.

Examples of the antibody may include an antibody for use in a rheumatoid therapeutic agent targeting an interleukin-6 (IL-6) receptor; an antibody for use in a therapeutic agent for multiple sclerosis targeting α4-integrin; an antibody having an anticancer effect targeting CD20, CD33, PD-1, CTLA-4, PD-L1, CD80, CD86, LAG3, TIM3 or KIR; an agonist antibody targeting e.g., OX40, CD137 or ICOS; and an antibody specifically binding to HER2, EGFR, CEA, HGF, EpCAM (CD326), cMET or CCR4.

Of them, the anti-PD-1 antibody can be preferably mentioned as an example, because it binds to a PD-1 receptor expressed on an activated lymphocyte (T cell, B cell) to inhibit the binding of PD-L1 and PD-L2 expressed by a cancer cell to the PD-1 receptor, with the result that the immune reaction to the tumor cell is enhanced. Furthermore, the anti-CTLA-4 antibody suppresses the function of CTLA-4, which is known as an autoimmune function suppression molecule, thereby enhancing an antitumor immune response. More specifically, the anti-CTLA-4 antibody can be preferably mentioned as an example, because the anti-CTLA-4 antibody is considered to enhance the antitumor immune response by inhibiting the binding of CTLA-4 to CD80 and CD86 expressed in an antigen presenting cell to inhibit negative down-regulation of an immune response induced by the interaction between these molecules. Moreover, the anti-HER-2 (human EGFR-related2) antibody can be preferably mentioned as an example, because it is considered to specifically bind to HER2 protein, which is a gene product of oncogene HER2/neu (c-erbB-2), to suppress a proliferation signal, thereby exerting an anti-tumor effect.

As the DNA encoding an antibody polypeptide as mentioned above, DNA encoding e.g., a chimeric antibody, a humanized antibody, Fab, Fab', F (ab')$_2$, and a single-chain antibody (scFv: single chain Fv) can be mentioned; however, DNA encoding a single-chain antibody, capable of recognizing and binding a target substance by itself, having an appropriate (not too big) molecular weight, and expressible when it is introduced into a bacterium of the genus *Bifidobacterium*, is preferable. DNAs encoding heterologous polypeptides including these antibodies can be also prepared by a method known in the art such as chemical synthesis and genetic engineering technique based on their sequence information appropriately obtained from published documents or database such as GenBank.

As the aforementioned combination of heterologous polypeptides of the present invention, it is preferable to employ a combination of heterologous polypeptides which are expected to produce a synergistic combinational effect at an anaerobic disease site when locally expressed. This is because when a bacterium of the genus *Bifidobacterium* is systemically administered, it does not proliferate in a normal tissue but is selectively distributed and colonized at an anaerobic site such as a solid tumor tissue and an ischemic disease site. Specific examples of the combination may include a combination of TNF-α and IFN-γ; a combination of an anti-PD-1 antibody and an anti-CTLA-4 antibody; a combination of an anti-HER2 antibody and IFN-γ; a combination of an anti-PD-1 antibody and IFN-γ; a combination of an anti-PD-1 antibody and an anti-HER2 antibody; and a combination of an anti-PD-1 antibody and an anti-EpCAM antibody.

The terminator DNA is not particularly limited as long as it is terminator DNA that functions in a bacterium of the genus *Bifidobacterium*. Specific examples thereof may include Hu terminator DNA derived from *Bifidobacterium longum*; d0013 terminator DNA, which is a terminator of a lactate dehydrogenase gene derived from *Bifidobacterium longum*; T572 terminator DNA derived from *Bifidobacterium animaris* (J. Microbiol Biotechnol. 2012 December; 22 (12): 1714-23); and BBa_B0015 (T2) terminator DNA, which is an artificially designed terminator. It is preferable to use different terminators for respective expression cassettes excellent in secretion of a heterologous polypeptide as mentioned above. Specific examples thereof may include Hu terminator DNA and d0013 terminator DNA in combination; Hu terminator DNA and T572 terminator DNA in combination; Hu terminator DNA and T2 terminator DNA in combination; d0013 terminator DNA and T572 terminator DNA in combination; d0013 terminator DNA and T2 terminator DNA in combination; and T572 terminator DNA and T2 terminator DNA in combination.

As a method for producing a secretory expression cassette of the present invention, preferably a secretory expression cassette comprising a DNA encoding a linker peptide, it is possible to mention a method of sequentially connecting the following DNAs:

(1) a promoter DNA functioning in a bacterium of the genus *Bifidobacterium*;

(2) a DNA encoding a secretory signal peptide consisting of the amino acid sequence described in a) or b) below:
  a) an amino acid sequence represented by any one of SEQ ID Nos. 57, 59, 61, 63, 65, 67, 69, 71, 73, 75 and 77;
  b) an amino acid sequence obtained by deleting, substituting or adding one or several amino acids in the amino acid sequence represented by any one of SEQ ID Nos. 57, 59, 61, 63, 65, 67, 69, 71, 73, 75 and 77, wherein a peptide consisting of the amino acid sequence serves as a signal peptide in the bacterium of the genus *Bifidobacterium*;

(3) a DNA encoding a linker peptide;

(4) a DNA encoding a heterologous polypeptide; and (5) a terminator DNA functioning in the bacterium of the genus *Bifidobacterium*, in the order of (1) to (5) from upstream to downstream. The secretory expression cassette of the present invention can be prepared in accordance with a method described in a commercially available experimental technique, for example, Gene Manual (Kodansha Ltd.); Gene Manipulation Experimental Technique, edited by Yasutaka Takagi, Kodansha Ltd.; Molecular Cloning [Cold Spring Harbor Laboratory (1982)]; Molecular cloning second edition [Cold Spring Harbor Laboratory (1989)]; Methods in enzymology 194 (1991); and Gene experimental technique by yeast, Experimental Medicine, supplemental vol., YODOSHA CO., LTD. (1994).

The plasmid vector that can be used for producing a co-expression plasmid comprising two types of secretory expression cassettes of the present invention is not particularly limited, as long as it is a plasmid vector into which two types of expression cassettes of the present invention can be inserted and as long as two types of secretory heterologous polypeptides are expressed when a bacterium of the genus Bifidobacterium is transformed with the plasmid vector. A shuttle plasmid vector further having an origin of replication such as a pUCori, which can function also in a bacterium other than a bacterium of the genus Bifidobacterium, for example, in E. coli, can be advantageously used.

Examples of the plasmid vector having a plasmid replication unit functioning in a bacterium of the genus Bifidobacterium include pTB6 (Biosci Biotechnol Biochem. 2005 February; 69 (2): 422-5); pMB1 (Lett Appl Microbiol. 1990 October; 11 (4): 220-3); pTB4 (structural analysis and application of Bifidobacterium longum-derived plasmid pTB4, general subject of speech, poster presentation program, Molecular Biology Society of Japan, 1994); pFI2576 (J Microbiol Biotechnol. 2009 April; 19 (4): 403-8); pCIBAO (Appl Environ Microbiol. 2007 December; 73 (24): 7858-66); pBC1 (Plasmid. 2007 March; 57 (2): 165-74); pDOJH10S (Appl Environ Microbiol. 2006 January; 72 (1): 527-35); and PKJ50 (Microbiology 1999 March; 145 (Pt): 585-92). As the replication unit, pTB6rep unit consisting of a pTB6-derived OriV region and RepB gene can be preferably mentioned. A shuttle plasmid vector further having an origin of replication such as a pUCori, which can function also in a bacterium other than a bacterium of the genus Bifidobacterium, for example in E. coli, can be used.

The plasmid may contain a marker gene such as a drug resistance gene. Examples of the drug resistance marker gene include spectinomycin, chloramphenicol, erythromycin and ampicillin resistance genes.

As a method for introducing the plasmid of the present invention into a bacterium of the genus Bifidobacterium, a gene introduction method known in the art, such as electroporation, may be mentioned.

Examples of the bacterium of the genus Bifidobacterium in the present invention include Bifidobacterium longum, Bifidobacterium breve (B. breve), Bifidobacterium adolescentis (B. adolescentis), Bifidobacterium bifidum (B. bifidum), Bifidobacterium pseudolongum (B. pseudolongum), Bifidobacterium thermophirum (B. thermophirum), Bifidobacterium infantis (B. infantis), Bifidobacterium animalis (B. animalis), Bifidobacterium angulatum (B. angulatum), Bifidobacterium asteroides (B. asteroides), Bifidobacterium boum (B. boum), Bifidobacterium catenulatum (B. catenulatum), Bifidobacterium choerinum (B. choerinum), Bifidobacterium coryneforme (B. coryneforme), Bifidobacterium cuniculi (B. cuniculi), Bifidobacterium denticolens (B. denticolens), Bifidobacterium dentium (B. dentium), Bifidobacterium gallicum (B. gallicum), Bifidobacterium gallinarum (B. gallinarum), Bifidobacterium globosum (B. globosum), Bifidobacterium indicum (B. indicum), Bifidobacterium inopinatum (B. inopinatum), Bifidobacterium lactis (B. lactis), Bifidobacterium lactentis (B. lactentis), Bifidobacterium magnum (B. magnum), Bifidobacterium merycicum (B. merycicum), Bifidobacterium minimum (B. minimum), Bifidobacterium Mongolia Enns (B. Mongolia Enns), Bifidobacterium parvulorum (B. parvulorum), Bifidobacterium pseudocatenulatum (B. pseudocatenulatum), Bifidobacterium psychraerophilum (B. psychraerophilum), Bifidobacterium pullorum (B. pullorum), Bifidobacterium ruminale (B. ruminale), Bifidobacterium ruminantium (B. ruminantium), Bifidobacterium saeculare (B. saeculare), Bifidobacterium scardovii (B. scardovii), Bifidobacterium subtile (B. subtile), Bifidobacterium suis (B. suis), and Bifidobacterium thermacidophilum (B. thermacidophilum). Of them, Bifidobacterium longum, Bifidobacterium breve, Bifidobacterium adolescentis, Bifidobacterium bifidum and Bifidobacterium infantis, which are known to be harbitually present within the human intestine regardless of age, are preferably used as a host cell, and Bifidobacterium longum is more preferably used. These bacteria all can be commercially available or can be easily obtained from e.g., a depository.

The strain of each bacterium is not particularly limited. Examples of the strain of Bifidobacterium longum include Bifidobacterium longum 105-A strain, Bifidobacterium longum aE-194b strain, Bifidobacterium longum bs-601 strain, Bifidobacterium longum M101-2 strain and Bifidobacterium longum ATCC-15707 strain. Of them, Bifidobacterium longum 105-A strain is preferable. As to Bifidobacterium breve, for example, Bifidobacterium breve standard strain (JCM1192), Bifidobacterium breve aS-1 strain and Bifidobacterium breve I-53-8W strain may be mentioned. Of them, Bifidobacterium breve standard strain and Bifidobacterium breve aS-1 strain are preferable. As to Bifidobacterium infantis, for example, Bifidobacterium infantis standard strain (JCM1222) and Bifidobacterium infantis I-10-5 strain may be mentioned. As to Bifidobacterium lactentis, for example, Bifidobacterium lactentis standard strain (JCM1210) may be mentioned. As to Bifidobacterium bifidum strain, for example, Bifidobacterium bifidum ATCC-11863 strain may be mentioned.

The plasmid and transformed bacterium of the genus Bifidobacterium of the present invention can be prepared in accordance with a method described in a published experimental text, for example, Gene Manual (Kodansha Ltd.); Gene Manipulation Experimental Technique, edited by Yasutaka Takagi, Kodansha Ltd.; Molecular Cloning [Cold Spring Harbor Laboratory (1982)]; Molecular cloning second edition [Cold Spring Harbor Laboratory (1989)]; Methods in enzymology 194 (1991); and Gene experimental technique by yeast, Experimental medicine, supplemental vol., YODOSHA CO., LTD. (1994).

The transformed bacterium of the genus Bifidobacterium does not proliferate in a normal tissue but proliferates only in a tumor tissue under an anaerobic environment and can express two types of heterologous polypeptides useful for therapy within the tumor tissue.

Accordingly, the transformed bacterium of the genus Bifidobacterium can be used in a pharmaceutical composition, in particular, an anticancer drug effective for treating a tumor under an anaerobic environment, preferably a solid tumor. Accordingly, the pharmaceutical composition of the present invention is not particularly limited as long as it contains the bacterium of the genus Bifidobacterium of the present invention capable of secreting heterologous polypeptides, preferably cytokines and antibodies having an anticancer effect, as an active ingredient, and may contain an optional ingredient such as a pharmacologically acceptable carrier, an excipient and a diluent as long as it does not prevent the action and effect of the polypeptide to be secreted.

The administration target of the pharmaceutical composition of the present invention is a mammalian, preferably a human. Examples of the applicable target of the pharmaceutical composition of the present invention include colon carcinoma, head and neck cancer, breast cancer, lung cancer, esophageal carcinoma, gastric carcinoma, liver carcinoma, gallbladder carcinoma, cholangiocarcinoma, pancreatic cancer, pancreatic islet cell carcinoma, choriocarcinoma, colon carcinoma, renal cell carcinoma, adrenal cortical carcinoma, bladder carcinoma, testicular carcinoma, prostate cancer, testis cancer, ovarian cancer, uterine cancer, choriocarcinoma, thyroid cancer, squamous cell carcinoma, skin cancer, brain tumor, malignant carcinoid tumor, osteosarcoma, soft tissue sarcoma, neuroblastoma, Wilms tumor, retinoblastoma and melanoma.

As the dosage form of the pharmaceutical composition of the present invention, a liquid formulation or a solid formulation can be mentioned. The liquid formulation can be prepared by purifying the culture of the bacterium of the genus *Bifidobacterium* of the present invention, applicably adding, if necessary, saline, a replacement fluid or a pharmaceutical additive(s) and charging e.g., ampoules or vials with the resultant suspension. The solid formulation can be prepared by adding a protecting agent to the liquid formulation, charging ampoules or vials with the mixture, and freezing the mixture to obtain a frozen formulation or freeze-drying the mixture to obtain a lyophilized formulation. As a method of administering the pharmaceutical composition of the present invention, oral administration and parenteral administration both can be employed; however, parenteral administration is preferable; for example, intravenous administration and local administration can be mentioned.

The dose of the pharmaceutical composition of the present invention is not particularly limited as long as a bacterium of the genus *Bifidobacterium* can grow in a diseased site and as long as it is a sufficient amount for the bacterium of the genus *Bifidobacterium* to express a therapeutically effective amount of e.g., a cytokine or active antibody. The dose of the pharmaceutical composition can be appropriately selected depending upon the severity of disease and the weight, age and sex of the patient, and appropriately increased or decreased depending upon the degree of improvement. From an economic point of view and in order to avoid a side effect as much as possible, the dose is preferably as low as possible within the range where a requisite therapeutic effect is obtained.

For example, in the case of intravenous administration, it is required to reduce a risk, in particular, e.g., embolization caused by bacterial mass. Thus, it is preferable that an injectable solution prepared to have a concentration as low as possible, is injected in a plurality of times by dividing the dose into the plural portions or continuously administered by diluting it with an appropriate replacement fluid. For example, in the case of an adult, the bifidobacterial cell of the present invention, a daily dose of $10^4$ to $10^{12}$ cfu per body weight (1 kg), is divided in a plurality of times and administered for one to several days continuously or non-continuously at appropriate time intervals. More specifically, a formulation comprising the bifidobacterial cell of the present invention in a concentration of $10^4$ to $10^{10}$ cfu/mL is directly administered or by diluting it with an appropriate replacement fluid, in a dose of 1 to 1000 mL per adult, once a day or by dividing the dose in a plurality of times per day continuously for one to several days.

For example, in the case of local administration, i.e., direct administration to a diseased tissue, a high-concentration injectable solution is desirably injected in a plurality of sites of the diseased tissue, since a bacterial cell is required to colonize and grow over the entire diseased tissue as much as possible. For example, in the case of an adult, the bifidobacterial cell of the present invention, more specifically, a daily dose of $10^4$ to $10^{12}$ cfu per body weight (1 kg), is administered once or in a plurality of times per day, if necessary, for one to several days, continuously or non-continuously at appropriate time intervals. More specifically, a formulation comprising the bifidobacterial cell of the present invention in a concentration of $10^4$ to $10^{10}$ cfu/mL is directly administered in a dose of 0.1 to 100 mL per adult, several times per day, if necessary, for one to several consecutive days.

Now, the present invention will be more specifically described by way of Examples below; however, the technical scope of the present invention is not limited by these examples.

Example 1

[Preparation of Human TNF-α and Human IFN-γ Co-Expression *Bifidobacterium*, AG8TL Strain]

(Outline)

A co-expression plasmid, pAG8TL was prepared, which contains an expression cassette for secretory human TNF-α (human TNF-α secretory expression cassette) and an expression cassette for secretory human IFN-γ (human IFN-γ secretory expression cassette) and which serves as an *E. coli-Bifidobacterium* shuttle vector. *Bifidobacterium longum* 105-A strain was transformed with pAG8TL thus prepared by electroporation to obtain a human TNF-α and human IFN-γ co-expression *Bifidobacterium*, AG8TL strain. The primers used in Examples 1 to 3 are shown in the following Table 1.

TABLE 1

| Primer Name | DNA sequence (5'→3') | SEQ ID No. |
|---|---|---|
| GA1_primer | gagcagaaggTCACTGGGAGGCGCGACGGCCAC | SEQ ID No. 18 |
| GA2_primer | AGTGAccttagctcgtagcg | SEQ ID No. 19 |
| GA5_primer_rev | ggtatgtaggcggtgctacag | SEQ ID No. 20 |
| GA6_primer | caccgcctacatacctcgct | SEQ ID No. 21 |
| GA100_primer | cggtgGTGCGCTCCTCCTCCCGTAC | SEQ ID No. 22 |
| GA101_primer | TCACAGGGCGATGATGCC | SEQ ID No. 23 |
| GA103_primer | AGGAGCGCACcaccgaactcgccttcgg | SEQ ID No. 24 |
| GA104_primer | ATCATCGCCCTGTGAAACCGCTTCTCATTTCCATTTGCG | SEQ ID No. 25 |
| GA113_primer | CGGTGCACACTAGTcctccaggacctc | SEQ ID No. 26 |
| GA116_primer | gACTAGTGTSCACCGAATCGCGCTG | SEQ ID No. 27 |
| IFNG1_primer | gaaggagctttATGCAGGACCCGTACGTCAAGG | SEQ ID No. 28 |

TABLE 1 -continued

| Primer Name | DNA sequence (5'→3') | SEQ ID No. |
|---|---|---|
| IFNG2_primer | CATCATCACCACCACTGAccttctgctcgtagcg | SEQ ID No. 29 |
| IFNG3_primer | GTGGTGGTGATGATGGTGCTGGGAGGCGCACGGCC | SEQ ID No. 30 |
| hIFNG4_primer | caggacccgtacgtcAAGG | SEQ ID No. 31 |
| SP69-ins_F1_primer | caagaaggatgctttATGAATTATTTACGACAAAAAATTTCGG | SEQ ID No. 32 |
| SP69-ins_R2_primer | gactacgggtcctgACCGCTATCAGTCGTGGTGTAAC | SEQ ID No. 33 |
| pCDshuttle_R1 primer | cataaagcatccttcttgggtcag | SEQ ID No. 34 |
| Hu-mCCL21-vecR1_primer | AAAGCATCCTTCTTGGGTCAGG | SEQ ID No. 35 |

(Constitution of Human TNF-α Secretory Expression Cassette)

As the human TNF-α secretory expression cassette, a cassette sequentially comprising (1) a P30 promoter DNA, (2) a DNA encoding a signal peptide-linker conjugate, SP7L20, (3) a DNA encoding the amino acid sequence of a human TNF-α protein and (4) a d0013 terminator DNA, was prepared such that DNA (1) was placed upstream (the 5' end) and DNA (4) downstream (the 3' end).

(Constitution of Human IFN-γ Secretory Expression Cassette)

As the human IFN-γ secretory expression cassette, a cassette sequentially comprising (1) a Hu promoter DNA, (2) a DNA encoding a signal peptide-linker conjugate, SP69L20, (3) a DNA encoding the amino acid sequence of human IFN-γ protein and (4) a Hu terminator DNA (derived from *Bifidobacterium longum*) was prepared such that DNA (1) was placed upstream (the 5' end) and DNA (4) downstream (the 3' end).

(Preparation of Plasmid pAG8TL)

In preparing plasmid pAG8TL, plasmid pAG8 was first prepared.

(Preparation of Plasmid pAG8)

(Preparation of hTNF-α Insert Fragment)

PCR amplification was carried out using plasmid pSP3B-TNFα (see, FIG. 1) (1 ng) described in International Publication No. WO2011/093465, as a template and a primer set of GA100_primer (forward) and GA101_primer (reverse) listed in Table 1. Each of the primer sequences was designed such that an insert fragment was overlapped with a vector fragment at the end of 15 bp. The PCR amplification was carried out by specifying the concentration of each primer as 0.2 μM and the reaction volume as 20 μL and using PrimeSTAR HS (Premix) kit (manufactured by Takara Bio Inc.) (hereinafter referred to as "STAR kit"). As the amplification program, a cycle consisting of a reaction at 98° C. for 10 seconds, a reaction at 65° C. for 5 seconds and a reaction at 75° C. for 40 seconds was repeated 30 times and then an elongation reaction was carried out at 72° C. for 30 seconds to prepare a h (human) TNF-α insert fragment amplified product of about 0.5 kbp.

(Preparation of Vector Fragment Comprising DNA Encoding the Amino Acid Sequence of Human IFN-γ Protein)

PCR amplification was carried out using a linearized fragment (SEQ ID No. 1) of plasmid pHG-2 (FIG. 2) as a template and a primer set of GA104_primer (forward) and GA103_primer (reverse) listed in Table 1. Each of the primer sequences was designed such that an insert fragment was overlapped with a vector fragment at the end of 15 bp. The PCR amplification was carried out by specifying the concentration of each primer as 0.2 μM and the reaction volume as 20 μL, and using STAR kit. As the amplification program, a cycle consisting of a reaction at 98° C. for 10 seconds, a reaction at 65° C. for 5 seconds and a reaction at 75° C. for 5 minutes was repeated 30 times and then an elongation reaction at 72° C. for 30 seconds was carried out to prepare a 5'-Hu promoter-SP69L20-human IFN-γ protein-His tag-Hu terminator-pTB rep unit-SPCM$^r$-pUCori-P30 promoter-SP7L20-3' vector fragment amplified product of about 5 kbp.

The plasmid pHG-2 linearized fragment is a nucleotide sequence from 1st nucleotide to 4975th nucleotide of SEQ ID No. 1 and constituted as follows.

d0013 terminator: a nucleotide sequence from 16th nucleotide to 129th nucleotide of SEQ ID No. 1, Hu promoter: a nucleotide sequence from 136th nucleotide to 496th nucleotide of SEQ ID No. 1, SP69L20: a nucleotide sequence from 497th nucleotide to 646th nucleotide of SEQ ID No. 1, human IFN-γ protein: a nucleotide sequence from 647th nucleotide to 1075th nucleotide of SEQ ID No. 1, His tag: a nucleotide sequence from 1076th nucleotide to 1093rd nucleotide of SEQ ID No. 1, Hu terminator: a nucleotide sequence from 1097th nucleotide to 1210th nucleotide of SEQ ID No. 1, a bacterium of the genus *Bifidobacterium*, origin of replication pTB6 rep unit: a nucleotide sequence from 1217th nucleotide to 2812nd nucleotide of SEQ ID No. 1, spectinomycin resistance gene SPCMr: a nucleotide sequence from 2819th nucleotide to 3897th nucleotide of SEQ ID No. 1,

*E. coli* origin of replication, pUCori: a nucleotide sequence from 3904th nucleotide to 4571st nucleotide of SEQ ID No. 1, P30 promoter: a nucleotide sequence from 4572nd nucleotide to 4806th nucleotide of SEQ ID No. 1, and SP7L20: a nucleotide sequence from 4807th nucleotide to 4965th nucleotide of SEQ ID No. 1.

(In-Fusion Reaction 1)

The vector fragment amplified product and insert fragment amplified product prepared above were ligated by use of In-Fusion (registered trademark) HD Cloning kit (manufactured by Takara Bio Inc.) (hereinafter referred to as "HD kit"). More specifically, in a micro tube, the vector fragment amplified product (50 ng) and the insert fragment amplified product (13 ng) were added, and 5× In-Fusion HD Enzyme premix (2 µL) and Cloning Enhancer (1 µL) contained in the kit were further added. The volume of the reaction solution was adjusted with 0.1×TE buffer (1 mM Tris-HCl, 0.1 mM EDTA, pH7.5) to be 10 µL. The reaction solution was kept warm at 37° C. for 15 minutes and further kept warm at 50° C. for 15 minutes. The procedure other than this was carried out in accordance with the product manual of the kit to prepare in-fusion reaction solution 1.

(Transformation of *E. coli* and Determination of DNA Sequence of Plasmid pAG8)

Using in-fusion reaction solution 1 (1 µL), *E. coli* HST16CR competent cells (manufactured by Takara Bio Inc.) were transformed in accordance with the product manual. After the transformation, the bacterial suspension was spread onto LB agar medium containing 75 µg/mL spectinomycin and cultured at 37° C. overnight with shaking. *E. coli* colony formed on the agar medium was cultured in LB liquid medium containing 75 µg/mL spectinomycin at 37° C. overnight. From this, a plasmid was extracted by use of QIAprepSpin Miniprep kit (manufactured by QIAGEN). In the plasmid extracted, the sequence of region 1 (5'-P30 promoter-SP7L20-human TNF-α protein-d0013 terminator-Hu promoter-SP69L20-human IFN-γ protein-His tag-Hu terminator-3') comprising the human TNF-α secretory expression cassette and the human IFN-γ secretory expression cassette, was determined by a sequencing reaction using Big Dye (registered trademark) Terminator v3.1 Cycle Sequencing kit (manufactured by Applied Biosystems). The plasmid extracted was designated as pAG8. The sequence of region 1 comprising the human TNF-α secretory expression cassette and the human IFN-γ secretory expression cassette of pAG8 is represented by SEQ ID No. 2.

(Preparation of pAG8TL Strain)

PCR amplification was carried out using pAG8 obtained above as a template and a primer set of GA2_primer (forward) and GA6_primer (reverse) listed in Table 1. The same procedure as in the above section (Preparation of plasmid pAG8) was repeated except that the amplification program, which is a cycle consisting of a reaction at 98° C. for 10 seconds, a reaction at 65° C. for 5 seconds and a reaction at 75° C. for 3 minutes and 15 seconds, was repeated 30 times and then an elongation reaction was carried out at 72° C. for 30 seconds, to prepare PCR amplification product A of about 3.3 kbp.

PCR amplification was carried out using pAG8 mentioned above as a template and a primer set of GA5_primer_rev (forward) and GA1_primer (reverse) listed in Table 1. The same procedure as in the above section (Preparation of plasmid pAG8) was repeated except that the amplification program, which is a cycle consisting of a reaction at 98° C. for 10 seconds, a reaction at 65° C. for 5 seconds and a reaction at 75° C. for 2 minutes and 10 seconds, was repeated 30 times, and then an elongation reaction was carried out at 72° C. for 30 seconds to prepare PCR amplification product B of about 2.2 kbp.

(In-Fusion Reaction 2)

The same procedure as in the above section (In-fusion reaction 1) was repeated except that PCR amplification product A (50 ng) and PCR amplification product B (33 ng) were used, to ligate PCR amplification product A and PCR amplification product B. In this manner, in-fusion reaction solution 2 was prepared.

(Transformation of *E. coli* and Determination of DNA Sequence of Plasmid pAG8TL)

Transformation of the *E. coli* HST16CR competent cells by using in-fusion reaction solution 2 obtained above and extraction of a plasmid from the recombinant *E. coli*. were carried out in the same procedure as in the above section (Transformation of *E. coli* and determination of DNA sequence of plasmid pAG8). In the plasmid extracted, the sequence of region 2 (5'-P30 promoter-SP7L20-human TNF-α protein-d0013 terminator-Hu promoter-SP69L20-human IFN-γ protein-Hu terminator-3') comprising the human TNF-α secretory expression cassette and human IFN-γ secretory expression cassette was determined in the same procedure as above. The plasmid extracted was designated as pAG8TL. The sequence of region 2 comprising the human TNF-α secretory expression cassette and human IFN-γ secretory expression cassette of pAG8TL is represented by SEQ ID No. 3.

(Transformation 1 of Bacterium of the Genus *Bifidobacterium*)

*Bifidobacterium longum* 105-A strain was transformed with plasmid pAG8TL (250 ng) extracted from the transformed *E. coli* by an electroporation system (Gene Pulser II, manufactured by Bio-Rad laboratories). Immediately after electric shock (2 kV, 25 µF, 200Ω), a mixture of 800 µL of IMR liquid medium and 50 µL of vitamin C solution was added to a cuvette (2 mm gap) and collected in (transferred to) in a sterilized 2 mL-micro tube. The 2 mL (micro) tube with the cap loosen was placed together with a deoxygen/carbon dioxide generator (AnaeroPack (registered trademark) Kenki manufactured by Mitsubishi Gas Chemical Company, Inc.) in an airtight container and kept warm for 3 hours in an incubator set at 37° C.

After kept warm, individual bacterial suspensions were each spread onto IMR agar medium containing 75 µg/mL spectinomycin. These plates were placed in an airtight container together with the deoxygen/carbon dioxide generator mentioned above and cultured in an incubator set at 37° C. for 2 days.

The colony formed on the IMR agar medium containing spectinomycin was determined as a transformant, *Bifidobacterium longum* 105-A/pAG8TL strain (hereinafter referred to as AG8TL strain).

Example 2

[Preparation of Human TNF-α Single-Expression Strain TNF11]

Human TNF-α single-expression strain TNF11 to be compared with co-expression *Bifidobacterium* AG8TL strain was prepared as follows.

PCR amplification was carried out using pAG12 as a template and a primer set of GA113_primer (forward) and GA6_primer (reverse) listed in Table 1. The same procedure as in the above section (Preparation of plasmid pAG8) was repeated except that the amplification program, which is a cycle consisting of a reaction at 98° C. for 10 seconds, a reaction at 65° C. for 5 seconds and a reaction at 75° C. for 3 minutes and 50 seconds was repeated 30 times and then an elongation reaction was carried out at 72° C. for 30 seconds to prepare PCR amplification product 60 of about 3.2 kbp.

PCR amplification was carried out using pAG12 as a template and a primer set of GA5_primer_rev (forward) and GA116_primer (reverse) listed in Table 1. The same procedure as in the above section (Preparation of plasmid pAG8) was repeated except that the amplification program, which is a cycle consisting of a reaction at 98° C. for 10 seconds, a reaction at 65° C. for 5 seconds and a reaction at 72° C. for one minute and 15 seconds, was repeated 30 times, and then an elongation reaction was carried out at 72° C. for 30 seconds to prepare PCR amplification product 61 of about 1.2 kbp. Note that, the plasmid pAG12 used as a template was obtained by replacing SP/Linker of hIFN-γ of pAG8TL, i.e., SP69L20, by SP56L20.

(In-Fusion Reaction 3)

The same procedure as in the above section (In-fusion reaction 1) was repeated except that PCR amplification product 60 (50 ng) and PCR amplification product 61 (20 ng) were used to ligate the PCR amplification product 60 and the PCR amplification product 61. In this manner, in-fusion reaction solution 3 was prepared.

(Transformation of E. coli and Determination of DNA Sequence of Plasmid pTNF11)

The same procedure as in the above section (Transformation of E. coli and determination of DNA sequence of plasmid pAG8) was repeated by using in-fusion reaction solution 3 obtained above to carry out transformation of the E. coli HST16CR competent cells obtained above and extraction of a plasmid from the recombinant E. coli. In the plasmid extracted, the sequence of the human TNF-α secretory expression cassette (5'-P30 promoter-SP7L20-human TNF-α protein-d0013 terminator) was determined. The plasmid extracted was designated as pTNF11. The constitution of pTNF11 plasmid is shown in FIG. 3.

(Transformation 2 of Bacterium of the Genus Bifidobacterium)

Bifidobacterium longum 105-A strain was transformed by the electroporation system in the same procedure as in the above section (Transformation 1 of bacterium of the genus Bifidobacterium) except that plasmid pTNF11 (500 ng) extracted from the transformed E. coli mentioned above was used. The transformant obtained was designated as Bifidobacterium longum 105-A/pTNF11 strain (hereinafter referred to as TNF11 strain).

Example 3

[Preparation of Human IFN-γ Single-Expression Strain hIFNg33TL]

Human IFN-γ single-expression strain hIFNg33TL to be compared with co-expression Bifidobacterium AG8TL strain was prepared as follows.

Human IFN-γ single-expression strain hIFNg33TL to be compared with co-expression AG8TL strain was prepared. In preparation of plasmid phIFNg33TL, plasmid phIFNg33 was first prepared.

(Artificial DNA Synthesis of hIFN-γ Gene)

Synthesis of hIFN-γ gene was ordered to GenScript Japan Inc. The codons of the hIFN-γ sequence were optimized for Bifidobacterium longum NCC2705 based on the amino acid sequence (Gln24-Gln166) of the mature protein of Accession # CAA31639 (plasmid delivered: pUC57-hIFNg). The DNA sequence of artificial synthesized hIFN-γ is represented by SEQ ID No. 4.

PCR amplification was carried out using pBEshuttle (SEQ ID No. 5) as a template and a primer set of pCDshuttle_R1_primer (reverse) and IFNG2_primer (forward) listed in Table 1. The same procedure as in the above section (Preparation of plasmid pAG8) was repeated except that the amplification program, which is a cycle consisting of a reaction at 98° C. for 10 seconds, a reaction at 55° C. for 5 seconds and a reaction at 75° C. for 3 minutes and 50 seconds, was repeated 30 times, and then an elongation reaction was carried out at 72° C. for 30 seconds to prepare PCR amplification product, vector 1 of about 3.9 kbp.

PCR amplification was carried out using pUC57-hIFNg (hIFNg in pUC57) mentioned above as a template and a primer set of IFNG1_primer (forward) and IFNG3_primer (reverse) listed in Table 1. The same procedure as in the above section (Preparation of plasmid pAG8) was repeated except that the amplification program, which is a cycle consisting of a reaction at 98° C. for 10 seconds, a reaction at 55° C. for 5 seconds and a reaction at 75° C. for 30 seconds, was repeated 30 times, and then an elongation reaction was carried out at 72° C. for 30 seconds to prepare PCR amplification product, insert 1 of about 0.5 kbp.

(In-Fusion Reaction 4)

The same procedure as in the above section (In-fusion reaction 1) was repeated except that PCR amplification product, vector 1 (50 ng) and PCR amplification product, insert 1 (12 ng) were used to ligate PCR amplification product, vector 1 and PCR amplification product, insert 1. In this manner, in-fusion reaction solution 4 was prepared.

(Transformation of E. coli and Determination of DNA Sequence of Non-Secretory Plasmid phIFNg)

E. coli HST16CR was transformed in the same manner as in the above section (Transformation of E. coli and determination of DNA sequence of plasmid pAG8) by using the in-fusion reaction solution 4 (2 μL). A plasmid was extracted from the recombinant E. coli and the sequence of full-length plasmid DNA was determined. The plasmid extracted was designated as phIFNg (non-secretory plasmid)

(Preparation of Secretory Plasmid hIFNg33)

PCR amplification was carried out using phIFNg mentioned above as a template and a primer set of hIFNG4_primer (forward) and Hu-mCCL21-vecR1_primer (reverse) listed in Table 1. The same procedure as in the above section (Preparation of plasmid pAG8) was repeated except that the amplification program, which is a cycle consisting of a reaction at 98° C. for 10 seconds, a reaction at 55° C. for 5 seconds and a reaction at 75° C. for 4 minutes and 20 seconds, was repeated 30 times, and then an elongation reaction was carried out at 72° C. for 30 seconds to prepare PCR amplification product, vector 2 of about 4.3 kbp.

PCR amplification was carried out using Bifidobacterium longum 105-A strain genomic DNA as a template and a primer set of SP69-ins_F1_primer (forward) and SP69-ins_R2_primer (reverse) listed in Table 1. The same procedure as in the above section (Preparation of plasmid pAG8) was repeated except that the amplification program, which is a cycle consisting of a reaction at 98° C. for 10 seconds, a reaction at 55° C. for 5 seconds and a reaction at 75° C. for 15 seconds, was repeated 30 times, and then an elongation reaction was carried out at 72° C. for 30 seconds to prepare PCR amplification product, insert 2 of about 0.2 kbp.

(In-Fusion Reaction 5)

The same procedure as in the above section (In-fusion reaction 1) was repeated except that PCR amplification product, vector 2 (50 ng) and PCR amplification product, insert 2 (5 ng) were used to ligate PCR amplification product, vector 2 and PCR amplification product, insert 2. In this manner, in-fusion reaction solution 5 was prepared.

(Transformation of E. coli and Determination of DNA Sequence of Plasmid phIFNg33)

The same procedure as in the above section (Transformation of E. coli and determination of DNA sequence of plasmid pAG8) was repeated by using in-fusion reaction solution 3 (2 μL) obtained above to carry out transformation of the E. coli HST16CR competent cells obtained above and extraction of a plasmid from the recombinant E. coli. In the plasmid extracted, the sequence of human IFN-γ secretory expression cassette (5'-Hu promoter-SP69L20-human IFN-γ protein-His tag-Hu terminator-3') was determined. The plasmid extracted was designated as phIFNg33. The constitution of plasmid phIFNg33 is shown in FIG. 4 (a).

(Transformation 3 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid phIFNg33 (605 ng) extracted from the transformed *E. coli* mentioned above was used. The transformant obtained was designated as *Bifidobacterium longum* 105-A/phIFNg33 strain (hereinafter referred to as hIFNg33 strain).

PCR amplification was carried out using phIFNg33 mentioned above as a template and a primer set of GA5_primer_rev (forward) and GA1_primer (reverse) listed in Table 1. The same procedure as in the above section (Preparation of plasmid pAG8) was repeated except that the amplification program, which is a cycle consisting of a reaction at 98° C. for 10 seconds, a reaction at 65° C. for 5 seconds and a reaction at 75° C. for 1 minute and 20 seconds, was repeated 30 times, and then an elongation reaction was carried out at 72° C. for 30 seconds to prepare PCR amplification product C of about 1.2 kbp.

PCR amplification was carried out using phIFNg33 mentioned above as a template and a primer set of GA2_primer (forward) and GA6_primer (reverse) listed in Table 1. The same procedure as in the above section (Preparation of plasmid pAG8) was repeated except that the amplification program, which is a cycle consisting of a reaction at 98° C. for 10 seconds, a reaction at 65° C. for 5 seconds and a reaction at 75° C. for 3 minutes and 20 seconds, was repeated 30 times, and then an elongation reaction was carried out at 72° C. for 30 seconds to prepare PCR amplification product D of about 3.3 kbp.

(In-Fusion Reaction 6)

The same procedure as in the above section (In-fusion reaction 1) was repeated except that PCR amplification product C (18 ng) and PCR amplification product D (50 ng) were used to ligate PCR amplification product C and PCR amplification product D. In this manner, in-fusion reaction solution 6 was prepared.

(Transformation of *E. coli* and Determination of DNA Sequence of Plasmid phIFNg33TL)

The same procedure as in the above section (Transformation of *E. coli* and determination of DNA sequence of plasmid pAG8) was repeated by using in-fusion reaction solution 6 obtained above to carry out transformation of the *E. coli* HST16CR competent cells obtained above and extraction of a plasmid from the recombinant *E. coli*. In the plasmid extracted, the sequence of human IFN-γ secretory expression cassette (5'-Hu promoter-SP69L20-human IFN-γ protein-Hu terminator-3') was determined. The plasmid extracted was designated as phIFNg33TL. The constitution of plasmid phIFNg33TL is shown in FIG. 4 (b).

(Transformation 4 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid phIFNg33TL (435 ng) extracted from the transformed *E. coli* mentioned above was used. The transformant obtained was designated as *Bifidobacterium longum* 105-A/phIFNg33TL strain (hereinafter referred to as hIFNg33TL strain).

Example 4

[Verification of hTNF-α and hIFN-γ Secretion in AG8TL strain]

The presence or absence of secretion of human TNF-α protein and human IFN-γ protein in the culture supernatant of AG8TL strain was checked by ELISA as follows. A negative control strain, *Bifidobacterium longum* 105A/pBEshuttle strain (hereinafter referred to as BEshuttle strain) was subjected to the same analysis.

(Culture of Recombinant Bacterium of the Genus *Bifidobacterium*)

AG8TL strain, TNF11 strain, hIFNg33TL strain and BEshuttle strain each were inoculated in MRS (manufactured by Becton, Dickinson and Company) liquid medium (10 mL) supplemented with spectinomycin (final concentration 75 μg/mL) and 100 μL of a vitamin C solution (solution comprising ascorbic acid (35 g) and L-cysteine hydrochloride monohydrate (2 g) and sodium carbonate (11 g)/100 mL), and anaerobically cultured at 37° C. for 24 hours. These were specified as activated culture solutions. Subsequently, to a medium (20 mL) obtained by adding DMEM (Cat No. 11885-084: manufactured by Life Technologies Corporation) and MRS in a ratio of 9:1, vitamin C solution (100 μL) and spectinomycin (so as to obtain a 75 μg/mL), the above activated culture solution (100 μL) was inoculated. The resultant medium was anaerobically cultured at 37° C. for 18 hours.

(Collection of Culture Supernatant and ELISA)

After the anaerobic culture, the culture solutions of the individual strains were centrifuged. The culture supernatants were separately collected and subjected to ELISA. The same operation was applied to the BEshuttle strain and used as a negative control. As the ELISA kit for TNF-α measurement, Quantikine Human TNFα/TNFSF1A Immunoassay (manufactured by R&D systems) was used. As the ELISA kit for hIFN-γ measurement, Quantikine Human IFN-γ Immunoassay (manufactured by R&D systems) was used. The operation of ELISA was carried out in accordance with the product manual of each ELISA kit. The results are shown in Table 2.

TABLE 2

| Recombinant *Bifidobacterium* strain | Amount of hTNF-α secreted | Amount of hIFN-γ secreted |
|---|---|---|
| | (ng/mL culture supernatant) | |
| AG8TL | 501 | 376 |
| TNF11 | 515 | N.D. |
| hIFNg33TL | N.D. | 346 |
| BEshuttle | N.D. | N.D. |

(Results)

As is apparent from Table 2, it was found that hTNF-α protein and hIFN-γ protein are both present in the culture supernatant of AG8TL strain. It was also found that hTNF-α protein is present in the culture supernatant of a positive control, i.e., single-expression strain TNF11; and that human IFN-γ protein is present in the culture supernatant of hIFNg33TL strain.

Example 5

[Investigation of Proliferative Inhibitory Activity of AG8TL Strain on KPL-1 Cell]

(Preparation of Culture-Supernatant Crude Purified Product)

Each (7 mL) of the culture supernatants of AG8TL strain, TNF11 strain and hIFNg33TL strain mentioned above prepared in the same manner as in Example 4 (Culture of recombinant bacterium of the genus *Bifidobacterium*) and (Collection of culture supernatant and ELISA) was concentrated by use of Amicon Ultra-4, MWCO: 10 k (manufactured by Millipore), washed three times with PBS buffer (pH7.4) and concentrated to prepare 0.5 mL of a culture-supernatant crude purified product. A crude purified product from the culture-supernatant of the negative control strain, i.e., *Bifidobacterium longum* 105A/pBEshuttle strain, was prepared in the same manner. The crude purified products from individual strains were subjected to measurement of cell proliferation inhibitory activity. The concentrations of hTNF-α and hIFN-γ were estimated by use of an ELISA kit for TNF-α measurement and an ELISA kit hIFN-γ measurement.

(Preparation of KPL-1 Cell and Addition of Test Sample)

Cell proliferation inhibitory activity was measured by using a human breast cancer cell strain, i.e., KPL-1 cell (provided by Prof. Junichi Kurebayashi, Kawasaki Medical School). KPL-1 cells were cultured in 10% fetal bovine serum (manufactured by EQUITECH-BIO)/Dulbecco's modified eagle medium (high glucose) (manufactured by Sigma Aldrich) in a 100-mm petri dish. After the (test) medium was removed, the cells were washed with PBS (−) (manufactured by Wako Pure Chemical Industries Ltd.). To the cells, 0.25% Trypsin-EDTA (manufactured by Life Technologies Corporation) was added. The cells were collected and centrifuged. The supernatant was removed and the cells were suspended in the test medium so as to obtain $6 \times 10^3$ cells/mL. In this manner, a cell suspension was prepared.

The cell suspension was dispensed in individual wells of a 96-well plate in an amount of 0.1 mL per well and cultured in a $CO_2$ incubator set at 37° C. In the following day, exchange was made with the medium prepared by further adding a crude purified product from culture-supernatant of AG8TL strain (comprising 20 ng/mL hIFN-γ and 51.1 ng/mL hTNF-α) to the test medium mentioned above. In this way, stimulation was started. Medium were prepared by separately adding crude purified products from culture-supernatant of TNF11 strain and hIFNg33TL strain so as to obtain the same concentration in the case of AG8TL strain and subjected to the same treatment as positive controls. Four days after initiation of stimulation, the medium was removed and exchanged for a medium (1/10 volume) supplemented with Cell Counting kit-8 (manufactured by Dojindo Molecular Technologies, Inc.) and the reaction was further carried out for 3 hours. After the reaction, absorbance at 450 nm and 630 nm (reference wavelength) was measured by a multi-mode plate reader (manufactured by DS Pharma Biomedical Co., Ltd.). The blank was calculated by subtracting the absorbance of a well comprising the medium and Cell Counting kit-8 alone and no cells. Note that, the value obtained from a test medium in which KPL-1 cells were continuously cultured without adding any one of the aforementioned culture-supernatant crude purified products was regarded as absorbance (100%) of an untreated district. The proliferation rate of KPL-1 cells in individual mediums was calculated. The results are shown in FIG. 5.

(Results)

As is apparent from FIG. 5, a secretion from AG8TL strain, significantly suppressed proliferation of KPL-1 cell, compared to a secretion from TNF11 strain alone or hIFNg33TL strain alone. More specifically, TNF11 strain secreting hTNF-α exhibited a proliferation rate of 89.9%; hIFNg33TL strain secreting hIFN-γ exhibited a proliferation rate of 83%; whereas AG8TL strain secreting hTNF-α and hIFN-γ, exhibited a relative cell viability of 35.5%. It was verified that AG8TL strain has a strong proliferation inhibitory effect on a human breast cancer cell strain. Such a result is conceivably due to a combinational effect of the hTNF-α secretion and the hIFN-γ secretion.

Example 6

[Investigation on Proliferation Inhibitory Activity of AG8TL Strain to MIA PaCa-2 Cell]

Cell proliferation inhibitory activity to MIA PaCa-2 cell was investigated in the same procedure as in Example 5 except that a human pancreas cancer-derived cell, i.e., MIA PaCa-2 cell (obtained from the independent administrative institution, RIKEN Bio Resource Center) was used in place of KPL-1 cell. Note that, the concentration of MIA PaCa-2 cells suspension dispensed and seeded in 96-well plates was specified as $1 \times 10^4$ cells/mL. The results are shown in FIG. 6.

(Results)

As is apparent from FIG. 6, a secretion from AG8TL strain, significantly suppressed proliferation of MIA PaCa-2 cell, compared to a secretion from TNF11 strain alone or hIFNg33TL strain alone. More specifically, TNF11 strain secreting hTNF-α exhibited a proliferation rate of 51.6%; hIFNg33TL strain secreting hIFN-γ exhibited a proliferation rate of 75.4%; whereas AG8TL strain secreting hTNF-α and hIFN-γ, exhibited a proliferation rate of 24.2%. It was verified that AG8TL strain has a strong proliferation inhibitory effect on the human pancreas cancer cell strain. Such a result is conceivably due to a combinational effect of the hTNF-α secretion and the hIFN-γ secretion.

Example 7

[Investigation of the Specificity in Cell Proliferation Inhibitory Activity of AG8TL Strain by Using Neutralizing Antibodies]

To verify that the cell proliferation inhibitory activity by crude purified product from the culture-supernatant of an AG8TL strain is due to secretion of hTNF-α and hIFN-γ, investigation using a neutralizing antibody, i.e., Human IFN-γ Antibody and Human TNF-α Antibody (both are manufactured by R&D systems) was made as follows.

In the same procedure as in Example 6, MIA PaCa-2 cells were seeded onto a 96-well plate. On the following day, exchange was made with a medium comprising any one of the crude purified products from culture-supernatant of AG8TL strain, TNF11 strain, hIFNg33TL strain and BEshuttle strain (negative control) and the antibody shown in the following Table 3, in combination. The materials added to the medium are shown in the following Table 3. Cell proliferation rate was calculated in the same procedure as in Example 5. The results are shown in FIG. 7.

TABLE 3

| Medium | culture-supernatant crude purified product | Secretion | Antibody |
|---|---|---|---|
| 1) | AG8TL strain | hIFN-γ (20 ng/mL) hTNF-α (51.1 ng/mL) | |

TABLE 3-continued

| Medium | culture-supernatant crude purified product | Secretion | Antibody |
|---|---|---|---|
| 2) | AG8TL strain | hIFN-γ (20 ng/mL) hTNF-α (51.1 ng/mL) | Anti-hTNF-α antibody (6 μg/mL) Anti-hIFN-γ antibody (1 μg/mL) |
| 3) | AG8TL strain | hIFN-γ (20 ng/mL) hTNF-α (51.1 ng/mL) | Anti-hTNF-α antibody (6 μg/mL) |
| 4) | AG8TL strain | hIFN-γ (20 ng/mL) hTNF-α (51.1 ng/mL) | Anti-hIFN-γ antibody (1 μg/mL) |
| 5) | TNF11 strain | hTNF-α (51.1 ng/mL) | |
| 6) | hIFNg33TL strain | hIFN-γ (20 ng/mL) | |
| 7) | BEshuttle strain | | |
| 8) | BEshuttle strain | | Anti-hTNF-α antibody (6 μg/mL) Anti-hIFN-γ antibody (1 μg/mL) |

(Results)

As is apparent from FIG. 7, MIA PaCa-2 cell proliferation rate was 15.3% at the time when the culture-supernatant crude purified product of an AG8TL strain was added; however, the cell proliferation rates at the time when the anti-hIFN-γ antibody alone and the anti-hTNF-α antibody alone were added increased to 31.8% and 44.4%, respectively. The cell proliferation rate increased to 74.1% at the time when both anti-hIFN-γ antibody and anti-hTNF-α antibody were added. This is because the bioactivities of hTNF-α and hIFN-γ secreted from AG8TL strain were neutralized by these antibodies. It is considered that proliferation inhibition of MIA PaCa-2 cell is due to hTNF-α and hIFN-γ secreted by AG8TL strain.

Example 8

[Preparation of Anti-hPD-1scFv03 and Anti-hCTLA-4scFv02 Co-Expression *Bifidobacterium* PC1 Strain and CP1 Strain]

(Outline)

Co-expression plasmids pPC1 and pCP1 were prepared, which contain an expression cassette for secretory anti-hPD-1scFv03 (anti-human PD-1scFv03 secretory expression cassette) and an expression cassette for secretory anti-hCTLA-4scFv02FLAG (anti-human CTLA-4scFv02FLAG secretory expression cassette), respectively and which serve as *E. coli-Bifidobacterium* shuttle vector. *Bifidobacterium longum* 105-A strain was transformed with these plasmids pPC1 and pCP1 in accordance with electroporation to obtain anti-hPD-1scFv03 and anti-hCTLA-4scFv02 co-expression *Bifidobacterium* PC1 strain and CP1 strain. The primers used in Example 8 are shown in the following Table 4.

TABLE 4

| Primer Name | DNA sequence (5'→3') | SEQ ID No. |
|---|---|---|
| Ins-hPD-1 scFv03-F1 | CAGGTCCAGCTGGTCGAATCGGGCGGCGGC | SEQ ID No. 36 |
| Ins-hPD-1 scFv03-R1 | ACGAGCAGAAGGTCAGTGGTGGTGATGATGGTGCTT | SEQ ID No. 37 |
| TGA-Hu-Terminator-F | TGACCTTCTGCTCGTAGCGATTAC | SEQ ID No. 38 |
| vec-SP7L20-R1 | GACCAGCTGGACCTGCACCGAACTCGCCTTCGGGAA | SEQ ID No. 39 |
| Ins-hCTLA-4 scFv02-F1 | CAGGTCCAGCTGGTCGAATCGGGCGGCGGC | SEQ ID No. 40 |
| Ins-hCTLA-4 scFv02-R1 | ACGAGCAGAAGGTCAGTGATGATGATGATGATGCTT | SEQ ID No. 41 |
| hCTLA-4 scFv02-FLAG-F1 | GACTACAAGGACGACGACGACAAGTGACCTTCTGCTCGTAGCGAT | SEQ ID No. 42 |
| hCTLA-4 scFv02-FLAG-R1 | GTCGTCCTTGTAGTCCTTGATTTCCACCTTGGT | SEQ ID No. 43 |
| Inf_pTB6 rep_F1 | ACTAGTCCTCCAGGACCTCGTCGACGAGGC | SEQ ID No. 44 |
| Inf_Hu Prom_F1 | GTCTTCCTGCTGGCCTATGCATTGGGTTCC | SEQ ID No. 45 |
| Inf_Hu Term-Hu Prom_R1 | GGCCAGCAGGAAGACCCGGAATAATACGGTTGGAC | SEQ ID No. 46 |
| Inf_Hu Term-pTB6_R1 | TCCTGGAGGACTAGTCCGGAATAATACGGTTGGAC | SEQ ID No. 47 |

(Preparation of Anti-Human PD-1scFv03 Secretion Plasmid pHuSP7L20-hPD-1scFv03)

In preparing pPC1 and pCP1, anti-human PD-1scFv03 secretion plasmid pHuSP7L20-hPD-1scFv03 was first prepared.

(Constitution of Anti-Human PD-1scFv03 Secretory Expression Cassette)

As an anti-human PD-1scFv03 secretory expression cassette, a cassette sequentially comprising (1) a Hu promoter DNA, (2) a DNA encoding a signal peptide-linker conjugate, SP7L20, (3) a DNA encoding the amino acid sequence of anti-hPD-1scFv03 (comprising a heavy chain sequence, a linker (GGGGS)$_3$ and a light chain sequence), (4) a DNA encoding a His tag sequence and (5) a Hu terminator DNA was prepared such that DNA (1) was placed upstream (the 5' end) and DNA (5) downstream (the 3' end). As to the nucleotide sequence of DNA encoding the amino acid sequence of anti-hPD-1scFv03 (comprising a heavy chain sequence, a linker (GGGGS)$_3$ and a light chain sequence), the document shown in Table 5 (1) was referred to.

(Artificial DNA Synthesis of Anti-hPD-1scFv03)

Anti-hPD-1scFv03 represented by SEQ ID No. 11 was sub-cloned to *E. coli* plasmid pUC57 by GenScript Japan Inc. and used as artificially synthesized plasmid, pUC57-hPD-1scFv03.

(In-Fusion Reaction 7)

The vector fragment (1) prepared above and the anti-hPD-1scFv03 insert fragment (1) were ligated by use of In-Fusion (registered trademark) HD Cloning kit. More specifically, the vector (fragment) and the insert (fragment) in the kit were added in a molar ratio of 1:5 in a micro tube; then, 2 μL of 5× In-Fusion HD Enzyme premix was added; and the volume of the reaction solution was adjusted to be 10 μL. The reaction solution was kept warm at 50° C. for 15 minutes. The procedure other than this was carried out in accordance with the product manual of the kit to prepare in-fusion reaction solution 7.

TABLE 5

| Antibody | | Reference document |
|---|---|---|
| (1) Anti-hPD-1 scFv03 | SEQ ID No. 11 (729 nucleotide sequence) Heavy chain sequence (1-342 nucleotides) (GGGGS)$_3$ linker (343-387 nucleotides) Light chain sequence (388-708 nucleotides) Histidine tag (709-726 nucleotides) | Japanese Patent No. 5028700 |
| (2) Anti-hCTLA-4 scFv02 | SEQ ID No. 12 (747 nucleotide sequence) Heavy chain sequence (1-357 nucleotides) (GGGGS)$_3$ linker (358-402 nucleotides) Light chain sequence (403-726 nucleotides) Histidine tag (727-744 nucleotides) | Japanese Patent No. 4093757 |
| (3) Anti-hCTLA-4 scFv02FLAG | SEQ ID No. 13 (753 nucleotide sequence) Heavy chain sequence (1-357 nucleotides) (GGGGS)$_3$ linker (358-402 nucleotides) Light chain sequence (403-726 nucleotides) FLAG tag (727-750 nucleotides) | Japanese Patent No. 4093757 |

(Preparation 1 of Anti-hPD-1scFv03 Insert Fragment)

PCR amplification was carried out using plasmid, pUC57-hPD-1scFv03 (500 μg) as a template and a primer set of Ins-hPD-1scFv03-F1 primer (forward) and Ins-hPD-1scFv03-R1 primer (reverse) listed in Table 4. Each of the primer sequences was designed such that an insert fragment was overlapped with a vector fragment at the end of 15 bp. The PCR amplification was carried out by specifying the concentration of each primer as 0.2 μM and the reaction volume as 30 μL and using STAR kit. As the amplification program, a cycle consisting of a reaction at 98° C. for 10 seconds, a reaction at 55° C. for 5 seconds and a reaction at 72° C. for 60 seconds was repeated 30 times. The insert PCR product amplified was electrophoresed on a 2% agarose gel and then purified by QIAquick Gel Extraction kit (hereinafter referred to as "QIAGel", manufactured by QIAGEN) to prepare an anti-hPD-1scFv03 insert fragment (1) of about 0.7 kbp.

(Preparation of Vector Fragment (1) Comprising DNA Encoding the Amino Acid Sequence of SP7L20)

PCR amplification was carried out using the vector linearized fragment (500 μg) represented by SEQ ID No. 14 as a template and a primer set of TGA-Hu-terminator-F primer (forward) and vec-SP7L20-R1 primer (reverse) listed in Table 4. The PCR amplification was carried out by specifying the concentration of each primer as 0.2 μM and the reaction volume as 30 μL and using STAR kit. As the amplification program, a cycle consisting of a reaction at 98° C. for 10 seconds, a reaction at 55° C. for 5 seconds and a reaction at 72° C. for 5 minutes, was repeated 30 times. The PCR product amplified was electrophoresed on a 0.8% agarose gel and then purified by QIAGel to prepare a 5'-Hu terminator-pTB6rep unit-SPCMr-pUCori-Hu promoter-SP7L20-3' vector fragment (1) of about 4.0 kbp.

(Transformation of *E. coli* and Determination of DNA Sequence of pHuSP7L20-hPD-1scFv03)

The same procedure as in the above section (Transformation of *E. coli* and determination of DNA sequence of plasmid pAG8) was repeated except that 5 μL of in-fusion reaction solution 7 was used to carry out transformation of the *E. coli* HST16CR competent cell obtained above and extraction of a plasmid from the recombinant *E. coli*. Note that, after the transformation, *E. coli* colony formed on an agar medium was picked up and cultured in LB liquid medium containing 75 μg/mL spectinomycin while shaking at 30° C. overnight. The sequence of anti-human PD-1scFv03 secretory expression cassette (5'-Hu promoter-SP7L20-anti-hPD-1scFv03-His tag-Hu terminator-3') in the plasmid extracted was determined in the same procedure as above. The plasmid extracted was designated as pHuSP7L20-hPD-1scFv03. The constitution of pHuSP7L20-hPD-1scFv03 is shown in FIG. 8 (A) and the sequence thereof is represented by SEQ ID No. 6.

(Transformation 5 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid pHuSP7L20-hPD-1scFv03 (550 ng) extracted from the transformed *E. coli* mentioned above was used. The transformant obtained was designated as *Bifidobacterium longum* 105-A/pHuSP7L20-hPD-1scFv03 strain (hereinafter referred to as hPD-1scFv03 strain).

(Preparation of Anti-hCTLA-4scFv02 Secretion Plasmid pHuSP7L20-hCTLA-4scFv02)

In preparing pPC1 and pCP1, anti-hCTLA-4scFv02 secretion plasmid pHuSP7L20-hCTLA-4scFv02 without FLAG tag was first prepared.

(Constitutions of Anti-Human CTLA-4scFv02 Secretory Expression Cassette and Anti-Human CTLA-4scFv02FLAG Secretory Expression Cassette)

As an anti-human CTLA-4scFv02 secretory expression cassette, a cassette sequentially comprising (1) a Hu promoter DNA, (2) a DNA encoding a signal peptide-linker conjugate, SP7L20, (3) a DNA encoding the amino acid sequence of anti-hCTLA-4scFv02 (comprising a heavy chain sequence, a linker (GGGGS)$_3$ and a light chain sequence), (4) a DNA encoding a His tag sequence and (5) a Hu terminator DNA, was prepared such that DNA (1) was placed upstream (the 5' end) and DNA (5) downstream (the 3' end). As to the nucleotide sequence of DNA encoding the amino acid sequence of anti-hCTLA-4scFv02 (comprising a heavy chain sequence, a linker (GGGGS)$_3$ and a light chain sequence), the document shown in Table 5 (2) was referred to.

As an anti-human CTLA-4scFv02FLAG secretory expression cassette, a cassette sequentially comprising (1) a Hu promoter DNA, (2) a DNA encoding a signal peptide-linker conjugate, SP7L20, (3) a DNA encoding the amino acid sequence of anti-hCTLA-4scFv02 (comprising a heavy chain sequence, a linker (GGGGS)$_3$ and a light chain sequence), (4) a DNA encoding a FLAG tag sequence and (5) a Hu terminator DNA, was prepared such that DNA (1) was placed upstream (the 5' end) and DNA (5) downstream (the 3' end). As to the nucleotide sequence of DNA encoding the amino acid sequence of anti-hCTLA-4scFv02 (comprising a heavy chain sequence, a linker (GGGGS)$_3$ and a light chain sequence), the document shown in Table 5 (3) was referred to.

(Artificial DNA Synthesis of hCTLA-4scFv02)

The fragment, hCTLA-4scFv02 represented by SEQ ID No. 12 was subcloned to *E. coli* plasmid pUC57 by GenScript Japan Inc. and used as artificially synthesized plasmid pUC57-hCTLA-4scFv02.

(Preparation of Anti-hCTLA-4scFv02 Insert Fragment)

The same procedure as in the above section (Preparation 1 of anti-hPD-1scFv03 insert fragment) was repeated except that the plasmid pUC57-hCTLA-4scFv02 as a template and a primer set of Ins-hCTLA-4scFv02-F1 (forward) and Ins-hCTLA-4scFv02-R1 (reverse) listed in Table 4 were used to prepare anti-hCTLA-4scFv02 insert fragment of about 0.8 kbp.

(In-Fusion Reaction 8)

An in-fusion reaction solution was prepared in the same procedure as in the in-fusion reaction in the above section (In-fusion reaction 7) except that the vector fragment (1) and the anti-hCTLA-4scFv02 insert fragment were used.

(Transformation of *E. coli* and Determination of DNA Sequence of pHuSP7L20-hCTLA-4scFv02)

The same procedure as in the above section (Transformation of *E. coli* and determination of DNA sequence of plasmid pHuSP7L20-hPD-1scFv03) was repeated except that 5 μL of in-fusion reaction solution 8 was used to carry out transformation of *E. coli* HST08 competent cell. A sequencing reaction was carried out for determining the sequence of anti-human CTLA-4scFv02 secretory expression cassette (5'-Hu promoter-SP7L20-anti-human CTLA-4scFv02-His tag-Hu terminator-3') in the plasmid extracted. The plasmid extracted was designated as pHuSP7L20-hCTLA-4scFv02. The constitution of pHuSP7L20-hCTLA-4scFv02 is shown in FIG. 8 (B) and the sequence thereof is represented by SEQ ID No. 7.

[Preparation of Anti-hCTLA-4scFv02FLAG Single Expression *Bifidobacterium* Strain]

(Preparation of Vector Fragment Comprising Anti-hCTLA-4scFv02FLAG Secretory Expression Cassette)

PCR amplification was carried out using plasmid pHuSP7L20-hCTLA-4scFv02 (500 μg) mentioned above as a template and a primer set of hCTLA-4scFv02-FLAG-F1 (forward) and hCTLA-4scFv02-FLAG-R1 (reverse) listed in Table 4. The primer sequences were designed such that both ends (15 bp.) of the PCR products were overlapped. The PCR amplification was carried out by specifying the concentration of each primer as 0.2 μM and the reaction volume as 30 μL and using the STAR kit. As the amplification program, a cycle consisting of a reaction at 98° C. for 10 seconds, a reaction at 55° C. for 5 seconds and a reaction at 72° C. for 5 minutes, was repeated 30 times to prepare a vector fragment amplified product of about 4.8 kbp comprising an anti-hCTLA-4scFv02FLAG secretory expression cassette.

(In-Fusion Reaction 9)

The vector fragment amplified product comprising the anti-human CTLA-4scFv02FLAG secretory expression cassette prepared above was subjected to an in-fusion reaction by use of In-Fusion (registered trademark) HD Cloning kit to close the ring by itself. More specifically, a reaction solution was prepared by mixing the vector fragment amplified product (5 μL) and Cloning Enhancer (2 μL), placed in a micro tube and kept warm at 37° C. for 15 minutes, subsequently at 80° C. for 15 minutes. Then, 0.5 μL of the reaction solution and 2 μL of 5× In-Fusion HD Enzyme premix were blended and the volume of the resultant reaction solution was adjusted to be 10 μL. The reaction solution was kept warm at 50° C. for 15 minutes. The procedure other than this was carried out in accordance with the production manual of the kit to prepare in-fusion reaction solution 9.

(Transformation of *E. coli* and Determination of DNA Sequence of pHuSP7L20-hCTLA-4scFv02FLAG)

The same procedure as in the above section (Transformation of *E. coli* and determination of DNA sequence of plasmid pHuSP7L20-hPD-1scFv03) was repeated except that 5 μL of in-fusion reaction solution 9 was used to carry out transformation of the *E. coli* HST08 competent cell obtained above and extraction of a plasmid from the recombinant *E. coli*. The sequence of anti-human CTLA-4scFv02FLAG secretory expression cassette (5'-Hu promoter-SP7L20-anti-human CTLA-4scFv02-FLAG tag-Hu terminator-3') in the plasmid extracted was determined in the same procedure as above. The plasmid extracted was designated as pHuSP7L20-hCTLA-4scFv02FLAG. The constitution of pHuSP7L20-hCTLA-4scFv02FLAG is shown in FIG. 8 (C) and the sequence thereof is represented by SEQ ID No. 8.

(Transformation 6 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid pHuSP7L20-hCTLA-4scFv02FLAG (256 ng) was used. The transformant obtained was designated as *Bifidobacterium longum* 105-A/pHuSP7L20-hCTLA-4scFv02FLAG strain (hereinafter referred to as hCTLA-4scFv02 strain).

[Preparation of Anti-hPD-1scFv03 and Anti-hCTLA-4scFv02 Co-Expression Strain]

PC1 strain and CP1 strain secreting both anti-hPD-1scFv03 and anti-hCTLA-4scFv02 were prepared. As is shown in FIG. 9 (*a*), PC1 strain has a plasmid having a secretory expression cassette following the 3' end side of the origin of replication, pUCori, of *E. coli*. This secretory expression cassette is anti-human PD-1scFv03 secretory expression cassette, which is followed by anti-human CTLA-4scFv02 secretory expression cassette. As shown in FIG. 9 (b), CP1 strain has a plasmid having a secretory expression cassette following the 3' end side of the origin of replication, pUCori, of E. coli. This secretory expression cassette is anti-human CTLA-4scFv02 secretory expression cassette which is followed by anti-human PD-1scFv03 secretory expression cassette.

[Preparation of PC1 Strain]

(Preparation of Anti-hCTLA-4scFv02FLAG Insert Fragment)

PCR amplification was carried out using plasmid pHuSP7L20-hCTLA-4scFv02FLAG (500 µg) (SEQ ID No. 8) as a template and a primer set of InF_Hu Prom_F1 (forward) and InF_Hu Term-pTB6_R1 (reverse) listed in Table 4. Each of the primer sequences was designed such that an insert fragment was overlapped with a vector fragment at the end of 15 bp. The PCR amplification was carried out by specifying the concentration of each primer as 0.2 µM and the reaction volume as 30 µL and using STAR kit. As the amplification program, a cycle consisting of a reaction at 98° C. for 10 seconds, a reaction at 55° C. for 5 seconds and a reaction at 72° C. for 2 minutes, was repeated 30 times. The insert PCR product amplified was electrophoresed on a 0.8% agarose gel and then purified by use of QIAGel to prepare an anti-human CTLA-4scFv02FLAG insert fragment of about 1.4 kbp.

(Preparation of Vector Fragment Comprising Anti-hPD-1scFv03 Secretory Expression Cassette)

PCR amplification was carried out using plasmid pHuSP7L20-hPD-1scFv03 (500 µg) (SEQ ID No. 6) mentioned above as a template and a primer set of InF_pTB6rep_F1 (forward) and InF_HuTerm-HuProm_R1 (reverse) listed in Table 4. Each of the primer sequences was designed such that an insert fragment was overlapped with a vector fragment at the end of 15 bp. The PCR amplification was carried out by specifying the concentration of each primer as 0.2 µM and the reaction volume as 30 µL and using PrimeSTAR HS (Premix) kit mentioned above. As the amplification program, a cycle consisting of a reaction at 98° C. for 10 seconds, a reaction at 55° C. for 5 seconds and a reaction at 72° C. for 5 minutes, was repeated 30 times. The insert PCR product amplified was electrophoresed on a 0.8% agarose gel and then purified by QIAquick Gel Extraction kit to prepare a vector fragment (2) of about 4.7 kbp comprising anti-hPD-1scFv03 secretory expression cassette.

(In-Fusion Reaction 10)

The vector fragment (2) prepared in the above and the anti-human CTLA-4scFv02FLAG insert fragment were ligated by use of In-Fusion (registered trademark) HD Cloning kit mentioned above. More specifically, the vector (fragment) and the insert (fragment) in the kit were added in a molar ratio of 1:3 in a micro tube; and then, 2 µL of 5× In-Fusion HD Enzyme premix was added; and the volume of the reaction solution was adjusted to be 10 µL. The reaction solution was kept warm at 50° C. for 15 minutes. The procedure other than this was carried out in accordance with the product manual of the kit to prepare in-fusion reaction solution 10.

(Transformation of E. coli and Determination of DNA Sequence of pPC1)

The same procedure as in the above section (Transformation of E. coli and determination of DNA sequence of plasmid pHuSP7L20-hPD-1scFv03) was repeated except that 2 µL of in-fusion reaction solution 10 was used to carry out transformation of the E. coli HST16CR competent cell obtained above and extraction of a plasmid from the recombinant E. coli. The sequences of anti-human PD-1scFv03 secretory expression cassette (5'-Hu promoter-SP7L20-anti-hPD-1scFv03-His tag-Hu terminator-3') and anti-human CTLA-4scFv02FLAG secretory expression cassette (5'-Hu promoter-SP7L20-anti-hCTLA-4scFv02-FLAG tag-Hu terminator-3') in the plasmid extracted were determined in the same procedure as above. The plasmid extracted was designated as pPC1. The constitution of pPC1 is shown in FIG. 9 (a) and the DNA sequence thereof is represented by SEQ ID No. 9.

(Transformation 7 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid pPC1 (250 ng) mentioned above was used. The transformant obtained was designated as *Bifidobacterium longum* 105-A/pPC1 strain (hereinafter referred to as PC1 strain).

[Preparation of CP1 Strain]

(Preparation 2 of Anti-hPD-1scFv03 Insert Fragment)

PCR amplification and purification by a gel extraction kit were carried out in the same procedure as in the above section (Preparation of anti-human CTLA-4scFv02FLAG insert fragment) except that plasmid pHuSP7L20-hPD-1scFv03 (500 µg) (SEQ ID No. 6) mentioned above was used as a template and a primer set of InF_HuProm_F1 (forward) and InF_HuTerm-pTB6_R1 (reverse) listed in Table 4 were used to prepare anti-hPD-1scFv03 insert fragment (2) of about 1.4 kbp.

(Preparation of Vector Fragment Comprising Anti-Human CTLA-4scFv02FLAG Secretory Expression Cassette)

PCR amplification and purification by a gel extraction kit were carried out in the same procedure as in the above section (Preparation 2 of anti-hPD-1scFv03 insert fragment) except that plasmid pHuSP7L20-hCTLA-4scFv02FLAG (SEQ ID No. 8) mentioned above was used as a template and a primer set of InF_pTB6rep_F1 (forward) and InF_HuTerm-HuProm_R1 (reverse) listed in Table 4 were used to prepare a vector fragment (3) of about 4.8 kbp comprising anti-human CTLA-4scFv02FLAG secretory expression cassette.

(In-Fusion Reaction 11)

In-fusion reaction solution 11 was prepared in the same procedure as in the above section (In-fusion reaction 10) except that the vector fragment (3) prepared above and the anti-hPD-1scFv03 insert fragment (2) were used.

(Transformation of E. coli and Determination of DNA Sequence of pCP1)

Transformation of E. coli HST16CR competent cell and plasmid extraction from recombinant E. coli were carried out in the same procedure as in the above section (Transformation of E. coli and determination of DNA sequence of plasmid pHuSP7L20-hPD-1scFv03) except that 2 µL of in-fusion reaction solution 11 was used. The sequences of anti-human PD-1scFv03 secretory expression cassette (5'-Hu promoter-SP7L20-anti-hPD-1scFv03-His tag-Hu terminator-3') and anti-human CTLA-4scFv02FLAG secretory expression cassette (5'-Hu promoter-SP7L20-anti-hCTLA-4scFv02-FLAG tag-Hu terminator-3') in the plasmid extracted were determined in the same procedure as the above section (Transformation of E. coli and determination of DNA sequence of pPC1). The plasmid extracted was designated as pCP1. The constitution of pCP1 is shown in FIG. 9 (b) and the DNA sequence of pCP1 is represented by SEQ ID No. 10.

(Transformation 8 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid pCP1 (250 ng) mentioned above was used. The transformant obtained was designated as *Bifidobacterium longum* 105-A/pCP1 strain (hereinafter referred to as CP1 strain).

Example 9

[Verification of Anti-hPD-1scFv and Anti-hCTLA-4scFv Secretion in PC1 Strain and CP1 Strain]

The presence or absence of anti-hPD-1scFv03 (labeled with a histidine tag) and anti-hCTLA-4scFv02 (labeled with FLAG tag) in the culture supernatants of PC1 strain and CP1 strain was checked by western blotting as follows. As a negative control strain, a BEshuttle strain was subjected to the same analysis.

(Culture of Recombinant Bacterium of the Genus *Bifidobacterium*)

*Bifidobacterium* strains, i.e., PC1 strain, CP1 strain, hPD-1scFv03 strain, hCTLA-4scFv02 strain and BEshuttle strain were cultured in the same procedure as in Example 4 (Culture of recombinant bacterium of the genus *Bifidobacterium*) and the culture supernatants were collected. The proteins in the culture supernatants were precipitated with trichloroacetic acid (TCA, manufactured by Wako Pure Chemical Industries Ltd.), washed with acetone, dissolved in a buffer for SDS-PAGE and treated with heat at 95° C. for 3 minutes to obtain culture supernatant concentrates.

(Western Analysis)

Each of the culture supernatant concentrates (corresponding to about 0.1 mL of the culture solution) was electrophoresed by Mini-PROTEAN (registered trademark) TGX™ gel (4 to 20%) (manufactured by Bio-Rad). The resultant gel was transferred to PVDF membrane (iBlot Transfer Stacks, manufactured by Life Technologies Corporation) by use of iBlot transfer device (manufactured by Life Technologies Corporation). After completion of blotting, the PVDF membrane was blocked with 2% ECL Prime Blocking agent (manufactured by GE Healthcare Japan) in TTBS. Electrophoresis and blotting to the membrane were carried out double. One of the PVDF membranes was used for detection of anti-hPD-1scFv03 using an anti-histidine antibody (THE His Tag Antibody, mAb, Mouse) (manufactured by GenScript) as a primary antibody and ECL peroxidase labelled anti-mouse antibody (manufactured by GE Healthcare) as a secondary antibody. The other PVDF membrane was used for detection of anti-hCTLA-4scFv02 using anti-FLAG antibody Monoclonal ANTI-FLAG M2 Antibody (produced in mouse) (manufactured by Sigma) as a primary antibody and an ECL peroxidase labelled anti-mouse antibody (manufactured by GE Healthcare) as a secondary antibody. After completion of the antibody reactions, the membranes were illuminated by Western Lightning Ultra (manufactured by PerkinElmer Co., Ltd.). These were analyzed by imaging equipment, MYECL Imager (manufactured by Thermo Scientific). The results are shown in FIG. 10.

(Results)

As is apparent from FIG. 10, both anti-hPD-1scFv03 and anti-hCTLA-4scFv02 were detected in the culture supernatants of PC1 strain (lane 1 both in A and B) and CP1 strain (lane 2 both in A and B) comprising anti-human PD-1scFv03 secretory expression cassette having a His tag fused to the C terminal of the anti-hPD-1scFv03 and anti-human CTLA-4scFv02FLAG secretory expression cassette having a FLAG tag fused to C terminal of the anti-hCTLA-4scFv02. The sizes of hPD-1scFv secretory proteins from PC1 strain (A: lane 1) and CP1 strain (A: lane 2) were the same as the size of hPD-1scFv secretory protein from hPD-1scFv03 single-expression strain (A: lane 3); and the sizes of hCTLA-4scFv secretory proteins from PC1 strain (B: lane 1) and CP1 strain (B: lane 2) were the same as the size of hCTLA-4scFv secretory protein from hCTLA-4scFv02 single-expression strain (B: lane 4). Accordingly, it was verified that co-expression *Bifidobacterium* strains, i.e., PC1 strain and CP1 strain, are recombinant *Bifidobacterium* strains capable of secreting both anti-hPD-1scFv and anti-hCTLA-4scFv in the culture supernatant.

Example 10

[Verification of Binding of Antibody Secreted from PC1 Strain to hPD-1 and hCTLA-4]

The presence or absence of binding activity of anti-hPD-1scFv03, which was purified from the culture supernatant of co-expression strain PC1, to human PD-1 (hPD-1); and the presence or absence of binding activity of anti-hCTLA-4scFv02 to human CTLA-4 were checked by ELISA.

To 96-well plates, hPD-1 (Recombinant Human hPD-1 Fc Chimera, manufactured by R&D systems); hCTLA-4 (Recombinant Human CTLA-4-Fc Chimera, manufactured by Biolegend); mPD-1 (Recombinant Human hPD-1 Fc Chimera, manufactured by R&D systems); and mCTLA-4 (Recombinant mouse CTLA-4-Fc Chimera, manufactured by Biolegend), which were adjusted to be 1 μg/mL with 1×PBS, were dispensed in an amount of 100 μL for each and incubated at 4° C. overnight for immobilization. After the liquid was removed, 1×PBS (350 μL) for each was dispensed and the liquid was removed. This operation was repeated three times for washing. To each of the plates, 1% BSA solution (350 μL) was dispensed at room temperature and incubated for 2 hours for blocking. After the liquid was removed, 1×PBS (350 μL) for each was dispensed and the liquid was removed. This operation was repeated three times for washing.

Anti-hPD-1scFv03 and anti-hCTLA-4scFv02 were adjusted to be 1000 ng/mL, 100 ng/mL, 10 ng/mL and 1 ng/mL with a signal enhancing reagent (Signal Enhancer HIKARI, manufactured by Nacalai Tesque) and dispensed to the plates each in an amount of 100 μL after completion of the blocking. To blank wells, the signal enhancing reagent alone was dispensed in an amount of 100 μL. A seal was attached to the plates and the plates were incubated at room temperature for 2 hours to allow anti-hPD-1scFv03 to react with immobilized hPD-1, mPD-1 and hCTLA-4. Similarly, anti-hCTLA-4scFv02 was allowed to react with immobilized hCTLA-4, mCTLA-4 and hPD-1. After the liquid was removed, 1×PBS (350 μL for each) was dispensed and the liquid was removed. This operation was repeated three times for washing.

The secondary antibody (Anti-Histag-Biotin, manufactured by MBL) was diluted with the signal enhancing reagent to 2000 fold. The dilution (100 μL) was dispensed to wells reacted with anti-hPD-1scFv03. Similarly, secondary antibody (THE (registered trademark) DYKDDDDK Tag Antibody [Biotin], mAb, mouse, manufactured by GenScript) was diluted with the signal enhancing reagent to 2500 fold. The dilution (100 μL) was dispensed to wells and allowed to react with anti-hCTLA-4scFv02. A seal was attached to the plates and the plates were incubated at room temperature for 2 hours. After the liquid was removed, 1×PBS (350 μL) was dispensed for each and the liquid was removed. This operation was repeated three times for washing.

Three drops of each of solution A and solution B serving as the avidin-biotin marker enzyme complex (VECTASTAIN ABC kit, manufactured by Vector) were added to the signal enhancing reagent (7.5 mL). The mixture was dispensed in an amount of 100 μL for each plate. Thereafter, a seal was attached to the plates and the plates were incubated at room temperature for 30 minutes. After the liquid was removed, 1×PBS (350 μL for each) was dispensed and the liquid was removed. This operation was repeated three times for washing.

A detection reagent was prepared by adding Color Solution A and Color Solution B (manufactured by R&D systems) in equal amounts, and dispensed in an amount of 200 μL for each. The plates were shielded from light and incubated at room temperature for 20 minutes. Accurately 20 minutes later, Stop Solution (R&D Systems) was added in an amount of 50 μL for each to terminate the coloring reaction. Absorbance was measured at 450 nm and 570 nm (reference wavelength). The results of binding of anti-hPD-1scFv03 to a human PD-1 immobilized plate determined by ELISA are shown in the following Table 6 and FIG. 11. Similarly, the results of binding of anti-hCTLA-4scFv02 to a human CTLA-4 immobilized plate are shown in the following Table 7 and FIG. 12.

TABLE 6

Binding of anti-hPD-1scFv03 to human PD-1 immobilized plate (OD value)

| Concentration of anti-hPD-1scFv03 | hPD-1 immobilized | hCTLA-4 immobilized | mPD-1 immobilized |
|---|---|---|---|
| 1 ng/mL | −0.030 | −0.062 | −0.059 |
| 10 ng/mL | 0.373 | −0.055 | −0.057 |
| 100 ng/mL | 3.774 | −0.018 | −0.049 |
| 1000 ng/mL | 3.788 | 0.341 | 0.107 |

TABLE 7

Binding of anti-hCTLA-4scFv02 to human CTLA-4 immobilized plate (OD value)

| Concentration of anti-hCTLA-4scFv02 | hPD-1 immobilized | hCTLA-4 immobilized | mCTLA-4 immobilized |
|---|---|---|---|
| 1 ng/mL | −0.018 | 0.009 | 0.026 |
| 10 ng/mL | −0.031 | 0.026 | 0.005 |
| 100 ng/mL | −0.038 | 0.255 | 0.001 |
| 1000 ng/mL | −0.001 | 1.419 | 0.051 |

(Results)

As is apparent from Table 6 and FIG. 11, anti-hPD-1scFv03 which was purified from the culture supernatant of co-expression strain PC1, bound to hPD-1. As is apparent from Table 7 and FIG. 12, anti-hCTLA-4scFv02 bound to hCTLA-4. In contrast, anti-hPD-1scFv03 bound to neither hCTLA-4 nor mPD-1; and anti-hCTLA-4scFv02 bound to neither hPD-1 nor mCTLA-4. From these, it was verified that anti-hPD-1scFv03 and anti-hCTLA-4scFv02 secreted from co-expression strain PC1, specifically bind to the corresponding antigen proteins.

Example 11

[Competitive Inhibitory Activity of Anti-hPD-1scFv in Binding Reaction of Human PD-L1 to Human PD-1]

It is said that when ligand PD-L1 binds to PD-1, a negative signal is transmitted to T cell to suppress an immune response (immune tolerance). Then, Competitive inhibitory activity of anti-hPD-1scFv in binding reaction of human PD-L1 to human PD-1 was investigated.

Whether anti-hPD-1scFv03 purified from the culture supernatant of co-expression strain PC1 has a competitive binding inhibition activity in binding of human PD-L1 (hPD-L1) to human PD-1 (hPD-1) was checked by ELISA. As a negative control, anti-hCTLA-4scFv02 was used.

To 96-well plates, hPD-1 (Recombinant HumanPD-1 Fc Chimera, manufactured by R&D systems), the concentration of which was adjusted to be 1 μg/mL with 1×PBS, was dispensed in an amount of 100 μL for each and incubated at 4° C. overnight for immobilization. After the liquid was removed, 1×PBS (350 μL) was dispensed and the liquid was removed. This operation was repeated three times for washing.

To the plates, 1% BSA solution (350 μL for each) was dispensed and incubated at room temperature for 2 hours for blocking. After the liquid was removed, 1×PBS (350 μL) for each was dispensed and the liquid was removed. This operation was repeated three times for washing. Ligand, hPD-L1 (R&D Systems, Recombinant HumanB7-H1/PD-L1 FcChimera) was adjusted to be 2000 ng/mL with the signal enhancing reagent.

Anti-hPD-1scFv03 purified from a bacterium of the genus Bifidobacterium was adjusted to be 20000 ng/mL, 2000 ng/mL, 200 ng/mL and 20 ng/mL with the signal enhancing reagent and mixed with hPD-L1 in equal amounts (120 μL). The resultant solutions was each (100 μL) dispensed to plates after completion of blocking. As a negative control, anti-hCTLA-4scFv02 purified from a bacterium of the genus Bifidobacterium was subjected to the same operation. To blank wells, the signal enhancing reagent alone (100 μL) was dispensed. A seal was attached to the plate and the plate was incubated at room temperature for 2 hours to allow hPD-L1 mixed with anti-hPD-1scFv03 to react with immobilized hPD-1. After the liquid was removed, 1×PBS (350 μL) was dispensed and the liquid was removed. This operation was repeated three times for washing. A secondary antibody (Biotinanti-human CD274, manufactured by Biolegend) to hPD-L1 was adjusted to be 0.2 μg/mL with the signal enhancing reagent and dispensed in an amount of 100 μL for each. A seal was attached to the plate and the plate was incubated at room temperature for 30 minutes. After the liquid was removed, 1×PBS (350 μL) was dispensed and the liquid was removed. This operation was repeated three times for washing.

One drop of solution A and solution B serving as the avidin-biotin marker enzyme complex were added to the signal enhancing reagent (2.5 mL). This was dispensed in an amount of 100 μL for each. Then, a seal was attached to the plate and the plate was incubated at room temperature for 30 minutes. After the liquid was removed, 1×PBS (350 μL) was dispensed and the liquid was removed. This operation was repeated three times for washing. A detection reagent was prepared by adding Color Solution A and Color Solution B (manufactured by R&D systems) in equal amounts and dispensed in an amount of 200 μL for each. The plate was shielded from light and incubated at room temperature for 20 minutes. Accurately 20 minutes later, 50 μL of Stop Solution (R&D Systems) for each was added to terminate the coloring reaction. Absorbance was measured at 450 nm and 570 nm (reference wavelength). The measurement results are shown in the following Table 8 and FIG. 13.

TABLE 8

Competitive inhibitory activity of anti-hPD-1scFv03
in binding reaction of human PD-L1 to human PD-1

| Concentration of scFv | Binding (OD) to hPD-L1 (1000 ng/mL) and Inhibition rate (%) | |
|---|---|---|
| | Anti- hPD-1 scFv03 | Anti- hCTLA-4 scFv02 |
| 10 ng/mL | 3.479 (−0.7%) | 3.697 (−7.0%) |
| 100 ng/mL | 3.503 (−1.4%) | 3.473 (−0.5%) |
| 1000 ng/mL | 3.309 (4.2%) | 3.555 (−2.9%) |
| 10000 ng/mL | 1.062 (69.3%) | 3.596 (−4.1%) |
| Non-scFv | 3.455 (0%) | |

(Results)

As is apparent from Table 8 and FIG. 13, the inhibition rate of anti-hPD-1scFv03 (10000 ng/mL) to the binding of hPD-L1 (1000 ng/mL) to hPD-1 was 69.3%. From the result, it was demonstrated that anti-hPD-1scFv03 competitively inhibits the binding of hPD-L1 (1000 ng/mL) to hPD-1 at a concentration of 10000 ng/mL or more.

Example 11-1

[Verification of Competitive Inhibitory Activity of hCTLA-4scFv in Binding Reactions of Human CD80 and Human CD86 to Human CTLA-4]

Using anti-hCTLA-4scFv02 purified from the culture supernatant of co-expression strain PC1 mentioned above, competitive inhibitory activity thereof in binding of each of human CD80 (hCD80) and human CD86 (hCD86) to human CTLA-4 (hCTLA-4) was checked by ELISA. As a negative control, anti-hPD-1scFv03 was used.

To 96-well plates, hCTLA-4 (Recombinant Human CTLA-4-Fc Chimera, carrier-free, manufactured by BioLegend) adjusted to be 1 μg/mL with 1×PBS was dispensed in an amount of 100 μL for each and incubated at 4° C. overnight for immobilization. After the liquid was removed, 1×PBS (350 μL for each) was dispensed and the liquid was removed. This operation was repeated three times for washing.

To the plates, 1% BSA solution (350 μL for each) was dispensed, incubated at room temperature for 2 hours for blocking. After the liquid was removed, 1×PBS (350 μL for each) was dispensed and the liquid was removed. This operation was repeated three times for washing. Ligand hCD80 (R&D Systems, Recombinant Human B7-1/CD80 Fc Chimera) and hCD86 (R&D Systems, Recombinant Human B7-2/CD86 Fc Chimera) were separately adjusted to be 2000 ng/mL with the signal enhancing reagent.

Anti-hCTLA-4scFv02 purified from a bacterium of the genus *Bifidobacterium* was adjusted to be 20000 ng/mL, 2000 ng/mL, 200 ng/mL and 20 ng/mL with the signal enhancing reagent, mixed with each of the hCD80 and hCD86 in equal amounts (120 μL). The resultant mixtures was each (100 μL) dispensed to the plates after completion of blocking. Anti-hPD-1scFv03 purified from a bacterium of the genus *Bifidobacterium* as a negative control was subjected to the same preparation. To blank wells, the signal enhancing reagent alone (100 μL) was dispensed. A seal was attached to the plates and the plates were incubated at room temperature for 2 hours. Each of hCD80 and hCD86, which were separately mixed with anti-hCTLA-4scFv02, was allowed to react with the hCTLA-4 immobilized. After the liquid was removed, 1×PBS (350 μL for each) was dispensed and the liquid was removed. This operation was repeated three times for washing.

A secondary antibody (R&D Systems, Human B7-1/CD80 Biotinylated Antibody) to hCD80 and a secondary antibody (R&D Systems, Biotinylated Anti-human B7-2 Antibody) to hCD86 were separately adjusted to be 2.5 μg/mL and 0.5 μg/mL with the signal enhancing reagent and each dispensed in an amount of 10 μL. A seal was attached to the plates and the plates were incubated at room temperature for 30 minutes. After the liquid was removed, 1×PBS (350 μL for each) was dispensed and the liquid was removed. This operation was repeated three times for washing.

Three drops of solution A and solution B mentioned above serving as the avidin-biotin marker enzyme complex were added to the signal enhancing reagent (7.5 mL). This was dispensed in an amount of 100 μL for each. Then, a seal was attached to the plates and the plates were incubated at room temperature for 30 minutes. After the liquid was removed, 1×PBS (350 μL for each) was dispensed and the liquid was removed. This operation was repeated three times for washing. A detection reagent was prepared by adding Color Solution A and Color Solution B (R&D) in equal amounts and dispensed in an amount of 200 μL for each. The plate was shielded from light and incubated at room temperature for 20 minutes. Accurately 20 minutes later, 50 μL of Stop Solution (R&D) was added to terminate the coloring reaction. Absorbance was measured at 450 nm and 570 nm (reference wavelength). The results are shown in the following Table 9 and Table 10 and FIG. 14 and FIG. 15.

TABLE 9

Competitive inhibitory activity of anti-hCTLA-4scFv02
in binding reaction of human CD80 to human CTLA-4

| Concentration of scFv | Binding (OD) to hCD80 (1000 ng/mL) and Inhibition rate (%) | |
|---|---|---|
| | Anti- hCTLA-4 scFv02 | Anti- hPD-1 scFv03 |
| 10 ng/mL | 2.656 (15.7%) | 2.638 (16.2%) |
| 100 ng/mL | 2.403 (23.7%) | 2.410 (23.5%) |
| 1000 ng/mL | 1.774 (43.7%) | 2.464 (21.8%) |
| 10000 ng/mL | 0.577 (81.7%) | 2.862 (9.1%) |
| Non-scFv | 3.149 (0%) | |

TABLE 10

Competitive inhibitory activity of anti-hCTLA-4scFv02
in binding reaction of human CD86 to human CTLA-4

| Concentration of scFv | Binding (OD) to hCD86 (1000 ng/mL) and Inhibition rate (%) | |
|---|---|---|
| | Anti- hCTLA-4 scFv02 | Anti- hPD-1 scFv03 |
| 10 ng/mL | 2.085 (0.3%) | 1.491 (28.7%) |
| 100 ng/mL | 1.421 (32.0%) | 1.396 (33.2%) |
| 1000 ng/mL | 0.627 (70.0%) | 1.265 (39.5%) |
| 10000 ng/mL | 0 (100.0%) | 1.526 (27.0%) |
| Non-scFv | 2.091 (0%) | |

(Results)

As is apparent from Table 9 and Table 10 and FIG. 14 and FIG. 15, the inhibition rates of anti-hCTLA-4scFv02 (1000 ng/mL) to the binding of hCD80 and hCD86 (1000 ng/mL) to hCTLA-4 are as follows. In the case of anti-hCTLA- 4scFv02 (1000 ng/mL), the inhibition rates thereof were 43.7% and 70.0%, respectively. In the case of anti-hCTLA-4scFv02 (10000 ng/mL), the inhibition rates thereof were 81.7% and 100.0%, respectively. It was demonstrated that anti-hCTLA-4scFv02 competitively inhibits the binding of each of hCD80 and hCD86 (1000 ng/mL) to hCTLA-4 at a concentration of 1000 ng/mL or more.

Example 12

[Investigation on Binding of Each of Anti-hPD-1scFv and Anti-hCTLA-4scFv Purified from a Co-Expression *Bifidobacterium* to Cells by Using Antigen Overexpressing Cell Strain]

The presence or absence of binding of anti-hPD-1scFv purified from the culture supernatant of co-expression strain PC1 mentioned above to a human PD-1 (hPD-1) expressing cells, and the presence or absence of binding of anti-hCTLA-4scFv to a human CTLA-4 (hCTLA-4) expressing cells were checked by using the following antigen-protein overexpressing cells in accordance with flow cytometry.

HEK293T cells overexpressing hPD-1 (hPD-1 and rat CD2 are bicistronically expressed) and HEK293T cells overexpressing hCTLA-4 (hCTLA-4 and rat CD2 are bicistronically expressed) were used. HEK293T cells overexpressing hPD-1 and HEK293T cells overexpressing hCTLA-4 were each cultured in DMEM medium containing inactivated 10% fetal bovine serum and seeded in a 100-mm dish (manufactured by Greiner Japan). After the culture supernatants of hPD-1 overexpressing HEK293T cells and hCTLA-4 overexpressing HEK293T cells were removed, these cells were separately washed twice with PBS ($Ca^{2+}$, $Mg^{2+}$-free phosphate buffer). A trypsin/EDTA solution (1 mL) (manufactured by Wako Pure Chemical Industries Ltd.) diluted 10 fold with PBS was added. The cells were incubated at room temperature for one minute. Thereafter, 10 mL of DMEM medium containing inactivated 10% fetal bovine serum was added. The resultant cells were transferred to 15 mL-centrifuge tubes (manufactured by BD FALCON) and spun by a low-speed centrifuge (manufactured by TOMY SEIKO CO., LTD.) at 1000 rpm for 5 minutes. After centrifugation, the supernatant was removed. DMEM medium (1 mL) containing inactivated 10% fetal bovine serum was added and the number of cells was counted. Further, the DMEM medium was added to prepare a cell suspension of $1\times10^5$ cells/mL and dispensed in 1.5-mL tubes (manufactured by Ina-optika Corporation) so as to contain $1\times10^5$ cells/mL/tube. The hPD-1 overexpressing HEK293T cells and hCTLA-4 overexpressing HEK293T cells dispensed in 1.5-mL tubes were each spun by a micro refrigerated centrifuge (manufactured by TOMY SEIKO CO., LTD.) at 5000 rpm and 4° C. for one minute and then the supernatants were removed. The remaining cell pellets in the tube were washed twice with 0.5 mL of PBS. Thereafter, anti-hPD-1scFv03 and anti-hCTLA-4scFv02 (100 µL for each), which were purified from a recombinant bacterium of the genus *Bifidobacterium* and prepared to be 10 µg/mL, were added to respective tubes and incubated on ice for 30 minutes. Thirty minutes later, FACS buffer (PBS containing 1% BSA and 0.1% $NaN_3$) was added in the tubes (500 µL). After centrifugation was carried out by a micro refrigerated centrifuge at 5000 rpm and 4° C. for one minute, the supernatants were removed and washing operation was carried out. The same operation was repeated once more and the washing operation was carried out twice. Anti-His-tag Alexa Fluor 488 antibody (manufactured by MBL) and anti-DDDDK-tag Alexa Fluor 488 antibody (manufactured by MBL) diluted with FACS buffer to be 0.5 µg/mL were added in an amount of 100 µL to the 1.5-mL tubes, sufficiently mixed by pipetting and incubated on ice for 30 minutes. Thirty minutes later, the FACS buffer was added to the tubes (500 µL), centrifuged by a micro refrigerated centrifuge at 5000 rpm and 4° C. for one minute. After the supernatants were removed, a washing operation was carried out. The same operation was repeated once more and the washing operation was carried out twice. After the FACS buffer (500 µL) was added, the cells suspended with the FACS buffer were transferred to 5 mL polystyrene round-bottom tubes (manufactured by Becton, Dickinson and Company). A propidium iodide solution (5 µL) diluted with the FACS buffer to be 5 µg/mL was added and analysis was carried out by use of BD FACS canto II flow cytometer (manufactured by Becton, Dickinson and Company) and flow cytometry analysis software Kaluza ver 1.2 (manufactured by Beckman Coulter, Inc.). The binding results of anti-PD-1scFv03 purified from PC1 strain to human PD-1 overexpressing cells are shown in FIG. 16. Similarly, the binding results of anti-CTLA-4scFv02 purified from co-expression strain PC1 to human CTLA-4 overexpressing cells are shown in FIG. 17.

(Results)

As is apparent form FIG. 16, it was verified that anti-PD-1scFv03 purified from PC1 strain specifically binds to human PD-1 high expressing cells (rat CD2 high expressing cells). Similarly, as is apparent form FIG. 17, it was verified that anti-CTLA-4scFv02 purified from PC1 strain specifically binds to a human CTLA-4 high expressing cells (rat CD2 high expressing cell). From these results, it was verified that the scFv purified from co-expression strain PC1, specifically binds to human PD-1 and human CTLA-4 overexpressing cells.

Example 13

[Preparation of Anti-HER2scFv and hIFN-γ Co-Expression *Bifidobacterium* Strain, HG-2]

(Outline)

A co-expression plasmid, pHG-2, which contains an expression cassette for secretory anti-HER2scFv (anti-HER2scFv secretory expression cassette) and an expression cassette for secretory hIFN-γ (human IFN-γ secretory expression cassette), and which serves as an *E. coli-Bifidobacterium* shuttle vector, was prepared (FIG. 2). *Bifidobacterium longum* 105-A strain was transformed with pHG-2 thus prepared by electroporation to obtain an anti-HER2scFv and hIFN-γ co-expression *Bifidobacterium*, HG-2 strain. The primers used in Example 13 are shown in the following Table 11.

TABLE 11

| Primer Name | DNA sequence (5'→3') | SEQ ID No. |
|---|---|---|
| pTB6_Vec_F1 | ACTAGTCCTCCAGGACCTCGTCTAC | SEQ ID No. 48 |
| Hu-term_Vec_R1 | CCGGAATAATACGGTTGGACAAC | SEQ ID No. 49 |

TABLE 11-continued

| Primer Name | DNA sequence (5'→3') | SEQ ID No. |
|---|---|---|
| Hu-HuT_ins_F1 | accgtattattccggGGATCCGTCTTCCTGCTGG | SEQ ID No. 50 |
| HuT-pTB6_ins_R1 | tcctggaggactagtCCGGAATAATACGGTTGGACAAC | SEQ ID No. 51 |
| Hu_Vec_F1 | GGATCCGTCTTCCTGCTGG | SEQ ID No. 52 |
| bHER2-His_Vec_R1 | TCAGTGATGATGATGATGATGCTTG | SEQ ID No. 53 |
| d0013 + T_ins_F1 | catcatcatcactgaAACCGCTTCTCATTTCCATTTG | SEQ ID No. 54 |
| d0013 + T_ins_R1 | caggaagacggatccGTGCACCGAATCGCGCT | SEQ ID No. 55 |

As the anti-HER2scFv secretory expression cassette, a cassette sequentially comprising (1) a P30 promoter DNA, (2) a DNA encoding a signal peptide-linker conjugate, SP7L20, (3) a DNA encoding the amino acid sequence of anti-HER2scFv, (4) a DNA encoding a His tag sequence and (5) a d0013 terminator DNA was prepared such that DNA (1) was placed upstream (the 5' end) and DNA (5) downstream (the 3' end).

(Preparation of Plasmid pHG-2)

In preparing plasmid pHG-2, plasmid pHG-1 was first prepared.

(Preparation of Plasmid pHG-1)

(Preparation of hIFNg Insert Fragment)

PCR amplification was carried out using a plasmid phIFNg33 (SEQ ID No. 16) as a template and a primer set of Hu-HuT_ins_F1 (forward) and HuT-pTB6_ins_R1 (reverse) listed in Table 11. Each of the primer sequences was designed such that an insert fragment was overlapped with a vector fragment at the end of 15 bp. The PCR amplification was carried out by specifying the concentration of each primer as 0.2 µM and the reaction volume as 20 µL and using STAR kit. As the amplification program, a cycle consisting of a reaction at 98° C. for 10 seconds, a reaction at 65° C. for 5 seconds and a reaction at 72° C. for 72 seconds, was repeated 30 times and then an elongation reaction was carried out at 72° C. for 30 seconds to prepare hIFNg insert fragment amplified product of about 1.1 kbp.

(Preparation of Vector Fragment Comprising DNA Encoding the Amino Acid Sequence of Anti-HER2scFv Protein)

PCR amplification was carried out using pP30SP7L20-bHER2 (SEQ ID No. 15) as a template and a primer set of pTB6_Vec_F1 (forward) and Hu-term_Vec_R1 (reverse) listed in Table 11. Each of the primer sequences was designed such that an insert fragment was overlapped with a vector fragment at the end of 15 bp. The PCR amplification was carried out by specifying the concentration of each primer as 0.2 µM and the reaction volume as 20 µL and using STAR kit. As the amplification program, a cycle consisting of a reaction at 98° C. for 10 seconds, a reaction at 65° C. for 5 seconds and a reaction at 72° C. for 4 minutes 45 seconds, was repeated 30 times and then an elongation reaction was carried out at 72° C. for 30 seconds to prepare a vector fragment amplified product of about 4.6 kbp.

(In-Fusion Reaction 12)

The vector fragment amplified product of 4.6 kbp and the insert fragment amplified product of about 1.1 kbp prepared above were ligated by use of In-Fusion (registered trademark) HD Cloning kit (manufactured by Takara Bio Inc.). First, in the website of Clontech: In-Fusion (registered trademark) Molar Ratio Calculator (http://bioinfo.clontech.com/infusion/molarRatio.do), the requisite insert amount and vector amount were calculated and the molar ratio of the vector to the insert was specified as 1:2. Two µL of 5× In-Fusion HD Enzymes premix, Cloning Enhancer (1 µL) and the requisite amounts of insert and vector were mixed and the total amount of the reaction system was adjusted with 0.1×TE buffer (1 mM Tris-HCl, 0.1 mM EDTA, pH7.5) to be 10 µL. The reaction was carried out at 37° C. for 15 minutes and then 50° C. for 15 minutes. The reaction solution was incubated at 4° C. The procedure other than this was carried out in accordance with the product manual of the kit to prepare in-fusion reaction solution 12.

(Transformation of E. coli and Determination of DNA Sequence of Plasmid pHG-1)

The same procedure as in the above section (Transformation of E. coli and determination of DNA sequence of plasmid pAG8) was repeated by using in-fusion reaction solution 12 obtained above to carry out transformation of the E. coli HST16CR competent cell obtained above and extraction of a plasmid from the recombinant E. coli. In the plasmid extracted, the sequences of anti-HER2scFv secretory expression cassette and human IFN-γ secretory expression cassette were determined in the same procedure as above. The plasmid extracted was designated as pHG-1. The DNA sequence of plasmid pHG-1 is represented by SEQ ID No. 17.

(Preparation of pHG-2 Strain)

The terminator of anti-HER2scFv expression secretion cassette of plasmid pHG-1 was changed from Hu terminator to d0013 terminator. PCR amplification was carried out using pHG-1 mentioned above as a template and a primer set of Hu_Vec_F1 (forward) and bHER2-His_Vec_R1 (reverse) listed in Table 11. As the amplification program, a cycle consisting of a reaction at 98° C. for 10 seconds, a reaction at 65° C. for 5 seconds and a reaction at 72° C. for 5 minutes 45 seconds, was repeated 30 times, and then an elongation reaction was carried out at 72° C. for 30 seconds. Other than this, the same procedure as in the above section (Preparation of plasmid pAG8) was repeated to obtain a vector fragment amplified product of about 5.6 kbp.

PCR amplification was carried out using genomic DNA of Bifidobacterium longum 105-A as a template and a primer set of d0013+T_ins_F1 (forward) and d0013+T_ins_R1 (reverse) listed in Table 11. As the amplification program, a cycle consisting of a reaction at 98° C. for 10 seconds, a reaction at 65° C. for 5 seconds and a reaction at 72° C. for 35 seconds, was repeated 30 times, and then an elongation reaction was carried out at 72° C. for 30 seconds. Other than this, the same procedure as in the above section (Preparation of plasmid pAG8) was repeated to obtain an insert fragment amplified product of about 144 bp.

(In-Fusion Reaction 13)

The same procedure as in the above (In-fusion reaction 10) was repeated except that the vector fragment and the insert fragment prepared above were used to prepare in-fusion reaction solution 13.

(Transformation of E. coli and Determination of DNA Sequence of Plasmid pHG-2)

The same procedure as in the above section (Transformation of E. coli and determination of DNA sequence of plasmid pAG8) was repeated by using in-fusion reaction solution 13 to carry out transformation of the E. coli HST16CR competent cell obtained above and extraction of a plasmid from the recombinant E. coli. In the plasmid extracted, the DNA sequences of anti-HER2scFv secretory expression cassette and human IFN-γ secretory expression cassette were determined in the same procedure. The plasmid extracted was designated as pHG-2. The DNA sequence of plasmid pHG-2 is represented by SEQ ID No. 100.

(Transformation 9 of Bacterium of the Genus Bifidobacterium)

Bifidobacterium longum 105-A strain was transformed by the electroporation system in the same procedure as in the above section (Transformation 1 of bacterium of the genus Bifidobacterium) except that plasmid pHG-2 (500 ng) extracted from the transformed E. coli was used. The transformant obtained was designated as Bifidobacterium longum 105-A/pHG-2 (hereinafter referred to as HG-2 strain).

Example 14

[Verification of Anti-HER2scFv and hIFN-γ Secretion in HG-2 Strain]

The presence or absence of anti-HER2scFv and hIFN-γ in the culture supernatant of HG-2 strain was verified by western blotting as follows.

(Culture of Recombinant Bacterium of the Genus Bifidobacterium)

Bacteria of the genus Bifidobacterium, i.e., HG-2 strain; a single-expression strain P30SP7L20-bHER2 (plasmid pP30SP7L20-bHER2 introduced strain) having one of the human IFN-γ secretory expression cassettes; and hIFNg33 strain; were cultured in the same procedure as in Example 4, (Culture of recombinant bacterium of the genus Bifidobacterium) and the culture supernatants were collected. The proteins in the culture supernatants were precipitated by trichloroacetic acid (TCA, manufactured by Wako Pure Chemical Industries Ltd.), washed with acetone, dissolved in a buffer for SDS-PAGE and treated with heat at 95° C. for 3 minutes to obtain culture supernatant concentrates.

(Western Analysis)

Each of the culture supernatant concentrates (corresponding to 0.1 mL of the culture solution) was treated in the same manner as in Example 9, (Western analysis). After blotting, the membrane was treated with blocking reagent. Thereafter, using an anti-histidine antibody, namely, THE His Tag Antibody, mAb, Mouse as a primary antibody and ECL peroxidase labelled anti-mouse antibody (mentioned above) as a secondary antibody, an antibody reaction was carried out. After the reaction, the membrane was illuminated by Western Lightning Ultra. This was analyzed by imaging equipment, Fluor-S Max (manufactured by BIO-RAD). The results are shown in FIG. 18.

(Results)

As is apparent from FIG. 18, both anti-HER2scFv and hIFN-γ in HG-2 strain were detected. The sizes of these proteins were the same as those of the proteins separately secreted from the corresponding single-expression strains. Note that, lane M shows a marker; lane 1 shows a protein secreted from anti-HER2scFv single-expression strain (P30SP7L20-bHER2 strain); lane 2 shows a protein secreted from hIFN-γ single-expression strain (hIFNg33 strain); and lane 3 shows proteins secreted from anti-HER2scFv and hIFN-γ co-expression strain (HG-2 strain).

Example 15

[Investigation on Physiological Activity of Secretion from HG-2 Strain]

(Preparation of Culture Supernatant Concentrate and Determination of hINF-γ Protein Expression-Level)

Each of HG-2 strain, P30SP7L20-bHER2 strain, hIFNg33 strain, and BEshuttle strain was inoculated in MRS liquid medium (75 µg/mL spectinomycin and 1% vitamin C-added liquid) in a ratio of 1% and anaerobically cultured at 37° C. for 24 hours (activation culture). The activated culture solution (0.5%) was inoculated in DMEM/MRS (75 µg/mL spectinomycin, 0.5% vitamin C-added liquid) medium, which was prepared by adding MRS liquid medium (2 mL) to 18 mL of DMEM medium (low glucose, manufactured by Life technologies). This medium was anaerobically cultured (main culture) at 37° C. for 18 hours. The culture solution (20 mL) was centrifuged. The culture supernatant (13 mL) was collected and filtered by a filter having a pore size of 0.2 µm to remove bacterial cells. The culture supernatant (10 mL) was concentrated by Amicon Ultra-4 (manufactured by Millipore) and replaced with PBS (−) to obtain a concentrate of 500 µL (Bifidobacterium culture supernatant concentrate (PBS substitution)). Each of the bacterium culture supernatant concentrates was subjected to hIFN-γ measurement by an ELISA kit in accordance with ELISA to measure the amount of IFN-γ in the culture supernatant. The measurement results are shown in the following Table 12.

TABLE 12

Measurement of human IFN-γ concentration in bifidobacterium culture supernatant concentrate

| Sample name | hIFN-γ conc. (ng/mL) |
| --- | --- |
| BEshuttle strain | 0 |
| P30SP7L20-bHER2 strain (anti-HER2scFv single expression strain) | 0 |
| hIFNg33 strain (hIFN-γ single expression strain) | 3697 |
| HG-2 strain (anti-HER2scFv/hIFN-γ co-expression strain) | 6851 |

(Cancer Cell Proliferation Inhibitory Activity of Anti-HER2scFv in Secretion Form HG-2 Strain)

As the physiological activity of anti-HER2scFv, cell proliferation inhibitory activity thereof was measured by adding anti-HER2scFv (PBS substitution), which was obtained by His-tag purification from the culture supernatant of P30SP7L20-bHER2 strain, to HER2 positive cell (NCI-N87 (stomach cancer) cell). More specifically, NCI-N87 cells were cultured in RPMI 1640 medium (10% (v/v) FBS) at 37° C. in the condition of 5% $CO_2$, and then seeded in a 96-well plate in a ratio of $2\times10^4$ cells for each and cultured at 37° C. in the condition of 5% $CO_2$ for 24 hours. Thereafter, the old medium was removed by suction and fresh RPMI 1640 medium (10% (v/v) FBS) was added in an amount of 98 µL for each. Subsequently, measurement samples, PBS (−) and anti-HER2scFv, which were adjusted to have a concentration in the range of 244 ng/mL to 1 mg/mL, were added separately in an amount of 2 µL for each. This plate was cultured at 37° C. in a condition of 5% $CO_2$ for 5 days.

After 5-day culture, the medium was removed by suction, a mixture, which was obtained by adding Cell Counting kit-8 (1 mL) to 9 mL of fresh RPMI 1640 medium (10% (v/v) FBS), was added in an amount of 100 µL for each. The plate was kept warm for further three hours at 37° C. in the condition of 5% $CO_2$. The absorbance was measured at a wavelength of 450 nm and 630 nm (reference wavelength) to determine cell proliferation inhibitory activity to the HER2 positive cells. The measurement results are shown in FIG. 19.

(Results)

As is apparent from FIG. 19, anti-HER2scFv purified from the *Bifidobacterium longum* Re-105A/pP30SP7L20-bHER2 exhibited cell proliferation inhibitory activity to NCI-N87 stomach cancer cell in a dose dependent manner. Thus, it was verified that anti-HER2scFv secreted from recombinant bacterium of the genus *Bifidobacterium* has a physiological activity.

Example 16

(Cancer Cell Proliferation Inhibitory Activity 1 of Anti-HER2scFv and hIFN-γ Secreted from HG-2 Strain)

The physiological activities of anti-HER2scFv and hINF-γ, which were secreted from a co-expression strain, were checked by determining cell proliferation inhibitory activity thereof by adding the concentrate (PBS substitution) of the culture supernatant of a bacterium of the genus *Bifidobacterium* (HG-2 strain) obtained in Example 15 to HER2 positive cell (NCI-N87 cell). More specifically, NCI-N87 cells were cultured in RPMI 1640 medium (10% (v/v) FBS) at 37° C., in the condition of 5% $CO_2$, seeded in a 96-well plate in an amount of $2\times10^4$ cells for each and cultured at 37° C. in the condition of 5% $CO_2$ for 24 hours. From the cell culture solution, the old medium was removed by suction and fresh RPMI 1640 medium (10% (v/v) FBS) was added in an amount of 90 µL for each. Subsequently, as measurement samples, PBS (−), a BEshuttle strain culture supernatant concentrate (negative control), a P30SP7L20-bHER2 strain culture supernatant concentrate, a hINFg33 strain culture supernatant concentrate (prepared by diluting with PBS so as to have a hIFN-γ concentration of 2000 ng/mL), a HG-2 strain culture supernatant concentrate and recombinant hIFN-γ (positive control, the hIFN-γ concentration was adjusted so as to be 2000 ng/mL) were added in an amount of 10 µL for each. This plate was subjected to culture at 37° C. in the condition of 5% $CO_2$ for 5 days.

The cell proliferation inhibitory activity was measured in the same manner as described in the above section (Cell proliferation inhibitory activity of anti-HER2scFv). The results are shown in FIG. 20.

As is apparent from FIG. 20, the culture supernatant concentrate derived from anti-HER2scFv/hIFN-γ co-expression strain, i.e., HG-2 strain, exhibited extremely strong cell proliferation inhibitory activity to NCI-N87 cell. In contrast, the concentrate derived from the culture supernatant of hIFN-γ single-expression strain, i.e., hINFg33 strain, exhibited the same cell proliferation inhibitory activity as recombinant hIFN-γ (manufactured by PeploTech) used as a standard at a hIFN-γ concentration of 200 ng/mL. The concentrate derived from P30SP7L20-bHER2 strain was determined to have the same cell proliferation inhibitory activity as in Example 15. The cell proliferation inhibitory activity of anti-HER2scFv/hIFN-γ co-expression strain, i.e., HG-2 strain, is higher than the activity of either one of strains: hIFN-γ single-expression strain and P30SP7L20-bHER2 strain, simultaneously checked. This activity is conceivably due to synergistic combinational effect of both hIFN-γ and anti-HER2scFv proteins secreted together.

Example 17

[Verification of Secretion from Anti-HER2scFv and hIFN-γ Co-Expression Strain within Tumor]

Using a human stomach cancer cell strain NCI-N87 bearing nude mouse, localization of a bacterium of the genus *Bifidobacterium* within a tumor was checked by gram staining. The localization of anti-HER2scFv and hIFN-γ within the tumor was checked by immunohistochemical staining with an anti-histidine tag antibody and anti-hIFN-γ antibody.

Human stomach cancer cell strain NCI-N87 (ATCC) was cultured in RPMI 1640 medium (manufactured by Wako Pure Chemical Industries Ltd.) comprising 10% FBS (manufactured by EQUITECH-BIO, INC.) and transplanted into nude mice (produced by Japan SLC, Inc.) to prepare tumor bearing mice. To mice having a tumor size of about 470 $mm^3$, a simple frozen preparation of an anti-HER2scFv and hIFN-γ co-expression strain (HG-2 strain); and a simple frozen preparation of the BEshuttle strain expressing neither one of them and serving as a control, were administered in a dose of $6\times10^8$ cfu from the tail vein. Note that, a 10% maltose solution was administered in a dose of 1 mL at a frequency of two times a day for 5 days. On Day 7 after the administration, the tumor was excised out, embedded in O. C. T. compound (manufactured by Sakura Finetek) and frozen. Thin specimens were prepared by Cryostat microtome Leica CM1900 (manufactured by Leica), separately placed on slides and subjected to tissue staining.

(Gram Staining)

The thin specimens on slides were dried in air and soaked in 4% PFA (manufactured by Wako Pure Chemical Industries Ltd.) for 10 minutes to fix. After fixation, the thin specimens were pre-stained with Bartholomew & Mittwer M crystal violet solution (manufactured by MUTO PURE CHEMICALS Co., Ltd.) for 2 minutes, and allowed to react with Bartholomew & Mittwer M iodine/sodium hydroxide solution (manufactured by MUTO PURE CHEMICALS Co., Ltd.) for one minute. The thin specimens were decolored with Bartholomew & Mittwer M acetone/ethyl alcohol mixture (manufactured by MUTO PURE CHEMICALS Co., Ltd.) and stained with Bartholomew & Mittwer M 0.1% fuchsin solution (manufactured by MUTO PURE CHEMICALS Co., Ltd.) for one minute. After staining, the thin specimens were washed with purified water, dewatered with 99.5% ethanol (manufactured by Wako Pure Chemical Industries Ltd.), cleared in Lemosol (manufactured by Wako Pure Chemical Industries Ltd.) and enclosed with Entellan new (manufactured by MERCK KGaA). The results are shown in FIG. 21.

(Immunohistochemical Staining with Anti-Histidine Tag Antibody and Anti-hIFN-γ Antibody)

The thin specimens on slides were dried in air and soaked in 4% PFA (manufactured by Wako Pure Chemical Industries Ltd.) for about 4 hours to fix. After fixation, the thin specimens were washed with purified water for one minute and three times with 1×PBS (−) for 5 minutes. Moisture around the tissue was wiped out. A line was drawn around the tissue by Dako pen (manufactured by Dako). To the tissue, 3% BSA-PBS was added dropwise and allowed to react for 60 minutes to inhibit non-specific binding. Anti-His-tag mAb-Alexa Fluor (registered trademark) 594

(manufactured by MBL) and FITC Anti-human IFN-γ antibody (manufactured by BioLegend) were mixed and diluted with Can Get Signal (registered trademark) immunostain (manufactured by TOYOBO CO., LTD.) to prepare an antibody reaction solution. The antibody reaction solution was added dropwise onto the tissue and allowed to react at 4° C. overnight. After the antibody reaction, washing with 1×PBS (−) for 5 minutes was carried out three times. The specimen(s) was enclosed with VECTASHIELD (registered trademark) Mounting Medium with DAPI. The stained slice was observed by a microscope DM5000B (manufactured by Leica) and the image thereof was photographed. The results are shown in FIGS. 22 and 23.

(Results)

As is apparent from FIG. 21, in gram staining, bacterial cells, i.e., HG-2 strain (A) and BEshuttle strain (B) (FIGS. 21 (A) and (B), pointed by the arrow) each were found to be present in the tumor tissue. Also, in immunohistochemical staining with an anti-hIFN-γ antibody, hIFN-γ positive images were found in the tumor tissue of the mouse having a cancer and administered with a co-expression strain, i.e., HG-2 strain (FIG. 22, green color portions pointed by arrows). Furthermore, in immunohistochemical staining with a histidine tag, histidine tag positive images (anti-HER2scFv and hIFN-γ) were found (FIG. 23, red color portions pointed by arrows). From these results, it was verified that when HG-2 strain is intravenously administered to a mouse having a human stomach cancer NCI-N87, the HG-2 strain is colonized in the tumor and hIFN-γ and anti-HER2scFv proteins are secreted from the HG-2 strain and simultaneously present in the tumor.

Example 18

[Preparation of Co-Expression Strain for Anti-Human PD-1scFv03-his and Anti-Human CTLA-4scFv01-FLAG]

*E. coli-Bifidobacterium* shuttle vector secreting anti-human PD-1scFv03-His and anti-human CTLA-4scFv01-FLAG, i.e., co-expression plasmids pPC2, pPC3, pPC4, pPC5, pPC6, pPC7 and pPC8 were prepared. *Bifidobacterium longum* 105-A strain was separately transformed with these 7 types of co-expression plasmids.

The constitutions of anti-human PD-1scFv03-His expression cassettes and anti-human CTLA-4scFv01-FLAG expression cassettes in the 7 types of co-expression plasmids pPC2 to pPC8 are shown in Table 13-1 and Table 13-2. To avoid homologous sequences within a plasmid molecule, the promoter DNA, a terminator DNA and DNA sequences encoding a tag and signal peptide-linker peptide conjugate in each expression cassette were designed not to have the same constitution.

TABLE 13-1 anti-hPD-1 scFv03-His expression cassette

| plasmid | promoter | SP/Linker | scFv | tag | terminator |
|---|---|---|---|---|---|
| pPC2 | Hu | SP50L5 | anti-hPD-1 scFv03 | His | Hu |
| pPC3 | Hu | SP50L5 | anti-hPD-1 scFv03 | His | Hu |
| pPC4 | Hu | SP67L10 | anti-hPD-1 scFv03 | His | Hu |
| pPC5 | Hu | SP67L10 | anti-hPD-1 scFv03 | His | Hu |
| pPC6 | Hu | SP69L1 | anti-hPD-1 scFv03 | His | Hu |
| pPC7 | Hu | SP69L1 | anti-hPD-1 scFv03 | His | Hu |
| pPC8 | Hu | SP69L1 | anti-hPD-1 scFv03 | His | Hu |

TABLE 13-2 anti-hCTLA-4 scFv01-FLAG expression cassette

| plasmid | promoter | SP/Linker | scFv | tag | terminator |
|---|---|---|---|---|---|
| pPC2 | P30 | SP67L1 | anti-hCTLA-4 scFv01 | FLAG | T2 |
| pPC3 | P30 | SP68L1 | anti-hCTLA-4 scFv01 | FLAG | T2 |
| pPC4 | P30 | SP50L5 | anti-hCTLA-4 scFv01 | FLAG | T2 |
| pPC5 | P30 | SP68L1 | anti-hCTLA-4 scFv01 | FLAG | T2 |
| pPC6 | P30 | SP50L5 | anti-hCTLA-4 scFv01 | FLAG | T2 |
| pPC7 | P30 | SP67L1 | anti-hCTLA-4 scFv01 | FLAG | T2 |
| pPC8 | P30 | SP68L1 | anti-hCTLA-4 scFv01 | FLAG | T2 |

(Constitution of Anti-hPD-1scFv03-his Secretory Expression Cassette)

As the anti-hPD-1scFv03-His secretory expression cassette, a cassette sequentially comprising (1) a Hu promoter DNA, (2) a DNA encoding a signal peptide-linker peptide conjugate, (3) a DNA encoding an anti-hPD-1scFv03 amino acid sequence, (4) a DNA encoding a His tag sequence and (5) a Hu terminator DNA was prepared such that DNA (1) was placed upstream (the 5′ end) and DNA (5) downstream (the 3′ end). As the signal peptide-linker peptide conjugate, SP50L5 (secretory signal peptide-linker peptide conjugate obtained by binding a sequence consisting of the initial five amino acids (Ala Thr Leu Thr Pro) of the amino acid sequence represented by SEQ ID No. 83 to the amino acid sequence represented by SEQ ID No. 61); SP67L10 (secretory signal peptide-linker peptide conjugate obtained by binding a sequence consisting of initial ten amino acids (Ala Gly Val Asp Tyr Leu Pro Thr Ile Gly) of the amino acid sequence represented by SEQ ID No. 95 to the amino acid sequence represented by SEQ ID No. 73); or SP69L1 (secretory signal peptide-linker peptide conjugate obtained by binding the initial amino acid (Asp) of the amino acid sequence represented by SEQ ID No. 99 to the amino acid sequence represented by SEQ ID No. 77) was used.

(Constitution of Anti-hCTLA-4scFv01-FLAG Secretory Expression Cassette)

As the anti-hCTLA-4scFv01-FLAG secretory expression cassette, a cassette sequentially comprising (1) a P30 promoter DNA, (2) a DNA encoding signal peptide-linker peptide conjugate, (3) a DNA encoding an anti-hCTLA-4scFv01 amino acid sequence, (4) a DNA encoding a FLAG tag sequence and (5) a T2 terminator DNA was prepared such that DNA (1) was placed upstream (the 5′ end) and DNA (5) downstream (the 3′ end). As the signal peptide-linker peptide conjugate, SP50L5 (secretory signal peptide-linker peptide conjugate obtained by binding a sequence consisting of the initial five amino acids (Ala Thr Leu Thr Pro) of the amino acid sequence represented by SEQ ID No. 83 to the amino acid sequence represented by SEQ ID No. 61); SP67L1 (secretory signal peptide-linker peptide conjugate obtained by binding the initial amino acid (Ala) of the amino acid sequence represented by SEQ ID No. 95 to the amino acid sequence represented by SEQ ID No. 73); or SP68L1 (secretory signal peptide-linker peptide conjugate obtained by binding the initial amino acid (Asp) of the amino acid sequence represented by SEQ ID No. 97 to the amino acid sequence represented by SEQ ID No. 75) was used.

The basic constitutions of co-expression plasmids pPC2 to pPC8 are shown in FIG. 24.

The production method thereof is schematically shown in FIG. 25.

(1) In the first step, template plasmids (pHuSPxLy-hPD-1scFv03-His (SPxLy=SP50L5, SP67L10, SP69L1)) to be used in preparation of co-expression plasmids pPC2 to pPC8 was prepared.

(2) In the second step, plasmid pHuSPxLy-hPD-1scFv03-His-T2 (SPxLy=SP50L5, SP67L10, SP69L1) was prepared by inserting T2 terminator fragment downstream of an anti-hPD-1scFv03-His expression cassette of an anti-hPD-1scFv03-His expression plasmid, pHuSPxLy-hPD-1scFv03-His (SPxLy=SP50L5, SP67L10, SP69L1).

(3) In the third step, an anti-hCTLA-4scFv01-FLAG expression cassette (except a terminator) was inserted between Hu terminator and T2 terminator of the plasmid prepared in the second step to prepare co-expression plasmids pPC2 to pPC8.

(First Step)

Step A: PCR products of a linear vector (vector) prepared by using plasmid pHuSP7L20-hPD-1scFv03 (histidine tag is added to the 3' end of scFv sequence) prepared in Example 8 as template DNA and SP50 insert (insert), SP67 insert and SP69 insert prepared from 105-A genomic DNA, were prepared. A primer was designed such that terminal 15 bp of a PCR product has the same sequence as that of the terminal 15 bp to the adjacent PCR product to be ligated in the in-fusion reaction of the next step. The elongation reaction time was set assuming that one minute is required for elongation of 1 kbp. The PCR amplification step herein is referred to as "PCR amplification step 1".

The linear vector and each of the inserts were ligated by an in-fusion reaction using HD kit. In the same manner as in (Example 1: Transformation of *E. coli* and determination of DNA sequence of plasmid pAG8), the *E. coli* HST16CR competent cells were transformed by using the in-fusion reaction solution; a plasmid was extracted from recombinant *E. coli*; and the sequence of "anti-hPD-1scFv03-His expression cassette region" (including Hu promoter to Hu terminator) in the plasmid extracted, was determined (hereinafter, the step from the in-fusion reaction to the sequence determination will be carried out in the same procedure as this). The plasmids extracted were designated as pHuSP50L20-hPD-1scFv03-His, pHuSP67L20-hPD-1scFv03-His and pHuSP69L20-hPD-1scFv03-His.

Step B: PCR products of SP50L5 insert, SP67L10 insert and SP69L1 insert, which were prepared respectively from the pHuSP50L20-hPD-1scFv03-His, pHuSP67L20-hPD-1scFv03-His and pHuSP69L20-hPD-1scFv03-His, were prepared.

The linear vector prepared in Step A and each of the SP50L5 insert, SP67L10 insert and SP69L1 insert prepared above were ligated by the HD kit in the same manner as above and the sequence of the "anti-hPD-1scFv03-His expression cassette region" was determined. The plasmids extracted were designated as pHuSP50L5-hPD-1scFv03-His, pHuSP67L10-hPD-1scFv03-His and pHuSP69L1-hPD-1scFv03-His.

(Second Step)

(Preparation of T2 Terminator)

Synthesis of the sequence (SEQ ID No. 101) was ordered to GenScript Japan Inc. and the sequence was designated as T2 terminator, which was integrated in plasmid vector pUC57 (Bba-B0015 in pUC57) and delivered.

Using the pHuSP50L5-hPD-1scFv03-His, pHuSP67L10-hPD-1scFv03-His and pHuSP69L1-hPD-1scFv03-His separately as template DNA and PC1_primer (SEQ ID No. 102) as a forward primer and PC2_primer (SEQ ID No. 103) as a reverse primer, PCR products were prepared in the same manner as in the above step "PCR amplification 1" and designated as A1, A2 and A3 linear vectors. The sizes of the PCR products were 4751 bp, 4697 bp and 4661 bp, respectively.

Using the Bba-B0015 in pUC57 as template DNA, and PC3_primer (SEQ ID No. 104) as a forward primer and PC4_primer (SEQ ID No. 105) as a reverse primer, PCR product B (159 bp) was prepared.

TABLE 14

| Plasmid to be constructed | Combination in in-fusion reaction |
|---|---|
| pHuSP50L5-hPD-1 scFv03-His-T2 | A1 and B |
| pHuSP67L10-hPD-1 scFv03-His-T2 | A2 and B |
| pHuSP69L1-hPD-1 scFv03-His-T2 | A3 and B |

PCR products were ligated in accordance with the combinations shown in Table 14 by use of the HD kit and the sequence of each of "anti-hPD-1scFv03-His expression cassette-T2 terminator regions" (5'-Hu promoter-SPxLy-human PD-1scFv03-His-T2 terminator-3') was determined. The plasmids extracted were designated as pHuSP50L5-hPD-1scFv03-His-T2, pHuSP67L10-hPD-1scFv03-His-T2 and pHuSP69L1-hPD-1scFv03-His-T2.

[Preparation of Plasmid phCTLAz]

The Hu promoter of the plasmid pHuSP7L20-hCTLA-4scFv02FLAG prepared in Example 8 was replaced by P30 promoter, as schematically shown in FIG. 26.

A PCR product (4410 bp) of a linear vector was prepared by using pHuSP7L20-hCTLA-4scFv02FLAG as template DNA, and vec_F5_primer (SEQ ID No. 106) as a forward primer and vec_R2_primer (SEQ ID No. 107) as a reverse primer. A PCR product (245 bp) of an insert was prepared by using 105-A genomic DNA as a template, and P30_F1_primer (SEQ ID No. 108) as a forward primer and P30_R1_primer (SEQ ID No. 109) as a reverse primer. The linear vector and insert thus prepared were ligated as mentioned above by use of the HD kit and the sequence of the full-length plasmid extracted was determined. The plasmid extracted was designated as phCTLA1.

(Preparation of Plasmid phCTLAz (z=4, 10, 11))

The signal peptide sequence of the plasmid phCTLA1 prepared above was changed from SP7 to SP50, SP67 and SP68.

PCR amplification was carried out in the same manner as in the above step "PCR amplification 1" using template DNA molecules and primers listed in Table 15 to prepare a vector and inserts.

TABLE 15

| | Template and primer used in PCR | | | |
|---|---|---|---|---|
| PCR product | Template DNA | Fow. Primer (Forward primer) | Rev. primer (Reverse primer) | Size of PCR product |
| Vector | phCTLA1 | hCTLA3_primer (SEQ ID No. 110) | P30_R1_primer (SEQ ID No. 109) | 4466 bp |

TABLE 15-continued

Template and primer used in PCR

| PCR product | Template DNA | Fow. Primer (Forward primer) | Rev. primer (Reverse primer) | Size of PCR product |
|---|---|---|---|---|
| Insert-SP50 | B. longum 105A genome | SP50-ins_F2_primer (SEQ ID No. 111) | SP50-ins_R6_primer (SEQ ID No. 112) | 258 bp |
| Insert-SP67 | B. longum 105A genome | SP67-ins_F2_primer (SEQ ID No. 113) | SP67-ins_R6_primer (SEQ ID No. 114) | 189 bp |
| Insert-SP68 | B. longum 105A genome | SP68-ins_F2_primer (SEQ ID No. 115) | SP68-ins_R6_primer (SEQ ID No. 116) | 219 bp |

The vector and each of the inserts listed in Table 15 were ligated in the same manner as above by using HD kit, and the sequences of "anti-hCTLA-4scFv02-FLAG cassette regions" were determined. The plasmids extracted were designated as phCTLA4 (in the case of SP50), phCTLA10 (in the case of SP67) and phCTLA11 (in the case of SP68).

(Preparation of pP30SPx'Ly'-hCTLA-4scFv01-his)

Preparation is schematically shown in FIG. 27.

(Preparation of Anti-CTLA-4 Single-Chain Antibody Expression Cassette)

Referring to [Preparation of pHuSP7L20-scFv-CTLA-4-1] in WO2015/166640, pHuSP7L20-scFv-CTLA-4-1 was prepared and designated as pHuSP7L20-hCTLA-4scFv01-His in this Example.

PCR products were prepared in the same manner as in the above step "PCR amplification 1" by using template DNA molecules and primers listed in Table 16.

TABLE 16

| PCR product | Template DNA | Fow. primer | Rev. primer | Size of PCR product |
|---|---|---|---|---|
| A | pHuSP7L20-hCTLA-4scFv01-His | hCTLA3_primer | GA6_primer (SEQ ID No. 117) | 4020 bp |
| B-SP50LS | phCTLA4 | GA5_primer_rev (SEQ ID No. 118) | SP50L5-ins_R1_hPD1_03 (SEQ ID No. 128) | 671 bp |
| B-SP67L1 | phCTLA10 | GA5_primer_rev | SP67L1-ins_R1_hPD1_03 (SEQ ID No. 129) | 590 bp |
| B-SP68L1 | phCTLA11 | GA5_primer_rev | SP68L1-ins_R1_hPD1_03 (SEQ ID No. 130) | 620 bp |

The PCR product A and each of PCR products B listed in Table 16 were ligated in the same manner as above by using HD kit, and the sequences of "anti-hCTLA-4scFv01-His cassette regions" were determined. The plasmids extracted were designated as pP30SP50L5-hCTLA-4scFv001-His, pP30SP67L1-hCTLA-4scFv01-His and pP30SP68L1-hCTLA-4scFv01-His.

[Preparation of Plasmid pP30SPx'Ly'-hCTLA-4scFv01-FLAG]

The histidine tag of plasmid pP30SPx'Ly'-hCTLA-4scFv01-His (SPx'Ly'=SP50L5, SP67L1, SP68L1) prepared above was changed to FLAG tag as schematically shown in FIG. 28. Hereinafter, in the case of anti-hCTLA-4scFv, expression "SPx'Ly'" may be sometimes employed.

PCR products were prepared by using the template DNA molecules and primers listed in Table 17 in the same manner as in the above step "PCR amplification 1".

TABLE 17

| PCR product | Template DNA | Fow. primer | Rev. primer | Size of PCR product |
|---|---|---|---|---|
| A | pP30SP50L5-hCTLA-4scFv01-His | hCTLA15_primer (SEQ ID No. 120) | GA6_primer | 3280 bp |
| B-SP50L5 | pP30SP50L5-hCTLA-4scFv01-His | GA5_primer_rev | hCTLA16_primer (SEQ ID No. 119) | 1417 bp |
| B-SP67L1 | pP30SP67L1-hCTLA-4scFv01-His | GA5_primer_rev | hCTLA16_primer | 1336 bp |
| B-SP68L1 | pP30SP68L1-hCTLA-4scFv01-His | GA5_primer_rev | hCTLA16_primer | 1366 bp |

PCR product A and each of PCR products B listed in Table 17 were ligated by using HD kit in the same manner as mentioned above and the sequences of "anti-hCTLA-4 scFv01-FLAG cassette regions" were determined. The plasmids extracted were designated as pP30SP50L5-hCTLA-4scFv01-FLAG (hereinafter referred to as pC1F), pP30SP67L1-hCTLA-4scFv01-FLAG (hereinafter referred to as pC2F) and pP30SP68L1-hCTLA-4scFv01-FLAG (hereinafter referred to as pC3F).

(Third Step)

PCR products were prepared by using the template DNA and primers listed in Table 18 in the same manner as in the above step "PCR amplification 1".

TABLE 18

| PCR product | Template DNA | Fow. primer | Rev. primer | Size of PCR product |
|---|---|---|---|---|
| A7 | pHuSP50L5-hPD-1scFv03-His-T2 | PC5_primer | PC2_primer (SEQ ID No. 121) | 4886 bp |
| A8 | pHuSP67L10-hPD-1scFv03-His-T2 | PC5_primer | PC2_primer | 4832 bp |
| A9 | pHuSP69L1-hPD-1scFv03-His-T2 | PC5_primer | PC2_primer | 4796 bp |
| B1 | pC1F | PC6_primer (SEQ ID No. 122) | PC7_primer (SEQ ID No. 123) | 1210 bp |
| B2 | pC2F | PC6_primer | PC7_primer | 1129 bp |
| B3 | pC3F | PC6_primer | PC7_primer | 1159 bp |

TABLE 19

| Plasmid to be constructed | Combination in in-fusion reaction |
|---|---|
| pPC2 | A7 and B2 |
| pPC3 | A7 and B3 |
| pPC4 | A8 and B1 |
| pPC5 | A8 and B3 |
| pPC6 | A9 and B1 |
| pPC7 | A9 and B2 |
| pPC8 | A9 and B3 |

The PCR products listed in Table 18 were ligated in accordance with the combinations listed in Table 19 by using HD kit in the same manner as mentioned above and DNA sequences of the full-length plasmids extracted were determined. The plasmids extracted were designated as pPC2, pPC3, pPC4, pPC5, pPC6, pPC7 and pPC8. The individual plasmids will be outlined below.

(pPC2 scFv expression cassette sequences (2618 bp) (SEQ ID No. 131))

| | |
|---|---|
| 1 ... 1384 | Anti-human PD-1scFv03-His expression cassette |
| 1 ... 361 | Hu promoter |
| 362 ... 544 | SP50L5 |
| 545 ... 1249 | anti-human PD-1scFv03 |
| 1250 ... 1267 | His tag |
| 1268 ... 1270 | stop codon |
| 1271 ... 1384 | Hu terminator |
| 1385 ... 2618 | Anti-human CTLA-4scFv01-FLAG expression cassette |
| 1385 ... 1619 | P30 promoter |
| 1620 ... 1721 | SP67L1 |
| 1722 ... 2462 | anti-human CTLA-4scFv01 |
| 2463 ... 2486 | FLAG tag |
| 2487 ... 2489 | stop codon |
| 2490 ... 2618 | T2 terminator |

(pPC3 scFv expression cassette sequences (2648 bp) (SEQ ID No. 132))

| | |
|---|---|
| 1 ... 1384 | Anti-human PD-1scFv03-His expression cassette |
| 1 ... 361 | Hu promoter |
| 362 ... 544 | SP50L5 |
| 545 ... 1249 | anti-human PD-1scFv03 |
| 1250 ... 1267 | His tag |
| 1268 ... 1270 | stop codon |
| 1271 ... 1384 | Hu terminator |
| 1385 ... 2648 | Anti-human CTLA-4scFv01-FLAG expression cassette |
| 1385 ... 1619 | P30 promoter |
| 1620 ... 1751 | SP68L1 |
| 1752 ... 2492 | anti-human CTLA-4scFv01 |
| 2493 ... 2516 | FLAG tag |
| 2517 ... 2519 | stop codon |
| 2520 ... 2648 | T2 terminator |

(pPC4 scFv expression cassette sequences (2645 bp) (SEQ ID No. 133))

| | |
|---|---|
| 1 ... 1330 | Anti-human PD-1scFv03-His expression cassette |
| 1 ... 361 | Hu promoter |
| 362 ... 490 | SP67L10 |
| 491 ... 1195 | anti-human PD-1scFv03 |
| 1196 ... 1213 | His tag |
| 1214 ... 1216 | stop codon |
| 1217 ... 1330 | Hu terminator |
| 1331 ... 2645 | Anti-human CTLA-4scFv01-FLAG expression cassette |
| 1331 ... 1565 | P30 promoter |
| 1566 ... 1748 | SP50L5 |
| 1749 ... 2489 | anti-human CTLA-4scFv01 |
| 2490 ... 2513 | FLAG tag |
| 2514 ... 2516 | stop codon |
| 2517 ... 2645 | T2 terminator |

(pPC5 scFv expression cassette sequences (2594 bp) (SEQ ID No. 134))

| | |
|---|---|
| 1 ... 1330 | Anti-human PD-1scFv03-His expression cassette |
| 1 ... 361 | Hu promoter |
| 362 ... 490 | SP67L10 |
| 491 ... 1195 | anti-human PD-1scFv03 |
| 1196 ... 1213 | His tag |
| 1214 ... 1216 | stop codon |
| 1217 ... 1330 | Hu terminator |
| 1331 ... 2594 | Anti-human CTLA-4scFv01-FLAG expression cassette |
| 1331 ... 1565 | P30 promoter |
| 1566 ... 1697 | SP68L1 |
| 1698 ... 2438 | anti-human CTLA-4scFv01 |
| 2439 ... 2462 | FLAG tag |
| 2463 ... 2465 | stop codon |
| 2466 ... 2594 | T2 terminator |

| (pPC6 scFv expression cassette sequences (2609 bp) (SEQ ID No. 135)) | |
|---|---|
| 1 ... 1294 | Anti-human PD-1scFv03-His expression cassette |
| 1 ... 361 | Hu promoter |
| 362 ... 454 | SP69L1 |
| 455 ... 1159 | anti-human PD-1scFv03 |
| 1160 ... 1177 | His tag |
| 1178 ... 1180 | stop codon |
| 1181 ... 1294 | Hu terminator |
| 1295 ... 2609 | Anti-human CTLA-4scFv01-FLAG expression cassette |
| 1295 ... 1529 | P30 promoter |
| 1530 ... 1712 | SP50L5 |
| 1713 ... 2453 | anti-human CTLA-4scFv01 |
| 2454 ... 2477 | FLAG tag |
| 2478 ... 2480 | stop codon |
| 2481 ... 2609 | T2 terminator |

| (pPC7 scFv expression cassette sequences (2528 bp) (SEQ ID No. 136)) | |
|---|---|
| 1 ... 1294 | Anti-human PD-1scFv03-His expression cassette |
| 1 ... 361 | Hu promoter |
| 362 ... 454 | SP69L1 |
| 455 ... 1159 | anti-human PD-1scFv03 |
| 1160 ... 1177 | His tag |
| 1178 ... 1180 | stop codon |
| 1181 ... 1294 | Hu terminator |
| 1295 ... 2528 | Anti-human CTLA-4scFv01-FLAG expression cassette |
| 1295 ... 1529 | P30 promoter |
| 1530 ... 1631 | SP67L1 |
| 1632 ... 2372 | anti-human CTLA-4scFv01 |
| 2373 ... 2396 | FLAG tag |
| 2397 ... 2399 | stop codon |
| 2400 ... 2528 | T2 terminator |

| (pPC8 scFv expression cassette sequences (2558 bp) (SEQ ID No. 137)) | |
|---|---|
| 1 ... 1294 | Anti-human PD-1scFv03-His expression cassette |
| 1 ... 361 | Hu promoter |
| 362 ... 454 | SP69L1 |
| 455 ... 1159 | anti-human PD-1scFv03 |
| 1160 ... 1177 | His tag |
| 1178 ... 1180 | stop codon |
| 1181 ... 1294 | Hu terminator |
| 1295 ... 2558 | Anti-human CTLA-4scFv01-FLAG expression cassette |
| 1295 ... 1529 | P30 promoter |
| 1530 ... 1661 | SP68L1 |
| 1662 ... 2402 | anti-human CTLA-4scFv01 |
| 2403 ... 2426 | FLAG tag |
| 2427 ... 2429 | stop codon |
| 2430 ... 2558 | T2 terminator |

(Transformation 10 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that the plasmids pPC2, pPC3, pPC4, pPC5, pPC6, pPC7 and pPC8, extracted from the transformed *E. coli* mentioned above were used each in an amount of 5 μL. The transformants obtained were designated as *Bifidobacterium longum* 105-A/pPC2 (hereinafter referred to as PC2 strain); *Bifidobacterium longum* 105-A/pPC3 (hereinafter referred to as PC3 strain); *Bifidobacterium longum* 105-A/pPC4 (hereinafter referred to as PC4 strain); *Bifidobacterium longum* 105-A/pPC5 (hereinafter referred to as PC5 strain); *Bifidobacterium longum* 105-A/pPC6 (hereinafter referred to as PC6 strain); *Bifidobacterium longum* 105-A/pPC7 (hereinafter referred to as PC7 strain) and *Bifidobacterium longum* 105-A/pPC8 (hereinafter referred to as PC8 strain).

Example 19

[Preparation of PC2TL Strain to PC8TL Strain]

In view of clinical development, from the plasmids prepared in Example 18, scFv marker tag (histidine tag/FLAG tag) and a plasmid origin of replication pUCori, working in *E. coli* were removed to prepare anti-human PD-1scFv03 and anti-human CTLA-4scFv01 co-expression plasmids, pPC2TL to pPC8TL. *Bifidobacterium longum* 105-A was transformed with each of these plasmids to obtain co-expression strains, PC2TL strain to PC8TL strain.

Basic constitution of the plasmid in co-expression strains, PC2TL strain to PC8TL strain, is shown in FIG. 29. In 7 types of non-tagged co-expression plasmids pPC2TL to pPC8TL, the constitutions of anti-human PD-1scFv03 expression cassette and anti-human CTLA-4scFv01 expression cassette are shown in the following Table 20 and Table 21.

TABLE 20

Anti-hPD-1 scFv03 expression cassette (not tagged)

| Plasmid | Promoter | SP/Linker | scFv | Tag | Terminator |
|---|---|---|---|---|---|
| pPC2TL | Hu | SP50L5 | anti-hPD-1 scFv03 | — | Hu |
| pPC3TL | Hu | SP50L5 | anti-hPD-1 scFv03 | — | Hu |
| pPC4TL | Hu | SP67L10 | anti-hPD-1 scFv03 | — | Hu |
| pPC5TL | Hu | SP67L10 | anti-hPD-1 scFv03 | — | Hu |
| pPC6TL | Hu | SP69L1 | anti-hPD-1 scFv03 | — | Hu |
| pPC7TL | Hu | SP69L1 | anti-hPD-1 scFv03 | — | Hu |
| pPC8TL | Hu | SP69L1 | anti-hPD-1 scFv03 | — | Hu |

TABLE 21

Anti-hCTLA-4 scFv01 expression cassette (not tagged)

| Plasmid | Promoter | SP/Linker | scFv | Tag | Terminator |
|---|---|---|---|---|---|
| pPC2TL | P30 | SP67L1 | anti-hCTLA-4 scFv01 | — | T2 |
| pPC3TL | P30 | SP68L1 | anti-hCTLA-4 scFv01 | — | T2 |
| pPC4TL | P30 | SP50L5 | anti-hCTLA-4 scFv01 | — | T2 |
| pPC5TL | P30 | SP68L1 | anti-hCTLA-4 scFv01 | — | T2 |
| pPC6TL | P30 | SP50L5 | anti-hCTLA-4 scFv01 | — | T2 |
| pPC7TL | P30 | SP67L1 | anti-hCTLA-4 scFv01 | — | T2 |
| pPC8TL | P30 | SP68L1 | anti-hCTLA-4 scFv01 | — | T2 |

(Constitution of Anti-hPD-1scFv03 Secretory Expression Cassette)

As anti-hPD-1scFv03 secretory expression cassette, a cassette sequentially comprising (1) a Hu promoter DNA, (2) a DNA encoding a signal peptide-linker peptide conjugate, (3) a DNA encoding an anti-hPD-1scFv03 amino acid sequence and (4) a Hu terminator DNA was prepared such that DNA (1) was placed upstream (the 5' end) and DNA (4) downstream (the 3' end). As the signal peptide-linker peptide conjugate, SP50L5, SP67L10 or SP69L1 was used.

(Constitution of Anti-hCTLA-4scFv01 Secretory Expression Cassette)

As anti-hCTLA-4scFv01 secretory expression cassette, a cassette sequentially comprising (1) a P30 promoter DNA, (2) a DNA encoding a signal peptide-linker peptide conjugate, (3) a DNA encoding an anti-hCTLA-4scFv01 amino acid sequence and (4) a T2 terminator DNA was prepared such that DNA (1) was placed upstream (the 5' end) and DNA (4) downstream (the 3' end). As the signal peptide-linker peptide conjugate, SP50L5, SP67L1 or SP68L1 was used.

(Method for Producing pPC2TL to pPC8TL)

The method for producing a plasmid is constituted of the following 4 steps as schematically shown in FIG. 30.

(1) In the first step, a template plasmid, pHuSPxLy-hPD-1scFv03TL to be used in preparation of co-expression plasmids, pPC2TL-pPC8TL was prepared.

(2) In the second step, a T2 terminator fragment was inserted downstream of anti-PD-1scFv03 expression cassette of anti-hPD-1scFv03 (not tagged) expression plasmid to prepare plasmid pHuSPxLy-hPD-1scFv03TL-T2 (SPxLy=SP50L5, SP67L10, SP69L1).

(3) In the third step, anti-hCTLA-4scFv01 (not tagged) expression cassette (note that a terminator is excluded) was inserted between Hu terminator and T2 terminator of the plasmid prepared in the second step to prepare plasmids pPC2TLS to pPC8TLS.

(4) In the fourth step, the fragment of pUCori, which serves as a plasmid origin of replication in *E. coli*, of the plasmid prepared in the third step, was cleaved out with a restriction enzyme(s). Thereafter, the plasmid was allowed to self-close to prepare a co-expression plasmids (not tagged, non-shuttle) pPC2TL to pPC8TL.

(First Step)

PCR product A-1 (3261 bp) was prepared in the same manner as in the above step "PCR amplification 1" using pHuSP50L5-hPD-1scFv03-His as mentioned above as template DNA, pCDshuttle_F1_primer (SEQ ID No. 126) as a forward primer and GA6_primer as a reverse primer. PCR products, B-SP50L5 (1502 bp), B-SP67L10 (1448 bp) and B-SP69L1 (1412 bp) were prepared in the same manner as in the above step "PCR amplification 1" using pHuSP50L5-hPD-1scFv03-His, pHuSP67L10-hPD-1scFv03-His and pHuSP69L1-hPD-1scFv03-His, respectively as template DNA, and GA5_primer_rev primer as a forward primer and hPD1scFv03-1_primer (SEQ ID No. 127) as a reverse primer.

PCR product A-1 and each of B-SP50L5, B-SP67L10 and B-SP69L1 were ligated by using HD kit in the same manner as mentioned above and the sequences of "anti-hPD-1scFv03 expression cassette regions" (including from Hu promoter to Hu terminator) were determined. The plasmids extracted were designated as pHuSP50L5-hPD-1scFv03TL, pHuSP67L10-hPD-1scFv03TL and pHuSP69L1-hPD-1scFv03TL.

(Second Step)

PCR products were prepared by using the template DNA and primers listed in Table 22, in the same manner as in the above step "PCR amplification 1".

TABLE 22

| PCR product | Template DNA | Fow. primer | Rev. primer | Size of PCR product |
|---|---|---|---|---|
| A4 | pHuSP50L5-hPD-1scFv03TL | PC1_primer | PC2_primer | 4733 bp |
| A5 | pHuSP67L10-hPD-1scFv03TL | PC1_primer | PC2_primer | 4679 bp |
| A6 | pHuSP69L1-hPD-1scFv03TL | PC1_primer | PC2_primer | 4643 bp |
| B | Bba-B0015 in pUC57 | PC3_primer | PC4_primer | 159 bp |

TABLE 23

| Plasmid to be constructed | Combination in in-fusion reaction |
|---|---|
| pHuSP50L5-hPD-1 scFv03TL-T2 | A4 and B |
| pHuSP67L10-hPD-1 scFv03TL-T2 | A5 and B |
| pHuSP69L1-hPD-1 scFv03TL-T2 | A6 and B |

The PCR products listed in Table 22 were ligated in accordance with the combinations listed in Table 23 by using HD kit in the same manner as mentioned above and the sequence of "anti-hPD-1scFv03 (not tagged) expression cassette-T2 terminator region" (5'-Hu promoter-SPxLy-human PD-1scFv03-Hu terminator-T2 terminator-3') was determined. The plasmids extracted were designated as pHuSP50L5-hPD-1scFv03TL-T2, pHuSP67L10-hPD-1scFv03TL-T2 and pHuSP69L1-hPD-1scFv03TL-T2.

(Third Step)

PCR products were prepared by using the template DNA and primers listed in Table 24 in the same manner as in the above step "PCR amplification 1".

TABLE 24

| PCR product | Template DNA | Fow. primer | Rev. primer | Size of PCR product |
|---|---|---|---|---|
| A10 | pHuSP50L5-hPD-1scFv03TL-T2 | PC8_primer (SEQ ID No. 124) | PC2_primer | 4868 bp |
| A11 | pHuSP67L10-hPD-1scFv03TL-T2 | PC_primer | PC2_primer | 4814 bp |
| A12 | pHuSP69L1-hPD-1scFv03TL-T2 | PC8_primer | PC2_primer | 4778 bp |
| B4 | pP30SP50L5-hCTLA-4scFv01-FLAG | PC6_primer (SEQ ID No. 122) | PC9_primer (SEQ ID No. 125) | 1186 bp |
| B5 | pP30SP67L1-hCTLA-4scFv01-FLAG | PC6_primer | PC9_primer | 1105 bp |
| B6 | pP30SP68L1-hCTLA-4scFv01-FLAG | PC6_primer | PC9_primer | 1135 bp |

TABLE 25

| Plasmid to be constructed | Combination in in-fusion reaction |
|---|---|
| pPC2TLS | A10 and B5 |
| pPC3TLS | A10 and B6 |
| pPC4TLS | A11 and B4 |
| pPC5TLS | A11 and B6 |
| pPC6TLS | A12 and B4 |
| pPC7TLS | A12 and B5 |
| pPC8TLS | A12 and B6 |

The PCR products listed in Table 24 were ligated in accordance with the combinations listed in Table 25 by using HD kit in the same manner as mentioned above and DNA sequences of the full-length plasmids extracted were determined in the same manner as above.

The plasmids extracted were designated as pPC2TLS, pPC3TLS, pPC4TLS, pPC5TLS, pPC6TLS, pPC7TLS and pPC8TLS.

(Fourth Step)

To plasmids pPC2TLS to pPC8TLS (2 μg for each), which were prepared in the third step of the plasmid preparation, restriction enzymes, BamHI and BglII (manufactured by Thermo Scientific Inc.) were added each in an amount of 10 units. The mixture was kept warm at 37° C. for 3 hours to cleave the plasmids. BamHI and BglII recognition sites are present one for each in the adjacent portions to pUCori, which is the plasmid origin of replication in *E. coli*, as shown in FIG. 30. After the treatment with the restriction enzymes, an aliquot was taken from the DNA solution and subjected to 0.8% agarose gel electrophoresis. In this manner, it was verified that the plasmid DNA was cleaved into fragments having predetermined sizes (about 5.3 kbp and about 0.7 kbp).

(Separation and Purification by Agarose Gel Electrophoresis)

After the treatment with the restriction enzymes, the DNA fragments were separated by agarose gel electrophoresis. DNA band of about 5.3 kbp was cut out and DNA was extracted by use of QIAGel. The concentration of DNA was estimated by agarose gel electrophoresis.

(Self-Closing of DNA)

The purified DNA mentioned above (about 5.3 kbp) was subjected to a self-ligation reaction using Rapid DNA Ligation kit (manufactured by Thermo Scientific Inc.). After completion of the reaction, the solution was purified by QIAquick PCR Purification Kit (manufactured by QIAGEN) to prepare pPC2TL, pPC3TL, pPC4TL, pPC5TL, pPC6TL, pPC7TL and pPC8TL.

(Transformation 11 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) except that plasmid pPC2TL, pPC3TL, pPC4TL, pPC5TL, pPC6TL, pPC7TL and pPC8TL prepared in the fourth step of the plasmid preparation were used each in an amount of 5 μL. The transformants obtained were designated as *Bifidobacterium longum* 105-A/pPC2TL (hereinafter referred to as PC2TL strain); *Bifidobacterium longum* 105-A/pPC3TL (hereinafter referred to as PC3TL strain); *Bifidobacterium longum* 105-A/pPC4TL (hereinafter referred to as PC4TL strain); *Bifidobacterium longum* 105-A/pPC5TL (hereinafter referred to as PC5TL strain); *Bifidobacterium longum* 105-A/pPC6TL (hereinafter referred to as PC6TL strain); *Bifidobacterium longum* 105-A/pPC7TL (hereinafter referred to as PC7TL strain); and *Bifidobacterium longum* 105-A/pPC8TL (hereinafter referred to as PC8TL strain).

(Determination of Plasmid DNA Sequence)

To each of the bacterium of the genus *Bifidobacterium* transformant cells obtained in the above section (Transformation 11 of the genus *Bifidobacterium*), 1.5 mL of a lysozyme-Proteinase K mixture, which was prepared by adding lysozyme (manufactured by Wako Pure Chemical Industries Ltd.) and Proteinase K (manufactured by QIAGEN) in a concentration of 40 mg/mL and 0.4 mg/mL, respectively with the addition of 1 mM Tris-HCl-0.1 mM EDTA buffer (pH8.0), was added and suspended. Each of the mixtures was kept warm at 37° C. for about 1.5 hours. After centrifugal separation was carried out and the supernatant was removed, the resultant bacterial cells were subjected to extraction of plasmid DNA by QIAprep Spin Miniprep Kit (manufactured by QIAGEN). In the same manner as in the above section (Example 1: Transformation of *E. coli* and determination of DNA sequence of plasmid pAG8), the DNA sequence of the full-length plasmid extracted was determined. The plasmids extracted were designated as plasmid pPC2TL, pPC3TL, pPC4TL, pPC5TL, pPC6TL, pPC7TL and pPC8TL as outlined below. The sequences of expression cassettes of plasmids pPC2TL, pPC3TL, pPC4TL, pPC5TL, pPC6TL, pPC7TL and pPC8TL are the same as in pPC2, pPC3, pPC4, pPC5, pPC6, pPC7 and pPC8 sequences except that neither of the sequences of expression cassettes of anti-hPD-1scFv03 and anti-hCTLA-4scFv01 contain a tag sequence.

| (pPC2TL: scFv expression cassette sequence (2576 bp) (SEQ ID No. 138)) | |
|---|---|
| 1 ... 1366 | Anti-human PD-1scFv03 expression cassette |
| 1 ... 361 | Hu promoter |
| 362 ... 544 | SP50L5 |
| 545 ... 1249 | anti-human PD-1scFv03 |
| 1250 ... 1252 | stop codon |
| 1253 ... 1366 | Hu terminator |
| 1367 ... 2576 | Anti-human CTLA-4scFv01 expression cassette |
| 1367 ... 1601 | P30 promoter |
| 1602 ... 1703 | SP67L1 |
| 1704 ... 2444 | anti-human CTLA-4scFv01 |
| 2445 ... 2447 | stop codon |
| 2448 ... 2576 | T2 terminator |

| (pPC3TL scFv expression cassette sequence (2606 bp) (SEQ ID No. 139)) | |
|---|---|
| 1 ... 1366 | Anti-human PD-1scFv03 expression cassette |
| 1 ... 361 | Hu promoter |
| 362 ... 544 | SP50L5 |
| 545 ... 1249 | anti-human PD-1scFv03 |
| 1250 ... 1252 | stop codon |
| 1253 ... 1366 | Hu terminator |
| 1367 ... 2606 | Anti-human CTLA-4scFv01 expression cassette |
| 1367 ... 1601 | P30 promoter |
| 1602 ... 1733 | SP68L1 |
| 1734 ... 2474 | anti-human CTLA-4scFv01 |
| 2475 ... 2477 | stop codon |
| 2478 ... 2606 | T2 terminator |

| (pPC4TL scFv expression cassette sequence (2603 bp) (SEQ ID No. 140)) | |
|---|---|
| 1 ... 1312 | Anti-human PD-1scFv03 expression cassette |
| 1 ... 361 | Hu promoter |
| 362 ... 490 | SP67L10 |
| 491 ... 1195 | anti-human PD-1scFv03 |
| 1196 ... 1198 | stop codon |
| 1199 ... 1312 | Hu terminator |

| | | |
|---|---|---|
| 1313 ... 2603 | Anti-human CTLA-4scFv01 expression cassette | |
| 1313 ... 1547 | P30 promoter | |
| 1548 ... 1730 | SP50L5 | |
| 1731 ... 2471 | anti-human CTLA-4scFv01 | |
| 2472 ... 2474 | stop codon | |
| 2475 ... 2603 | T2 terminator | |

| (pPC5TL scFv expression cassette sequence (2552 bp) (SEQ ID No. 141)) | |
|---|---|
| 1 ... 1312 | Anti-human PD-1scFv03 expression cassette |
| 1 ... 361 | Hu promoter |
| 362 ... 490 | SP67L10 |
| 491 ... 1195 | anti-human PD-1scFv03 |
| 1196 ... 1198 | stop codon |
| 1199 ... 1312 | Hu terminator |

| | |
|---|---|
| 1313 ... 2552 | Anti-human CTLA-4scFv01 expression cassette |
| 1313 ... 1547 | P30 promoter |
| 1548 ... 1679 | SP68L1 |
| 1680 ... 2420 | anti-human CTLA-4scFv01 |
| 2421 ... 2423 | stop codon |
| 2424 ... 2552 | T2 terminator |

| (pPC6TL scFv expression cassette sequence (2567 bp) (SEQ ID No. 142)) | |
|---|---|
| 1 ... 1276 | Anti-human PD-1scFv03 expression cassette |
| 1 ... 361 | Hu promoter |
| 362 ... 454 | SP69L1 |
| 455 ... 1159 | anti-human PD-1scFv03 |
| 1160 ... 1162 | stop codon |
| 1163 ... 1276 | Hu terminator |

| | |
|---|---|
| 1277 ... 2567 | Anti-human CTLA-4scFv01 expression cassette |
| 1277 ... 1511 | P30 promoter |
| 1512 ... 1694 | SP50L5 |
| 1695 ... 2435 | anti-human CTLA-4scFv01 |
| 2436 ... 2438 | stop codon |
| 2439 ... 2567 | T2 terminator |

| (pPC7TL scFv expression cassette sequence (2486 bp) (SEQ ID No. 143)) | |
|---|---|
| 1 ... 1276 | anti-human PD-1scFv03 expression cassette |
| 1 ... 361 | Hu promoter |
| 362 ... 454 | SP69L1 |
| 455 ... 1159 | anti-human PD-1scFv03 |
| 1160 ... 1162 | stop codon |
| 1163 ... 1276 | Hu terminator |

| | |
|---|---|
| 1277 ... 2486 | anti-human CTLA-4scFv01 expression cassette |
| 1277 ... 1511 | P30 promoter |
| 1512 ... 1613 | SP67L1 |
| 1614 ... 2354 | anti-human CTLA-4scFv01 |
| 2355 ... 2357 | stop codon |
| 2358 ... 2486 | T2 terminator |

| (pPC8TL scFv expression cassette sequence (2516 bp) (SEQ ID No. 144)) | |
|---|---|
| 1 ... 1276 | Anti-human PD-1scFv03 expression cassette |
| 1 ... 361 | Hu promoter |
| 362 ... 454 | SP69L1 |
| 455 ... 1159 | anti-human PD-1scFv03 |
| 1160 ... 1162 | stop codon |
| 1163 ... 1276 | Hu terminator |

| | |
|---|---|
| 1277 ... 2516 | Anti-human CTLA-4scFv01 expression cassette |
| 1277 ... 1511 | P30 promoter |
| 1512 ... 1643 | SP68L1 |
| 1644 ... 2384 | anti-human CTLA-4scFv01 |
| 2385 ... 2387 | stop codon |
| 2388 ... 2516 | T2 terminator |

Example 20

[Verification of scFv Secretion in Co-Expression *Bifidobacterium* Strain]

The presence or absence of secretions of anti-hPD-1scFv03-His and anti-hCTLA-4scFv01-FLAG in culture supernatants of co-expression strains, PC2 to PC8, was checked by western blotting as follows. The BEshuttle strain mentioned above was used as a negative control strain and subjected to the same analysis.

(Culture of Recombinant Bacterium of the Genus *Bifidobacterium*)

PC2 strain to PC8 strain, PC1 strain prepared in Example 8 and BEshuttle strain were cultured in the same procedure as in Example 4 (Culture of recombinant bacterium of the genus *Bifidobacterium*) and the culture supernatants were collected. The culture supernatants were concentrated by TCA in the same procedure as in Example 9 (Culture of recombinant bacterium of the genus *Bifidobacterium*) to obtain individual culture supernatant concentrates.

(Western Analysis)

Western analysis using each of the culture supernatant concentrates (corresponding to about 0.01 mL of the culture solution) was carried out in the same manner as in Example 9 (Western analysis). Note that transferring from the gel to membrane was carried out by using Trans-Blot Turbo (manufactured by Bio-Rad) and the 2% ECL Advance Blocking Agent mentioned above was used as a blocking solution. The results for anti-hPD-1scFv03-His are shown in FIG. 31 (A) and the results for anti-hCTLA-4scFv01-FLAG are shown in FIG. 31 (B).

(Results)

As is apparent from FIGS. 31A and B, both secretions of anti-hPD-1scFv03-His and anti-hCTLA-4scFv01-FLAG were observed in the culture supernatants of PC2 strain (lane 1 both in A and B), PC3 strain (lane 2 both in A and B), PC4 strain (lane 3 both in A and B), PC5 strain (lane 4 both in A and B), PC6 strain (lane 5 both in A and B), PC7 strain (lane 6 both in A and B), PC8 strain (lane 7 both in A and B) and PC1 strain (lane 9 both in A and B) (note that in PC1 strain, anti-hCTLA-4scFv02-FLAG was secreted). The amounts of anti-hPD-1scFv03-His and anti-hCTLA-4scFv01-FLAG secreted from PC2 strain to PC8 strain were each larger than the amount of single-chain antibody secreted from PC1 strain.

From the above results, it was verified that co-expression *Bifidobacterium* strains, PC2 strain to PC8 strain, are recombinant *Bifidobacterium* strains that can secrete both antihPD-1scFv and anti-hCTLA-4scFv in the culture supernatants and secrete a single-chain antibody in a larger amount than PC1 strain.

Example 21

[Verification of scFv Secretion in Co-Expression Strains, PC2TL Strain to PC8TL Strain]

The antibodies secreted from the co-expression strains, PC2TL strain to PC8TL strain, were subjected to ELISA for checking the presence or absence of binding activity to human PD-1 (hPD-1) and binding activity to human CTLA-4.

(Culture of Recombinant Bacterium of the Genus *Bifidobacterium*)

Co-expression bifidobacteria, PC2TL strain to PC8TL strain prepared in Example 19 above and BEshuttle strain were cultured in the same procedure as in Example 4 (Culture of recombinant bacterium of the genus *Bifidobacterium*) and the culture supernatants were collected. The culture supernatants of PC2TL strain to PC8TL strain were appropriately diluted with the culture supernatant of BEshuttle strain and used as samples for ELISA.

(Evaluation on Secretion of Anti-hPD-1scFv03)

To 96-well plates (MaxiSorp, Type C, manufactured by Nunc), 1 μg/mL hPD-1 solution (using Recombinant Human PD-1 Fc Chimera (R&D Systems) as an antigen and prepared with 1×PBS) was dispensed in an amount of 100 μL for each. To the upper portion of the plates, a seal was attached and the plates were incubated at 4° C. overnight to immobilize the antigen. After the solution was removed from the plates, 1×PBS was dispensed in an amount of 400 μL for each and the liquid was removed. This operation was repeated three times for washing (hereinafter referred to as "PBS washing").

To the plates washed, 1% BSA solution (350 μL for each) was dispensed. The plates were incubated at room temperature for 2 hours for blocking and PBS washing was carried out.

To the plates, the samples for ELISA were dispensed. To the blank wells, the culture supernatant (100 μL) of BEshuttle strain was dispensed. As a positive control, a solution (100 μL), which was prepared by adding anti-hPD-1scFv03 purified product to the culture supernatant of BEshuttle strain so as to obtain a concentration of 100 ng/mL, was dispensed. A seal was attached to the upper portions of the plates and the plates were incubated at room temperature for 2 hours to carry out the scFv binding reaction to the antigen immobilized and PBS washing was carried out.

After completion of the scFv binding reaction to the antigen immobilized, 100 μL of 0.2 μg/mL biotinylated Protein L solution (prepared by diluting Biotinylated Protein L: manufactured by Thermo Scientific with Solution B of Signal Enhancer HIKARI: manufactured by Nacalai Tesque Inc., up to a concentration of 0.2 μg/mL) was added to the plates. A seal was attached to the upper portions of the plates and the plates were incubated at room temperature for one hour (binding reaction of biotinylated Protein L to scFv light chain, κ chain) and PBS washing was carried out.

After the binding reaction of the biotinylated Protein L, 100 μL of an avidin-biotin marker enzyme complex preparation solution (prepared by adding Solution A and B (30 μL for each) of avidin-biotin marker enzyme complex VECTASTAIN ABC Kit: manufactured by VECTOR Laboratories, to Solution B (7.5 mL) of Signal Enhancer HIKARI, followed by stirring) was added to the plates. A seal was attached to the upper portions of the plates and the plates were incubated at room temperature for 30 minutes and PBS washing was carried out.

To the plates to which the enzyme was bound, 200 μL of a detection reagent (comprising Color Reagent A and Color Reagent B: both are manufactured by R&D systems and blended in equal amounts) was added. The plates were shielded from light and incubated at room temperature. Accurately 20 minutes later, the stop solution (50 μL) mentioned above was added to terminate a color reaction. Absorbance was measured at 450 nm and 570 nm (reference wavelength) by a plate reader.

(Evaluation on Secretion of Anti-hCTLA-4scFv01)

Evaluation was carried out in the same manner as in the above section (Evaluation on secretion of anti-hPD-1scFv03) except the points: 1) the antigen was immobilized to a plate by using a 1 μg/mL hCTLA-4 solution (Recombinant Human CTLA-4-Fc Chimera (manufactured by BioLegend) prepared in the addition of 1×PBS), 2) as the positive control, anti-hCTLA-4scFv01 purified product added in the culture supernatant of BEshuttle strain was used and 3) the concentration of biotinylated Protein L solution was specified as 0.05 μg/mL. The results are shown in Table 26.

TABLE 26

Binding activity of scFv to immobilized antigen

| | Binding (OD450-570) to immobilized antigen | |
|---|---|---|
| Sample | hPD-1 immobilized | hCTLA-4 immobilized |
| PC2TL | 0.812 | 1.312 |
| PC3TL | 0.792 | 1.286 |
| PC4TL | 0.363 | 1.788 |
| PC5TL | 0.305 | 1.39 |
| PC6TL | 0.528 | 1.116 |
| PC7TL | 0.549 | 1.457 |
| PC8TL | 0.733 | 1.320 |
| P.C. 1 (anti-hPD-1 scFv03) | 0.667 | n.t. |
| P.C. 2 (anti-hCTLA-4 scFv01) | n.t. | 1.074 | n.t.: not treated,
P.C.: Positive control (Results)

As is apparent from Table 26, culture supernatants of ELISA co-expression strains, PC2TL strain to PC8TL strain, had binding activities to both of human PD-1 and human CTLA-4 immobilized. Note that it was already verified that the binding activities of such scFv molecules are specific to the corresponding antigens (data are not shown).

Example 22

Anti-hPD-1scFv03-His single-expression strain and anti-hCTLA-4scFv01-FLAG single-expression strain to be compared with co-expression bifidobacteria, PC2 strain to PC8 strain, are shown in Table 27.

TABLE 27

| Co-expression strain | Comparable anti-hPD-1scFv03-His single expression strain | Comparable anti-hCTLA-4scFv01-FLAG single expression strain |
|---|---|---|
| PC2 | P1H | C2F |
| PC3 | P1H | C3F |
| PC4 | P2H | C1F |

TABLE 27-continued

| Co-expression strain | Comparable anti-hPD-1scFv03-His single expression strain | Comparable anti-hCTLA-4scFv01-FLAG single expression strain |
| --- | --- | --- |
| PC5 | P2H | C3F |
| PC6 | P3H | C1F |
| PC7 | P3H | C2F |
| PC8 | P3H | C3F |

(Transformation 12 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) by using plasmid pHuSP50L5-hPD-1scFv03-His, pHuSP67L10-hPD-1scFv03-His and pHuSP69L1-hPD-1scFv03-His prepared in Example 18. The transformants obtained were designated as *Bifidobacterium longum* 105-A/pHuSP50L5-hPD-1scFv03-His (hereinafter referred to as P1H strain); *Bifidobacterium longum* 105-A/pHuSP67L10-hPD-1scFv03-His (hereinafter referred to as P2H strain); and *Bifidobacterium longum* 105-A/pHuSP69L1-hPD-1scFv03-His (hereinafter referred to as P3H strain).

Similarly, *Bifidobacterium longum* 105-A strain was transformed by using plasmid pC1F, pC2F and pC3F prepared in Example 18 to obtain *Bifidobacterium longum* 105-A/pC1F (hereinafter referred to as C1F strain); *Bifidobacterium longum* 105-A/pC2F (hereinafter referred to as C2F strain); and *Bifidobacterium longum* 105-A/pC3F (hereinafter referred to as C3F strain).

Example 23

Anti-hPD-1scFv03 single-expression strain and anti-hCTLA-4scFv01 single-expression strain to be compared with co-expression bifidobacteria PC2TL-PC8TL strain are shown in Table 28.

TABLE 28

| Co-expression strain | Comparable anti-hPD-1scFv03 single expression strain | Comparable anti-hCTLA-4scFv01 single expression strain |
| --- | --- | --- |
| PC2TL | P1TL | C2TLB |
| PC3TL | P1TL | C3TLB |
| PC4TL | P2TL | C1TLB |
| PC5TL | P2TL | C3TLB |
| PC6TL | P3TL | C1TLB |
| PC7TL | P3TL | C2TLB |
| PC8TL | P3TL | C3TLB |

(Transformation 13 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) by using plasmid pHuSP50L5-hPD-1scFv03TL, pHuSP67L10-hPD-1scFv03TL and pHuSP69L1-hPD-1scFv03TL prepared in Example 19. The transformants obtained were designated as *Bifidobacterium longum* 105-A/pHuSP50L5-hPD-1scFv03TL (hereinafter referred to as P1TL strain); *Bifidobacterium longum* 105-A/pHuSP67L10-hPD-1scFv03TL (hereinafter referred to as P2TL strain); and *Bifidobacterium longum* 105-A/pHuSP69L1-hPD-1scFv03TL (hereinafter referred to as P3TL strain).

(Preparation of Anti-hCTLA-4scFv01 Single-Expression Strain)

A method for producing anti-hCTLA-4scFv01 expression plasmids pC1TLB, pC2TLB and pC3TLB is schematically shown in FIG. 32. The method consists of two steps: T2 substitution step of removing FLAG tag from plasmids pC1F, pC2F and pC3F and replacing with T2 terminator; and pUCori removal step of removing pUCori from plasmids pC1TL, pC2TL and pC3TL.

(T2 Substitution Step)

Using the template DNA and primers listed in Table 29, PCR products were prepared in the same manner as in the above step "PCR amplification 1".

TABLE 29

| PCR product | Template DNA | Fow. primer | Rev. primer | Size of PCR product |
| --- | --- | --- | --- | --- |
| A1 | pC1F | PC1_primer | PC9_primer | 4538 bp |
| A2 | pC2F | PC1_primer | PC9_primer | 4457 bp |
| A3 | pC3F | PC1_primer | PC9_primer | 4487 bp |
| B | BBa-B0015 in pUC57 | PC8_primer | PC4_primer | 150 bp |

PCR products were used in combination in accordance with the following three types: A1 and B (for preparation of pC1TL), A2 and B (for preparation of pC2TL) and A3 and B (for preparation of pC3TL preparation) and ligated by using HD kit in the same manner as mentioned above. The DNA sequences of the full-length plasmids extracted were determined in the same procedure as above. The plasmids extracted were designated as pC1TL, pC2TL and pC3TL.

(pUCori Removal Step)

pUCori was removed from pC1TL, pC2TL and pC3TL in the same manner as in the third step of the method for producing co-expression plasmids, pPC2TL to pPC8TL in Example 19 to obtain pC1TLB, pC2TLB and pC3TLB.

(Transformation 14 of Bacterium of the Genus *Bifidobacterium*)

*Bifidobacterium longum* 105-A strain was transformed by the electroporation system in the same procedure as in the above section (Transformation 1 of bacterium of the genus *Bifidobacterium*) by using plasmid pC1TLB, pC2TLB and pC3TLB. The transformants obtained were designated as *Bifidobacterium longum* 105-A/pC1TLB (hereinafter referred to as C1TLB strain); *Bifidobacterium longum* 105-A/pC2TLB (hereinafter referred to as C2TLB strain); and *Bifidobacterium longum* 105-A/pC3TLB (hereinafter referred to as C3TLB strain).

Example 24

(Binding to Cell)

Binding of anti-hCTLA-4scFv01-FLAG purified from the anti-hCTLA-4scFv01-FLAG single-expression strain to be compared with co-expression strains, PC2 to PC8 was investigated.

Anti-hCTLA-4scFv01-FLAG was purified from each of the culture supernatants of anti-hCTLA-4scFv01-FLAG single expression *Bifidobacterium* C1F strain, C2F strain and C3F strain by Protein L column. The purified scFv (100 μL) prepared to have a concentration of 1 μg/mL was added to HEK293T cells, in which intracellular domain deficient hCTLA-4 was overexpressed by use of a retrovirus vector, and incubated on ice for 30 minutes. After the cells were washed, biotinylated Protein L (100 μL) was added and incubated for 30 minutes to allow protein L to bind to scFv bound to the cell. After the cells were washed, Brilliant Violet 421 Streptavidin (100 μL) prepared to have a concentration of 0.5 μg/mL was added and incubated for 30 minutes. The cells were washed and then analysis was carried out by flow cytometry. The results are shown in FIG. 33.

(Results)

As is apparent from FIG. 33, scFv molecules derived from C1F strain, C2F strain and C3F strain all bound to intracellular domain deficient hCTLA-4 expression HEK293T cells. From this, it was presumed that anti-hCTLA-4scFv01-FLAG secreted from each of co-expression strains, PC4 and PC6, which secrete the same scFv as in C1F strain; co-expression strains, PC2 strain and PC7 strain, which secrete the same scFv as in C2F strain; and co-expression strains, PC3 strain, PC5 strain and PC8 strain, which secrete the same scFv as in C3F strain can also bind to hCTLA-4 expressing cells. From FIG. 33 (a), binding to a Mock cells not expressing hCTLA-4 was slightly observed; however, binding of anti-hCTLA-4scFv01-FLAG purified from co-expression PC4 strain to the Mock cells were not observed from the results of FIG. 37 (d). From this, binding to scFv molecules derived from C1F strain, C2F strain and C3F strain to the Mock cells is considered as non-specific binding.

Example 25

(Binding of Anti-hCTLA-4scFv01 Purified from Anti-hCTLA-4scFv01 Single-Expression Strain to Cells)

Anti-hCTLA-4scFv01 was purified from each of the culture supernatants of anti-hCTLA-4scFv01 single-expression strains, C1TLB, C2TLB and C3TLB to be compared with co-expression strains, PC2TL to PC8TL, by Protein L column. To HEK293T cells in which intracellular domain deficient hCTLA-4 was overexpressed by use of a retrovirus vector, purified scFv (100 μL) prepared to have a concentration of 1 μg/mL was added and incubated on ice for 30 minutes. After the cells were washed, biotinylated Protein L (100 μL) was added and incubated for 30 minutes to allow protein L to bind to scFv bound to the cells. After the cells were washed, Brilliant Violet 421 Streptavidin (100 μL) prepared to have a concentration of 0.5 μg/mL was added and incubated for 30 minutes. The cells were washed and then analysis was carried out by flow cytometry. The results are shown in FIG. 34.

(Results)

As is apparent form FIG. 34, scFv molecules derived from C1TLB strain, C2TLB strain and C3TLB strain all bound to hCTLA-4 expressing cells. From this, it was presumed that anti-hCTLA-4scFv01 secreted from each of co-expression strains, PC4TL strain and PC6TL strain, which secrete the same scFv as in C1TLB strain; co-expression strains, PC2TL strain and PC7TL strain, which secrete the same scFv as in C2TLB strain; and co-expression strains, PC3TL strain, PC5TL strain and PC8TL strain, which secrete the same scFv as in C3TLB strain can also bind to hCTLA-4 expressing cells.

Example 26

(Binding of Anti-PD-1scFv03-his Purified from Anti-hPD-1scFv03-his Single-Expression Strain to Cells)

Anti-PD-1scFv03-His was purified from each of the culture supernatants of anti-PD-1scFv03-His single-expression strains, P1H, P2H and P3H to be compared with co-expression strains, PC2 to PC8, by Protein L. To HEK293T cells in which hPD-1 was overexpressed by use of a retrovirus vector, purified scFv (100 μL) prepared to have a concentration of 1 μg/mL was added and incubated on ice for 30 minutes. After the cells were washed, biotinylated Protein L (100 μL) was added, incubated for 30 minutes to allow protein L to bind to scFv bound to the cells. After the cells were washed, Brilliant Violet 421 Streptavidin (100 μL) prepared to have a concentration of 0.5 μg/mL was added and incubated for 30 minutes. The cells were washed and then analysis was carried out by flow cytometry. The results are shown in FIG. 35.

(Results)

As is apparent form FIG. 35, scFv molecules derived from P1H strain, P2H strain and P3H strain all bound to hPD-1 expressing cells. From this, it was presumed that anti-PD-1scFv03-His secreted from each of co-expression strains, PC2 and PC3, which secrete the same scFv as in P1H strain; co-expression strains, PC4 and PC5, which secrete the same scFv as in P2H strain; and co-expression strains, PC6, PC7 and PC8, which secrete the same scFv as in P3H strain can also bind to hPD-1 expressing cells.

Example 27

(Binding of Anti-hPD-1scFv03 Purified from Anti-hPD-1scFv03 Single-Expression Strain to Cells)

Anti-hPD-1scFv03 was purified from each of the culture supernatants of PD-1scFv03 single expression bifidobacteria, P1TL strain, P2TL strain and P3TL strain, to be compared with co-expression strains, PC2TL strain to PC8TL strain, by Protein L column. To HEK293T cells in which hPD-1 was overexpressed by use of a retrovirus vector, purified scFv (100 μL) prepared to have a concentration of 1 μg/mL was added and incubated on ice for 30 minutes. After the cells were washed, biotinylated Protein L (100 μL) was added and incubated for 30 minutes to allow protein L to bind to scFv bound to the cells. After the cells were washed, Brilliant Violet 421 Streptavidin (100 μL) prepared to have a concentration of 0.5 μg/mL was added and incubated for 30 minutes. The cells were washed and then analysis was carried out by flow cytometry. The results are shown in FIG. 36.

(Results)

As is apparent from FIG. 36, scFv molecules derived from P1TL strain, P2TL strain and P3TL strain all bound to hPD-1 expressing cells. From this, it was presumed that anti-PD-1scFv03 secreted from each of co-expression strains, PC2TL and PC3TL, which secrete the same scFv as in P1TL strain; co-expression strains, PC4TL and PC5TL, which secrete the same scFv as in P2TL strain; and co-expression strains, PC6TL, PC7TL and PC8TL, which secrete the same scFv as in P3TL strain can bind to hPD-1 expressing cells.

Example 28

(Binding of scFv Purified from Co-Expression Strain PC4 to Cells)

From the culture supernatant of co-expression strain PC4, anti-hPD-1scFv03-His was purified by use of a purification column for His-tag; and anti-hCTLA-4scFv01-FLAG was purified by use of a purification column for FLAG tag. Binding of anti-hPD-1scFv03 to hPD-1 expressing cells were checked in the same manner as in [Example 26]. Binding of anti-hCTLA-4scFv01 to hCTLA-4 expressing cells were checked in the same manner as in [Example 24]. As positive controls, PE-labeled anti-hPD-1 antibody (clone: EH12.2H7) and PE-labeled anti-hCTLA-4 antibody (clone: L3D10) were used. The results are shown in FIG. 37.

From FIG. 37 (a), it was found that a positive control, i.e., PE-labeled anti-hPD-1 antibody (clone: EH12.2H7) binds to hPD-1 expressing cells and binds to neither Mock cells nor hCTLA-4 expressing cells. From (b), it was found that PE-labeled anti-hCTLA-4 antibody (clone: L3D10) binds to hCTLA-4 expressing cells and binds to neither Mock cells nor hPD-1 expressing cells. As is apparent from FIGS. 37 (c) and (d), it was found that anti-hPD-1scFv03-His and anti-hCTLA-4scFv01-FLAG purified from co-expression strain PC4 bind to the corresponding antigen expressing cells.

Example 29

(Affinity of Anti-hCTLA-4scFv01-FLAG Purified from Anti-hCTLA-4scFv01-FLAG Single-Expression Strain for Antigen (Biacore))

Anti-hCTLA-4scFv01-FLAG was purified by Protein L column from each of the culture supernatants of anti-hCTLA-4scFv01-FLAG single expression bifidobacteria C1F, C2F and C3F to be compared with co-expression strains, PC2 to PC8. The binding kinetic parameter of each hCTLA-4scFv01-FLAG purified to hCTLA-4 (fusion protein with human IgG1Fc) was measured by surface plasmon resonance using Biacore system (manufactured by GE Healthcare). To a substrate having a carboxyl methyl dextran-coated gold membrane, a mouse anti-human IgG (Fc) monoclonal antibody (manufactured by GE Healthcare) was bound in accordance with amine coupling, and Fc-fused recombinant hCTLA-4 (Biolegend) was captured as a ligand. As an analyte, scFv purified was used. Samples of scFv having a concentration of 0.7404, 2.2222, 6.6667, 20 and 60 nM were prepared and sequentially subjected to binding in order of increasing concentration in accordance with single cycle kinetics. Data obtained were analyzed by BIA evaluation software (manufactured by GE Healthcare). The results are shown in Table 30.

TABLE 30

| sample | ka (1/Ms) | kd (1/s) | KD (M) |
| --- | --- | --- | --- |
| C1F | 9.18E+05 | 9.96E−04 | 1.08E−09 |
| C2F | 4.52E+05 | 1.03E−03 | 2.28E−09 |
| C3F | 3.47E+05 | 1.03E−03 | 2.97E−09 |
| C1TLB | 6.61E+05 | 9.80E−04 | 1.48E−09 |
| C2TLB | 9.81E+05 | 9.61E−04 | 9.80E−10 |
| C3TLB | 7.73E+05 | 9.96E−04 | 1.29E−09 |

(Results)

As is apparent from Table 30, scFvs secreted from each of the single-expression strains C1F, C2F and C3F exhibits a high KD value, meaning that scFvs have affinity for hCTLA-4. It is presumed that anti-hCTLA-4scFv secreted from each of co-expression strains, PC4 and PC6, also has affinity for hCTLA-4, similarly to scFv derived from C1F strain. It is also presumed that scFv secreted from each of co-expression strains, PC2 and PC7, presumably has affinity for hCTLA-4 similarly to scFv derived from C2F strain; and that scFv secreted from each of co-expression strains, PC3, PC5 and PC8, has affinity for hCTLA-4 similarly to scFv derived from C3F strain.

Example 30

(Affinity of Anti-hCTLA-4scFv01 Purified from Anti-hCTLA-4scFv01 Single-Expression Strain for Antigen (Biacore))

Anti-hCTLA-4scFv01 was purified by Protein L column from each of the culture supernatants of anti-hCTLA-4scFv01 single expression bifidobacteria, C1TLB strain, C2TLB strain and C3TLB strain to be compared with co-expression strains, PC2TL to PC8TL. The binding kinetic parameter to hCTLA-4 (fusion protein with human IgG1Fc) was measured by surface plasmon resonance using Biacore system. Thereafter, analysis was carried out in the same manner as in Example 29. The results are shown in Table 30.

(Results)

As is apparent from Table 30, scFvs secreted from each of single-expression strains, C1TLB, C2TLB and C3TLB exhibits a high KD value, meaning that scFvs have affinity for hCTLA-4. It is presumed that scFv secreted from each of co-expression strains, PC4TL and PC6TL, also has affinity for hCTLA-4, similarly to scFv derived from C1TLB strain. It is also presumed that scFv secreted from each of co-expression strains, PC2TL and PC7TL, has affinity for hCTLA-4 similarly to scFv derived from C2TLB strain; and that scFv secreted from each of co-expression strains, PC3TL, PC5TL and PC8TL, has affinity for hCTLA-4 similarly to scFv derived from C3TLB strain.

Example 31

(Affinity of Anti-hPD-1scFv03-his Purified from Anti-hPD-1scFv03-his Single-Expression Strain for Antigen (Biacore))

Anti-hPD-1scFv03-His was purified by Protein L column from each of the culture supernatants of anti-hPD-1scFv03-His single expression bifidobacteria, P1H strain, P2H strain and P3H strain, to be compared with co-expression strains, PC2 to PC8. The binding kinetic parameter with hPD-1 (fusion protein with human IgG1Fc) was measured by surface plasmon resonance using Biacore system. Analysis was carried out in the same manner as in Example 29 except that Fc fused recombinant hPD-1 (R&D) was captured as a ligand. The results are shown in Table 31.

TABLE 31

| sample | ka (1/Ms) | kd (1/s) | KD (M) |
| --- | --- | --- | --- |
| P1H | 4.79E+05 | 1.29E−03 | 2.69E−09 |
| P2H | 4.60E+05 | 1.86E−03 | 4.04E−09 |
| P3H | 4.33E+05 | 1.99E−03 | 4.60E−09 |
| P1TL | 3.44E+05 | 1.34E−03 | 3.89E−09 |
| P2TL | 3.35E+05 | 1.96E−03 | 5.85E−09 |
| P3TL | 3.03E+05 | 2.07E−03 | 6.83E−09 |

(Results)

As is apparent from Table 31, scFvs secreted from each of single-expression strains, P1H, P2H and P3H exhibited a high KD value, meaning that scFvs have affinity for hPD-1. It is presumed that scFv secreted from each of co-expression strains, PC2 and PC3, also has affinity for hPD-1, similarly to scFv derived from P1H strain. It is also presumed that scFv secreted from each of co-expression strains, PC4 and PC5 has affinity for hPD-1, similarly to scFv derived from P2H strain; and that scFv secreted from each of co-expression strains, PC6, PC7 and PC8 has affinity for hPD-1, similarly to scFv derived from P3H strain.

Example 32

(Affinity of Anti-hPD-1scFv03 Purified from Anti-hPD-1scFv03 Single-Expression Strain for Antigen (Biacore))

Anti-hPD-1scFv03 was purified by Protein L column from each of the culture supernatants of anti-hPD-1scFv03 single expression bifidobacteria, P1TL strain, P2TL strain and P3TL strain to be compared with co-expression strains, PC2TL to PC8TL. The binding kinetic parameter with hPD-1 (fusion protein with human IgG1Fc) was measured by surface plasmon resonance using Biacore system. Analysis was carried out in the same manner as in Example 29 except that Fc fused recombinant hPD-1 (R&D) was captured as a ligand. The results are shown in Table 31.

(Results)

As is apparent from Table 31, scFvs secreted from each of single-expression strains P1TL, P2TL and P3TL exhibited a high KD value, meaning that scFvs have affinity for hPD-1. It is presumed that scFv secreted from each of co-expression strains, PC2TL and PC3TL, also has affinity for hPD-1, similarly to scFv derived from P1TL strain. It is also presumed that scFv secreted from each of co-expression strains, PC4TL and PC5TL has affinity for hPD-1, similarly to scFv derived from P2TL strain; and that scFv secreted from each of co-expression strains, PC6TL, PC7TL and PC8TL has affinity for hPD-1, similarly to scFv derived from P3TL strain.

Example 33

(Inhibitory Activity of scFv Derived from Co-Expression Strain PC4 to Antigen-Ligand Binding)

From the culture supernatant of co-expression strain PC4, anti-hPD-1scFv03-His was purified by the purification column for His-tag and anti-hCTLA-4scFv01-FLAG was purified by the purification column for FLAG-tag. Competitive activities (ELISA) of these with a ligand in binding to the corresponding antigens were evaluated.

(Competitive Activity of Human PD-L1 to Binding Between Anti-hPD-1scFv03 to Antigen)

The same operation as in Example 21 (Evaluation on secretion of anti-hPD-1scFv03) was repeated except the sample addition operation. As a sample, a mixture of 2 nM (immobilization concentration) of anti-hPD-1scFv03-His obtained by His-tag purification of the culture supernatant of co-expression strain PC4 and a human PD-L1 solution (Recombinant Human B7-H1/PD-L1Fc Chimera, R&D systems, hereinafter referred to as hPD-L1) different in concentration (640 nM, 320 nM, 160 nM, 80 nM, 40 nM, 20 nM, 5 nM, 0.5 nM, 0 nM) was used. In control wells, a sample of 2 nM anti-hCTLA-4scFv01-FLAG (derived from C1F strain) and a sample of 640 nM hPD-L1 were added. The binding inhibition rate of hPD-L1 to binding of hPD-1/anti-hPD-1scFv03-His was calculated in accordance with Expression 1. The resultant (binding) inhibitory activities of hPD-L1 to the binding between hPD-1scFv03 purified from PC4 strain and hPD-1 are shown in Table 32.

[Expression 1]

Binding inhibition rate (%) = $100 - \frac{(\text{Absorbance in the presence of } hPD\text{-}L1)}{(\text{Absorbance in the absence of } hPD\text{-}L1)} \times 100$ (Formula 1)

TABLE 32

| Sample | | Binding | Inhibition rate |
|---|---|---|---|
| hPD-1 scFv03-His | hPD-L1 | A450-570 | (%) |
| 2 nM | 0 nM | 1.942 | 0 |
| 2 nM | 0.5 nM | 1.426 | 26.6 |
| 2 nM | 5 nM | 1.359 | 30 |
| 2 nM | 20 nM | 1.481 | 23.7 |
| 2 nM | 40 nM | 1.021 | 47.4 |
| 2 nM | 80 nM | 0.851 | 56.2 |
| 2 nM | 160 nM | 0.649 | 66.6 |
| 2 nM | 320 nM | 0.396 | 79.6 |
| 2 nM | 640 nM | 0.272 | 86 |
| no | 640 nM | 0 | — |
| hCTLA-4 scFv | no | −0.001 | — |

As is apparent from Table 32, as the hPD-L1 concentration increased, absorbance decreased. Binding of anti-hPD-1scFv03-His to an antigen decreased in a hPD-L1-concentration dependent manner. In contrast, in the case where 2 nM anti-hCTLA-4scFv01-FLAG was added, binding to the plate was not observed. From this, binding of anti-hPD-1scFv03-His to human PD-1 immobilized can be said to be specific binding. In the case where hPD-L1 alone was added, binding to the plate was not observed. From this, what was bound to the plate when anti-hPD-1scFv03-His/hPD-L1 mixture was added can be said to be anti-hPD-1scFv03-His. The binding inhibition rate of hPD-L1 against the binding between hPD-1 and anti-hPD-1scFv03-His is shown in FIG. 38. The binding between hPD-1 and anti-hPD-1scFv03-His is inhibited by hPD-L1 in a concentration-dependent manner.

(Competitive Activity of Ligand to Binding Between Anti-hCTLA-4scFv01 and Antigen)

The same operation as in Example 21 (Evaluation on secretion of anti-hCTLA-4scFv01) was repeated except the sample addition operation. As samples, a mixture of 1 nM anti-hCTLA-4scFv01-FLAG obtained by FLAG-tag purification from co-expression strain PC4 and human CD80 (Recombinant Human B7-1/CD80 Fc Chimera, R&D Systems, hereinafter referred to as hCD80) different in concentration (30 nM, 20 nM, 10 nM, 5 nM, 3 nM and 0 nM); and a mixture of 1 nM anti-hCTLA-4 scFv01-FLAG and human CD86 (Recombinant Human B7-1/CD86 Fc Chimera, R&D Systems, hereinafter referred to as hCD86) different in concentration (100 nM, 80 nM, 60 nM, 40 nM, 20 nM and 0 nM) were used. In control wells, 1 nM anti-hPD-1scFv03-His (derived from P2H strain), 30 nM hCD80 alone, or 100 nM hCD86 alone were added. The binding inhibition rate of hCD80 or hCD86 to binding of hCTLA-4/anti-hCTLA-4scFv01-FLAG was calculated in accordance with Expression 2.

[Expression 2]

Binding inhibition rate (%) = (Formula 2)

$$100 - \frac{\text{(Absorbance in the presence of ligand*)}}{\text{(Absorbance in the absence of ligand*)}} \times 100$$

*Ligand: hCD80 or hCD86

(Results)

The results of competitive ELISA are shown in Table 33 (hCD80 was used as a ligand) and Table 34 (hCD86 was used as a ligand).

TABLE 33

Binding inhibitory activity of hCD80 to binding between hCTLA-4scFv01-FLAG purified from PC4 strain and hCTLA-4

| Sample | | Binding | Inhibition |
|---|---|---|---|
| hCTLA-4scFv01-FLAG | hCD80 | A450-570 | (%) |
| 1 nM | 0 nM | 1.027 | 0 |
| 1 nM | 3 nM | 1.352 | −31.6 |
| 1 nM | 5 nM | 0.489 | 52.4 |
| 1 nM | 10 nM | 0.407 | 60.4 |
| 1 nM | 20 nM | 0.248 | 75.9 |
| 1 nM | 30 nM | 0.185 | 82 |
| no | 30 nM | 0.004 | — |
| hPD-1 scFv | no | −0.020 | — |

TABLE 34

Binding inhibitory activity of hCD86 to binding between hCTLA-4scFv01-FLAG purified from PC4 strain and hCTLA-4

| Sample | | Binding | Inhibition |
|---|---|---|---|
| hCTLA-4scFv01-FLAG | hCD86 | A450-570 | (%) |
| 1 nM | 0 nM | 1.027 | 0 |
| 1 nM | 20 nM | 1.084 | −5.6 |
| 1 nM | 40 nM | 0.799 | 22.2 |
| 1 nM | 60 nM | 0.614 | 40.2 |
| 1 nM | 80 nM | 0.521 | 49.3 |
| 1 nM | 100 nM | 0.374 | 63.6 |
| no | 100 nM | 0.009 | — |
| hPD-1 scFv | no | −0.020 | — |

As is apparent from Table 33 and Table 34, as the concentration of hCD80 or hCD86 increased, absorbance decreased. Binding of anti-hCTLA-4scFv01-FLAG to an antigen decreased in a hCD80- or hCD86-concentration dependent manner. In contrast, in the case where 1 nM anti-hPD-1scFv03-His was added, binding to the plate was not observed. From this, the binding of hCTLA-4scFv01-FLAG to human CTLA-4 immobilized can be said to be specific binding. In the case where hCD80 alone or hCD86 alone was added, binding to the plate was not observed. From this, what was bound to the plate when the mixture of anti-hCTLA-4scFv01-FLAG and hCD80 or the mixture of anti-hCTLA-4scFv01-FLAG and hCD86 was added, can be said to be anti-hCTLA-4scFv01-FLAG.

The binding inhibition rates of hCD80 and hCD86 to binding between hCTLA-4 and anti-hCTLA-4scFv01-FLAG are shown in FIG. 39 and FIG. 40, respectively. The binding between hCTLA-4 and anti-hCTLA-4scFv01-FLAG is inhibited by hCD80 or hCD86 in a concentration-dependent manner.

From the results mentioned above, it was successfully verified that anti-hPD-1scFv03-His and anti-hCTLA-4scFv01-FLAG secreted from co-expression strain PC4 have activities to competitively bind to the corresponding antigens with the respective ligands.

The invention claimed is:

1. A co-expression plasmid comprising two types of secretory expression cassettes each sequentially comprising the following DNAs (1) to (4) and expressed within a bacterium of the genus *Bifidobacterium*:
   (1) a promoter DNA functioning in the bacterium of the genus *Bifidobacterium*;
   (2) a DNA encoding a secretory signal peptide consisting of an amino acid sequence represented by any one of SEQ ID Nos: 61, 69, 73, 75, 77, 57, 59, 63, 65, 67, and 71;
   (3) a DNA encoding a heterologous polypeptide; and
   (4) a terminator DNA functioning in the bacterium of the genus *Bifidobacterium*.

2. The co-expression plasmid according to claim 1, wherein a DNA encoding a linker peptide is ligated downstream of the DNA encoding a secretory signal peptide.

3. The co-expression plasmid according to claim 1, wherein the promoter functioning in the bacterium of the genus *Bifidobacterium* is one or two promoters selected from P30 promoter, P54 promoter and Hu promoter.

4. The co-expression plasmid according to claim 1, wherein the terminator functioning in the bacterium of the genus *Bifidobacterium* is one or two terminators selected from Hu terminator and T2 terminator.

5. The co-expression plasmid according to claim 1, wherein the heterologous polypeptide is a single-chain antibody.

6. The co-expression plasmid according to claim 5, wherein the single-chain antibody is an anti-PD-1 antibody.

7. The co-expression plasmid according to claim 5, wherein the single-chain antibody is an anti-CTLA-4 antibody.

8. The co-expression plasmid according to claim 5, wherein the single-chain antibody is an anti-HER2 antibody.

9. The co-expression plasmid according to claim 1, wherein the heterologous polypeptide is a cytokine.

10. The co-expression plasmid according to claim 9, wherein the cytokine is TNF-$\alpha$.

11. The co-expression plasmid according to claim 9, wherein the cytokine is IFN-$\gamma$.

12. The co-expression plasmid according to claim 1, comprising two types of secretory expression cassettes, wherein the heterologous polypeptide of one of the secretory expression cassettes is an anti-PD-1 antibody and the heterologous polypeptide of the other of the secretory expression cassettes is an anti-CTLA-4 antibody.

13. The co-expression plasmid according to claim 1, comprising two types of secretory expression cassettes, wherein the heterologous polypeptide of one of the secretory expression cassettes is TNF-$\alpha$ and the heterologous polypeptide of the other of the secretory expression cassettes is IFN-$\gamma$.

14. The co-expression plasmid according to claim 1, comprising two types of secretory expression cassettes, wherein the heterologous polypeptide of one of the secretory expression cassettes is an anti-HER2 antibody and the heterologous polypeptide of the other of the secretory expression cassettes is IFN-$\gamma$.

15. A bacterium of the genus *Bifidobacterium* transformed with the co-expression plasmid according to claim 1.

16. The bacterium of the genus *Bifidobacterium* according to claim 15, wherein the bacterium is *Bifidobacterium longum*.

17. A pharmaceutical composition comprising the bacterium of the genus *Bifidobacterium* according to claim 15.

18. The co-expression plasmid according to claim 2, wherein the promoter functioning in the bacterium of the genus *Bifidobacterium* is one or two promoters selected from P30 promoter, P54 promoter and Hu promoter.

19. The co-expression plasmid according to claim 2, wherein the terminator functioning in the bacterium of the genus *Bifidobacterium* is one or two terminators selected from Hu terminator and T2 terminator.

* * * * *

SEQUENCE LISTING

```
<160> NUMBER OF SEQ ID NOS: 144

<210> SEQ ID NO 1
<211> LENGTH: 4975
<212> TYPE: DNA
<213> ORGANISM: Artificial
<220> FEATURE:
<223> OTHER INFORMATION: Linearized pHG-2 fragment
<220> FEATURE:
<221> NAME/KEY: misc_feature
<223> OTHER INFORMATION: Inventor:KOSEKI, Koichi; SHIOYA, Koichiro;
      KOBAYASHI, Satoshi; SHIMATANI, Yuko ;MASAKI, Takeshi; SHIMIZU,
      Hitomi; MATSUMURA, Tomio; OKABE, Masami; INOUE, Kengo

<400> SEQUENCE: 1
atcatcgccc tgtgaaaccg cttctcattt ccatttgcga tatggtctga atacgacgaa      60 acccccggcgc gaggccgggg tttcgtaagc tgtgcgtgac tatagcacga ccagcgcgat     120
tcggtgcacg gatccgtctt cctgctggcc tatgcattgg gttccgcagt gcccactcca     180
ggcggtctgg gcggtgtgga agcggcgctg acattcgcgt tcgtggcggt cggagtgccg     240
cagggcgtgg cgctttccgc cactttgctg caccgcgtgg tgttctactg gctgcgcatt     300
```

```
ccgctgggcg cggcggccat gaagtggctt gacaagcata atcttgtctg attcgtctat    360
tttcataccc ccttcgggga aatagatgtg aaaacccttta taaaacgcgg gttttcgcag   420
aaacatgcgc tagtatcatt gatgacaaca tggactaagc aaaagtgctt gtcccctgac   480
ccaagaagga tgctttatga attatttacg acaaaaaatt tcggctagtg ctatcgcggt   540
gttgtcgact tgtgggttga ttttggcgcc aatgccggtc tttgcggatg attcaacgcc   600
atcttcaacg ccatcggatg gcagttacac cacgactgat agcggtcagg acccgtacgt   660
caaggaagcc gaaaacctga agaagtactt caacgccggc catagcgatg tcgccgataa   720
cggcaccctg ttcctgggca tcctgaagaa ctggaaggaa gagtccgacc gcaagatcat   780
gcagtcccag atcgtgagct tctacttcaa gctgttcaag aacttcaagg acgatcagtc   840
gatccagaag tccgtggaga ccatcaagga agacatgaac gtcaagttct tcaacagcaa   900
caagaagaag cgcgacgatt tcgagaagct gaccaactac tccgtgaccg atctgaacgt   960
ccagcgtaag gccatccacg agctgatcca ggtcatggcc gaactgtccc cggccgccaa  1020
gaccggcaag cgtaagcgtt cccagatgct gttccgtggc cgtcgcgcct cccagcacca  1080
tcatcaccac cactgacctt ctgctcgtag cgattacttc gagcattact gacgacaaag  1140
accccgaccg agatggtcgg ggtctttttg ttgtggtgct gtgacgtgtt gtccaaccgt  1200
attattccgg actagtcctc caggacctcg tctacgaggc gctgagcgag gaatggcgca  1260
aaagggacgg cgagatcagc gacccatggg ccaacgacga ggcggacgga taccagccgc  1320
cctcatacga gccggtcaac cccgaacgca ggactcccca cgacgccctcc gatggcctga  1380 tctgacgtcc gaaaaaaggc gctgtgcgcc ctttttaaat cttttataaa tcttttttaca  1440 ttcttttagc ccctccgcag ccttactctc caacgggtt tcagccgaaa cctacaccaa  1500
aaggggagcg aacctacacc aaaaggggag cgaacctaca ccaaaagggg agcgaaccta  1560
caccaaaagg ggagctatat acaccttttg ttatttaagg tgcaagttgt gctatgctga  1620
ggccatgtcc aatgagatcg tgaagttcag caaccagttc aacaacgtcg cgctgaagaa  1680
gttcgacgcc gtgcacctgg acgtgctcat ggcgatcgcc tcaagggtga gggagaaggg  1740
cacggccacg gtggagttct cgttcgagga gctgcgcggc ctcatgcgat tgaggaagaa  1800
cctgaccaac aagcagctgg ccgacaagat cgtgcagacg aacgcgcgcc tgctggcgct  1860
gaactacatg ttcgaggatt cgggcaagat catccagttc gcgctgttca cgaagttcgt  1920
caccgacccg caggaggcga ctctcgcggt tggggtcaac gaggagttcg cgttcctgct  1980
caacgacctg accagccagt tcacgcgctt cgagctggcc gagttcgccg acctcaagag  2040
caagtacgcc aaggagttct accgcagggc caagcagtac cgcagctccg gaatctggaa  2100
gatcggccgc gacgagttct gccgactgct tggcgttcca ccgtcggcaa taacccagac  2160
acgatatctg aatcagaagg ttcttcagcc aattcaggag gagtgtgggc ctctccttgg  2220
cctgaagatc gagcgccagt acgtgaaacg caggctgtcg ggcttcgtgt tcacattcgc  2280
ccgcgagacc cctccggtga tcgacgccag gcccgtggga gcgaggaaga cggacggcga  2340
cggcaagggc cattggacga gcgttgccgg gtacggcgag gtgttcacga ccacggcgtt  2400
gttcgacgtg acggccgccc gggctcactt cgacggcacc gttgaagccg gggagtgccg  2460
tttctgcgcg tttgacgcgc gcaaccgcga acatcatgcg cggaacgccg gaaggctgtt  2520
ctagcggccc tgtccgcgcc tctggggcgg ttgcgcctgc catgggtcga tctgccgctg  2580
ttcggcctca cgctggtctg tgcgctgcct gatctccctg agcaggtcgg ccttggtcct  2640
gggggcgctt cgctcctcga acgggccgct ctccccagg tcctcgggct cgctcaggtc  2700
```

```
caacggctcg tcaccggacg gctcgggccg gttctctccc tgtgccgggt tctccgcctg   2760
tgcgcgttgt tcggccatgc gcagtgcgag ggccttcacc tgttcggggc ttgtcgactc   2820
gattttcgtt cgtgaataca tgttataata actataacta ataacgtaac gtgactggca   2880
agagatattt ttaaaacaat gaataggttt acacttactt tagttttatg gaatgaaag    2940 atcatatcat atataatcta gaataaaatt aactaaaata attattatct agataaaaaa   3000
tttagaagcc aatgaaatct ataaataaac taaattaagt ttatttaatt aacaactatg   3060
gatataaaat aggtactaat caaaatagtg aggaggatat atttgaatac atacgaacaa   3120
attaataaag tgaaaaaaat acttcggaaa catttaaaaa ataaccttat tggtacttac   3180
atgtttggat caggagttga gagtggacta aaaccaaata gtgatcttga cttttttagtc  3240 gtcgtatctg aaccattgac agatcaaagt aaagaaatac ttatacaaaa aattagacct   3300
atttcaaaaa aataggaga taaaagcaac ttacgatata ttgaattaac aattattatt   3360
cagcaagaaa tggtaccgtg gaatcatcct cccaaacaag aatttattta tggagaatgg   3420
ttacaagagc tttatgaaca aggatacatt cctcagaagg aattaaattc agatttaacc   3480
ataatgcttt accaagcaaa acgaaaaaat aaagaatat acggaaatta tgacttagag    3540
gaattactac ctgatattcc attttctgat gtgagaagag ccattatgga ttcgtcagag   3600
gaattaatag ataattatca ggatgatgaa accaactcta tattaacttt atgccgtatg   3660
attttaacta tggacacggg taaaatcata ccaaaagata ttgcgggaaa tgcagtggct   3720
gaatcttctc cattagaaca tagggagaga attttgttag cagttcgtag ttatcttgga   3780
gagaatattg aatggactaa tgaaaatgta aatttaacta taaactattt aaataacaga   3840 ttaaaaaat tataaaaaaa ttgaaaaaat ggtggaaaca cttttttcaa ttttttttaga   3900 tcttgagcaa aaggccagca aaaggccagg aaccgtaaaa aggccgcgtt gctggcgttt   3960
ttccataggc tccgcccccc tgacgagcat cacaaaaatc gacgctcaag tcagaggtgg   4020
cgaaacccga caggactata agataccag gcgtttcccc ctggaagctc cctcgtgcgc    4080
tctcctgttc cgaccctgcc gcttaccgga tacctgtccg cctttctccc ttcgggaagc   4140
gtggcgcttt ctcatagctc acgctgtagg tatctcagtt cggtgtaggt cgttcgctcc   4200
aagctgggct gtgtgcacga accccccgtt cagcccgacc gctgcgcctt atccggtaac   4260
tatcgtcttg agtccaaccc ggtaagacac gacttatcgc cactggcagc agccactggt   4320
aacaggatta gcagagcgag gtatgtaggc ggtgctacag agttcttgaa gtggtggcct   4380
aactacggct acactagaag aacagtattt ggtatctgcg ctctgctgaa gccagttacc   4440
ttcggaaaaa gagttggtag ctcttgatcc ggcaaacaaa ccaccgctgg tagcggtggt   4500
ttttttgttt gcaagcagca gattacgcgc agaaaaaaag gatctcaaga agatcctttg   4560
atcttttcta ctagccggca ttttcgcgat acattccccg gaatgttgcg caacggggaa   4620
cgcgcaccac accgcaacca cagtgcgcca cgcccagtcc ggccctgtgc gctataatag   4680
gtcagttatt cgcgcgcgcg tggcgccctc tacacccga gccgcgagga cacgtggatt    4740
ccggacggcc atgccccaca tggcaaaccg agaaccgca cacctagcat tacaaggaga   4800
gccattatgg cgttgatgat gagcgttaag actattattt ccacatcagt ggcgattatc   4860
gccacgggtg ccatgtttgc gtgcgtagcc ccgtttgcct ctgccgattc cgcgcagacg   4920
agtgctgtgg tgtcctcacg ttctttcccg aaggcgagtt cggtggtgcg ctcct         4975
```

<210> SEQ ID NO 2

<211> LENGTH: 2063
<212> TYPE: DNA
<213> ORGANISM: Artificial
<220> FEATURE:
<223> OTHER INFORMATION: pAG8 hTNF-[? expression cassette-hIFN-[A
      expression cassette

<400> SEQUENCE: 2

```
tagccggcat tttcgcgata cattccccgg aatgttgcgc aacggggaac gcgcaccaca      60
ccgcaaccac agtgcgccac gcccagtccg gccctgtgcg ctataatagg tcagttattc     120
gcgcgcgcgt ggcgccctct acaccccgag ccgcgaggac acgtggattc cggacggcca     180
tgccccacat ggcaaaccga gaacccgcac acctagcatt acaaggagag ccattatggc     240
gttgatgatg agcgttaaga ctattatttc cacatcagtg gcgattatcg ccacgggtgc     300
catgtttgcg tgcgtagccc cgtttgcctc tgccgattcc gcgcagacga gtgctgtggt     360
gtcctcacgt tctttcccga aggcgagttc ggtggtgcgc tcctcctccc gtaccccgtc     420
cgataagccg gtcgcccatg tggtcgccaa cccgcaggcc gagggccagc tgcagtggct     480
gaaccgtcgc gccaacgccc tgctggccaa cggcgtggaa ctgcgcgaca accagctggt     540
cgtgccgtcc gagggcctgt acctgatcta ctcccaggtg ctgttcaagg gccagggctg     600
cccgtccacc cacgtcctgc tgacccatac catctcccgc atcgccgtgt cctaccagac     660
caaggtcaac ctgctgtccg ccatcaagtc ccgtgccag cgtgagaccc cggaaggcgc     720
cgaggccaag ccgtggtacg aaccgatcta cctgggcggc gtgttccagc tggaaaaggg     780
cgatcgtctg tccgccgaga tcaaccgtcc ggactacctg gatttcgccg agtccggcca     840
ggtctacttc ggcatcatcg ccctgtgaaa ccgcttctca tttccatttg cgatatggtc     900
tgaatacgac gaaaccccgg cgcgaggccg gggtttcgta agctgtgcgt gactatagca     960
cgaccagcgc gattcggtgc acggatccgt cttcctgctg gcctatgcat tgggttccgc    1020
agtgccact ccaggcggtc tgggcggtgt ggaagcggcg ctgacattcg cgttcgtggc    1080
ggtcggagtg ccgcagggcg tggcgctttc cgccactttg ctgcaccgcg tggtgttcta    1140
ctggctgcgc attccgctgg gcgcggcggc catgaagtgg cttgacaagc ataatcttgt    1200
ctgattcgtc tattttcata cccccttcgg ggaaatagat gtgaaaaccc ttataaaacg    1260
cgggttttcg cagaaacatg cgctagtatc attgatgaca acatggacta agcaaaagtg    1320
cttgtccccct gacccaagaa ggatgcttta tgaattattt acgacaaaaa atttcggcta    1380
gtgctatcgc ggtgttgtcg acttgtgggt tgattttggc gccaatgccg gtctttgcgg    1440
atgattcaac gccatcttca acgccatcgg atggcagtta caccacgact gatagcggtc    1500
aggacccgta cgtcaaggaa gccgaaaacc tgaagaagta cttcaacgcc ggccatagcg    1560
atgtcgccga taacggcacc ctgttcctgg gcatcctgaa gaactggaag gaagagtccg    1620
accgcaagat catgcagtcc cagatcgtga gcttctactt caagctgttc aagaacttca    1680
aggacgatca gtcgatccag aagtccgtgg agaccatcaa ggaagacatg aacgtcaagt    1740
tcttcaacag caacaagaag aagcgcgacg atttcgagaa gctgaccaac tactccgtga    1800
ccgatctgaa cgtccagcgt aaggccatcc acgagctgat ccaggtcatg gccgaactgt    1860
ccccggccgc caagaccggc aagcgtaagc gttcccagat gctgttccgt ggccgtcgcg    1920
cctcccagca ccatcatcac caccactgac cttctgctcg tagcgattac ttcgagcatt    1980
actgacgaca aagaccccga ccgagatggt cggggtcttt tgttgtggt gctgtgacgt    2040
gttgtccaac cgtattattc cgg                                             2063
```

<210> SEQ ID NO 3
<211> LENGTH: 2045
<212> TYPE: DNA
<213> ORGANISM: Artificial
<220> FEATURE:
<223> OTHER INFORMATION: pAG8TL hTNF-[? expression cassette-hIFN-[A
      expression cassette

<400> SEQUENCE: 3

```
tagccggcat tttcgcgata cattccccgg aatgttgcgc aacggggaac gcgcaccaca      60
ccgcaaccac agtgcgccac gcccagtccg gccctgtgcg ctataatagg tcagttattc     120
gcgcgcgcgt ggcgccctct acaccccgag ccgcgaggac acgtggattc cggacggcca     180
tgccccacat ggcaaaccga gaacccgcac acctagcatt acaaggagag ccattatggc     240
gttgatgatg agcgttaaga ctattatttc cacatcagtg gcgattatcg ccacgggtgc     300
catgtttgcg tgcgtagccc cgtttgcctc tgccgattcc gcgcagacga gtgctgtggt     360
gtcctcacgt tctttcccga aggcgagttc ggtggtgcgc tcctcctccc gtaccccgtc     420
cgataagccg gtcgcccatg tggtcgccaa cccgcaggcc gagggccagc tgcagtggct     480
gaaccgtcgc gccaacgccc tgctggccaa cggcgtggaa ctgcgcgaca accagctggt     540
cgtgccgtcc gagggcctgt acctgatcta ctcccaggtg ctgttcaagg gccagggctg     600
cccgtccacc cacgtcctgc tgacccatac catctcccgc atcgccgtgt cctaccagac     660
caaggtcaac ctgctgtccg ccatcaagtc cccgtgccag cgtgagaccc cggaaggcgc     720
cgaggccaag ccgtggtacg aaccgatcta cctgggcggc gtgttccagc tggaaaaggg     780
cgatcgtctg tccgccgaga tcaaccgtcc ggactacctg gatttcgccg agtccggcca     840
ggtctacttc ggcatcatcg ccctgtgaaa ccgcttctca tttccatttg cgatatggtc     900
tgaatacgac gaaaccccgg cgcgaggccg gggtttcgta agctgtgcgt gactatagca     960
cgaccagcgc gattcggtgc acggatccgt cttcctgctg gcctatgcat gggttccgc    1020
agtgcccact ccaggcggtc tgggcggtgt ggaagcggcg ctgacattcg cgttcgtggc    1080
ggtcggagtg ccgcagggcg tggcgctttc cgccactttg ctgcaccgcg tggtgttcta    1140
ctggctgcgc attccgctgg gcgcggcggc catgaagtgg cttgacaagc ataatcttgt    1200
ctgattcgtc tattttcata ccccttcgg ggaaatagat gtgaaaaccc ttataaaacg    1260
cgggttttcg cagaaacatg cgctagtatc attgatgaca acatggacta agcaaaagtg    1320
cttgtcccct gacccaagaa ggatgcttta tgaattattt acgacaaaaa atttcggcta    1380
gtgctatcgc ggtgttgtcg acttgtgggt tgattttggc gccaatgccg gtctttgcgg    1440
atgattcaac gccatcttca acgccatcgg atggcagtta caccacgact gatagcggtc    1500
aggacccgta cgtcaaggaa gccgaaaacc tgaagaagta cttcaacgcc ggccatagcg    1560
atgtcgccga taacggcacc ctgttcctgg gcatcctgaa gaactggaag gaagagtccg    1620
accgcaagat catgcagtcc cagatcgtga gcttctactt caagctgttc aagaacttca    1680
aggacgatca gtcgatccag aagtccgtgg agaccatcaa ggaagacatg aacgtcaagt    1740
tcttcaacag caacaagaag aagcgcgacg atttcgagaa gctgaccaac tactccgtga    1800
ccgatctgaa cgtccagcgt aaggccatcc acgagctgat ccaggtcatg gccgaactgt    1860
ccccggccgc caagaccggc aagcgtaagc gttcccagat gctgttccgt ggccgtcgcg    1920
cctcccagtg accttctgct cgtagcgatt acttcgagca ttactgacga caaagacccc    1980
gaccgagatg gtcggggtct ttttgttgtg gtgctgtgac gtgttgtcca accgtattat    2040
```

```
tccgg                                                            2045

<210> SEQ ID NO 4
<211> LENGTH: 432
<212> TYPE: DNA
<213> ORGANISM: Artificial
<220> FEATURE:
<223> OTHER INFORMATION: hIFN-⌊A

<400> SEQUENCE: 4
caggacccgt acgtcaagga agccgaaaac ctgaagaagt acttcaacgc cggccatagc     60
gatgtcgccg ataacggcac cctgttcctg ggcatcctga gaactggaa ggaagagtcc    120
gaccgcaaga tcatgcagtc ccagatcgtg agcttctact tcaagctgtt caagaacttc    180
aaggacgatc agtcgatcca agtccgtg gagaccatca aggaagacat gaacgtcaag     240
ttcttcaaca gcaacaagaa gaagcgcgac gatttcgaga agctgaccaa ctactccgtg    300
accgatctga acgtccagcg taaggccatc cacgagctga tccaggtcat ggccgaactg    360
tccccggccg ccaagaccgg caagcgtaag cgttcccaga tgctgttccg tggccgtcgc    420
gcctcccagt ga                                                       432

<210> SEQ ID NO 5
<211> LENGTH: 3863
<212> TYPE: DNA
<213> ORGANISM: Artificial
<220> FEATURE:
<223> OTHER INFORMATION: pBEshuttle

<400> SEQUENCE: 5
ggatccgtct tcctgctggc ctatgcattg ggttccgcag tgcccactcc aggcggtctg     60
ggcggtgtgg aagcggcgct gacattcgcg ttcgtggcgg tcggagtgcc gcagggcgtg    120
gcgctttccg ccactttgct gcaccgcgtg gtgttctact ggctgcgcat tccgctgggc    180
gcggcggcca tgaagtggct tgacaagcat aatcttgtct gattcgtcta ttttcatacc    240
cccttcgggg aaatagatgt gaaaacccTT ataaaacgcg gttttcgca gaaacatgcg    300
ctagtatcat tgatgacaac atggactaag caaaagtgct tgtcccctga cccaagaagg    360
atgctttatg aagcttatcc tgcagtgacc ttctgctcgt agcgattact tcgagcatta    420
ctgacgacaa agaccccgac cgagatggtc ggggtctttt tgttgtggtg ctgtgacgtg    480
ttgtccaacc gtattattcc ggactagtcc tccaggacct cgtctacgag gcgctgagcg    540
aggaatggcg caaaagggac ggcgagatca gcgacccatg gccaacgac gaggcggacg     600
gataccagcc gccctcatac gagccggtca accccgaacg caggactccc cagacgccct    660
ccgatggcct gatctgacgt ccgaaaaaag gcgctgtgcg cccttttTaa atcttttata    720
aatcttttta cattctttta gcccctccgc agccttactc tcccaacggg tttcagccga    780
aacctacacc aaaaggggag cgaacctaca ccaaaagggg agcgaaccta caccaaaagg    840
ggagcgaacc tacaccaaaa ggggagctat atacaccttt tgttatttaa ggtgcaagtt    900
gtgctatgct gaggccatgt ccaatgagat cgtgaagttc agcaaccagt tcaacaacgt    960
cgcgctgaag aagttcgacg ccgtgcacct ggacgtgctc atggcgatcg cctcaagggt   1020
gagggagaag ggcacggcca cggtggagtt ctcgttcgag gagctgcgcg gcctcatgcg   1080
attgaggaag aacctgacca caagcagctg ggccgacaag atcgtgcaga cgaacgcgcg   1140
cctgctggcg ctgaactaca tgttcgagga ttcgggcaag atcatccagt tcgcgctgtt   1200
cacgaagttc gtcaccgacc cgcaggaggc gactctcgcg gttgggtca acgaggagtt   1260
```

```
cgcgttcctg ctcaacgacc tgaccagcca gttcacgcgc ttcgagctgg ccgagttcgc    1320
cgacctcaag agcaagtacg ccaaggagtt ctaccgcagg gccaagcagt accgcagctc    1380
cggaatctgg aagatcggcc gcgacgagtt ctgccgactg cttggcgttc accgtcggc    1440 aataacccag acacgatatc tgaatcagaa ggttcttcag ccaattcagg aggagtgtgg    1500
gcctctcctt ggcctgaaga tcgagcgcca gtacgtgaaa cgcaggctgt cgggcttcgt    1560
gttcacattc ccccgcgaga cccctccggt gatcgacgcc aggcccgtgg aggcgaggaa    1620
gacggacggc gacggcaagg ccattggac gagcgttgcc gggtacggcg aggtgttcac    1680
gaccacggcg ttgttcgacg tgacggccgc ccgggctcac ttcgacggca ccgttgaagc    1740
cggggagtgc cgtttctgcg cgtttgacgc gcgcaaccgc gaacatcatg cgcggaacgc    1800
cggaaggctg ttctagcggc cgtgtccgcg cctctgggc ggttgcgcct gccatgggtc    1860
gatctgccgc tgttcggcct cacgctggtc tgtgcgctgc ctgatctccc tgagcaggtc    1920
ggccttggtc ctggggcgc ttcgctcctc gaacgggccg ctctccccca ggtcctcggg    1980
ctcgctcagg tccaacggct cgtcaccgga cggctcgggc cggttctctc cctgtgccgg    2040
gttctccgcc tgtgcgcgtt gttcggccat cgcagtgcg agggccttca cctgttcggg    2100
gcttgtcgac tcgattttcg ttcgtgaata catgttataa taactataac taataacgta    2160
acgtgactgg caagagatat ttttaaaaca atgaataggt ttacacttac tttagtttta    2220
tggaaatgaa agatcatatc atatataatc tagaataaaa ttaactaaaa taattattat    2280
ctagataaaa aatttagaag ccaatgaaat ctataaataa actaaattaa gtttatttaa    2340
ttaacaacta tggatataaa ataggtacta atcaaaatag tgaggaggat atatttgaat    2400
acatacgaac aaattaataa agtgaaaaaa atacttcgga aacatttaaa aaataacctt    2460
attggtactt acatgtttgg atcaggagtt gagagtggac taaaaccaaa tagtgatctt    2520 gacttttttag tcgtcgtatc tgaaccattg acagatcaaa gtaaagaaat acttatacaa    2580
aaaattagac ctatttcaaa aaaaatagga gataaaagca acttacgata tattgaatta    2640
acaattatta ttcagcaaga aatggtaccg tggaatcatc ctcccaaaca agaatttatt    2700
tatggagaat ggttacaaga gctttatgaa caaggataca ttcctcagaa ggaattaaat    2760
tcagatttaa ccataatgct ttaccaagca aaacgaaaaa ataaaagaat atacggaaat    2820
tatgacttag aggaattact acctgatatt ccatttctg atgtgagaag agccattatg    2880
gattcgtcag aggaattaat agataattat caggatgatg aaaccaactc tatattaact    2940
ttatgccgta tgattttaac tatggacacg ggtaaaatca taccaaaaga tattgcggga    3000
aatgcagtgg ctgaatcttc tccattagaa cataggagga aatttttgtt agcagttcgt    3060
agttatcttg gagagaatat tgaatggact aatgaaaatg taaatttaac tataaactat    3120
ttaaataaca gattaaaaaa attataaaaa aattgaaaaa atggtggaaa cacttttttc    3180 aatttttta gatcttgagc aaaaggccag caaaaggcca ggaaccgtaa aaaggccgcg    3240
ttgctggcgt ttttccatag gctccgcccc cctgacgagc atcacaaaaa tcgacgctca    3300
agtcagaggt ggcgaaaccc gacaggacta taaagatacc aggcgtttcc ccctggaagc    3360
tccctcgtgc gctctcctgt tccgaccctg ccgcttaccg gatacctgtc cgcctttctc    3420
ccttcgggaa gcgtggcgct ttctcatagc tcacgctgta ggtatctcag ttcggtgtag    3480
gtcgttcgct ccaagctggg ctgtgtgcac gaaccccccg ttcagcccga ccgctgcgcc    3540
ttatccggta actatcgtct tgagtccaac ccggtaagac acgacttatc gccactggca    3600
```

```
gcagccactg gtaacaggat tagcagagcg aggtatgtag gcggtgctac agagttcttg    3660
aagtggtggc ctaactacgg ctacactaga agaacagtat ttggtatctg cgctctgctg    3720
aagccagtta ccttcggaaa aagagttggt agctcttgat ccggcaaaca aaccaccgct    3780
ggtagcggtg gttttttgt ttgcaagcag cagattacgc gcagaaaaaa aggatctcaa    3840
gaagatcctt tgatcttttc tac                                           3863

<210> SEQ ID NO 6
<211> LENGTH: 4727
<212> TYPE: DNA
<213> ORGANISM: Artificial
<220> FEATURE:
<223> OTHER INFORMATION: pHuSP7L20-hPD-1scFv03

<400> SEQUENCE: 6
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaaccctt ataaaacgcg gttttcgca gaaacatgcg     300 ctagtatcat tgatgacaac atggactaag caaaagtgct tgtcccctga cccaagaagg     360
atgctttatg gcgttgatga tgagcgttaa gactattatt ccacatcag tggcgattat      420 cgccacgggt gccatgtttg cgtgcgtagc cccgtttgcc tctgccgatt ccgcgcagac     480
gagtgctgtg tgtcctcac gttctttccc gaaggcgagt tcggtgcagg tccagctggt      540
cgaatcgggc ggcggcgtcg tccagccggg ccgttccctg cgtctggatt gcaaggcctc     600
gggcatcacc ttctcgaact ccggcatgca ctgggtgcgc caggcccgg gcaagggcct      660 ggaatgggtc gccgtgatct ggtacgatgg ctcgaagcgc tactacgccg attccgtgaa     720
gggccgcttc accatctcgc gcgacaactc caagaacacc ctgttcctgc agatgaactc     780
cctgcgcgcc gaagacaccg ccgtgtacta ctgcgccacc aacgatgact actggggcca     840
gggcaccctg gtcaccgtgt ccagcggcgg cggcggctcc ggcggcggcg gctcgggcgg     900
cggcggcagc gaaatcgtgc tgacccagtc cccggccacc ctgtccctgt ccccgggcga     960
acgtgccacc ctgtcgtgcc gcgcctccca gtcggtgtcc agctacctgg cctggtacca    1020
gcagaagccg ggccaggccc cgcgtctgct gatctacgac gcctccaacc gcgccaccgg    1080
catcccggcc cgcttctccg gctcgggctc cggcaccgac ttcaccctga ccatctcgtc    1140
cctggaaccg gaggacttcg ccgtctacta ctgccagcag tcctcgaact ggccgcgcac    1200
cttcggccag ggcaccaagg tcgagatcaa gcaccatcat caccaccact gaccttctgc    1260
tcgtagcgat tacttcgagc attactgacg acaaagaccc cgaccgagat ggtcggggtc    1320
tttttgttgt ggtgctgtga cgtgttgtcc aaccgtatta ttccggacta gtcctccagg    1380
acctcgtcta cgaggcgctg agcgaggaat ggcgcaaaag ggacggcgag atcagcgacc    1440
catgggccaa cgacgaggcg gacggatacc agccgccctc atacgagccg gtcaaccccg    1500
aacgcaggac tccccagacg ccctccgatg gcctgatctg acgtccgaaa aaggcgctg    1560 tgcgcccttt ttaaatcttt tataaatctt tttacattct tttagcccct ccgcagcctt    1620
actctcccaa cgggtttcag ccgaaaccta caccaaaagg ggagcgaacc tacaccaaaa    1680
ggggagcgaa cctacaccaa aaggggagcg aacctacacc aaaaggggag ctatatacac    1740
cttttgttat ttaaggtgca agttgtgcta tgctgaggcc atgtccaatg agatcgtgaa    1800
```

```
gttcagcaac cagttcaaca acgtcgcgct gaagaagttc gacgccgtgc acctggacgt    1860
gctcatggcg atcgcctcaa gggtgaggga gaagggcacg gccacggtgg agttctcgtt    1920
cgaggagctg cgcggcctca tgcgattgag gaagaacctg accaacaagc agctggccga    1980
caagatcgtg cagacgaacg cgcgcctgct ggcgctgaac tacatgttcg aggattcggg    2040
caagatcatc cagttcgcgc tgttcacgaa gttcgtcacc gacccgcagg aggcgactct    2100
cgcggttggg gtcaacgagg agttcgcgtt cctgctcaac gacctgacca gccagttcac    2160
gcgcttcgag ctggccgagt tcgccgacct caagagcaag tacgccaagg agttctaccg    2220
cagggccaag cagtaccgca gctccggaat ctggaagatc ggccgcgacg agttctgccg    2280
actgcttggc gttccaccgt cggcaataac ccagacacga tatctgaatc agaaggttct    2340
tcagccaatt caggaggagt gtgggcctct ccttggcctg aagatcgagc gccagtacgt    2400
gaaacgcagg ctgtcgggct tcgtgttcac attcgcccgc gagacccctc cggtgatcga    2460
cgccaggccc gtggaggcga ggaagacgga cggcgacggc aagggccatt ggacgagcgt    2520
tgccgggtac ggcgaggtgt tcacgaccac ggcgttgttc gacgtgacgg ccgcccgggc    2580
tcacttcgac ggcaccgttg aagccgggga gtgccgtttc tgcgcgtttg acgcgcgcaa    2640
ccgcgaacat catgcgcgga acgccggaag gctgttctag cggccgtgtc cgcgcctctg    2700
gggcggttgc gcctgccatg ggtcgatctg ccgctgttcg gcctcacgct ggtctgtgcg    2760
ctgcctgatc tccctgagca ggtcggcctt ggtcctgggg gcgcttcgct cctcgaacgg    2820
gccgctctcc cccaggtcct cgggctcgct caggtccaac ggctcgtcac cggacggctc    2880
gggccggttc tctccctgtg ccgggttctc cgcctgtgcg cgttgttcgg ccatgcgcag    2940
tgcgagggcc ttcacctgtt cggggcttgt cgactcgatt ttcgttcgtg aatacatgtt    3000
ataataacta taactaataa cgtaacgtga ctggcaagag atattttttaa aacaatgaat    3060 aggtttacac ttactttagt tttatggaaa tgaaagatca tatcatatat aatctagaat    3120
aaaattaact aaaataatta ttatctagat aaaaaattta gaagccaatg aaatctataa    3180
ataaactaaa ttaagtttat ttaattaaca actatggata taaaataggt actaatcaaa    3240
atagtgagga ggatatattt gaatacatac gaacaaatta ataaagtgaa aaaaatactt    3300
cggaaacatt taaaaaataa ccttattggt acttacatgt ttggatcagg agttgagagt    3360
ggactaaaac caaatagtga tcttgacttt ttagtcgtcg tatctgaacc attgacagat    3420
caaagtaaag aaatacttat acaaaaaatt agacctattt caaaaaaaat aggagataaa    3480
agcaacttac gatatattga attaacaatt attattcagc aagaaatggt accgtggaat    3540
catcctccca aacaagaatt tatttatgga gaatggttac aagagcttta tgaacaagga    3600
tacattcctc agaaggaatt aaattcagat ttaaccataa tgctttacca agcaaaacga    3660
aaaaataaaa gaatatacgg aaattatgac ttagaggaat tactacctga tattccattt    3720
tctgatgtga gaagagccat tatggattcg tcagaggaat aatagataaa ttatcaggat    3780
gatgaaacca actctatatt aactttatgc cgtatgattt taactatgga cacgggtaaa    3840
atcataccaa aagatattgc gggaaatgca gtggctgaat cttctccatt agaacatagg    3900
gagagaattt tgttagcagt tcgtagttat cttggagaga atattgaatg gactaatgaa    3960
aatgtaaatt taactataaa ctatttaaat aacagattaa aaaattata aaaaattga    4020 aaaaatggtg gaaacacttt tttcaatttt tttagatctt gagcaaaagg ccagcaaaag    4080
gccaggaacc gtaaaaggc cgcgttgctg gcgtttttcc ataggctccg ccccctgac    4140
```

| | |
|---|---|
| gagcatcaca aaaatcgacg ctcaagtcag aggtggcgaa acccgacagg actataaaga | 4200 |
| taccaggcgt ttccccctgg aagctccctc gtgcgctctc ctgttccgac cctgccgctt | 4260 |
| accggatacc tgtccgcctt tctcccttcg ggaagcgtgg cgctttctca tagctcacgc | 4320 |
| tgtaggtatc tcagttcggt gtaggtcgtt cgctccaagc tgggctgtgt gcacgaaccc | 4380 |
| cccgttcagc ccgaccgctg cgccttatcc ggtaactatc gtcttgagtc caacccggta | 4440 |
| agacacgact tatcgccact ggcagcagcc actggtaaca ggattagcag agcgaggtat | 4500 |
| gtaggcggtg ctacagagtt cttgaagtgg tggcctaact acggctacac tagaagaaca | 4560 |
| gtatttggta tctgcgctct gctgaagcca gttaccttcg gaaaaagagt tggtagctct | 4620 |
| tgatccggca acaaaccac cgctggtagc ggtggttttt ttgtttgcaa gcagcagatt | 4680 |
| acgcgcagaa aaaaggatc tcaagaagat cctttgatct tttctac | 4727 |

<210> SEQ ID NO 7
<211> LENGTH: 4745
<212> TYPE: DNA
<213> ORGANISM: Artificial
<220> FEATURE:
<223> OTHER INFORMATION: pHuSP7L20-hCTLA-4scFv02

<400> SEQUENCE: 7

| | |
|---|---|
| ggatccgtct tcctgctggc ctatgcattg ggttccgcag tgcccactcc aggcggtctg | 60 |
| ggcggtgtgg aagcggcgct gacattcgcg ttcgtggcgg tcggagtgcc gcagggcgtg | 120 |
| gcgctttccg ccactttgct gcaccgcgtg gtgttctact ggctgcgcat tccgctgggc | 180 |
| gcggcggcca tgaagtggct tgacaagcat aatcttgtct gattcgtcta ttttcatacc | 240 |
| cccttcgggg aaatagatgt gaaaacccct ataaaacgcg gttttcgca gaaacatgcg | 300 |
| ctagtatcat tgatgacaac atggactaag caaaagtgct tgtcccctga cccaagaagg | 360 |
| atgctttatg gcgttgatga tgagcgttaa gactattatt ccacatcag tggcgattat | 420 |
| cgccacgggt gccatgtttg cgtgcgtagc ccgtttgcc tctgccgatt ccgcgcagac | 480 |
| gagtgctgtg gtgtcctcac gttctttccc gaaggcgagt tcggtgcagg tccagctggt | 540 |
| cgaatcgggc ggcggcgtcg tccagccggg ccgtagcctg cgtctgtcgt gcgccgcctc | 600 |
| gggcttcacc ttctccagct acaccatgca ctgggtgcgt caggccccgg gcaagggcct | 660 |
| ggagtgggtc accttcatct cctacgacgg caacaacaag tactacgccg attccgtgaa | 720 |
| gggccgcttc accatctccc gtgacaacag caagaacacc ctgtacctgc agatgaactc | 780 |
| cctgcgcgcc gaagacaccg ccatctacta ctgcgcccgt accggctggc tgggcccgtt | 840 |
| cgattactgg ggccagggca ccctggtgac cgtctcgtcg ggcggcggcg gctcgggcgg | 900 |
| cggcggctcc ggcggcggcg gcagcgagat cgtgctgacc cagtcccggg caccctgtc | 960 |
| gctgtccccg ggcgaacgcg ccacccgtc ctgccgtgcc agccagtcgg tcggcagctc | 1020 |
| gtacctggcc tggtaccagc agaagccggg ccaggcccg cgtctgctga tctacgcgc | 1080 |
| cttctcccgt gccaccggca tcccggaccg tttctccggc agcggctcgg gcaccgattt | 1140 |
| caccctgacc atctcccgcc tggagccgga agatttcgcc gtctactact gccagcagta | 1200 |
| cggctccagc ccgtggacct tcggccaggg caccaaggtg gaaatcaagc atcatcatca | 1260 |
| tcatcactga ccttctgctc gtagcgatta cttcgagcat tactgacgac aaagaccccg | 1320 |
| accgagatgg tcggggtctt tttgttgtgg tgctgtgacg tgttgtccaa ccgtattatt | 1380 |
| ccggactagt cctccaggac ctcgtctacg aggcgctgag cgaggaatgg cgcaaaaggg | 1440 |
| acggcgagat cagcgaccca tgggccaacg acgaggcgga cggataccag ccgccctcat | 1500 |

```
acgagccggt caaccccgaa cgcaggactc cccagacgcc ctccgatggc ctgatctgac    1560
gtccgaaaaa aggcgctgtg cgcccttttt aaatctttta taaatctttt tacattcttt    1620
tagcccctcc gcagccttac tctcccaacg ggtttcagcc gaaacctaca ccaaaagggg    1680
agcgaaccta caccaaaagg ggagcgaacc tacaccaaaa ggggagcgaa cctacaccaa    1740
aaggggagct atatacacct tttgttattt aaggtgcaag ttgtgctatg ctgaggccat    1800
gtccaatgag atcgtgaagt tcagcaacca gttcaacaac gtcgcgctga agaagttcga    1860
cgccgtgcac ctggacgtgc tcatggcgat cgcctcaagg gtgagggaga agggcacggc    1920
cacggtggag ttctcgttcg aggagctgcg cggcctcatg cgattgagga gaacctgac     1980 caacaagcag ctggccgaca gatcgtgca gacgaacgcg cgcctgctgg cgctgaacta     2040
catgttcgag gattcgggca agatcatcca gttcgcgctg ttcacgaagt tcgtcaccga    2100
cccgcaggag gcgactctcg cggttggggt caacgaggag ttcgcgttcc tgctcaacga    2160
cctgaccagc cagttcacgc gcttcgagct ggccgagttc gccgacctca agagcaagta    2220
cgccaaggag ttctaccgca gggccaagca gtaccgcagc tccggaatct ggaagatcgg    2280
ccgcgacgag ttctgccgac tgcttggcgt tccaccgtcg gcaataaccc agacacgata    2340
tctgaatcag aaggttcttc agccaattca ggaggagtgt gggcctctcc ttggcctgaa    2400
gatcgagcgc cagtacgtga acgcaggct gtcgggcttc gtgttcacat tcgcccgcga    2460 gaccccctccg gtgatcgacg ccaggcccgt ggaggcgagg aagacggacg cgacggcaa    2520 gggccattgg acgagcgttg ccgggtacgg cgaggtgttc acgaccacgg cgttgttcga    2580
cgtgacggcc gcccgggctc acttcgacgg caccgttgaa gccggggagt gccgtttctg    2640
cgcgtttgac gcgcgcaacc gcgaacatca tgcgcggaac gccggaaggc tgttctagcg    2700
gccgtgtccg cgcctctggg gcggttgcgc ctgccatggg tcgatctgcc gctgttcggc    2760
ctcacgctgg tctgtgcgct gcctgatctc cctgagcagg tcggccttgg tcctgggggc    2820
gcttcgctcc tcgaacgggc cgctctcccc caggtcctcg ggctcgctca ggtccaacgg    2880
ctcgtcaccg gacggctcgg gccggttctc tccctgtgcc gggttctccg cctgtgcgcg    2940
ttgttcggcc atgcgcagtg cgagggcctt cacctgttcg gggcttgtcg actcgatttt    3000
cgttcgtgaa tacatgttat aataactata actaataacg taacgtgact ggcaagagat    3060 attttttaaaa caatgaatag gtttacactt actttagttt tatggaaatg aaagatcata    3120
tcatatataa tctagaataa aattaactaa aataattatt atctagataa aaaatttaga    3180
agccaatgaa atctataaat aaactaaatt aagtttattt aattaacaac tatggatata    3240
aaataggtac taatcaaaat agtgaggagg atatatttga atacatacga acaaattaat    3300
aaagtgaaaa aaatacttcg gaaacattta aaaaataacc ttattggtac ttacatgttt    3360
ggatcaggag ttgagagtgg actaaaacca aatagtgatc ttgacttttt agtcgtcgta    3420
tctgaaccat tgacagatca agtaaagaa atacttatac aaaaaattag acctatttca    3480
aaaaaaatag gagataaaag caacttacga tatattgaat taacaattat tattcagcaa    3540
gaaatggtac cgtggaatca tcctcccaaa caagaattta tttatggaga atggttacaa    3600
gagctttatg aacaaggata cattcctcag aaggaattaa attcagattt aaccataatg    3660
ctttaccaag caaaacgaaa aaataaaaga atatacgaaa attatgactt agaggaatta    3720
ctacctgata ttccattttc tgatgtgaga agagccatta tggattcgtc agaggaatta    3780
atagataatt atcaggatga tgaaaccaac tctatattaa ctttatgccg tatgatttta    3840
```

```
actatggaca cgggtaaaat cataccaaaa gatattgcgg gaaatgcagt ggctgaatct    3900
tctccattag aacataggga gagaattttg ttagcagttc gtagttatct tggagagaat    3960
attgaatgga ctaatgaaaa tgtaaattta actataaact atttaaataa cagattaaaa    4020
aaattataaa aaaattgaaa aaatggtgga aacacttttt tcaattttt tagatcttga     4080 gcaaaaggcc agcaaaggc caggaaccgt aaaaaggccg cgttgctggc gttttccat     4140 aggctccgcc cccctgacga gcatcacaaa aatcgacgct caagtcagag gtggcgaaac    4200
ccgacaggac tataaagata ccaggcgttt ccccctggaa gctccctcgt gcgctctcct    4260
gttccgaccc tgccgcttac cggatacctg tccgcctttc tcccttcggg aagcgtggcg    4320
ctttctcata gctcacgctg taggtatctc agttcggtgt aggtcgttcg ctccaagctg    4380
ggctgtgtgc acgaaccccc cgttcagccc gaccgctgcg ccttatccgg taactatcgt    4440
cttgagtcca acccggtaag acacgactta tcgccactgg cagcagccac tggtaacagg    4500
attagcagag cgaggtatgt aggcggtgct acagagttct tgaagtggtg cctaactac     4560 ggctacacta agaacagt atttggtatc tgcgctctgc tgaagccagt taccttcgga     4620
aaaagagttg gtagctcttg atccggcaaa caaaccaccg ctggtagcgg tggtttttt    4680 gtttgcaagc agcagattac gcgcagaaaa aaaggatctc aagaagatcc tttgatcttt    4740
tctac                                                              4745

<210> SEQ ID NO 8
<211> LENGTH: 4751
<212> TYPE: DNA
<213> ORGANISM: Artificial
<220> FEATURE:
<223> OTHER INFORMATION: pHuSP7L20-hCTLA-4scFv02FLAG

<400> SEQUENCE: 8
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca gaaacatgcg     300 ctagtatcat tgatgacaac atggactaag caaaagtgct tgtcccctga cccaagaagg    360
atgctttatg gcgttgatga tgagcgttaa gactattatt tccacatcag tggcgattat     420
cgccacgggt gccatgtttg cgtgcgtagc cccgtttgcc tctgccgatt ccgcgcagac    480
gagtgctgtg gtgtcctcac gttctttccc gaaggcgagt tcggtgcagg tccagctggt    540
cgaatcgggc ggcggcgtcg tccagccggg ccgtagcctg cgtctgtcgt gcgccgcctc    600
gggcttcacc ttctccagct acaccatgca ctgggtgcgt caggccccgg gcaagggcct    660
ggagtgggtc accttcatct cctacgacgg caacaacaag tactacgccg attccgtgaa    720
gggccgcttc accatctccc gtgacaacag caagaacacc ctgtacctgc agatgaactc    780
cctgcgcgcc gaagacaccg ccatctacta ctgcgcccgt accggctggc tgggcccgtt    840
cgattactgg ggccagggca ccctggtgac cgtctcgtcg ggcggcggcg gctcgggcgg    900
cggcggctcc ggcggcggcg gcagcgagat cgtgctgacc cagtccccgg gcaccctgtc    960 gctgtcccg ggcgaacgcg ccaccctgtc ctgccgtgcc agccagtcgg tcggcagctc    1020
gtacctggcc tggtaccagc agaagccggg ccaggccccg cgtctgctga tctacggcgc    1080
cttctcccgt gccaccggca tcccggaccg tttctccggc agcggctcgg gcaccgattt    1140
```

```
caccctgacc atctcccgcc tggagccgga agatttcgcc gtctactact gccagcagta    1200
cggctccagc ccgtggacct tcggccaggg caccaaggtg gaaatcaagg actacaagga    1260
cgacgacgac aagtgacctt ctgctcgtag cgattacttc gagcattact gacgacaaag    1320
accccgaccg agatggtcgg ggtcttttg ttgtggtgct gtgacgtgtt gtccaaccgt    1380
attattccgg actagtcctc caggacctcg tctacgaggc gctgagcgag aatggcgca    1440 aaagggacgg cgagatcagc gacccatggg ccaacgacga ggcggacgga taccagccgc    1500
cctcatacga gccggtcaac cccgaacgca ggactcccca cacgccctcc gatggcctga    1560
tctgacgtcc gaaaaaaggc gctgtgcgcc ctttttaaat cttttataaa tcttttaca    1620 ttcttttagc ccctccgcag ccttactctc caacgggtt tcagccgaaa cctacaccaa    1680
aaggggagcg aacctacacc aaaaggggag cgaacctaca ccaaaagggg agcgaaccta    1740
caccaaaagg ggagctatat acacctttg ttatttaagg tgcaagttgt gctatgctga    1800
ggccatgtcc aatgagatcg tgaagttcag caaccagttc aacaacgtcg cgctgaagaa    1860
gttcgacgcc gtgcacctgg acgtgctcat ggcgatcgcc tcaagggtga gggagaaggg    1920 cacgccacg gtggagttct cgttcgagga gctgcgcggc ctcatgcgat tgaggaagaa    1980
cctgaccaac aagcagctgg ccgacaagat cgtgcagacg aacgcgcgcc tgctggcgct    2040
gaactacatg ttcgaggatt cgggcaagat catccagttc cgcgctgttca cgaagttcgt    2100 caccgacccg caggaggcga ctctcgcggt tgggtcaac gaggagttcg cgttcctgct    2160
caacgacctg accagccagt tcacgcgctt cgagctggcc gagttcgccg acctcaagag    2220
caagtacgcc aaggagttct accgcagggc caagcagtac cgcagctccg aatctggaa    2280 gatcggccgc gacgagttct gccgactgct tggcgttcca ccgtcggcaa taacccagac    2340
acgatatctg aatcagaagg ttcttcagcc aattcaggag gagtgtgggc ctctccttgg    2400
cctgaagatc gagcgccagt acgtgaaacg caggctgtcg ggcttcgtgt tcacattcgc    2460
ccgcgagacc cctccggtga tcgacgccag gcccgtggag gcgaggaaga cggacggcga    2520
cggcaagggc cattggacga cgttgccgg gtacggcgag gtgttcacga ccacggcgtt    2580
gttcgacgtg acggccgccc gggctcactt cgacggcacc gttgaagccg gggagtgccg    2640
tttctgcgcg tttgacgcgc gcaaccgcga acatcatgcg cggaacgccg gaaggctgtt    2700
ctagcggccg tgtccgcgcc tctggggcgg ttgcgcctgc catgggtcga tctgccgctg    2760
ttcggcctca cgctggtctg tgcgctgcct gatctccctg agcaggtcgg ccttggtcct    2820
gggggcgctt cgctcctcga acgggccgct ctccccagg tcctcgggct cgctcaggtc    2880
caacggctcg tcaccggacg gctcgggccg gttctctccc tgtgccgggt tctccgcctg    2940
tgcgcgttgt tcgccatgc gcagtgcgag ggccttcacc tgttcgggc ttgtcgactc    3000 gattttcgtt cgtgaataca tgttataata actataacta ataacgtaac gtgactggca    3060
agagatattt ttaaaacaat gaataggttt acacttactt tagttttatg gaatgaaag    3120 atcatatcat atataatcta gaataaaatt aactaaaata attattatct agataaaaaa    3180
tttagaagcc aatgaaatct ataaatataaac taaattaagt ttatttaatt aacaactatg    3240
gatataaaat aggtactaat caaaatagtg aggaggatat atttgaatac atacgaacaa    3300
attaataaag tgaaaaaaat acttcggaaa catttaaaaa ataaccttat tggtacttac    3360
atgtttggat caggagttga gagtggacta aaaccaaata gtgatcttga ctttttagtc    3420
gtcgtatctg aaccattgac agatcaaagt aaagaaatac ttatacaaaa aattagacct    3480
```

| | |
|---|---:|
| atttcaaaaa aaataggaga taaaagcaac ttacgatata ttgaattaac aattattatt | 3540 |
| cagcaagaaa tggtaccgtg aatcatcct cccaaacaag aatttattta tggagaatgg | 3600 |
| ttacaagagc tttatgaaca aggatacatt cctcagaagg aattaaattc agatttaacc | 3660 |
| ataatgcttt accaagcaaa acgaaaaaat aaaagaatat acggaaatta tgacttagag | 3720 |
| gaattactac ctgatattcc attttctgat gtgagaagag ccattatgga ttcgtcagag | 3780 |
| gaattaatag ataattatca ggatgatgaa accaactcta tattaacttt atgccgtatg | 3840 |
| attttaacta tggacacggg taaaatcata ccaaaagata ttgcgggaaa tgcagtggct | 3900 |
| gaatcttctc cattagaaca tagggagaga attttgttag cagttcgtag ttatcttgga | 3960 |
| gagaatattg aatggactaa tgaaaatgta aatttaacta taaactattt aaataacaga | 4020 |
| ttaaaaaaat tataaaaaaa ttgaaaaaat ggtggaaaca cttttttcaa ttttttttaga | 4080 |
| tcttgagcaa aaggccagca aaaggccagg aaccgtaaaa aggccgcgtt gctggcgttt | 4140 |
| ttccataggc tccgcccccc tgacgagcat cacaaaaatc gacgctcaag tcagaggtgg | 4200 |
| cgaaacccga caggactata agataccag gcgtttcccc ctggaagctc cctcgtgcgc | 4260 |
| tctcctgttc cgaccctgcc gcttaccgga tacctgtccg cctttctccc ttcgggaagc | 4320 |
| gtggcgcttt ctcatagctc acgctgtagg tatctcagtt cggtgtaggt cgttcgctcc | 4380 |
| aagctgggct gtgtgcacga accccccgtt cagcccgacc gctgcgcctt atccggtaac | 4440 |
| tatcgtcttg agtccaaccc ggtaagacac gacttatcgc cactggcagc agccactggt | 4500 |
| aacaggatta gcagagcgag gtatgtaggc ggtgctacag agttcttgaa gtggtggcct | 4560 |
| aactacggct acactagaag aacagtattt ggtatctgcg ctctgctgaa gccagttacc | 4620 |
| ttcggaaaaa gagttggtag ctcttgatcc ggcaaacaaa ccaccgctgg tagcggtggt | 4680 |
| ttttttgttt gcaagcagca gattacgcgc agaaaaaaag gatctcaaga agatcctttg | 4740 |
| atcttttcta c | 4751 |

<210> SEQ ID NO 9
<211> LENGTH: 6111
<212> TYPE: DNA
<213> ORGANISM: Artificial
<220> FEATURE:
<223> OTHER INFORMATION: pPC1

<400> SEQUENCE: 9

| | |
|---|---:|
| ggatccgtct tcctgctggc ctatgcattg ggttccgcag tgcccactcc aggcggtctg | 60 |
| ggcggtgtgg aagcggcgct gacattcgcg ttcgtggcgg tcggagtgcc gcagggcgtg | 120 |
| gcgctttccg ccactttgct gcaccgcgtg gtgttctact ggctgcgcat tccgctgggc | 180 |
| gcggcggcca tgaagtggct tgacaagcat aatcttgtct gattcgtcta ttttcatacc | 240 |
| cccttcgggg aaatagatgt gaaaaccctt ataaaacgcg gttttcgca gaaacatgcg | 300 |
| ctagtatcat tgatgacaac atggactaag caaaagtgct tgtcccctga cccaagaagg | 360 |
| atgctttatg gcgttgatga tgagcgttaa gactattatt ccacatcag tggcgattat | 420 |
| cgccacgggt gccatgtttg cgtgcgtagc cccgtttgcc tctgccgatt ccgcgcagac | 480 |
| gagtgctgtg gtgtcctcac gttctttccc gaaggcgagt tcggtgcagg tccagctggt | 540 |
| cgaatcgggc ggcggcgtcg tccagccggg ccgttccctg cgtctggatt gcaaggcctc | 600 |
| gggcatcacc ttctcgaact ccggcatgca ctgggtgcgc caggcccggg caagggcct | 660 |
| ggaatgggtc gccgtgatct ggtacgatgg ctcgaagcgc tactacgccg attccgtgaa | 720 |
| gggccgcttc accatctcgc gcgacaactc caagaacacc ctgttcctgc agatgaactc | 780 |

```
cctgcgcgcc gaagacaccg ccgtgtacta ctgcgccacc aacgatgact actggggcca      840
gggcaccctg gtcaccgtgt ccagcggcgg cggcggctcc ggcggcggcg gctcgggcgg      900
cggcggcagc gaaatcgtgc tgacccagtc cccggccacc ctgtccctgt cccgggcga      960 acgtgccacc ctgtcgtgcc gcgcctccca gtcggtgtcc agctacctgg cctggtacca     1020
gcagaagccg ggccaggccc cgcgtctgct gatctacgac gcctccaacc gcgccaccgg     1080
catcccggcc cgcttctccg gctcgggctc cggcaccgac ttcaccctga ccatctcgtc     1140
cctggaaccg gaggacttcg ccgtctacta ctgccagcag tcctcgaact ggccgcgcac     1200
cttcggccag ggcaccaagg tcgagatcaa gcaccatcat caccaccact gaccttctgc     1260
tcgtagcgat tacttcgagc attactgacg acaaagaccc cgaccgagat ggtcggggtc     1320 ttttgttgt ggtgctgtga cgtgttgtcc aaccgtatta ttccgggtct tcctgctggc      1380
ctatgcattg ggttccgcag tgcccactcc aggcggtctg ggcggtgtgg aagcggcgct     1440
gacattcgcg ttcgtggcgg tcggagtgcc gcagggcgtg gcgctttccg ccactttgct     1500
gcaccgcgtg gtgttctact ggctgcgcat tccgctgggc gcggcggcca tgaagtggct     1560
tgacaagcat aatcttgtct gattcgtcta ttttcatacc cccttcgggg aaatagatgt     1620
gaaaaccctt ataaaacgcg ggttttcgca gaaacatgcg ctagtatcat tgatgacaac     1680
atggactaag caaagtgct tgtcccctga cccaagaagg atgctttatg gcgttgatga      1740
tgagcgttaa gactattatt tccacatcag tggcgattat cgccacgggt gccatgtttg     1800
cgtgcgtagc cccgttttgcc tctgccgatt ccgcgcagac gagtgctgtg gtgtcctcac    1860
gttctttccc gaaggcgagt tcggtgcagg tccagctggt cgaatcgggc ggcggcgtcg     1920
tccagccggg ccgtagcctg cgtctgtcgt gcgccgcctc gggcttcacc ttctccagct     1980
acaccatgca ctgggtgcgt caggcccgg gcaagggcct ggagtgggtc accttcatct      2040
cctacgacgg caacaacaag tactacgccg attccgtgaa gggccgcttc accatctccc     2100
gtgacaacag caagaacacc ctgtacctgc agatgaactc cctgcgcgcc gaagacaccg     2160
ccatctacta ctgcgcccgt accggctggc tgggcccgtt cgattactgg ggccagggca     2220
ccctggtgac cgtctcgtcg ggcggcggcg gctcgggcgg cggcggctcc ggcggcggcg     2280
gcagcgagat cgtgctgacc cagtcccccgg gcaccctgtc gctgtccccg ggcgaacgcg    2340
ccaccctgtc ctgccgtgcc agccagtcgg tcggcagctc gtacctggcc tggtaccagc     2400
agaagccggg ccaggccccg cgtctgctga tctacggcgc cttctcccgt gccaccggca     2460
tcccggaccg tttctccggc agcggctcgg gcaccgattt caccctgacc atctcccgcc     2520
tggagccgga agatttcgcc gtctactact gccagcagta cggctccagc ccgtggacct     2580
tcggccaggg caccaaggtg gaaatcaagg actacaagga cgacgacgac aagtgacctt     2640
ctgctcgtag cgattacttc gagcattact gacgacaaag accccgaccg agatggtcgg     2700
ggtctttttg ttgtggtgct gtgacgtgtt gtccaaccgt attattccgg actagtcctc     2760
caggacctcg tctacgaggc gctgagcgag gaatggcgca aaagggacgg cgagatcagc     2820
gacccatggg ccaacgacga ggcggacgga taccagccgc cctcatacga gccggtcaac     2880
cccgaacgca ggactcccca gacgccctcc gatggcctga tctgacgtcc gaaaaaggc     2940 gctgtgcgcc ctttttaaat cttttataaa tcttttttaca ttcttttagc ccctccgcag    3000
ccttactctc ccaacgggtt tcagccgaaa cctacaccaa aagggagcg aacctacacc      3060 aaaagggag cgaacctaca ccaaaagggg agcgaaccta caccaaaagg ggagctatat     3120
```

```
acaccttttg ttatttaagg tgcaagttgt gctatgctga ggccatgtcc aatgagatcg    3180
tgaagttcag caaccagttc aacaacgtcg cgctgaagaa gttcgacgcc gtgcacctgg    3240
acgtgctcat ggcgatcgcc tcaagggtga gggagaaggg cacggccacg gtggagttct    3300
cgttcgagga gctgcgcggc ctcatgcgat tgaggaagaa cctgaccaac aagcagctgg    3360
ccgacaagat cgtgcagacg aacgcgcgcc tgctggcgct gaactacatg ttcgaggatt    3420
cgggcaagat catccagttc gcgctgttca cgaagttcgt caccgacccg caggaggcga    3480
ctctcgcggt tggggtcaac gaggagttcg cgttcctgct caacgacctg accagccagt    3540
tcacgcgctt cgagctggcc gagttcgccg acctcaagag caagtacgcc aaggagttct    3600
accgcagggc caagcagtac cgcagctccg gaatctggaa gatcggccgc gacgagttct    3660
gccgactgct tggcgttcca ccgtcggcaa taacccagac acgatatctg aatcagaagg    3720
ttcttcagcc aattcaggag gagtgtgggc ctctccttgg cctgaagatc gagcgccagt    3780
acgtgaaacg caggctgtcg ggcttcgtgt tcacattcgc ccgcgagacc cctccggtga    3840
tcgacgccag gcccgtggag gcgaggaaga cggacgcgca cggcaagggc cattggacga    3900
gcgttgccgg gtacggcgag gtgttcacga ccacggcgtt gttcgacgtg acggccgccc    3960
gggctcactt cgacggcacc gttgaagccg gggagtgccg tttctgcgcg tttgacgcgc    4020
gcaaccgcga acatcatgcg cggaacgccg gaaggctgtt ctagcggccg tgtccgcgcc    4080
tctggggcgg ttgcgcctgc catgggtcga tctgccgctg ttcggcctca cgctggtctg    4140
tgcgctgcct gatctccctg agcaggtcgg ccttggtcct gggggcgctt cgctcctcga    4200
acgggccgct ctcccccagg tcctcgggct cgctcaggtc caacggctcg tcaccggacg    4260
gctcgggccg gttctctccc tgtgccgggt tctccgcctg tgcgcgttgt tcggccatgc    4320
gcagtgcgag ggccttcacc tgttcggggc ttgtcgactc gattttcgtt cgtgaataca    4380
tgttataata actataacta ataacgtaac gtgactggca agagatattt ttaaaacaat    4440
gaataggttt acacttactt tagttttatg gaaatgaaag atcatatcat atataatcta    4500
gaataaaatt aactaaaata attattatct agataaaaaa tttagaagcc aatgaaatct    4560
ataaataaac taaattaagt ttatttaatt aacaactatg gatataaaat aggtactaat    4620
caaaatagtg aggaggatat atttgaatac atacgaacaa attaataaag tgaaaaaaat    4680
acttcggaaa catttaaaaa ataaccttat tggtacttac atgtttggat caggagttga    4740
gagtggacta aaaccaaata gtgatcttga cttttttagtc gtcgtatctg aaccattgac    4800
agatcaaagt aaagaaatac ttatacaaaa aattagacct atttcaaaaa aataggaga    4860 taaaagcaac ttacgatata ttgaattaac aattattatt cagcaagaaa tggtaccgtg    4920
gaatcatcct cccaaacaag aatttattta tggagaatgg ttacaagagc tttatgaaca    4980
aggatacatt cctcagaagg aattaaattc agatttaacc ataatgcttt accaagcaaa    5040
acgaaaaaat aaaagaatat acggaaatta tgacttagag gaattactac ctgatattcc    5100
attttctgat gtgagaagag ccattatgga ttcgtcagag gaattaatag ataattatca    5160
ggatgatgaa accaactcta tattaacttt atgccgtatg attttaacta tggacacggg    5220
taaaatcata ccaaaagata ttgcgggaaa tgcagtggct gaatcttctc cattagaaca    5280
tagggagaga attttgttag cagttcgtag ttatcttgga gagaatattg aatggactaa    5340
tgaaaatgta aatttaacta taaactattt aaataacaga ttaaaaaaat tataaaaaaa    5400
ttgaaaaaat ggtggaaaca cttttttcaa ttttttttaga tcttgagcaa aaggccagca    5460
aaaggccagg aaccgtaaaa aggccgcgtt gctggcgttt ttccataggc tccgcccccc    5520
```

```
tgacgagcat cacaaaaatc gacgctcaag tcagaggtgg cgaaacccga caggactata    5580
aagataccag gcgtttcccc ctggaagctc cctcgtgcgc tctcctgttc cgaccctgcc    5640
gcttaccgga tacctgtccg cctttctccc ttcgggaagc gtggcgcttt ctcatagctc    5700
acgctgtagg tatctcagtt cggtgtaggt cgttcgctcc aagctgggct gtgtgcacga    5760
accccccgtt cagcccgacc gctgcgcctt atccggtaac tatcgtcttg agtccaaccc    5820
ggtaagacac gacttatcgc cactggcagc agccactggt aacaggatta gcagagcgag    5880
gtatgtaggc ggtgctacag agttcttgaa gtggtggcct aactacggct acactagaag    5940
aacagtattt ggtatctgcg ctctgctgaa gccagttacc ttcggaaaaa gagttggtag    6000
ctcttgatcc ggcaaacaaa ccaccgctgg tagcggtggt ttttttgttt gcaagcagca    6060
gattacgcgc agaaaaaaag gatctcaaga agatcctttg atcttttcta c            6111
```

<210> SEQ ID NO 10
<211> LENGTH: 6111
<212> TYPE: DNA
<213> ORGANISM: Artificial
<220> FEATURE:
<223> OTHER INFORMATION: pCP1

<400> SEQUENCE: 10

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca gaaacatgcg     300 ctagtatcat tgatgacaac atggactaag caaaagtgct tgtcccctga cccaagaagg     360
atgctttatg gcgttgatga tgagcgttaa gactattatt ccacatcag tggcgattat     420 cgccacgggt gccatgtttg cgtgcgtagc cccgtttgcc tctgccgatt ccgcgcagac     480
gagtgctgtg gtgtcctcac gttctttccc gaaggcgagt tcggtgcagg tccagctggt     540
cgaatcgggc ggcggcgtcg tccagccggg ccgtagcctg cgtctgtcgt gcgccgcctc     600
gggcttcacc ttctccagct acaccatgca ctgggtgcgt caggccccgg gcaagggcct     660
ggagtgggtc accttcatct cctacgacgg caacaacaag tactacgccg attccgtgaa     720
gggccgcttc accatctccc gtgacaacag caagaacacc ctgtacctgc agatgaactc     780
cctgcgcgcc gaagacaccg ccatctacta ctgcgcccgt accggctggc tgggcccgtt     840
cgattactgg ggccagggca ccctggtgac cgtctcgtcg ggcggcggcg gctcgggcgg     900
cggcggctcc ggcggcggcg gcagcgagat cgtgctgacc cagtcccggg caccctgtc     960 gctgtccccg ggcgaacgcg ccaccctgtc ctgccgtgcc agccagtcgg tcggcagctc    1020
gtacctggcc tggtaccagc agaagccggg ccaggccccg cgtctgctga tctacgcgc    1080 cttctcccgt gccaccggca tcccggaccg tttctccggc agcggctcgg gcaccgattt    1140 cacccctgacc atctcccgcc tggagccgga agatttcgcc gtctactact gccagcagta    1200
cggctccagc ccgtggacct tcggccaggg caccaaggtg gaaatcaagg actacaagga    1260
cgacgacgac aagtgacctt ctgctcgtag cgattacttc gagcattact gacgacaaag    1320
accccgaccg agatggtcgg ggtctttttg ttgtggtgct gtgacgtgtt gtccaaccgt    1380
attattccgg gtcttcctgc tggcctatgc attgggttcc gcagtgccca ctccaggcgg    1440
```

-continued

| | |
|---|---|
| tctgggcggt gtggaagcgg cgctgacatt cgcgttcgtg gcggtcggag tgccgcaggg | 1500 |
| cgtggcgctt ccgccactt tgctgcaccg cgtggtgttc tactggctgc gcattccgct | 1560 |
| gggcgcggcg gccatgaagt ggcttgacaa gcataatctt gtctgattcg tctattttca | 1620 |
| tacccccttc ggggaaatag atgtgaaaac ccttataaaa cgcgggtttt cgcagaaaca | 1680 |
| tgcgctagta tcattgatga caacatggac taagcaaaag tgcttgtccc ctgacccaag | 1740 |
| aaggatgctt tatggcgttg atgatgagcg ttaagactat tatttccaca tcagtggcga | 1800 |
| ttatcgccac gggtgccatg tttgcgtgcg tagccccgtt tgcctctgcc gattccgcgc | 1860 |
| agacgagtgc tgtggtgtcc tcacgttctt tcccgaaggc gagttcggtg caggtccagc | 1920 |
| tggtcgaatc gggcggcggc gtcgtccagc cgggccgttc cctgcgtctg gattgcaagg | 1980 |
| cctcgggcat caccttctcg aactccggca tgcactgggt gcgccaggcc ccgggcaagg | 2040 |
| gcctggaatg ggtcgccgtg atctggtacg atggctcgaa cgctactac gccgattccg | 2100 |
| tgaagggccg cttcaccatc tcgcgcgaca actccaagaa caccctgttc ctgcagatga | 2160 |
| actccctgcg cgccgaagac accgccgtgt actactgcgc caccaacgat gactactggg | 2220 |
| gccagggcac cctggtcacc gtgtccagcg gcggcggcgg ctccggcggc ggcggctcgg | 2280 |
| gcggcggcg cagcgaaatc gtgctgaccc agtccccggc caccctgtcc ctgtccccgg | 2340 |
| gcgaacgtgc caccctgtcg tgccgcgcct cccagtcggt gtccagctac ctggcctggt | 2400 |
| accagcagaa gccgggccag gccccgcgtc tgctgatcta cgacgcctcc aaccgcgcca | 2460 |
| ccggcatccc ggcccgcttc tccggctcgg gctccggcac cgacttcacc ctgaccatct | 2520 |
| cgtccctgga accggaggac ttcgccgtct actactgcca gcagtcctcg aactggccgc | 2580 |
| gcaccttcgg ccagggcacc aaggtcgaga tcaagcacca tcatcaccac cactgaccttt | 2640 |
| ctgctcgtag cgattacttc gagcattact gacgacaaag accccgaccg agatggtcgg | 2700 |
| ggtctttttg ttgtggtgct gtgacgtgtt gtccaaccgt attattccgg actagtcctc | 2760 |
| caggacctcg tctacgaggc gctgagcgag gaatggcgca aaaggggacgg cgagatcagc | 2820 |
| gacccatggg ccaacgacga ggcggacgga taccagccgc cctcatacga gccggtcaac | 2880 |
| cccgaacgca ggactcccca gacgcccctcc gatggcctga tctgacgtcc gaaaaaggc | 2940 |
| gctgtgcgcc cttttttaaat cttttataaa tcttttttaca ttcttttagc ccctccgcag | 3000 |
| ccttactctc ccaacgggtt tcagccgaaa cctacaccaa aaggggagcg aacctacacc | 3060 |
| aaaaggggag cgaacctaca ccaaaagggg agcgaaccta caccaaaagg ggagctatat | 3120 |
| acaccttttg ttatttaagg tgcaagttgt gctatgctga ggccatgtcc aatgagatcg | 3180 |
| tgaagttcag caaccagttc aacaacgtcg cgctgaagaa gttcgacgcc gtgcacctgg | 3240 |
| acgtgctcat ggcgatcgcc tcaagggtga gggagaaggg cacggccacg gtggagttct | 3300 |
| cgttcgagga gctgcgcggc ctcatgcgat tgaggaagaa cctgaccaac aagcagctgg | 3360 |
| ccgacaagat cgtgcagacg aacgcgcgcc tgctggcgct gaactacatg ttcgaggatt | 3420 |
| cgggcaagat catccagttc gcgctgttca cgaagttcgt caccgacccg caggaggcga | 3480 |
| ctctcgcggt tggggtcaac gaggagttcg cgttcctgct caacgacctg accagccagt | 3540 |
| tcacgcgctt cgagctggcc gagttcgccg acctcaagag caagtacgcc aaggagttct | 3600 |
| accgcagggc caagcagtac cgcagctccg gaatctggaa gatcggccgc gacgagttct | 3660 |
| gccgactgct tggcgttcca ccgtcggcaa taacccagac acgatatctg aatcagaagg | 3720 |
| ttcttcagcc aattcaggag gagtgtgggc ctctccttgg cctgaagatc gagcgccagt | 3780 |
| acgtgaaacg caggctgtcg ggcttcgtgt tcacattcgc ccgcgagacc cctccggtga | 3840 |

-continued

```
tcgacgccag gcccgtggag gcgaggaaga cggacggcga cggcaagggc cattggacga    3900
gcgttgccgg gtacgcgag gtgttcacga ccacggcgtt gttcgacgtg acggccgccc    3960
gggctcactt cgacggcacc gttgaagccg gggagtgccg tttctgcgcg tttgacgcgc    4020
gcaaccgcga acatcatgcg cggaacgccg gaaggctgtt ctagcggccg tgtccgcgcc    4080
tctggggcgg ttgcgcctgc catgggtcga tctgccgctg ttcggcctca cgctggtctg    4140
tgcgctgcct gatctccctg agcaggtcgg ccttggtcct gggggcgctt cgctcctcga    4200
acgggccgct ctcccccagg tcctcgggct cgctcaggtc caacggctcg tcaccggacg    4260
gctcgggccg gttctctccc tgtgccgggt ctccgcctg tgcgcgttgt tcggccatgc    4320
gcagtgcgag ggccttcacc tgttcggggc ttgtcgactc gattttcgtt cgtgaataca    4380
tgttataata actataacta ataacgtaac gtgactggca agagatattt ttaaaacaat    4440
gaataggttt acacttactt tagttttatg gaaatgaaag atcatatcat atataatcta    4500
gaataaaatt aactaaaata attattatct agataaaaaa tttagaagcc aatgaaatct    4560
ataaataaac taaattaagt ttatttaatt aacaactatg gatataaaat aggtactaat    4620
caaaatagtg aggaggatat atttgaatac atacgaacaa attaataaag tgaaaaaaat    4680
acttcggaaa catttaaaaa ataaccttat tggtacttac atgtttggat caggagttga    4740
gagtggacta aaaccaaata gtgatcttga cttttttagtc gtcgtatctg aaccattgac    4800
agatcaaagt aaagaaatac ttatacaaaa aattagacct atttcaaaaa aataggaga    4860 taaaagcaac ttcgatata ttgaattaac aattattatt cagcaagaaa tggtaccgtg    4920
gaatcatcct cccaaacaag aatttattta tggagaatgg ttacaagagc tttatgaaca    4980
aggatacatt cctcagaagg aattaaattc agatttaacc ataatgcttt accaagcaaa    5040
acgaaaaaat aaaagaatat acggaaatta tgacttagag gaattactac ctgatattcc    5100
attttctgat gtgagaagag ccattatgga ttcgtcagag gaattaatag ataattatca    5160
ggatgatgaa accaactcta tattaacttt atgccgtatg attttaacta tggacacggg    5220
taaaatcata ccaaaagata ttgcgggaaa tgcagtggct gaatcttctc cattagaaca    5280
tagggagaga atttttgttag cagttcgtag ttatcttgga gagaatattg aatggactaa    5340
tgaaaatgta aatttaacta taaactattt aaataacaga ttaaaaaaat tataaaaaaa    5400
ttgaaaaaat ggtggaaaca cttttttcaa tttttttaga tcttgagcaa aaggccagca    5460
aaaggccagg aaccgtaaaa aggccgcgtt gctggcgttt ttccataggc tccgcccccc    5520
tgacgagcat cacaaaaatc gacgctcaag tcagaggtgg cgaaacccga caggactata    5580
aagataccag gcgtttcccc ctggaagctc cctcgtgcgc tctcctgttc cgaccctgcc    5640
gcttaccgga tacctgtccg cctttctccc ttcgggaagc gtggcgcttt ctcatagctc    5700
acgctgtagg tatctcagtt cggtgtaggt cgttcgctcc aagctgggct gtgtgcacga    5760
accccccgtt cagcccgacc gctgcgcctt atccggtaac tatcgtcttg agtccaaccc    5820
ggtaagacac gacttatcgc cactggcagc agccactggt aacaggatta gcagagcgag    5880
gtatgtaggc ggtgctacag agttcttgaa gtggtggcct aactacggct acactagaag    5940
aacagtattt ggtatctgcg ctctgctgaa gccagttacc ttcggaaaaa gagttggtag    6000
ctcttgatcc ggcaaacaaa ccaccgctgg tagcggtggt ttttttgttt gcaagcagca    6060
gattacgcgc agaaaaaaag gatctcaaga agatcctttg atcttttcta c            6111
```

<210> SEQ ID NO 11

<211> LENGTH: 729
<212> TYPE: DNA
<213> ORGANISM: Artificial
<220> FEATURE:
<223> OTHER INFORMATION: hPD-1scFv03

<400> SEQUENCE: 11

| | | | | | |
|---|---|---|---|---|---|
| atgcaggtcc | agctggtcga | atcgggcggc | ggcgtcgtcc | agccgggccg | ttccctgcgt | 60 |
| ctggattgca | aggcctcggg | catcaccttc | tcgaactccg | gcatgcactg | ggtgcgccag | 120 |
| gccccgggca | agggcctgga | atgggtcgcc | gtgatctggt | acgatggctc | gaagcgctac | 180 |
| tacgccgatt | ccgtgaaggg | ccgcttcacc | atctcgcgcg | acaactccaa | gaacaccctg | 240 |
| ttcctgcaga | tgaactccct | gcgcgccgaa | gacaccgccg | tgtactactg | cgccaccaac | 300 |
| gatgactact | ggggccaggg | caccctggtc | accgtgtcca | gcggcggcgg | cggctccggc | 360 |
| ggcggcggct | cgggcggcgg | cggcagcgaa | atcgtgctga | cccagtcccc | ggccaccctg | 420 |
| tccctgtccc | cgggcgaacg | tgccaccctg | tcgtgccgcg | cctcccagtc | ggtgtccagc | 480 |
| tacctggcct | ggtaccagca | gaagccgggc | caggccccgc | gtctgctgat | ctacgacgcc | 540 |
| tccaaccgcg | ccaccggcat | cccggcccgc | ttctccggct | cgggctccgg | caccgacttc | 600 |
| accctgacca | tctcgtccct | ggaaccgaga | gacttcgccg | tctactactg | ccagcagtcc | 660 |
| tcgaactggc | cgcgcacctt | cggccagggc | accaaggtcg | agatcaagca | ccatcatcac | 720 |
| caccactga | | | | | | 729 |

<210> SEQ ID NO 12
<211> LENGTH: 747
<212> TYPE: DNA
<213> ORGANISM: Artificial
<220> FEATURE:
<223> OTHER INFORMATION: hCTLA-4scFv02

<400> SEQUENCE: 12

| | | | | | |
|---|---|---|---|---|---|
| atgcaggtcc | agctggtcga | atcgggcggc | ggcgtcgtcc | agccgggccg | tagcctgcgt | 60 |
| ctgtcgtgcg | ccgcctcggg | cttcaccttc | tccagctaca | ccatgcactg | ggtgcgtcag | 120 |
| gccccgggca | agggcctgga | gtgggtcacc | ttcatctcct | acgacggcaa | caacaagtac | 180 |
| tacgccgatt | ccgtgaaggg | ccgcttcacc | atctcccgtg | acaacagcaa | gaacaccctg | 240 |
| tacctgcaga | tgaactccct | gcgcgccgaa | gacaccgcca | tctactactg | cgcccgtacc | 300 |
| ggctggctgg | gcccgttcga | ttactggggc | cagggcaccc | tggtgaccgt | ctcgtcgggc | 360 |
| ggcggcggct | cgggcggcgg | cggctccggc | ggcggcggca | gcgagatcgt | gctgacccag | 420 |
| tccccgggca | ccctgtcgct | gtcccgggc | gaacgcgcca | ccctgtcctg | ccgtgccagc | 480 |
| cagtcggtcg | gcagctcgta | cctggcctgg | taccagcaga | agccgggcca | ggccccgcgt | 540 |
| ctgctgatct | acggcgcctt | ctcccgtgcc | accggcatcc | cggaccgttt | ctccggcagc | 600 |
| ggctcgggca | ccgatttcac | cctgaccatc | tcccgcctgg | agccggaaga | tttcgccgtc | 660 |
| tactactgcc | agcagtacgg | ctccagcccg | tggaccttcg | gccagggcac | caaggtggaa | 720 |
| atcaagcatc | atcatcatca | tcactga | | | | 747 |

<210> SEQ ID NO 13
<211> LENGTH: 753
<212> TYPE: DNA
<213> ORGANISM: Artificial
<220> FEATURE:
<223> OTHER INFORMATION: hCTLA-4 scFv02FLAG

<400> SEQUENCE: 13

| atgcaggtcc | agctggtcga | atcgggcggc | ggcgtcgtcc | agccgggccg | tagcctgcgt | 60 |
| ctgtcgtgcg | ccgcctcggg | cttcaccttc | tccagctaca | ccatgcactg | ggtgcgtcag | 120 |
| gccccgggca | agggcctgga | gtgggtcacc | ttcatctcct | acgacggcaa | caacaagtac | 180 |
| tacgccgatt | ccgtgaaggg | ccgcttcacc | atctcccgtg | acaacagcaa | gaacaccctg | 240 |
| tacctgcaga | tgaactccct | gcgcgccgaa | gacaccgcca | tctactactg | cgcccgtacc | 300 |
| ggctggctgg | gcccgttcga | ttactggggc | cagggcaccc | tggtgaccgt | ctcgtcgggc | 360 |
| ggcggcggct | cgggcggcgg | cggctccggc | ggcggcggca | gcgagatcgt | gctgacccag | 420 |
| tccccgggca | ccctgtcgct | gtccccgggc | gaacgcgcca | ccctgtcctg | ccgtgccagc | 480 |
| cagtcggtcg | gcagctcgta | cctggcctgg | taccagcaga | agccgggcca | ggccccgcgt | 540 |
| ctgctgatct | acggcgcctt | ctcccgtgcc | accggcatcc | cggaccgttt | ctccggcagc | 600 |
| ggctcgggca | ccgatttcac | cctgaccatc | tcccgcctgg | agccggaaga | tttcgccgtc | 660 |
| tactactgcc | agcagtacgg | ctccagcccg | tggaccttcg | gccagggcac | caaggtggaa | 720 |
| atcaaggact | acaaggacga | cgacgacaag | tga | | | 753 |

<210> SEQ ID NO 14
<211> LENGTH: 4019
<212> TYPE: DNA
<213> ORGANISM: Artificial
<220> FEATURE:
<223> OTHER INFORMATION: Linearized vector fragment

<400> SEQUENCE: 14

| tgaccttctg | ctcgtagcga | ttacttcgag | cattactgac | gacaaagacc | ccgaccgaga | 60 |
| tggtcggggt | cttttttgttg | tggtgctgtg | acgtgttgtc | caaccgtatt | attccggact | 120 |
| agtcctccag | gacctcgtct | acgaggcgct | gagcgaggaa | tggcgcaaaa | gggacggcga | 180 |
| gatcagcgac | ccatgggcca | acgacgaggc | ggacggatac | cagccgccct | catacgagcc | 240 |
| ggtcaacccc | gaacgcagga | ctccccagac | gccctccgat | ggcctgatct | gacgtccgaa | 300 |
| aaaaggcgct | gtgcgccctt | tttaaatctt | ttataaatct | ttttacattc | ttttagcccc | 360 |
| tccgcagcct | tactctccca | acgggtttca | gccgaaacct | acaccaaaag | gggagcgaac | 420 |
| ctacaccaaa | aggggagcga | acctacacca | aaagggagc | gaacctacac | caaaagggga | 480 |
| gctatataca | ccttttgtta | tttaaggtgc | aagttgtgct | atgctgaggc | catgtccaat | 540 |
| gagatcgtga | agttcagcaa | ccagttcaac | aacgtcgcgc | tgaagaagtt | cgacgccgtg | 600 |
| cacctggacg | tgctcatggc | gatcgcctca | agggtgaggg | agaagggcac | ggccacggtg | 660 |
| gagttctcgt | tcgaggagct | gcgcggcctc | atgcgattga | ggaagaacct | gaccaacaag | 720 |
| cagctggccg | acaagatcgt | gcagacgaac | gcgcgcctgc | tggcgctgaa | ctacatgttc | 780 |
| gaggattcgg | gcaagatcat | ccagttcgcg | ctgttcacga | agttcgtcac | cgacccgcag | 840 |
| gaggcgactc | tcgcggttgg | ggtcaacgag | gagttcgcgt | tcctgctcaa | cgacctgacc | 900 |
| agccagttca | cgcgcttcga | gctggccgag | ttcgccgacc | tcaagagcaa | gtacgccaag | 960 |
| gagttctacc | gcagggccaa | gcagtaccgc | agctccggaa | tctggaagat | cggccgcgac | 1020 |
| gagttctgcc | gactgcttgg | cgttccaccg | tcggcaataa | cccagacacg | atatctgaat | 1080 |
| cagaaggttc | ttcagccaat | tcaggaggag | tgtgggcctc | tccttggcct | gaagatcgag | 1140 |
| cgccagtacg | tgaaacgcag | gctgtcgggc | ttcgtgttca | cattcgcccg | cgagacccct | 1200 |
| ccggtgatcg | acgccaggcc | cgtggaggcg | aggaagacgg | acggcgacgg | caagggccat | 1260 |

```
tggacgagcg ttgccgggta cggcgaggtg ttcacgacca cggcgttgtt cgacgtgacg    1320
gccgcccggg ctcacttcga cggcaccgtt gaagccgggg agtgccgttt ctgcgcgttt    1380
gacgcgcgca accgcgaaca tcatgcgcgg aacgccggaa ggctgttcta gcggccgtgt    1440
ccgcgcctct ggggcggttg cgcctgccat gggtcgatct gccgctgttc ggcctcacgc    1500
tggtctgtgc gctgcctgat ctccctgagc aggtcggcct tggtcctggg ggcgcttcgc    1560
tcctcgaacg ggccgctctc ccccaggtcc tcgggctcgc tcaggtccaa cggctcgtca    1620
ccggacggct cgggccggtt ctctccctgt gccgggttct ccgcctgtgc gcgttgttcg    1680
gccatgcgca gtgcgagggc cttcacctgt tcggggcttg tcgactcgat tttcgttcgt    1740
gaatacatgt tataataact ataactaata acgtaacgtg actggcaaga gatatttta     1800
aaacaatgaa taggtttaca cttactttag ttttatggaa atgaaagatc atatcatata    1860
taatctagaa taaaattaac taaaataatt attatctaga taaaaaattt agaagccaat    1920
gaaatctata aataaactaa attaagttta tttaattaac aactatggat ataaaatagg    1980
tactaatcaa aatagtgagg aggatatatt tgaatacata cgaacaaatt aataaagtga    2040
aaaaaatact tcggaaacat ttaaaaaata accttattgg tacttacatg tttggatcag    2100
gagttgagag tggactaaaa ccaaatagtg atcttgactt tttagtcgtc gtatctgaac    2160
cattgacaga tcaaagtaaa gaaatactta tacaaaaaat tagacctatt tcaaaaaaaa    2220
taggagataa aagcaactta cgatatattg aattaacaat tattattcag caagaaatgg    2280
taccgtggaa tcatcctccc aaacaagaat ttatttatgg agaatggtta caagagcttt    2340
atgaacaagg atacattcct cagaaggaat taaattcaga tttaaccata atgctttacc    2400
aagcaaaacg aaaaaataaa agaatatacg gaaattatga cttagaggaa ttactacctg    2460
atattccatt ttctgatgtg agaagagcca ttatggattc gtcagaggaa ttaatagata    2520
attatcagga tgatgaaacc aactctatat taactttatg ccgtatgatt ttaactatgg    2580
acacgggtaa aatcatacca aaagatattg cgggaaatgc agtggctgaa tcttctccat    2640
tagaacatag ggagagaatt ttgttagcag ttcgtagtta tcttggagag aatattgaat    2700
ggactaatga aaatgtaaat ttaactataa actatttaaa taacagatta aaaaaattat    2760
aaaaaaattg aaaaaatggt ggaaacactt ttttcaattt ttttagatct tgagcaaaag    2820
gccagcaaaa ggccaggaac cgtaaaaagg ccgcgttgct ggcgtttttc cataggctcc    2880
gcccccctga cgagcatcac aaaaatcgac gctcaagtca gaggtggcga aacccgacag    2940
gactataaag ataccaggcg tttccccctg gaagctccct cgtgcgctct cctgttccga    3000
cccctgccgct taccggatac ctgtccgcct ttctcccttc gggaagcgtg gcgctttctc    3060
atagctcacg ctgtaggtat ctcagttcgg tgtaggtcgt tcgctccaag ctgggctgtg    3120
tgcacgaacc ccccgttcag cccgaccgct gcgccttatc cggtaactat cgtcttgagt    3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
agcagcagat tacgcgcaga aaaaaggat ctcaagaaga tcctttgatc ttttctacgg    3480
atccgtcttc ctgctggcct atgcattggg ttccgcagtg cccactccag gcggtctggg    3540
cggtgtggaa gcgcgctga cattcgcgtt cgtggcggtc ggagtgccgc agggcgtggc    3600
gctttccgcc actttgctgc accgcgtggt gttctactgg ctgcgcattc cgctgggcgc    3660
```

```
ggcggccatg aagtggcttg acaagcataa tcttgtctga ttcgtctatt ttcataccc    3720 cttcggggaa atagatgtga aaacccttat aaaacgcggg ttttcgcaga aacatgcgct    3780
agtatcattg atgacaacat ggactaagca aaagtgcttg tccctgacc caagaaggat    3840 gctttatggc gttgatgatg agcgttaaga ctattatttc cacatcagtg gcgattatcg    3900
ccacgggtgc catgtttgcg tgcgtagccc cgtttgcctc tgccgattcc gcgcagacga    3960
gtgctgtggt gtcctcacgt tctttcccga aggcgagttc ggtgcaggtc cagctggtc    4019
```

<210> SEQ ID NO 15
<211> LENGTH: 4616
<212> TYPE: DNA
<213> ORGANISM: Artificial
<220> FEATURE:
<223> OTHER INFORMATION: pP30SP7L20-bHER2

<400> SEQUENCE: 15

```
tagccggcat tttcgcgata cattcccgg aatgttgcgc aacggggaac gcgcaccaca      60
ccgcaaccac agtgcgccac gcccagtccg gccctgtgcg ctataatagg tcagttattc     120
gcgcgcgcgt ggcgccctct acaccccgag ccgcgaggac acgtggattc cggacggcca    180
tgccccacat ggcaaaccga gaacccgcac acctagcatt acaaggagag ccattatggc    240
gttgatgatg agcgttaaga ctattatttc cacatcagtg gcgattatcg ccacgggtgc    300
catgtttgcg tgcgtagccc cgtttgcctc tgccgattcc gcgcagacga gtgctgtggt    360
gtcctcacgt tctttcccga aggcgagttc ggtggaagtg cagctggtcg aatcgggcgg    420
cggcctggtg cagccgggcg gctccctgcg tctgtcgtgc gccgctcgg gcttcaacat    480 caaggatacc tacatccact gggtgcgcca ggccccgggc aagggcctgg aatgggtggc    540
ccgtatctac ccgaccaacg gctacacccg ctacgccgat tccgtgaagg gccgcttcac    600
catctccgcc gataccagca gaacaccgc ctacctgcag atgaactccc tgcgcgccga    660
agataccgcc gtgtactact gctcgcgctg ggcggcgac ggcttctacg ccatggacta    720
ctggggccag ggcaccctgg tgaccgtgtc cagcggcggc ggcggctccg gcggcggcgg    780
ctcgggcggc ggcggctccg acatccagat gacccagtcc ccgtcgtccc tgagcgcctc    840
ggtgggcgat cgcgtgacca tcacctgccg cgcctcccag gatgtgaaca ccgccgtggc    900
ctggtaccag cagaagccgg gcaaggcccc gaagctgctg atctactcgg cctccttcct    960
gtactccggc gtgccgtccc gtttctccgg ctcccgctcg ggcaccgact tcaccctgac   1020
catctcgtcc ctgcagccgg aagacttcgc cacctactac tgccagcagc attacaccac   1080
cccgccgacc ttcggccagg gcaccaaggt ggaaatcaag catcatcatc atcatcactg   1140
accttctgct cgtagcgatt acttcgagca ttactgacga caaagacccc gaccgagatg   1200
gtcggggtct ttttgttgtg gtgctgtgac gtgttgtcca accgtattat tccggactag   1260
tcctccagga cctcgtctac gaggcgctga gcgaggaatg gcgcaaaagg gacggcgaga   1320
tcagcgaccc atgggccaac gacgaggcgg acggatacca gccgccctca tacgagccgg   1380
tcaaccccga acgcaggact ccccagacgc cctccgatgg cctgatctga cgtccgaaaa   1440
aaggcgctgt gcgcccttt taaatctttt ataaatcttt ttacattctt ttagcccctc   1500
cgcagcctta ctctcccaac gggtttcagc cgaaacctac accaaagggg agcgaacct   1560 acaccaaaag gggagcgaac ctacaccaaa aggggagcga acctacacca aaaggggagc   1620
tatatacacc ttttgttatt taaggtgcaa gttgtgctat gctgaggcca tgtccaatga   1680
```

```
gatcgtgaag ttcagcaacc agttcaacaa cgtcgcgctg aagaagttcg acgccgtgca      1740
cctggacgtg ctcatggcga tcgcctcaag ggtgagggag aagggcacgg ccacggtgga      1800
gttctcgttc gaggagctgc gcggcctcat gcgattgagg aagaacctga ccaacaagca      1860
gctggccgac aagatcgtgc agacgaacgc gcgcctgctg gcgctgaact acatgttcga      1920
ggattcgggc aagatcatcc agttcgcgct gttcacgaag ttcgtcaccg acccgcagga      1980
ggcgactctc gcggttgggg tcaacgagga gttcgcgttc ctgctcaacg acctgaccag      2040
ccagttcacg cgcttcgagc tggccgagtt cgccgacctc aagagcaagt acgccaagga      2100
gttctaccgc agggccaagc agtaccgcag ctccggaatc tggaagatcg ccgcgacga      2160
gttctgccga ctgcttggcg ttccaccgtc ggcaataacc agacacgat atctgaatca      2220
gaaggttctt cagccaattc aggaggagtg tgggcctctc cttggcctga agatcgagcg      2280
ccagtacgtg aaacgcaggc tgtcgggctt cgtgttcaca ttcgcccgcg agacccctcc      2340
ggtgatcgac gccaggcccg tggaggcgag gaagacggac ggcgacggca agggccattg      2400
gacgagcgtt gccgggtacg gcgaggtgtt cacgaccacg cgttgttcg acgtgacggc      2460
cgcccgggct cacttcgacg gcaccgttga agccggggag tgccgtttct gcgcgtttga      2520
cgcgcgcaac cgcgaacatc atgcgcgcgaa cgccggaagg ctgttctagc ggccgtgtcc      2580
gcgcctctgg ggcggttgcg cctgccatgg gtcgatctgc cgctgttcgg cctcacgctg      2640
gtctgtgcgc tgcctgatct ccctgagcag gtcggccttg gtcctggggg cgcttcgctc      2700
ctcgaacggg ccgctctccc ccaggtcctc gggctcgctc aggtccaacg gctcgtcacc      2760
ggacggctcg ggccggttct ctccctgtgc cgggttctcc gcctgtgcgc gttgttcggc      2820
catgcgcagt gcgagggcct tcacctgttc ggggcttgtc gactcgattt tcgttcgtga      2880
atacatgtta taataactat aactaataac gtaacgtgac tggcaagaga tatttttaaa      2940
acaatgaata ggtttacact tactttagtt ttatggaaat gaaagatcat atcatatata      3000
atctagaata aaattaacta aaataattat tatctagata aaaaatttag aagccaatga      3060
aatctataaa taaactaaat taagtttatt taattaacaa ctatggatat aaaataggta      3120
ctaatcaaaa tagtgaggag gatatatttg aatacatacg aacaaattaa taaagtgaaa      3180
aaaatacttc ggaaacattt aaaaaataac cttattggta cttacatgtt tggatcagga      3240
gttgagagtg gactaaaacc aaatagtgat cttgacttt tagtcgtcgt atctgaacca      3300
ttgacagatc aaagtaaaga aatacttata caaaaaatta gacctatttc aaaaaaaata      3360
ggagataaaa gcaacttacg atatattgaa ttaacaatta ttattcagca agaaatggta      3420
ccgtggaatc atcctcccaa acaagaattt atttatggag aatggttaca agagctttat      3480
gaacaaggat acattcctca gaaggaatta aattcagatt taaccataat gctttaccaa      3540
gcaaaacgaa aaaataaaag aatatacgga aattatgact tagaggaatt actacctgat      3600
attccatttt ctgatgtgag aagagccatt atggattcgt cagaggaatt aatagataat      3660
tatcaggatg atgaaaccaa ctctatatta actttatgcc gtatgatttt aactatggac      3720
acgggtaaaa tcataccaaa agatattgcg ggaaatgcag tggctgaatc ttctccatta      3780
gaacataggg agagaatttt gttagcagtt cgtagttatc ttggagagaa tattgaatgg      3840
actaatgaaa atgtaaattt aactataaac tatttaaata acagattaaa aaaattataa      3900
aaaaattgaa aaaatggtgg aaacacttt ttcaattttt ttagatcttg agcaaaaggc      3960
cagcaaaagg ccaggaaccg taaaaggcc gcgttgctgg cgttttttcca taggctccgc      4020
cccctgacg agcatcacaa aaatcgacgc tcaagtcaga ggtggcgaaa cccgacagga      4080
```

```
ctataaagat accaggcgtt tccccctgga agctccctcg tgcgctctcc tgttccgacc    4140
ctgccgctta ccggatacct gtccgccttt ctcccttcgg aagcgtggc gctttctcat    4200 agctcacgct gtaggtatct cagttcggtg taggtcgttc gctccaagct gggctgtgtg    4260
cacgaacccc ccgttcagcc cgaccgctgc gccttatccg gtaactatcg tcttgagtcc    4320
aacccggtaa gacacgactt atcgccactg gcagcagcca ctggtaacag gattagcaga    4380
gcgaggtatg taggcggtgc tacagagttc ttgaagtggt ggcctaacta cggctacact    4440
agaagaacag tatttggtat ctgcgctctg ctgaagccag ttaccttcgg aaaaagagtt    4500
ggtagctctt gatccggcaa acaaaccacc gctggtagcg gtggtttttt tgtttgcaag    4560
cagcagatta cgcgcagaaa aaaggatct caagaagatc ctttgatctt ttctac        4616
```

<210> SEQ ID NO 16
<211> LENGTH: 4442
<212> TYPE: DNA
<213> ORGANISM: Artificial
<220> FEATURE:
<223> OTHER INFORMATION: phIFNg33

<400> SEQUENCE: 16

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca gaaacatgcg     300 ctagtatcat tgatgacaac atggactaag caaaagtgct tgtcccctga cccaagaagg     360
atgctttatg aattatttac gacaaaaaat ttcggctagt gctatcgcgg tgttgtcgac     420
ttgtgggttg attttggcgc caatgccggt ctttgcggat gattcaacgc catcttcaac     480
gccatcggat ggcagttaca ccacgactga tagcggtcag gacccgtacg tcaaggaagc     540
cgaaaacctg aagaagtact caacgccgg ccatagcgat gtcgccgata acggcaccct     600
gttcctgggc atcctgaaga actggaagga agagtccgac cgcaagatca tgcagtccca     660
gatcgtgagc ttctacttca agctgttcaa gaacttcaag gacgatcagt cgatccagaa     720
gtccgtggag accatcaagg aagacatgaa cgtcaagttc ttcaacagca acaagaagaa     780
gcgcgacgat ttcgagaagc tgaccaacta ctccgtgacc gatctgaacg tccagcgtaa     840
ggccatccac gagctgatcc aggtcatggc cgaactgtcc ccggccgcca agaccggcaa     900
gcgtaagcgt tcccagatgc tgttccgtgg ccgtcgcgcc tcccagcacc atcatcacca     960
ccactgacct tctgctcgta gcgattactt cgagcattac tgacgacaaa gaccccgacc    1020
gagatggtcg gggtcttttt gttgtggtgc tgtgacgtgt tgtccaaccg tattattccg    1080
gactagtcct ccaggacctc gtctacgagg cgctgagcga ggaatggcgc aaaagggacg    1140
gcgagatcag cgacccatgg gccaacgacg aggcggacgg ataccagccg ccctcatacg    1200
agccggtcaa ccccgaacgc aggactcccc agacgccctc cgatggcctg atctgacgtc    1260
cgaaaaaagg cgctgtgcgc cctttttaaa tcttttataa atcttttac attctttag     1320 cccctccgca gccttactct cccaacgggt ttcagccgaa acctacacca aaggggagc     1380 gaacctacac caaagggga gcgaacctac accaaagggg agcgaaccta caccaaaag     1440 gggagctata tacaccttt gttatttaag gtgcaagttg tgctatgctg aggccatgtc     1500
```

```
caatgagatc gtgaagttca gcaaccagtt caacaacgtc gcgctgaaga agttcgacgc    1560
cgtgcacctg gacgtgctca tggcgatcgc ctcaagggtg agggagaagg gcacggccac    1620
ggtggagttc tcgttcgagg agctgcgcgg cctcatgcga ttgaggaaga acctgaccaa    1680
caagcagctg gccgacaaga tcgtgcagac gaacgcgcgc ctgctggcgc tgaactacat    1740
gttcgaggat tcgggcaaga tcatccagtt cgcgctgttc acgaagttcg tcaccgaccc    1800
gcaggaggcg actctcgcgg ttggggtcaa cgaggagttc gcgttcctgc tcaacgacct    1860
gaccagccag ttcacgcgct tcgagctggc cgagttcgcc gacctcaaga gcaagtacgc    1920
caaggagttc taccgcaggg ccaagcagta ccgcagctcc ggaatctgga agatcggccg    1980
cgacgagttc tgccgactgc ttggcgttcc accgtcggca ataacccaga cacgatatct    2040
gaatcagaag gttcttcagc caattcagga ggagtgtggg cctctccttg gcctgaagat    2100
cgagcgccag tacgtgaaac gcaggctgtc gggcttcgtg ttcacattcg cccgcgagac    2160
ccctccggtg atcgacgcca ggcccgtgga ggcgaggaag acggacggcg acggcaaggg    2220
ccattggacg agcgttgccg ggtacggcga ggtgttcacg accacggcgt tgttcgacgt    2280
gacggccgcc cgggctcact tcgacggcac cgttgaagcc ggggagtgcc gtttctgcgc    2340
gtttgacgcg cgcaaccgcg aacatcatgc gcggaacgcc ggaaggctgt tctagcggcc    2400
gtgtccgcgc tctgggggcg gttgcgcctg ccatgggtcg atctgccgct gttcggcctc    2460
acgctggtct gtgcgctgcc tgatctccct gagcaggtcg gccttggtcc tgggggcgct    2520
tcgctcctcg aacgggccgc tctcccccag gtcctcgggc tcgctcaggt ccaacggctc    2580
gtcaccggac ggctcgggcc ggttctctcc ctgtgccggg ttctccgcct gtgcgcgttg    2640
ttcggccatg cgcagtgcga gggccttcac ctgttcgggg cttgtcgact cgattttcgt    2700
tcgtgaatac atgttataat aactataact aataacgtaa cgtgactggc aagagatatt    2760
tttaaaacaa tgaataggtt tacacttact ttagttttat ggaaatgaaa gatcatatca    2820
tatataatct agaataaaat taactaaaat aattattatc tagataaaaa atttagaagc    2880
caatgaaatc tataaataaa ctaaattaag tttatttaat taacaactat ggatataaaa    2940
taggtactaa tcaaaatagt gaggaggata tatttgaata catacgaaca aattaataaa    3000
gtgaaaaaaa tacttcggaa acatttaaaa aataaccta ttggtactta catgtttgga    3060
tcaggagttg agagtggact aaaaccaaat agtgatcttg acttttagt cgtcgtatct    3120
gaaccattga cagatcaaag taaagaaata cttatacaaa aaattagacc tatttcaaaa    3180
aaaataggag ataaaagcaa cttacgatat attgaattaa caattattat tcagcaagaa    3240
atggtaccgt ggaatcatcc tcccaaacaa gaatttattt atggagaatg gttacaagag    3300
ctttatgaac aaggatacat tcctcagaag gaattaaatt cagatttaac cataatgctt    3360
taccaagcaa aacgaaaaaa taaaagaata tacggaaatt atgacttaga ggaattacta    3420
cctgatattc cattttctga tgtgagaaga gccattatgg attcgtcaga ggaattaata    3480
gataattatc aggatgatga aaccaactct atattaactt tatgccgtat gattttaact    3540
atggacacgg gtaaaatcat accaaaagat attgcgggaa atgcagtggc tgaatcttct    3600
ccattagaac ataggagag aattttgtta gcagttcgta gttatcttgg agagaatatt    3660
gaatggacta atgaaaatgt aaatttaact ataaactatt taaataacag attaaaaaaa    3720
ttataaaaaa attgaaaaaa tggtggaaac acttttttca attttttag atcttgagca    3780
aaaggccagc aaaaggccag gaaccgtaaa aaggccgcgt tgctggcgtt tttccatagg    3840
ctccgccccc ctgacgagca tcacaaaaat cgacgctcaa gtcagaggtg gcgaaacccg    3900
```

```
acaggactat aaagatacca ggcgtttccc cctggaagct ccctcgtgcg ctctcctgtt    3960
ccgaccctgc cgcttaccgg atacctgtcc gcctttctcc cttcgggaag cgtggcgctt    4020
tctcatagct cacgctgtag gtatctcagt tcggtgtagg tcgttcgctc caagctgggc    4080
tgtgtgcacg aaccccccgt tcagcccgac cgctgcgcct tatccggtaa ctatcgtctt    4140
gagtccaacc cggtaagaca cgacttatcg ccactggcag cagccactgg taacaggatt    4200
agcagagcga ggtatgtagg cggtgctaca gagttcttga agtggtggcc taactacggc    4260
tacactagaa gaacagtatt tggtatctgc gctctgctga agccagttac cttcggaaaa    4320
agagttggta gctcttgatc cggcaaacaa accaccgctg gtagcggtgg ttttttgtt    4380 tgcaagcagc agattacgcg cagaaaaaaa ggatctcaag aagatccttt gatcttttct    4440
ac                                                                   4442

<210> SEQ ID NO 17
<211> LENGTH: 5697
<212> TYPE: DNA
<213> ORGANISM: Artificial
<220> FEATURE:
<223> OTHER INFORMATION: pHG-1

<400> SEQUENCE: 17
tagccggcat tttcgcgata cattccccgg aatgttgcgc aacggggaac gcgcaccaca      60
ccgcaaccac agtgcgccac gcccagtccg gccctgtgcg ctataatagg tcagttattc     120
gcgcgcgcgt ggcgccctct acaccccgag ccgcgaggac acgtggattc cggacggcca     180
tgccccacat ggcaaaccga gaacccgcac acctagcatt acaaggagag ccattatggc     240
gttgatgatg agcgttaaga ctattatttc cacatcagtg gcgattatcg ccacgggtgc     300
catgtttgcg tgcgtagccc cgtttgcctc tgccgattcc gcgcagacga gtgctgtggt     360
gtcctcacgt tctttcccga aggcgagttc ggtggaagtg cagctggtcg aatcgggcgg     420
cggcctggtg cagccgggcg gctccctgcg tctgtcgtgc gccgcctcgg gcttcaacat     480
caaggatacc tacatccact gggtgcgcca ggccccgggc aagggcctgg aatgggtggc     540
ccgtatctac ccgaccaacg gctacacccg ctacgccgat tccgtgaagg gccgcttcac     600
catctccgcc gataccagca gaacaccgc ctacctgcag atgaactccc tgcgcgccga     660
agataccgcc gtgtactact gctcgcgctg ggcggcgac ggcttctacg ccatggacta     720
ctggggccag ggcaccctgg tgaccgtgtc cagcggcggc ggcggctccg gcggcggcgg     780
ctcgggcggc ggcggctccg acatccagat gacccagtcc ccgtcgtccc tgagcgcctc     840
ggtgggcgat cgcgtgacca tcacctgccg cgcctcccag gatgtgaaca ccgccgtggc     900
ctggtaccag cagaagccgg gcaaggcccc gaagctgctg atctactcgg cctccttcct     960
gtactccggc gtgccgtccc gtttctccgg ctcccgctcg ggcaccgact tcaccctgac    1020
catctcgtcc ctgcagccgg aagacttcgc cacctactac tgccagcagc attacaccac    1080
cccgccgacc ttcggccagg gcaccaaggt ggaaatcaag catcatcatc atcatcactg    1140
accttctgct cgtagcgatt acttcgagca ttactgacga caaagacccc gaccgagatg    1200
gtcggggtct ttttgttgtg gtgctgtgac gtgttgtcca accgtattat tccgggatc    1260 cgtcttcctg ctggcctatg cattgggttc cgcagtgccc actccaggcg gtctgggcgg    1320
tgtggaagcg gcgctgacat tcgcgttcgt ggcggtcgga gtgccgcagg gcgtggcgct    1380
ttccgccact ttgctgcacc gcgtggtgtt ctactggctg cgcattccgc tgggcgcggc    1440
```

```
ggccatgaag tggcttgaca agcataatct tgtctgattc gtctatttc ataccccctt    1500
cggggaaata gatgtgaaaa cccttataaa acgcgggttt tcgcagaaac atgcgctagt   1560
atcattgatg acaacatgga ctaagcaaaa gtgcttgtcc cctgacccaa gaaggatgct   1620
ttatgaatta tttacgacaa aaaatttcgg ctagtgctat cgcggtgttg tcgacttgtg   1680
ggttgatttt ggcgccaatg ccggtctttg cggatgattc aacgccatct tcaacgccat   1740
cggatggcag ttacaccacg actgatagcg gtcaggaccc gtacgtcaag gaagccgaaa   1800
acctgaagaa gtacttcaac gccggccata gcgatgtcgc cgataacggc accctgttcc   1860
tgggcatcct gaagaactgg aaggaagagt ccgaccgcaa gatcatgcag tcccagatcg   1920
tgagcttcta cttcaagctg ttcaagaact tcaaggacga tcagtcgatc cagaagtccg   1980
tggagaccat caaggaagac atgaacgtca agttcttcaa cagcaacaag aagaagcgcg   2040
acgatttcga gaagctgacc aactactccg tgaccgatct gaacgtccag cgtaaggcca   2100
tccacgagct gatccaggtc atggccgaac tgtccccggc cgccaagacc ggcaagcgta   2160
agcgttccca gatgctgttc cgtggccgtc gcgcctccca gcaccatcat caccaccact   2220
gaccttctgc tcgtagcgat tacttcgagc attactgacg acaaagaccc cgaccgagat   2280
ggtcggggtc tttttgttgt ggtgctgtga cgtgttgtcc aaccgtatta ttccggacta   2340
gtcctccagg acctcgtcta cgaggcgctg agcgaggaat ggcgcaaaag ggacggcgag   2400
atcagcgacc catgggccaa cgacgaggcg gacggatacc agccgccctc atacgagccg   2460
gtcaaccccg aacgcaggac tccccagacg ccctccgatg gcctgatctg acgtccgaaa   2520
aaaggcgctg tgcgcccttt ttaaatcttt tataaatctt tttacattct tttagcccct   2580
ccgcagcctt actctcccaa cgggtttcag ccgaaaccta caccaaaagg ggagcgaacc   2640
tacaccaaaa ggggagcgaa cctacaccaa aaggggagcg aacctacacc aaaggggag    2700
ctatatacac cttttgttat ttaaggtgca agttgtgcta tgctgaggcc atgtccaatg   2760
agatcgtgaa gttcagcaac cagttcaaca acgtcgcgct gaagaagttc gacgccgtgc   2820
acctggacgt gctcatggcg atcgcctcaa gggtgaggga aagggcacg gccacggtgg    2880
agttctcgtt cgaggagctg cgcggcctca tgcgattgag gaagaacctg accaacaagc   2940
agctggccga caagatcgtg cagacgaacg cgcgcctgct ggcgctgaac tacatgttcg   3000
aggattcggg caagatcatc cagttcgcgc tgttcacgaa gttcgtcacc gacccgcagg   3060
aggcgactct cgcggttggg gtcaacgagg agttcgcgtt cctgctcaac gacctgacca   3120
gccagttcac gcgcttcgag ctggccgagt tcgccgacct caagagcaag tacgccaagg   3180
agttctaccg cagggccaag cagtaccgca gctccggaat ctggaagatc ggccgcgacg   3240
agttctgccg actgcttggc gttccaccgt cggcaataac ccagacacga tatctgaatc   3300
agaaggttct tcagccaatt caggaggagt gtgggcctct ccttggcctg aagatcgagc   3360
gccagtacgt gaaacgcagg ctgtcgggct tcgtgttcac attcgcccgc gagacccctc   3420
cggtgatcga cgccaggccc gtggaggcga ggaagacgga cggcgacggc aagggccatt   3480
ggacgagcgt tgccgggtac ggcgaggtgt tcacgaccac ggcgttgttc gacgtgacgg   3540
ccgcccgggc tcacttcgac ggcaccgttg aagccgggga gtgccgtttc tgcgcgtttg   3600
acgcgcgcaa ccgcgaacat catgcgcgga acgccggaag gctgttctag cggccgtgtc   3660
cgcgcctctg gggcggttgc gcctgccatg ggtcgatctg ccgctgttcg gcctcacgct   3720
ggtctgtgcg ctgcctgatc tccctgagca ggtcggcctt ggtcctgggg gcgcttcgct   3780
cctcgaacgg gccgctctcc cccaggtcct cgggctcgct caggtccaac ggctcgtcac   3840
```

-continued

```
cggacggctc gggccggttc tctccctgtg ccgggttctc cgcctgtgcg cgttgttcgg      3900
ccatgcgcag tgcgagggcc ttcacctgtt cggggcttgt cgactcgatt ttcgttcgtg      3960
aatacatgtt ataataacta taactaataa cgtaacgtga ctggcaagag atatttttaa      4020
aacaatgaat aggtttacac ttactttagt tttatggaaa tgaaagatca tatcatatat      4080
aatctagaat aaaattaact aaaataatta ttatctagat aaaaaattta gaagccaatg      4140
aaatctataa ataaactaaa ttaagtttat ttaattaaca actatggata taaaataggt      4200
actaatcaaa atagtgagga ggatatattt gaatacatac gaacaaatta ataaagtgaa      4260
aaaaatactt cggaaacatt taaaaaataa ccttattggt acttacatgt ttggatcagg      4320
agttgagagt ggactaaaac caaatagtga tcttgacttt ttagtcgtcg tatctgaacc      4380
attgacagat caaagtaaag aaatacttat acaaaaaatt agacctattt caaaaaaaat      4440
aggagataaa agcaacttac gatatattga attaacaatt attattcagc aagaaatggt      4500
accgtggaat catcctccca aacaagaatt tatttatgga gaatggttac aagagcttta      4560
tgaacaagga tacattcctc agaaggaatt aaattcagat ttaaccataa tgctttacca      4620
agcaaaacga aaaaataaaa gaatatacgg aaattatgac ttagaggaat tactacctga      4680
tattccattt tctgatgtga gaagagccat tatggattcg tcagaggaat aatagataa       4740 ttatcaggat gatgaaacca actctatatt aactttatgc cgtatgattt taactatgga      4800
cacgggtaaa atcataccaa agatattgc gggaaatgca gtggctgaat cttctccatt       4860
agaacatagg gagagaattt tgttagcagt tcgtagttat cttggagaga atattgaatg      4920
gactaatgaa aatgtaaatt taactataaa ctatttaaat aacagattaa aaaaattata      4980
aaaaaattga aaaatggtg gaaacacttt tttcaattt tttagatctt gagcaaaagg        5040
ccagcaaaag gccaggaacc gtaaaaaggc cgcgttgctg cgttttttcc ataggctccg      5100
cccccctgac gagcatcaca aaaatcgacg ctcaagtcag aggtggcgaa acccgacagg      5160
actataaaga taccaggcgt ttccccctgg aagctccctc gtgcgctctc ctgttccgac      5220
cctgccgctt accggatacc tgtccgcctt tctcccttcg ggaagcgtgg cgctttctca      5280
tagctcacgc tgtaggtatc tcagttcggt gtaggtcgtt cgctccaagc tgggctgtgt      5340
gcacgaaccc cccgttcagc ccgaccgctg cgccttatcc ggtaactatc gtcttgagtc      5400
caacccggta agacacgact tatcgccact ggcagcagcc actggtaaca ggattagcag      5460
agcgaggtat gtaggcggtg ctacagagtt cttgaagtgg tggcctaact acggctacac      5520
tagaagaaca gtatttggta tctgcgctct gctgaagcca gttaccttcg aaaaagagt       5580 tggtagctct tgatccggca aacaaaccac cgctggtagc ggtggttttt tgtttgcaa       5640 gcagcagatt acgcgcagaa aaaaggatc tcaagaagat cctttgatct tttctac         5697
```

<210> SEQ ID NO 18
<211> LENGTH: 33
<212> TYPE: DNA
<213> ORGANISM: Artificial
<220> FEATURE:
<223> OTHER INFORMATION: GA1_primer

<400> SEQUENCE: 18
gagcagaagg tcactgggag gcgcgacggc cac                                    33

<210> SEQ ID NO 19
<211> LENGTH: 21
<212> TYPE: DNA

```
<213> ORGANISM: Artificial
<220> FEATURE:
<223> OTHER INFORMATION: GA2_primer

<400> SEQUENCE: 19
agtgaccttc tgctcgtagc g                                              21

<210> SEQ ID NO 20
<211> LENGTH: 21
<212> TYPE: DNA
<213> ORGANISM: Artificial
<220> FEATURE:
<223> OTHER INFORMATION: GA5_primer_rev

<400> SEQUENCE: 20
ggtatgtagg cggtgctaca g                                              21

<210> SEQ ID NO 21
<211> LENGTH: 20
<212> TYPE: DNA
<213> ORGANISM: Artificial
<220> FEATURE:
<223> OTHER INFORMATION: GA6_primer

<400> SEQUENCE: 21
caccgcctac atacctcgct                                                20

<210> SEQ ID NO 22
<211> LENGTH: 25
<212> TYPE: DNA
<213> ORGANISM: Artificial
<220> FEATURE:
<223> OTHER INFORMATION: GA100_primer

<400> SEQUENCE: 22
cggtggtgcg ctcctcctcc cgtac                                          25

<210> SEQ ID NO 23
<211> LENGTH: 18
<212> TYPE: DNA
<213> ORGANISM: Artificial
<220> FEATURE:
<223> OTHER INFORMATION: GA101_primer

<400> SEQUENCE: 23
tcacagggcg atgatgcc                                                  18

<210> SEQ ID NO 24
<211> LENGTH: 28
<212> TYPE: DNA
<213> ORGANISM: Artificial
<220> FEATURE:
<223> OTHER INFORMATION: GA103_primer

<400> SEQUENCE: 24
aggagcgcac caccgaactc gccttcgg                                       28

<210> SEQ ID NO 25
<211> LENGTH: 39
<212> TYPE: DNA
<213> ORGANISM: Artificial
<220> FEATURE:
<223> OTHER INFORMATION: GA104_primer

<400> SEQUENCE: 25
atcatcgccc tgtgaaaccg cttctcattt ccatttgcg                           39
```

<210> SEQ ID NO 26
<211> LENGTH: 27
<212> TYPE: DNA
<213> ORGANISM: Artificial
<220> FEATURE:
<223> OTHER INFORMATION: GA113_primer

<400> SEQUENCE: 26
cggtgcacac tagtcctcca ggacctc                               27

<210> SEQ ID NO 27
<211> LENGTH: 25
<212> TYPE: DNA
<213> ORGANISM: Artificial
<220> FEATURE:
<223> OTHER INFORMATION: GA116_primer

<400> SEQUENCE: 27
gactagtgtg caccgaatcg cgctg                                 25

<210> SEQ ID NO 28
<211> LENGTH: 34
<212> TYPE: DNA
<213> ORGANISM: Artificial
<220> FEATURE:
<223> OTHER INFORMATION: IFNG1_primer

<400> SEQUENCE: 28
gaaggatgct ttatgcagga cccgtacgtc aagg                       34

<210> SEQ ID NO 29
<211> LENGTH: 34
<212> TYPE: DNA
<213> ORGANISM: Artificial
<220> FEATURE:
<223> OTHER INFORMATION: IFNG2_primer

<400> SEQUENCE: 29
catcatcacc accactgacc ttctgctcgt agcg                       34

<210> SEQ ID NO 30
<211> LENGTH: 36
<212> TYPE: DNA
<213> ORGANISM: Artificial
<220> FEATURE:
<223> OTHER INFORMATION: IFNG3_primer

<400> SEQUENCE: 30
gtggtggtga tgatggtgct gggaggcgcg acggcc                     36

<210> SEQ ID NO 31
<211> LENGTH: 19
<212> TYPE: DNA
<213> ORGANISM: Artificial
<220> FEATURE:
<223> OTHER INFORMATION: hIFNG4_primer

<400> SEQUENCE: 31
caggacccgt acgtcaagg                                        19

<210> SEQ ID NO 32
<211> LENGTH: 43
<212> TYPE: DNA
<213> ORGANISM: Artificial
<220> FEATURE:

<223> OTHER INFORMATION: SP69-ins_F1_primer

<400> SEQUENCE: 32
caagaaggat gctttatgaa ttatttacga caaaaatttt cgg             43

<210> SEQ ID NO 33
<211> LENGTH: 38
<212> TYPE: DNA
<213> ORGANISM: Artificial
<220> FEATURE:
<223> OTHER INFORMATION: SP69-ins_R2_primer

<400> SEQUENCE: 33
gacgtacggg tcctgaccgc tatcagtcgt ggtgtaac             38

<210> SEQ ID NO 34
<211> LENGTH: 24
<212> TYPE: DNA
<213> ORGANISM: Artificial
<220> FEATURE:
<223> OTHER INFORMATION: pCDshuttle_R1_primer

<400> SEQUENCE: 34
cataaagcat ccttcttggg tcag             24

<210> SEQ ID NO 35
<211> LENGTH: 22
<212> TYPE: DNA
<213> ORGANISM: Artificial
<220> FEATURE:
<223> OTHER INFORMATION: Hu-mCCL21-vecR1_primer

<400> SEQUENCE: 35
aaagcatcct tcttgggtca gg             22

<210> SEQ ID NO 36
<211> LENGTH: 30
<212> TYPE: DNA
<213> ORGANISM: Artificial
<220> FEATURE:
<223> OTHER INFORMATION: Ins-hPD-1scFv03-F1

<400> SEQUENCE: 36
caggtccagc tggtcgaatc gggcggcggc             30

<210> SEQ ID NO 37
<211> LENGTH: 36
<212> TYPE: DNA
<213> ORGANISM: Artificial
<220> FEATURE:
<223> OTHER INFORMATION: Ins-hPD-1scFv03-R1

<400> SEQUENCE: 37
acgagcagaa ggtcagtggt ggtgatgatg gtgctt             36

<210> SEQ ID NO 38
<211> LENGTH: 24
<212> TYPE: DNA
<213> ORGANISM: Artificial
<220> FEATURE:
<223> OTHER INFORMATION: TGA-Hu-Terminator-F

<400> SEQUENCE: 38
tgaccttctg ctcgtagcga ttac             24

<210> SEQ ID NO 39
<211> LENGTH: 36
<212> TYPE: DNA
<213> ORGANISM: Artificial
<220> FEATURE:
<223> OTHER INFORMATION: vec-SP7L20-R1

<400> SEQUENCE: 39
gaccagctgg acctgcaccg aactcgcctt cgggaa                                36

<210> SEQ ID NO 40
<211> LENGTH: 30
<212> TYPE: DNA
<213> ORGANISM: Artificial
<220> FEATURE:
<223> OTHER INFORMATION: Ins-hCTLA-4scFv02-F1

<400> SEQUENCE: 40
caggtccagc tggtcgaatc gggcggcggc                                        30

<210> SEQ ID NO 41
<211> LENGTH: 36
<212> TYPE: DNA
<213> ORGANISM: Artificial
<220> FEATURE:
<223> OTHER INFORMATION: Ins-hCTLA-4scFv02-R1

<400> SEQUENCE: 41
acgagcagaa ggtcagtgat gatgatgatg atgctt                                36

<210> SEQ ID NO 42
<211> LENGTH: 45
<212> TYPE: DNA
<213> ORGANISM: Artificial
<220> FEATURE:
<223> OTHER INFORMATION: hCTLA-4scFv02-FLAG-F1

<400> SEQUENCE: 42
gactacaagg acgacgacga caagtgacct tctgctcgta gcgat                      45

<210> SEQ ID NO 43
<211> LENGTH: 33
<212> TYPE: DNA
<213> ORGANISM: Artificial
<220> FEATURE:
<223> OTHER INFORMATION: hCTLA-4scFv02-FLAG-R1

<400> SEQUENCE: 43
gtcgtccttg tagtccttga tttccacctt ggt                                    33

<210> SEQ ID NO 44
<211> LENGTH: 30
<212> TYPE: DNA
<213> ORGANISM: Artificial
<220> FEATURE:
<223> OTHER INFORMATION: InF_pTB6 rep_F1

<400> SEQUENCE: 44
actagtcctc caggacctcg tctacgaggc                                        30

<210> SEQ ID NO 45
<211> LENGTH: 30
<212> TYPE: DNA
<213> ORGANISM: Artificial
<220> FEATURE:
<223> OTHER INFORMATION: InF_Hu Prom_F1

<400> SEQUENCE: 45
gtcttcctgc tggcctatgc attgggttcc                                30

<210> SEQ ID NO 46
<211> LENGTH: 35
<212> TYPE: DNA
<213> ORGANISM: Artificial
<220> FEATURE:
<223> OTHER INFORMATION: InF_Hu Term-Hu Prom_R1

<400> SEQUENCE: 46
ggccagcagg aagacccgga ataatacggt tggac                          35

<210> SEQ ID NO 47
<211> LENGTH: 35
<212> TYPE: DNA
<213> ORGANISM: Artificial
<220> FEATURE:
<223> OTHER INFORMATION: InF_Hu Term-pTB6_R1

<400> SEQUENCE: 47
tcctggagga ctagtccgga ataatacggt tggac                          35

<210> SEQ ID NO 48
<211> LENGTH: 25
<212> TYPE: DNA
<213> ORGANISM: Artificial
<220> FEATURE:
<223> OTHER INFORMATION: pTB6_Vec_F1

<400> SEQUENCE: 48
actagtcctc caggacctcg tctac                                     25

<210> SEQ ID NO 49
<211> LENGTH: 23
<212> TYPE: DNA
<213> ORGANISM: Artificial
<220> FEATURE:
<223> OTHER INFORMATION: Hu-term_Vec_R1

<400> SEQUENCE: 49
ccggaataat acggttggac aac                                       23

<210> SEQ ID NO 50
<211> LENGTH: 34
<212> TYPE: DNA
<213> ORGANISM: Artificial
<220> FEATURE:
<223> OTHER INFORMATION: Hu-HuT_ins_F1

<400> SEQUENCE: 50
accgtattat tccggggatc cgtcttcctg ctgg                           34

<210> SEQ ID NO 51
<211> LENGTH: 38
<212> TYPE: DNA
<213> ORGANISM: Artificial
<220> FEATURE:
<223> OTHER INFORMATION: HuT-pTB6_ins_R1

<400> SEQUENCE: 51
tcctggagga ctagtccgga ataatacggt tggacaac                       38

<210> SEQ ID NO 52
<211> LENGTH: 19

```
<212> TYPE: DNA
<213> ORGANISM: Artificial
<220> FEATURE:
<223> OTHER INFORMATION: Hu_Vec_F1

<400> SEQUENCE: 52
ggatccgtct tcctgctgg                                                19

<210> SEQ ID NO 53
<211> LENGTH: 25
<212> TYPE: DNA
<213> ORGANISM: Artificial
<220> FEATURE:
<223> OTHER INFORMATION: bHER2-His_Vec_R1

<400> SEQUENCE: 53
tcagtgatga tgatgatgat gcttg                                         25

<210> SEQ ID NO 54
<211> LENGTH: 37
<212> TYPE: DNA
<213> ORGANISM: Artificial
<220> FEATURE:
<223> OTHER INFORMATION: d0013+T_ins_F1

<400> SEQUENCE: 54
catcatcatc actgaaaccg cttctcattt ccatttg                            37

<210> SEQ ID NO 55
<211> LENGTH: 32
<212> TYPE: DNA
<213> ORGANISM: Artificial
<220> FEATURE:
<223> OTHER INFORMATION: d0013+T_ins_R1

<400> SEQUENCE: 55
caggaagacg gatccgtgca ccgaatcgcg ct                                 32

<210> SEQ ID NO 56
<211> LENGTH: 99
<212> TYPE: DNA
<213> ORGANISM: Bifidobacterium spp.
<220> FEATURE:
<221> NAME/KEY: CDS
<222> LOCATION: (1)..(99)
<223> OTHER INFORMATION:
<220> FEATURE:
<221> NAME/KEY: misc_feature
<223> OTHER INFORMATION: SP7

<400> SEQUENCE: 56 atg gcg ttg atg atg agc gtt aag act att att tcc aca tca gtg gcg    48
Met Ala Leu Met Met Ser Val Lys Thr Ile Ile Ser Thr Ser Val Ala
1               5                   10                  15 att atc gcc acg ggt gcc atg ttt gcg tgc gta gcc ccg ttt gcc tct    96
Ile Ile Ala Thr Gly Ala Met Phe Ala Cys Val Ala Pro Phe Ala Ser
            20                  25                  30 gcc                                                                99
Ala

<210> SEQ ID NO 57
<211> LENGTH: 33
<212> TYPE: PRT
<213> ORGANISM: Bifidobacterium spp.

<400> SEQUENCE: 57
```

```
Met Ala Leu Met Met Ser Val Lys Thr Ile Ser Thr Ser Val Ala
1               5                   10                  15

Ile Ile Ala Thr Gly Ala Met Phe Ala Cys Val Ala Pro Phe Ala Ser
            20                  25                  30

Ala

<210> SEQ ID NO 58
<211> LENGTH: 102
<212> TYPE: DNA
<213> ORGANISM: Bifidobacterium spp.
<220> FEATURE:
<221> NAME/KEY: CDS
<222> LOCATION: (1)..(102)
<223> OTHER INFORMATION:
<220> FEATURE:
<221> NAME/KEY: misc_feature
<223> OTHER INFORMATION: SP45

<400> SEQUENCE: 58 atg aag cac ctc tcc cac cgc acc atc gcc atc atc gtc gcg ttg ctc      48
Met Lys His Leu Ser His Arg Thr Ile Ala Ile Ile Val Ala Leu Leu
1               5                   10                  15 tcc acg ctg tca ctg gca ctt gcc gtc atc tcc ctt ccg cac cag gcg      96
Ser Thr Leu Ser Leu Ala Leu Ala Val Ile Ser Leu Pro His Gln Ala
            20                  25                  30 tac gca                                                             102
Tyr Ala

<210> SEQ ID NO 59
<211> LENGTH: 34
<212> TYPE: PRT
<213> ORGANISM: Bifidobacterium spp.

<400> SEQUENCE: 59

Met Lys His Leu Ser His Arg Thr Ile Ala Ile Ile Val Ala Leu Leu
1               5                   10                  15

Ser Thr Leu Ser Leu Ala Leu Ala Val Ile Ser Leu Pro His Gln Ala
            20                  25                  30

Tyr Ala

<210> SEQ ID NO 60
<211> LENGTH: 168
<212> TYPE: DNA
<213> ORGANISM: Bifidobacterium spp.
<220> FEATURE:
<221> NAME/KEY: CDS
<222> LOCATION: (1)..(168)
<223> OTHER INFORMATION:
<220> FEATURE:
<221> NAME/KEY: misc_feature
<223> OTHER INFORMATION: SP50

<400> SEQUENCE: 60 atg atc gtg gcc tac ccg cac aca gtg cag tat gcg ggg aaa cgt acc      48
Met Ile Val Ala Tyr Pro His Thr Val Gln Tyr Ala Gly Lys Arg Thr
1               5                   10                  15 agg aaa gga cga atg atg ata acg aca tgg cgg caa cgg ggc atg gcc      96
Arg Lys Gly Arg Met Met Ile Thr Thr Trp Arg Gln Arg Gly Met Ala
            20                  25                  30 atc gta gcg atg ctg acc ggt ctg ata ata atg gtg gga gtg gtg ttc     144
Ile Val Ala Met Leu Thr Gly Leu Ile Ile Met Val Gly Val Val Phe
        35                  40                  45 ggc tcg gcg aat acg gcg tat gcc                                     168
Gly Ser Ala Asn Thr Ala Tyr Ala
```

```
        50               55

<210> SEQ ID NO 61
<211> LENGTH: 56
<212> TYPE: PRT
<213> ORGANISM: Bifidobacterium spp.

<400> SEQUENCE: 61

Met Ile Val Ala Tyr Pro His Thr Val Gln Tyr Ala Gly Lys Arg Thr
1               5                   10                  15

Arg Lys Gly Arg Met Met Ile Thr Thr Trp Arg Gln Arg Gly Met Ala
            20                  25                  30

Ile Val Ala Met Leu Thr Gly Leu Ile Ile Met Val Gly Val Val Phe
        35                  40                  45

Gly Ser Ala Asn Thr Ala Tyr Ala
    50                  55

<210> SEQ ID NO 62
<211> LENGTH: 105
<212> TYPE: DNA
<213> ORGANISM: Bifidobacterium spp.
<220> FEATURE:
<221> NAME/KEY: CDS
<222> LOCATION: (1)..(105)
<223> OTHER INFORMATION:
<220> FEATURE:
<221> NAME/KEY: misc_feature
<223> OTHER INFORMATION: SP52

<400> SEQUENCE: 62 atg agt ttc cat gta tcc gcg caa tcg gtt cgc gcg gtg gcc ggt gga    48
Met Ser Phe His Val Ser Ala Gln Ser Val Arg Ala Val Ala Gly Gly
1               5                   10                  15 ctc gtc gcc gca gcg aca ttg ctg tca ggc ctt gcc ctt gcg ccg acc    96
Leu Val Ala Ala Ala Thr Leu Leu Ser Gly Leu Ala Leu Ala Pro Thr
            20                  25                  30 gca atg gcc                                                        105
Ala Met Ala
        35

<210> SEQ ID NO 63
<211> LENGTH: 35
<212> TYPE: PRT
<213> ORGANISM: Bifidobacterium spp.

<400> SEQUENCE: 63

Met Ser Phe His Val Ser Ala Gln Ser Val Arg Ala Val Ala Gly Gly
1               5                   10                  15

Leu Val Ala Ala Ala Thr Leu Leu Ser Gly Leu Ala Leu Ala Pro Thr
            20                  25                  30

Ala Met Ala
        35

<210> SEQ ID NO 64
<211> LENGTH: 144
<212> TYPE: DNA
<213> ORGANISM: Bifidobacterium spp.
<220> FEATURE:
<221> NAME/KEY: CDS
<222> LOCATION: (1)..(144)
<223> OTHER INFORMATION:
<220> FEATURE:
<221> NAME/KEY: misc_feature
<223> OTHER INFORMATION: SP55
```

```
<400> SEQUENCE: 64 atg gtt cgt cgc gcc cag gct gct ctt cgg tcc gtt gaa cac acc agc     48
Met Val Arg Arg Ala Gln Ala Ala Leu Arg Ser Val Glu His Thr Ser
 1               5                  10                  15 gtg agg cag ctg cga gtc ctg gct gcg att gta ttt ctg ttc gcc atg     96
Val Arg Gln Leu Arg Val Leu Ala Ala Ile Val Phe Leu Phe Ala Met
             20                  25                  30 gtc atc gcc act gtg gct cct gca gtc acg gct ccg atg gcc ttc gcc    144
Val Ile Ala Thr Val Ala Pro Ala Val Thr Ala Pro Met Ala Phe Ala
         35                  40                  45

<210> SEQ ID NO 65
<211> LENGTH: 48
<212> TYPE: PRT
<213> ORGANISM: Bifidobacterium spp.

<400> SEQUENCE: 65

Met Val Arg Arg Ala Gln Ala Ala Leu Arg Ser Val Glu His Thr Ser
 1               5                  10                  15

Val Arg Gln Leu Arg Val Leu Ala Ala Ile Val Phe Leu Phe Ala Met
             20                  25                  30

Val Ile Ala Thr Val Ala Pro Ala Val Thr Ala Pro Met Ala Phe Ala
         35                  40                  45

<210> SEQ ID NO 66
<211> LENGTH: 96
<212> TYPE: DNA
<213> ORGANISM: Bifidobacterium spp.
<220> FEATURE:
<221> NAME/KEY: CDS
<222> LOCATION: (1)..(96)
<223> OTHER INFORMATION:
<220> FEATURE:
<221> NAME/KEY: misc_feature
<223> OTHER INFORMATION: SP58

<400> SEQUENCE: 66 atg gca atg gca cgg cgt tgg acc ccg cag cgg ttt gtt aca ctg cgt     48
Met Ala Met Ala Arg Arg Trp Thr Pro Gln Arg Phe Val Thr Leu Arg
 1               5                  10                  15 cgc atc cgc gta atc gcc tgt atc gcg gcg acc agt atc gcg ctg gct     96
Arg Ile Arg Val Ile Ala Cys Ile Ala Ala Thr Ser Ile Ala Leu Ala
             20                  25                  30

<210> SEQ ID NO 67
<211> LENGTH: 32
<212> TYPE: PRT
<213> ORGANISM: Bifidobacterium spp.

<400> SEQUENCE: 67

Met Ala Met Ala Arg Arg Trp Thr Pro Gln Arg Phe Val Thr Leu Arg
 1               5                  10                  15

Arg Ile Arg Val Ile Ala Cys Ile Ala Ala Thr Ser Ile Ala Leu Ala
             20                  25                  30

<210> SEQ ID NO 68
<211> LENGTH: 93
<212> TYPE: DNA
<213> ORGANISM: Bifidobacterium spp.
<220> FEATURE:
<221> NAME/KEY: CDS
<222> LOCATION: (1)..(93)
<223> OTHER INFORMATION:
<220> FEATURE:
<221> NAME/KEY: misc_feature
```

<223> OTHER INFORMATION: SP64

<400> SEQUENCE: 68

```
atg aag tca cta atc agg aat gta gcg gcg ggc gtc ctc gca gcc gcc    48
Met Lys Ser Leu Ile Arg Asn Val Ala Ala Gly Val Leu Ala Ala Ala
1               5                   10                  15 acg atg ctc ggc atc gcc ggc ctc ggc gcc acc acc gcc tcc gcg        93
Thr Met Leu Gly Ile Ala Gly Leu Gly Ala Thr Thr Ala Ser Ala
            20                  25                  30
```

<210> SEQ ID NO 69
<211> LENGTH: 31
<212> TYPE: PRT
<213> ORGANISM: Bifidobacterium spp.

<400> SEQUENCE: 69

```
Met Lys Ser Leu Ile Arg Asn Val Ala Ala Gly Val Leu Ala Ala Ala
1               5                   10                  15

Thr Met Leu Gly Ile Ala Gly Leu Gly Ala Thr Thr Ala Ser Ala
            20                  25                  30
```

<210> SEQ ID NO 70
<211> LENGTH: 78
<212> TYPE: DNA
<213> ORGANISM: Bifidobacterium spp.
<220> FEATURE:
<221> NAME/KEY: CDS
<222> LOCATION: (1)..(78)
<223> OTHER INFORMATION:
<220> FEATURE:
<221> NAME/KEY: misc_feature
<223> OTHER INFORMATION: SP66

<400> SEQUENCE: 70

```
gtg aag cat tgg aag aag atg gca gca tcg ttg att gca ata tca acg    48
Val Lys His Trp Lys Lys Met Ala Ala Ser Leu Ile Ala Ile Ser Thr
1               5                   10                  15 atg gtg gca gta gtt ccg acg acg tat gcc                            78
Met Val Ala Val Val Pro Thr Thr Tyr Ala
            20                  25
```

<210> SEQ ID NO 71
<211> LENGTH: 26
<212> TYPE: PRT
<213> ORGANISM: Bifidobacterium spp.

<400> SEQUENCE: 71

```
Val Lys His Trp Lys Lys Met Ala Ala Ser Leu Ile Ala Ile Ser Thr
1               5                   10                  15

Met Val Ala Val Val Pro Thr Thr Tyr Ala
            20                  25
```

<210> SEQ ID NO 72
<211> LENGTH: 99
<212> TYPE: DNA
<213> ORGANISM: Bifidobacterium spp.
<220> FEATURE:
<221> NAME/KEY: CDS
<222> LOCATION: (1)..(99)
<223> OTHER INFORMATION:
<220> FEATURE:
<221> NAME/KEY: misc_feature
<223> OTHER INFORMATION: SP67

<400> SEQUENCE: 72

```
atg aag ata aac aat aag ggc aag ggc gct ctt atc gcg gca att acc    48
```

```
Met Lys Ile Asn Asn Lys Gly Lys Gly Ala Leu Ile Ala Ala Ile Thr
1               5                   10                  15 gcc gcg gca acg cta ttg tca tgc ggg ctg gcc gct gca agt gcc agt        96
Ala Ala Ala Thr Leu Leu Ser Cys Gly Leu Ala Ala Ala Ser Ala Ser
                20                  25                  30 gcg                                                                     99
Ala

<210> SEQ ID NO 73
<211> LENGTH: 33
<212> TYPE: PRT
<213> ORGANISM: Bifidobacterium spp.

<400> SEQUENCE: 73

Met Lys Ile Asn Asn Lys Gly Lys Gly Ala Leu Ile Ala Ala Ile Thr
1               5                   10                  15

Ala Ala Ala Thr Leu Leu Ser Cys Gly Leu Ala Ala Ala Ser Ala Ser
                20                  25                  30

Ala

<210> SEQ ID NO 74
<211> LENGTH: 129
<212> TYPE: DNA
<213> ORGANISM: Bifidobacterium spp.
<220> FEATURE:
<221> NAME/KEY: CDS
<222> LOCATION: (1)..(129)
<223> OTHER INFORMATION:
<220> FEATURE:
<221> NAME/KEY: misc_feature
<223> OTHER INFORMATION: SP68

<400> SEQUENCE: 74 atg gtt tat aac att cac ata ttg caa aca agg aaa acc ggt cgt gtg        48
Met Val Tyr Asn Ile His Ile Leu Gln Thr Arg Lys Thr Gly Arg Val
1               5                   10                  15 gtt gct gct gcg gct gca tcc gtg ctg tgt tgc atg ggg gct gta ttt        96
Val Ala Ala Ala Ala Ala Ser Val Leu Cys Cys Met Gly Ala Val Phe
                20                  25                  30 cca gcg act atc gga gtg act gcg gcg tcg gcc                           129
Pro Ala Thr Ile Gly Val Thr Ala Ala Ser Ala
        35                  40

<210> SEQ ID NO 75
<211> LENGTH: 43
<212> TYPE: PRT
<213> ORGANISM: Bifidobacterium spp.

<400> SEQUENCE: 75

Met Val Tyr Asn Ile His Ile Leu Gln Thr Arg Lys Thr Gly Arg Val
1               5                   10                  15

Val Ala Ala Ala Ala Ala Ser Val Leu Cys Cys Met Gly Ala Val Phe
                20                  25                  30

Pro Ala Thr Ile Gly Val Thr Ala Ala Ser Ala
        35                  40

<210> SEQ ID NO 76
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
```

```
<220> FEATURE:
<221> NAME/KEY: misc_feature
<223> OTHER INFORMATION: SP69

<400> SEQUENCE: 76 atg aat tat tta cga caa aaa att tcg gct agt gct atc gcg gtg ttg      48
Met Asn Tyr Leu Arg Gln Lys Ile Ser Ala Ser Ala Ile Ala Val Leu
1               5                   10                  15 tcg act tgt ggg ttg att ttg gcg cca atg ccg gtc ttt gcg              90
Ser Thr Cys Gly Leu Ile Leu Ala Pro Met Pro Val Phe Ala
            20                  25                  30

<210> SEQ ID NO 77
<211> LENGTH: 30
<212> TYPE: PRT
<213> ORGANISM: Bifidobacterium spp.

<400> SEQUENCE: 77

Met Asn Tyr Leu Arg Gln Lys Ile Ser Ala Ser Ala Ile Ala Val Leu
1               5                   10                  15

Ser Thr Cys Gly Leu Ile Leu Ala Pro Met Pro Val Phe Ala
            20                  25                  30

<210> SEQ ID NO 78
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP7)

<400> SEQUENCE: 78 gat tcc gcg cag acg agt gct gtg gtg tcc tca cgt tct ttc ccg aag      48
Asp Ser Ala Gln Thr Ser Ala Val Val Ser Ser Arg Ser Phe Pro Lys
1               5                   10                  15 gcg agt tcg gtg aag aag aat ttg ttc gcc gaa tcc acc tcc              90
Ala Ser Ser Val Lys Lys Asn Leu Phe Ala Glu Ser Thr Ser
            20                  25                  30

<210> SEQ ID NO 79
<211> LENGTH: 30
<212> TYPE: PRT
<213> ORGANISM: Bifidobacterium spp.

<400> SEQUENCE: 79

Asp Ser Ala Gln Thr Ser Ala Val Val Ser Ser Arg Ser Phe Pro Lys
1               5                   10                  15

Ala Ser Ser Val Lys Lys Asn Leu Phe Ala Glu Ser Thr Ser
            20                  25                  30

<210> SEQ ID NO 80
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP45)

<400> SEQUENCE: 80
```

```
gtc gac ggc aca gac ggc aca agc ggc acg aac agt acg tct cag gga        48
Val Asp Gly Thr Asp Gly Thr Ser Gly Thr Asn Ser Thr Ser Gln Gly
1               5                   10                  15 agc gac ggc gat tcc gcg cca atc gcc ggc ccg gtg ccg aac              90
Ser Asp Gly Asp Ser Ala Pro Ile Ala Gly Pro Val Pro Asn
            20                  25                  30
```

<210> SEQ ID NO 81
<211> LENGTH: 30
<212> TYPE: PRT
<213> ORGANISM: Bifidobacterium spp.

<400> SEQUENCE: 81

```
Val Asp Gly Thr Asp Gly Thr Ser Gly Thr Asn Ser Thr Ser Gln Gly
1               5                   10                  15

Ser Asp Gly Asp Ser Ala Pro Ile Ala Gly Pro Val Pro Asn
            20                  25                  30
```

<210> SEQ ID NO 82
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP50)

<400> SEQUENCE: 82

```
gcg acg ttg acg ccc gcc gac gaa aga tat cac gtg gcg ttt cca tac        48
Ala Thr Leu Thr Pro Ala Asp Glu Arg Tyr His Val Ala Phe Pro Tyr
1               5                   10                  15 aac gat atg gaa tat tac gtc ggt gtc gcg ggg ctg gac gct              90
Asn Asp Met Glu Tyr Tyr Val Gly Val Ala Gly Leu Asp Ala
            20                  25                  30
```

<210> SEQ ID NO 83
<211> LENGTH: 30
<212> TYPE: PRT
<213> ORGANISM: Bifidobacterium spp.

<400> SEQUENCE: 83

```
Ala Thr Leu Thr Pro Ala Asp Glu Arg Tyr His Val Ala Phe Pro Tyr
1               5                   10                  15

Asn Asp Met Glu Tyr Tyr Val Gly Val Ala Gly Leu Asp Ala
            20                  25                  30
```

<210> SEQ ID NO 84
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP52)

<400> SEQUENCE: 84

```
gcc gat tca gcc acc gct gac aac gcg ccc agc gtt gcc ggt cac gcg        48
Ala Asp Ser Ala Thr Ala Asp Asn Ala Pro Ser Val Ala Gly His Ala
1               5                   10                  15
```

```
tat aac gaa ctg ccg tat aac aat cct gat gtc acc gtc acc        90
Tyr Asn Glu Leu Pro Tyr Asn Asn Pro Asp Val Thr Val Thr
             20                  25                  30
```

<210> SEQ ID NO 85
<211> LENGTH: 30
<212> TYPE: PRT
<213> ORGANISM: Bifidobacterium spp.

<400> SEQUENCE: 85

```
Ala Asp Ser Ala Thr Ala Asp Asn Ala Pro Ser Val Ala Gly His Ala
1               5                   10                  15

Tyr Asn Glu Leu Pro Tyr Asn Asn Pro Asp Val Thr Val Thr
             20                  25                  30
```

<210> SEQ ID NO 86
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP55)

<400> SEQUENCE: 86

```
gac agc agc acc agc tcg tcc agt tca tca agc tcg tcc agc gtt gac        48
Asp Ser Ser Thr Ser Ser Ser Ser Ser Ser Ser Ser Ser Ser Val Asp
1               5                   10                  15 tac gcc acc tgg gcc gaa gtc tcc aag gcg atg gac aag cag                90
Tyr Ala Thr Trp Ala Glu Val Ser Lys Ala Met Asp Lys Gln
             20                  25                  30
```

<210> SEQ ID NO 87
<211> LENGTH: 30
<212> TYPE: PRT
<213> ORGANISM: Bifidobacterium spp.

<400> SEQUENCE: 87

```
Asp Ser Ser Thr Ser Ser Ser Ser Ser Ser Ser Ser Ser Ser Val Asp
1               5                   10                  15

Tyr Ala Thr Trp Ala Glu Val Ser Lys Ala Met Asp Lys Gln
             20                  25                  30
```

<210> SEQ ID NO 88
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP58)

<400> SEQUENCE: 88

```
gga tca ttc gcg ttc acc gcg cgt aaa tcc gtg gcc ctg aac atc aac        48
Gly Ser Phe Ala Phe Thr Ala Arg Lys Ser Val Ala Leu Asn Ile Asn
1               5                   10                  15 ggg caa acc acc caa gtc acc aca tat gcg atg acg gcc acc                90
Gly Gln Thr Thr Gln Val Thr Thr Tyr Ala Met Thr Ala Thr
             20                  25                  30
```

```
<210> SEQ ID NO 89
<211> LENGTH: 30
<212> TYPE: PRT
<213> ORGANISM: Bifidobacterium spp.

<400> SEQUENCE: 89

Gly Ser Phe Ala Phe Thr Ala Arg Lys Ser Val Ala Leu Asn Ile Asn
1               5                   10                  15

Gly Gln Thr Thr Gln Val Thr Thr Tyr Ala Met Thr Ala Thr
            20                  25                  30

<210> SEQ ID NO 90
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP64)

<400> SEQUENCE: 90 gaa gat gct acc ggc acg ctg acc gtc acc agc tcg gat gcc gcg ttc      48
Glu Asp Ala Thr Gly Thr Leu Thr Val Thr Ser Ser Asp Ala Ala Phe
1               5                   10                  15 aac ggc aag aag gtg aac gcc tac cag atg ttc tcc gct tcc              90
Asn Gly Lys Lys Val Asn Ala Tyr Gln Met Phe Ser Ala Ser
            20                  25                  30

<210> SEQ ID NO 91
<211> LENGTH: 30
<212> TYPE: PRT
<213> ORGANISM: Bifidobacterium spp.

<400> SEQUENCE: 91

Glu Asp Ala Thr Gly Thr Leu Thr Val Thr Ser Ser Asp Ala Ala Phe
1               5                   10                  15

Asn Gly Lys Lys Val Asn Ala Tyr Gln Met Phe Ser Ala Ser
            20                  25                  30

<210> SEQ ID NO 92
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP66)

<400> SEQUENCE: 92 atg gaa tcg gaa gat tcc caa cca cag aca acc gat acc gcg aca gtg      48
Met Glu Ser Glu Asp Ser Gln Pro Gln Thr Thr Asp Thr Ala Thr Val
1               5                   10                  15 cag act act aag gct gct gaa ccg acg ctg ctc gcc agc tgg              90
Gln Thr Thr Lys Ala Ala Glu Pro Thr Leu Leu Ala Ser Trp
            20                  25                  30

<210> SEQ ID NO 93
<211> LENGTH: 30
<212> TYPE: PRT
<213> ORGANISM: Bifidobacterium spp.
```

<400> SEQUENCE: 93

Met Glu Ser Glu Asp Ser Gln Pro Gln Thr Thr Asp Thr Ala Thr Val
1               5                   10                  15

Gln Thr Thr Lys Ala Ala Glu Pro Thr Leu Leu Ala Ser Trp
            20                  25                  30

<210> SEQ ID NO 94
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP67)

<400> SEQUENCE: 94 gca ggt gtg gat tac ctg cct acc atc ggc caa gtg ccg aca tac acc    48
Ala Gly Val Asp Tyr Leu Pro Thr Ile Gly Gln Val Pro Thr Tyr Thr
1               5                   10                  15 aag ttc cag ccc aca gcc gat ccg ggc aag aac gct agc gat              90
Lys Phe Gln Pro Thr Ala Asp Pro Gly Lys Asn Ala Ser Asp
            20                  25                  30

<210> SEQ ID NO 95
<211> LENGTH: 30
<212> TYPE: PRT
<213> ORGANISM: Bifidobacterium spp.

<400> SEQUENCE: 95

Ala Gly Val Asp Tyr Leu Pro Thr Ile Gly Gln Val Pro Thr Tyr Thr
1               5                   10                  15

Lys Phe Gln Pro Thr Ala Asp Pro Gly Lys Asn Ala Ser Asp
            20                  25                  30

<210> SEQ ID NO 96
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP68)

<400> SEQUENCE: 96 gat gaa ccc gtc gaa ttg gtc gtc aac ggc gga ttc gaa gac gat ctt    48
Asp Glu Pro Val Glu Leu Val Val Asn Gly Gly Phe Glu Asp Asp Leu
1               5                   10                  15 aat ggt tgg aag tct gga acg gtg tgg aat agc tcc gca tcg              90
Asn Gly Trp Lys Ser Gly Thr Val Trp Asn Ser Ser Ala Ser
            20                  25                  30

<210> SEQ ID NO 97
<211> LENGTH: 30
<212> TYPE: PRT
<213> ORGANISM: Bifidobacterium spp.

<400> SEQUENCE: 97

Asp Glu Pro Val Glu Leu Val Val Asn Gly Gly Phe Glu Asp Asp Leu
1               5                   10                  15

```
Asn Gly Trp Lys Ser Gly Thr Val Trp Asn Ser Ser Ala Ser
             20                  25                  30

<210> SEQ ID NO 98
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION:
<220> FEATURE:
<221> NAME/KEY: misc_feature
<223> OTHER INFORMATION: Linker peptide (SP69)

<400> SEQUENCE: 98 gat gat tca acg cca tct tca acg cca tcg gat ggc agt tac acc acg     48
Asp Asp Ser Thr Pro Ser Ser Thr Pro Ser Asp Gly Ser Tyr Thr Thr
1               5                   10                  15 act gat agc ggt gat ggc acg tat tcc att ccc atg ttg aac             90
Thr Asp Ser Gly Asp Gly Thr Tyr Ser Ile Pro Met Leu Asn
             20                  25              30

<210> SEQ ID NO 99
<211> LENGTH: 30
<212> TYPE: PRT
<213> ORGANISM: Bifidobacterium spp.

<400> SEQUENCE: 99

Asp Asp Ser Thr Pro Ser Ser Thr Pro Ser Asp Gly Ser Tyr Thr Thr
1               5                   10                  15

Thr Asp Ser Gly Asp Gly Thr Tyr Ser Ile Pro Met Leu Asn
             20                  25              30

<210> SEQ ID NO 100
<211> LENGTH: 5697
<212> TYPE: DNA
<213> ORGANISM: Artificial
<220> FEATURE:
<223> OTHER INFORMATION: pHG-2

<400> SEQUENCE: 100
tagccggcat tttcgcgata cattccccgg aatgttgcgc aacggggaac gcgcaccaca    60
ccgcaaccac agtgcgccac gcccagtccg gccctgtgcg ctataatagg tcagttattc   120
gcgcgcgcgt ggcgccctct acaccccgag ccgcgaggac acgtggattc cggacggcca   180
tgccccacat ggcaaaccga gaacccgcac acctagcatt acaaggagag ccattatggc   240
gttgatgatg agcgttaaga ctattatttc cacatcagtg gcgattatcg ccacgggtgc   300
catgtttgcg tgcgtagccc cgtttgcctc tgccgattcc gcgcagacga gtgctgtggt   360
gtcctcacgt tctttcccga aggcgagttc ggtggaagtg cagctggtcg aatcgggcgg   420
cggcctggtg cagccgggcg gctccctgcg tctgtcgtgc gccgcctcgg gcttcaacat   480
caaggatacc tacatccact gggtgcgcca ggccccgggc aagggcctgg aatgggtggc   540
ccgtatctac ccgaccaacg gctacacccg ctacgccgat tccgtgaagg gccgcttcac   600
catctccgcc gataccagca gaacaccgc ctacctgcag atgaactccc tgcgcgccga   660
agataccgcc gtgtactact gctcgcgctg gggcggcgac ggcttctacg ccatggacta   720
ctggggccag ggcaccctgg tgaccgtgtc cagcggcggc ggcggctccg gcggcggcgg   780
ctcgggcggc ggcggctccg acatccagat gacccagtcc ccgtcgtccc tgagcgcctc   840
ggtgggcgat cgcgtgacca tcacctgccg cgcctcccag gatgtgaaca ccgccgtggc   900
```

```
ctggtaccag cagaagccgg gcaaggcccc gaagctgctg atctactcgg cctccttcct    960
gtactccggc gtgccgtccc gtttctccgg ctcccgctcg ggcaccgact tcaccctgac   1020
catctcgtcc ctgcagccgg aagacttcgc cacctactac tgccagcagc attacaccac   1080
cccgccgacc ttcggccagg gcaccaaggt ggaaatcaag catcatcatc atcatcactg   1140
aaaccgcttc tcatttccat ttgcgatatg gtctgaatac gacgaaaccc cggcgcgagg   1200
ccggggtttc gtaagctgtg cgtgactata gcacgaccag cgcgattcgg tgcacggatc   1260
cgtcttcctg ctggcctatg cattgggttc cgcagtgccc actccaggcg gtctgggcgg   1320
tgtggaagcg cgcgctgaca tcgcgttcgt ggcggtcgga gtgccgcagg gcgtggcgct   1380
ttccgccact tgctgcaccg cgtggtgtt ctactggctg cgcattccgc tgggcgcggc    1440
ggccatgaag tggcttgaca agcataatct tgtctgattc gtctattttc ataccccctt   1500
cggggaaata gatgtgaaaa cccttataaa acgcgggttt tcgcagaaac atgcgctagt   1560
atcattgatg acaacatgga ctaagcaaaa gtgcttgtcc cctgacccaa gaaggatgct   1620
ttatgaatta tttacgacaa aaaatttcgg ctagtgctat cgcggtgttg tcgacttgtg   1680
ggttgatttt ggcgccaatg ccggtctttg cggatgattc aacgccatct tcaacgccat   1740
cggatggcag ttacaccacg actgatagcg gtcaggaccc gtacgtcaag gaagccgaaa   1800
acctgaagaa gtacttcaac gccggccata gcgatgtcgc cgataacggc accctgttcc   1860
tgggcatcct gaagaactgg aaggaagagt ccgaccgcaa gatcatgcag tcccagatcg   1920
tgagcttcta cttcaagctg ttcaagaact tcaaggacga tcagtcgatc cagaagtccg   1980
tggagaccat caaggaagac atgaacgtca agttcttcaa cagcaacaag aagaagcgcg   2040
acgatttcga gaagctgacc aactactccg tgaccgatct gaacgtccag cgtaaggcca   2100
tccacgagct gatccaggtc atggccgaac tgtccccggc cgccaagacc ggcaagcgta   2160
agcgttccca gatgctgttc cgtggccgtc gcgcctccca gcaccatcat caccaccact   2220
gaccttctgc tcgtagcgat tacttcgagc attactgacg acaaagaccc cgaccgagat   2280
ggtcggggtc tttttgttgt ggtgctgtga cgtgttgtcc aaccgtatta ttccggacta   2340
gtcctccagg acctcgtcta cgaggcgctg agcgaggaat ggcgcaaaag ggacggcgag   2400
atcagcgacc catgggccaa cgacgaggcg gacggatacc agccgccctc atacgagccg   2460
gtcaaccccg aacgcaggac tccccagacg ccctccgatg gcctgatctg acgtccgaaa   2520
aaaggcgctg tgcgcccttt ttaaatcttt tataaatctt tttacattct tttagcccct   2580
ccgcagcctt actctcccaa cgggtttcag ccgaaaccta caccaaaagg ggagcgaacc   2640
tacaccaaaa ggggagcgaa cctacaccaa aaggggagcg aacctacacc aaaaggggag   2700
ctatatacac cttttgttat ttaaggtgca agttgtgcta tgctgaggcc atgtccaatg   2760
agatcgtgaa gttcagcaac cagttcaaca acgtcgcgct gaagaagttc gacgccgtgc   2820
acctggacgt gctcatggcg atcgcctcaa gggtgaggga aagggcacg gccacggtgg    2880
agttctcgtt cgaggagctg cgcggcctca tgcgattgag gaagaacctg accaacaagc   2940
agctggccga caagatcgtg cagacgaacg cgcgcctgct ggcgctgaac tacatgttcg   3000
aggattcggg caagatcatc cagttcgcgc tgttcacgaa gttcgtcacc gacccgcagg   3060
aggcgactct cgcggttggg gtcaacgagg agttcgcgtt cctgctcaac gacctgacca   3120
gccagttcac gcgcttcgag ctggccgagt tcgccgacct caagagcaag tacgccaagg   3180
agttctaccg cagggccaag cagtaccgca gctccggaat ctggaagatc ggccgcgacg   3240
```

```
agttctgccg actgcttggc gttccaccgt cggcaataac ccagacacga tatctgaatc    3300
agaaggttct tcagccaatt caggaggagt gtgggcctct ccttggcctg aagatcgagc    3360
gccagtacgt gaaacgcagg ctgtcgggct tcgtgttcac attcgcccgc gagacccctc    3420
cggtgatcga cgccaggccc gtggaggcga ggaagacgga cggcgacggc aagggccatt    3480
ggacgagcgt tgccgggtac ggcgaggtgt tcacgaccac ggcgttgttc gacgtgacgg    3540
ccgcccgggc tcacttcgac ggcaccgttg aagccgggga gtgccgtttc tgcgcgtttg    3600
acgcgcgcaa ccgcgaacat catgcgcgga acgccggaag gctgttctag cggccgtgtc    3660
cgcgcctctg gggcggttgc gcctgccatg ggtcgatctg ccgctgttcg gcctcacgct    3720
ggtctgtgcg ctgcctgatc tccctgagca ggtcggcctt ggtcctgggg gcgcttcgct    3780
cctcgaacgg gccgctctcc cccaggtcct cgggctcgct caggtccaac ggctcgtcac    3840
cggacggctc gggccggttc tctccctgtg ccgggttctc cgcctgtgcg cgttgttcgg    3900
ccatgcgcag tgcgagggcc ttcacctgtt cggggcttgt cgactcgatt ttcgttcgtg    3960
aatacatgtt ataataacta taactaataa cgtaacgtga ctggcaagag atatttttaa    4020
aacaatgaat aggtttacac ttactttagt tttatggaaa tgaaagatca tatcatatat    4080
aatctagaat aaaattaact aaaataatta ttatctagat aaaaaattta gaagccaatg    4140
aaatctataa ataaactaaa ttaagtttat ttaattaaca actatggata taaaataggt    4200
actaatcaaa atagtgagga ggatatattt gaatacatac gaacaaatta ataaagtgaa    4260
aaaaatactt cggaaacatt taaaaaataa ccttattggt acttacatgt ttggatcagg    4320
agttgagagt ggactaaaac caaatagtga tcttgacttt ttagtcgtcg tatctgaacc    4380
attgacagat caaagtaaag aaatacttat acaaaaaatt agacctattt caaaaaaaat    4440
aggagataaa agcaacttac gatatattga attaacaatt attattcagc aagaaatggt    4500
accgtggaat catcctccca aacaagaatt tatttatgga gaatggttac aagagcttta    4560
tgaacaagga tacattcctc agaaggaatt aaattcagat ttaaccataa tgctttacca    4620
agcaaaacga aaaaataaaa gaatatacgg aaattatgac ttagaggaat tactacctga    4680 tattccatttt tctgatgtga gaagagccat tatggattcg tcagaggaat taatagataa    4740
ttatcaggat gatgaaacca actctatatt aactttatgc cgtatgattt taactatgga    4800
cacgggtaaa atcataccaa aagatattgc gggaaatgca gtggctgaat cttctccatt    4860
agaacatagg gagagaattt tgttagcagt tcgtagttat cttggagaga atattgaatg    4920
gactaatgaa aatgtaaatt taactataaa ctatttaaat aacagattaa aaaaattata    4980
aaaaaattga aaaaatggtg gaaacacttt tttcaatttt tttagatctt gagcaaaagg    5040
ccagcaaaag gccaggaacc gtaaaaaggc cgcgttgctg gcgttttttcc ataggctccg    5100 ccccccctgac gagcatcaca aaaatcgacg ctcaagtcag aggtggcgaa acccgacagg    5160
actataaaga taccaggcgt ttccccctgg aagctccctc gtgcgctctc ctgttccgac    5220
cctgccgctt accggatacc tgtccgcctt tctcccttcg ggaagcgtgg cgctttctca    5280
tagctcacgc tgtaggtatc tcagttcggt gtaggtcgtt cgctccaagc tgggctgtgt    5340
gcacgaaccc cccgttcagc ccgaccgctg cgccttatcc ggtaactatc gtcttgagtc    5400
caacccggta agacacgact tatcgccact ggcagcagcc actggtaaca ggattagcag    5460
agcgaggtat gtaggcggtg ctacagagtt cttgaagtgg tggcctaact acggctacac    5520
tagaagaaca gtatttggta tctgcgctct gctgaagcca gttaccttcg aaaaagagt    5580 tggtagctct tgatccggca aacaaaccac cgctggtagc ggtggttttt ttgtttgcaa    5640
```

```
gcagcagatt acgcgcagaa aaaaaggatc tcaagaagat cctttgatct tttctac    5697
```

<210> SEQ ID NO 101
<211> LENGTH: 129
<212> TYPE: DNA
<213> ORGANISM: Artificial
<220> FEATURE:
<223> OTHER INFORMATION: T2 terminator

<400> SEQUENCE: 101

```
ccaggcatca ataaaacga aaggctcagt cgaaagactg ggcctttcgt tttatctgtt    60
gtttgtcggt gaacgctctc tactagagtc acactggctc accttcgggt gggcctttct   120
gcgtttata                                                          129
```

<210> SEQ ID NO 102
<211> LENGTH: 22
<212> TYPE: DNA
<213> ORGANISM: Artificial
<220> FEATURE:
<223> OTHER INFORMATION: PC1_primer

<400> SEQUENCE: 102

```
actagtcctc caggacctcg tc                                            22
```

<210> SEQ ID NO 103
<211> LENGTH: 20
<212> TYPE: DNA
<213> ORGANISM: Artificial
<220> FEATURE:
<223> OTHER INFORMATION: PC2_primer

<400> SEQUENCE: 103

```
ccggaataat acggttggac                                               20
```

<210> SEQ ID NO 104
<211> LENGTH: 46
<212> TYPE: DNA
<213> ORGANISM: Artificial
<220> FEATURE:
<223> OTHER INFORMATION: PC3_primer

<400> SEQUENCE: 104

```
accgtattat tccggccagg catcaaataa acgaaaggc tcagtc                   46
```

<210> SEQ ID NO 105
<211> LENGTH: 36
<212> TYPE: DNA
<213> ORGANISM: Artificial
<220> FEATURE:
<223> OTHER INFORMATION: PC4_primer

<400> SEQUENCE: 105

```
tcctggagga ctagttataa acgcagaaag gcccac                             36
```

<210> SEQ ID NO 106
<211> LENGTH: 34
<212> TYPE: DNA
<213> ORGANISM: Artificial
<220> FEATURE:
<223> OTHER INFORMATION: vec_F5_primer

<400> SEQUENCE: 106

```
acaaggagag ccattatggc gttgatgatg agcg                               34
```

<210> SEQ ID NO 107
<211> LENGTH: 43
<212> TYPE: DNA
<213> ORGANISM: Artificial
<220> FEATURE:
<223> OTHER INFORMATION: vec_R2_primer

<400> SEQUENCE: 107
ggctaggatc cgtagaaaag atcaaaggat cttcttgaga tcc       43

<210> SEQ ID NO 108
<211> LENGTH: 36
<212> TYPE: DNA
<213> ORGANISM: Artificial
<220> FEATURE:
<223> OTHER INFORMATION: P30_F1_primer

<400> SEQUENCE: 108
ctacggatcc tagccggcat tttcgcgata cattcc       36

<210> SEQ ID NO 109
<211> LENGTH: 24
<212> TYPE: DNA
<213> ORGANISM: Artificial
<220> FEATURE:
<223> OTHER INFORMATION: P30_R1_primer

<400> SEQUENCE: 109
aatggctctc cttgtaatgc tagg       24

<210> SEQ ID NO 110
<211> LENGTH: 21
<212> TYPE: DNA
<213> ORGANISM: Artificial
<220> FEATURE:
<223> OTHER INFORMATION: hCTLA3_primer

<400> SEQUENCE: 110
caggtccagc tggtcgaatc g       21

<210> SEQ ID NO 111
<211> LENGTH: 33
<212> TYPE: DNA
<213> ORGANISM: Artificial
<220> FEATURE:
<223> OTHER INFORMATION: SP50-ins_F2_primer

<400> SEQUENCE: 111
acaaggagag ccattatgat cgtggcctac ccg       33

<210> SEQ ID NO 112
<211> LENGTH: 39
<212> TYPE: DNA
<213> ORGANISM: Artificial
<220> FEATURE:
<223> OTHER INFORMATION: SP50-ins_R6_primer

<400> SEQUENCE: 112
gaccagctgg acctgttcca tatcgttgta tggaaacgc       39

<210> SEQ ID NO 113
<211> LENGTH: 40
<212> TYPE: DNA
<213> ORGANISM: Artificial
<220> FEATURE:
<223> OTHER INFORMATION: SP67-ins_F2_primer

<400> SEQUENCE: 113
acaaggagag ccattatgaa gataaacaat aagggcaagg         40

<210> SEQ ID NO 114
<211> LENGTH: 37
<212> TYPE: DNA
<213> ORGANISM: Artificial
<220> FEATURE:
<223> OTHER INFORMATION: SP67-ins_R6_primer

<400> SEQUENCE: 114
gaccagctgg acctggggct ggaacttggt gtatgtc         37

<210> SEQ ID NO 115
<211> LENGTH: 44
<212> TYPE: DNA
<213> ORGANISM: Artificial
<220> FEATURE:
<223> OTHER INFORMATION: SP68-ins_F2_primer

<400> SEQUENCE: 115
acaaggagag ccattatggt ttataacatt cacatattgc aaac         44

<210> SEQ ID NO 116
<211> LENGTH: 40
<212> TYPE: DNA
<213> ORGANISM: Artificial
<220> FEATURE:
<223> OTHER INFORMATION: SP68-ins_R6_primer

<400> SEQUENCE: 116
gaccagctgg acctgcttcc aaccattaag atcgtcttcg         40

<210> SEQ ID NO 117
<211> LENGTH: 20
<212> TYPE: DNA
<213> ORGANISM: Artificial
<220> FEATURE:
<223> OTHER INFORMATION: GA6_primer

<400> SEQUENCE: 117
caccgcctac atacctcgct         20

<210> SEQ ID NO 118
<211> LENGTH: 21
<212> TYPE: DNA
<213> ORGANISM: Artificial
<220> FEATURE:
<223> OTHER INFORMATION: GA5_primer_rev

<400> SEQUENCE: 118
ggtatgtagg cggtgctaca g         21

<210> SEQ ID NO 119
<211> LENGTH: 39
<212> TYPE: DNA
<213> ORGANISM: Artificial
<220> FEATURE:
<223> OTHER INFORMATION: hCTLA16_primer

<400> SEQUENCE: 119
tcgtcgtcgt ccttgtagtc cttgatctcg accttggtg         39

<210> SEQ ID NO 120

```
<211> LENGTH: 38
<212> TYPE: DNA
<213> ORGANISM: Artificial
<220> FEATURE:
<223> OTHER INFORMATION: hCTLA15_primer

<400> SEQUENCE: 120
caaggacgac gacgacaagt gaccttctgc tcgtagcg                                38

<210> SEQ ID NO 121
<211> LENGTH: 37
<212> TYPE: DNA
<213> ORGANISM: Artificial
<220> FEATURE:
<223> OTHER INFORMATION: PC5_primer

<400> SEQUENCE: 121
aagtgaccag gcatcaaata aaacgaaagg ctcagtc                                 37

<210> SEQ ID NO 122
<211> LENGTH: 41
<212> TYPE: DNA
<213> ORGANISM: Artificial
<220> FEATURE:
<223> OTHER INFORMATION: PC6_primer

<400> SEQUENCE: 122
accgtattat tccggtagcc ggcattttcg cgatacattc c                            41

<210> SEQ ID NO 123
<211> LENGTH: 27
<212> TYPE: DNA
<213> ORGANISM: Artificial
<220> FEATURE:
<223> OTHER INFORMATION: PC7_primer

<400> SEQUENCE: 123
gatgcctggt cacttgtcgt cgtcgtc                                            27

<210> SEQ ID NO 124
<211> LENGTH: 37
<212> TYPE: DNA
<213> ORGANISM: Artificial
<220> FEATURE:
<223> OTHER INFORMATION: PC8_primer

<400> SEQUENCE: 124
aagtgaccag gcatcaaata aaacgaaagg ctcagtc                                 37

<210> SEQ ID NO 125
<211> LENGTH: 31
<212> TYPE: DNA
<213> ORGANISM: Artificial
<220> FEATURE:
<223> OTHER INFORMATION: PC9_primer

<400> SEQUENCE: 125
gatgcctggt cacttgatct cgaccttggt g                                       31

<210> SEQ ID NO 126
<211> LENGTH: 19
<212> TYPE: DNA
<213> ORGANISM: Artificial
<220> FEATURE:
<223> OTHER INFORMATION: pCDshuttle_F1_primer

<400> SEQUENCE: 126
```

-continued tgaccttctg ctcgtagcg					19

<210> SEQ ID NO 127
<211> LENGTH: 35
<212> TYPE: DNA
<213> ORGANISM: Artificial
<220> FEATURE:
<223> OTHER INFORMATION: hPD1scFv03-1_primer

<400> SEQUENCE: 127
acgagcagaa ggtcacttga tctcgacctt ggtgc					35

<210> SEQ ID NO 128
<211> LENGTH: 31
<212> TYPE: DNA
<213> ORGANISM: Artificial
<220> FEATURE:
<223> OTHER INFORMATION: SP50L5-ins_R1_hPD1_03

<400> SEQUENCE: 128
gaccagctgg acctggggcg tcaacgtcgc g					31

<210> SEQ ID NO 129
<211> LENGTH: 30
<212> TYPE: DNA
<213> ORGANISM: Artificial
<220> FEATURE:
<223> OTHER INFORMATION: SP68L1-ins_R1_hPD1_03

<400> SEQUENCE: 129
gaccagctgg acctgatcgg ccgacgccgc					30

<210> SEQ ID NO 130
<211> LENGTH: 32
<212> TYPE: DNA
<213> ORGANISM: Artificial
<220> FEATURE:
<223> OTHER INFORMATION: SP67L1-ins_R1_hPD1_03

<400> SEQUENCE: 130
gaccagctgg acctgtgccg cactggcact tg					32

<210> SEQ ID NO 131
<211> LENGTH: 2618
<212> TYPE: DNA
<213> ORGANISM: Artificial
<220> FEATURE:
<223> OTHER INFORMATION: pPC2 scFv expression cassettes sequence

<400> SEQUENCE: 131
gtcttcctgc tggcctatgc attgggttcc gcagtgccca ctccaggcgg tctgggcggt					60 gtggaagcgg cgctgacatt cgcgttcgtg gcggtcggag tgccgcaggg cgtggcgctt					120 tccgccactt tgctgcaccg cgtggtgttc tactggctgc gcattccgct gggcgcggcg					180 gccatgaagt ggcttgacaa gcataatctt gtctgattcg tctattttca tacccccttc					240 ggggaaatag atgtgaaaac ccttataaaa cgcgggtttt cgcagaaaca tgcgctagta					300 tcattgatga caacatggac taagcaaaag tgcttgtccc ctgacccaag aaggatgctt					360 tatgatcgtg gcctacccgc acacagtgca gtatgcgggg aaacgtacca ggaaaggacg					420 aatgatgata acgacatggc ggcaacgggg catggccatc gtagcgatgc tgaccggtct					480 gataataatg gtgggagtgg tgttcggctc ggcgaatacg gcgtatgccg cgacgttgac					540

```
gccccaggtc cagctggtcg aatcggcgg cggcgtcgtc cagccgggcc gttccctgcg     600
tctggattgc aaggcctcgg gcatcacctt ctcgaactcc ggcatgcact gggtgcgcca     660
ggccccgggc aagggcctgg aatgggtcgc cgtgatctgg tacgatggct cgaagcgcta     720
ctacgccgat tccgtgaagg gccgcttcac catctcgcgc gacaactcca agaacaccct     780
gttcctgcag atgaactccc tgcgcgccga agacaccgcc gtgtactact gcgccaccaa     840
cgatgactac tggggccagg gcaccctggt caccgtgtcc agcggcggcg gcggctccgg     900
cggcggcggc tcgggcggcg gcggcagcga atcgtgctg acccagtccc cggccaccct     960
gtccctgtcc ccgggcgaac gtgccaccct gtcgtgccgc gcctcccagt cggtgtccag    1020
ctacctggcc tggtaccagc agaagccggg ccaggccccg cgtctgctga tctacgacgc    1080
ctccaaccgc gccaccggca tcccggcccg cttctccggc tcgggctccg gcaccgactt    1140
caccctgacc atctcgtccc tggaaccgga ggacttcgcc gtctactact gccagcagtc    1200
ctcgaactgg ccgcgcacct tcggccaggg caccaaggtc gagatcaagc accatcatca    1260
ccaccactga ccttctgctc gtagcgatta cttcgagcat tactgacgac aaagaccccg    1320
accgagatgg tcggggtctt tttgttgtgg tgctgtgacg tgttgtccaa ccgtattatt    1380
ccggtagccg gcattttcgc gatacattcc ccggaatgtt gcgcaacggg gaacgcgcac    1440
cacaccgcaa ccacagtgcg ccacgcccag tccggcccctg tgcgctataa taggtcagtt    1500
attcgcgcgc gcgtggcgcc ctctacaccc cgagccgcga ggacacgtgg attccggacg    1560
gccatgcccc acatggcaaa ccgagaaccc gcacacctag cattacaagg agagccatta    1620
tgaagataaa caataagggc aagggcgctc ttatcgcggc aattaccgcc gcggcaacgc    1680
tattgtcatg cgggctggcc gctgcaagtg ccagtgcggc acaggtccag ctggtcgaat    1740
cgggcggcgg cgtcgtccag ccgggccgtt ccctgcgtct gtcgtgcgcc gcctcgggct    1800
tcaccttctc cagctacggc atgcactggg tgcgtcaggc cccgggcaag ggcctggagt    1860
gggtggccgt catctggtac gacggctcca acaagtacta cgccgattcc gtcaagggcc    1920
gcttcaccat ctcgcgtgac aactccaaga cacccctgta cctgcagatg aactccctgc    1980
gtgccgaaga caccgccgtg tactactgcg cccgcgatcc gcgtggcgcc accctgtact    2040
actactacta cggcatggat gtctggggcc agggcaccac cgtgaccgtc tcgtccggcg    2100
gcggcggctc cggcggcggc ggcagcgcgg cggcggctc cgacatccag atgacccagt    2160
ccccgagctc gctgagcgcc tcggtgggcg atcgcgtcac catcacctgc cgtgcctccc    2220
agagcatcaa ctcctacctg gactggtacc agcagaagcc gggcaaggcc ccgaagctgc    2280
tgatctacgc cgcctccagc ctgcagagcg gcgtgccgtc gcgcttctcg ggctccggca    2340
gcggcaccga cttcacctg accatctcgt ccctgcagcc ggaggatttc gccacctact    2400
actgccagca gtactactcc accccgttca ccttcggccc gggcaccaag gtcgagatca    2460
aggactacaa ggacgacgac gacaagtgac caggcatcaa ataaaacgaa aggctcagtc    2520
gaaagactgg gcctttcgtt ttatctgttg tttgtcggtg aacgctctct actagagtca    2580
cactggctca ccttcgggtg ggcctttctg cgtttata                            2618
```

<210> SEQ ID NO 132
<211> LENGTH: 2648
<212> TYPE: DNA
<213> ORGANISM: Artificial
<220> FEATURE:
<223> OTHER INFORMATION: pPC3 scFv expression cassettes sequence

<400> SEQUENCE: 132

```
gtcttcctgc tggcctatgc attgggttcc gcagtgccca ctccaggcgg tctgggcggt    60
gtggaagcgg cgctgacatt cgcgttcgtg gcggtcggag tgccgcaggg cgtggcgctt   120
tccgccactt tgctgcaccg cgtggtgttc tactggctgc gcattccgct gggcgcggcg   180
gccatgaagt ggcttgacaa gcataatctt gtctgattcg tctattttca taccccttc    240
ggggaaatag atgtgaaaac ccttataaaa cgcgggtttt cgcagaaaca tgcgctagta   300
tcattgatga caacatggac taagcaaaag tgcttgtccc ctgacccaag aaggatgctt   360
tatgatcgtg gcctacccgc acacagtgca gtatgcgggg aaacgtacca ggaaaggacg   420
aatgatgata cgacatggcg ggcaacgggg catggccatc gtagcgatgc tgaccggtct   480
gataataatg gtgggagtgg tgttcggctc ggcgaatacg gcgtatgccg cgacgttgac   540
gccccaggtc cagctggtcg aatcgggcgg cggcgtcgtc cagccgggcc gttccctgcg   600
tctggattgc aaggcctcgg gcatcacctt ctcgaactcc ggcatgcact gggtgcgcca   660
ggcccccggg caagggcctgg aatgggtcgc cgtgatctgg tacgatggct cgaagcgcta   720
ctacgccgat tccgtgaagg gccgcttcac catctcgcgc gacaactcca agaacaccct   780
gttcctgcag atgaactccc tgcgcgccga agacaccgcc gtgtactact gcgccaccaa   840
cgatgactac tggggccagg gcaccctggt caccgtgtcc agcggcggcg gcggctccgg   900
cggcggcggc tcgggcggcg gcggcagcga aatcgtgctg acccagtccc cggccaccct   960
gtccctgtcc ccgggcgaac gtgccaccct gtcgtgccgc gcctcccagt cggtgtccag  1020
ctacctggcc tggtaccagc agaagccggg ccaggccccg cgtctgctga tctacgacgc  1080
ctccaaccgc gccaccggca tcccggcccg cttctccggc tcgggctccg gcaccgactt  1140
caccctgacc atctcgtccc tggaaccgga ggacttcgcc gtctactact gccagcagtc  1200
ctcgaactgg ccgcgcacct tcggccaggg caccaaggtc gagatcaagc accatcatca  1260
ccaccactga ccttctgctc gtagcgatta cttcgagcat tactgacgac aaagaccccg  1320
accgagatgg tcggggtctt tttgttgtgg tgctgtgacg tgttgtccaa ccgtattatt  1380
ccggtagccg gcatttttcgc gatacattcc ccggaatgtt gcgcaacggg gaacgcgcac  1440
cacaccgcaa ccacagtgcg ccacgcccag tccggccctg tgcgctataa taggtcagtt  1500
attcgcgcgc gcgtggcgcc ctctacaccc cgagccgcga ggacacgtgg attccggacg  1560
gccatgcccc acatggcaaa ccgagaaccc gcacacctag cattacaagg agagccatta  1620
tggtttataa cattcacata ttgcaaacaa ggaaaaccgg tcgtgtggtt gctgctgcgg  1680
ctgcatccgt gctgtgttgc atgggggctg tatttccagc gactatcgga gtgactgcgg  1740
cgtcggccga tcaggtccag ctggtcgaat cgggcggcgg cgtcgtccag ccgggccgtt  1800
ccctgcgtct gtcgtgcgcc gcctcgggct tcaccttctc cagctacggc atgcactggg  1860
tgcgtcaggc cccgggcaag ggcctggagt gggtggccgt catctggtac gacggctcca  1920
acaagtacta cgccgattcc gtcaagggcc gcttcaccat ctcgcgtgac aactccaaga  1980
acaccctgta cctgcagatg aactccctgc gtgccgaaga caccgccgtg tactactgcg  2040
cccgcgatcc gcgtggcgcc accctgtact actactacta cggcatggat gtctggggcc  2100
agggcaccac cgtgaccgtc tcgtccgcg gcggcggctc cggcggcggc ggcagcggcg  2160
gcggcggctc cgacatccag atgacccagt ccccgagctc gctgagcgcc tcggtgggcg  2220
atcgcgtcac catcacctgc cgtgcctccc agagcatcaa ctcctacctg gactggtacc  2280
agcagaagcc gggcaaggcc ccgaagctgc tgatctacgc cgcctccagc ctgcagagcg  2340
```

```
gcgtgccgtc gcgcttctcg ggctccggca gcggcaccga cttcaccctg accatctcgt   2400
ccctgcagcc ggaggatttc gccacctact actgccagca gtactactcc accccgttca   2460
ccttcggccc gggcaccaag gtcgagatca aggactacaa ggacgacgac gacaagtgac   2520
caggcatcaa ataaaacgaa aggctcagtc gaaagactgg gcctttcgtt ttatctgttg   2580
tttgtcggtg aacgctctct actagagtca cactggctca ccttcgggtg ggcctttctg   2640
cgtttata                                                             2648
```

<210> SEQ ID NO 133
<211> LENGTH: 2645
<212> TYPE: DNA
<213> ORGANISM: Artificial
<220> FEATURE:
<223> OTHER INFORMATION: pPC4 scFv expression cassettes sequence

<400> SEQUENCE: 133

```
gtcttcctgc tggcctatgc attgggttcc gcagtgccca ctccaggcgg tctgggcggt     60
gtggaagcgg cgctgacatt cgcgttcgtg gcggtcggag tgccgcaggg cgtggcgctt    120
tccgccactt tgctgcaccg cgtggtgttc tactggctgc gcattccgct gggcgcggcg    180
gccatgaagt ggcttgacaa gcataatctt gtctgattcg tctattttca taccccccttc   240 ggggaaatag atgtgaaaac ccttataaaa cgcgggtttt cgcagaaaca tgcgctagta    300
tcattgatga caacatggac taagcaaaag tgcttgtccc ctgacccaag aaggatgctt    360
tatgaagata acaataagg caagggcgc tcttatcgcg gcaattaccg ccgcggcaac      420
gctattgtca tgcgggctgg ccgctgcaag tgccagtgcg gcaggtgtgg attacctgcc    480
taccatcggc caggtccagc tggtcgaatc gggcggcggc gtcgtccagc cgggccgttc    540
cctgcgtctg gattgcaagg cctcgggcat caccttctcg aactccggca tgcactgggt    600
gcgccaggcc ccgggcaagg gcctggaatg ggtcgccgtg atctggtacg atggctcgaa    660
gcgctactac gccgattccg tgaagggccg cttcaccatc tcgcgcgaca actccaagaa    720
caccctgttc ctgcagatga actccctgcg cgccgaagac accgccgtgt actactgcgc    780
caccaacgat gactactggg gccagggcac cctggtcacc gtgtccagcg gcggcggcgg    840
ctccggcggc ggcggctcgg gcggcggcgg cagcgaaatc gtgctgaccc agtccccggc    900
caccctgtcc ctgtccccgg gcgaacgtgc caccctgtcg tgccgcgcct ccagtcggt     960 gtccagctac ctggcctggt accagcagaa gccgggccag gccccgcgtc tgctgatcta   1020
cgacgcctcc aaccgcgcca ccggcatccc ggcccgcttc tccggctcgg gctccggcac   1080
cgacttcacc ctgaccatct cgtccctgga accggaggac ttcgccgtct actactgcca   1140
gcagtcctcg aactggccgc gcaccttcgg ccagggcacc aaggtcgaga tcaagcacca   1200
tcatcaccac cactgacctt ctgctcgtag cgattacttc gagcattact gacgacaaag   1260
accccgaccg agatggtcgg ggtctttttg ttgtggtgct gtgacgtgtt gtccaaccgt   1320
attattccgg tagccggcat tttcgcgata cattccccgg aatgttgcgc aacggggaac   1380
gcgcaccaca ccgcaaccac agtgcgccac gcccagtccg gccctgtgcg ctataatagg   1440
tcagttattc gcgcgcgcgt ggcgccctct acacccgag ccgcgaggac acgtggattc    1500
cggacggcca tgcccacat ggcaaaccga gaacccgcac acctagcatt acaaggagag     1560
ccattatgat cgtggcctac ccgcacacag tgcagtatgc ggggaaacgt accaggaaag   1620
gacgaatgat gataacgaca tggcggcaac ggggcatggc catcgtagcg atgctgaccg   1680
gtctgataat aatggtggga gtggtgttcg gctcggcgaa tacggcgtat gccgcgacgt   1740
```

```
tgacgcccca ggtccagctg gtcgaatcgg gcggcggcgt cgtccagccg ggccgttccc   1800
tgcgtctgtc gtgcgccgcc tcgggcttca ccttctccag ctacggcatg cactgggtgc   1860
gtcaggcccc gggcaagggc ctggagtggg tggccgtcat ctggtacgac ggctccaaca   1920
agtactacgc cgattccgtc aagggccgct tcaccatctc gcgtgacaac tccaagaaca   1980
ccctgtacct gcagatgaac tccctgcgtg ccgaagacac cgccgtgtac tactgcgccc   2040
gcgatccgcg tggcgccacc ctgtactact actactacgg catggatgtc tggggccagg   2100
gcaccaccgt gaccgtctcg tccggcggcg gcggctccgg cggcggcggc agcggcggcg   2160
gcggctccga catccagatg acccagtccc cgagctcgct gagcgcctcg gtgggcgatc   2220
gcgtcaccat cacctgccgt gcctcccaga gcatcaactc ctacctggac tggtaccagc   2280
agaagccggg caaggccccg aagctgctga tctacgccgc ctccagcctg cagagcggcg   2340
tgccgtcgcg cttctcgggc tccggcagcg gcaccgactt cacgctgacc atctcgtccc   2400
tgcagccgga ggatttcgcc acctactact gccagcagta ctactccacc ccgttcacct   2460
tcggcccggg caccaaggtc gagatcaagg actacaagga cgacgacgac aagtgaccag   2520
gcatcaaata aaacgaaagg ctcagtcgaa agactgggcc tttcgtttta tctgttgttt   2580
gtcggtgaac gctctctact agagtcacac tggctcacct tcgggtgggc ctttctgcgt   2640
ttata                                                                2645
```

<210> SEQ ID NO 134
<211> LENGTH: 2594
<212> TYPE: DNA
<213> ORGANISM: Artificial
<220> FEATURE:
<223> OTHER INFORMATION: pPC5 scFv expression cassettes sequence

<400> SEQUENCE: 134

```
gtcttcctgc tggcctatgc attgggttcc gcagtgccca ctccaggcgg tctgggcggt     60
gtggaagcgg cgctgacatt cgcgttcgtg gcggtcggag tgccgcaggg cgtggcgctt    120
tccgccactt tgctgcaccg cgtggtgttc tactggctgc gcattccgct gggcgcggcg    180
gccatgaagt ggcttgacaa gcataatctt gtctgattcg tctattttca tacccccttc    240
ggggaaatag atgtgaaaac ccttataaaa cgcgggtttt cgcagaaaca tgcgctagta    300
tcattgatga caacatggac taagcaaaag tgcttgtccc ctgacccaag aaggatgctt    360
tatgaagata acaataagg caagggcgc tcttatcgcg gcaattaccg ccgcggcaac    420
gctattgtca tgcgggctgg ccgctgcaag tgccagtgcg gcaggtgtgg attacctgcc    480
taccatcggc caggtccagc tggtcgaatc gggcggcggc gtcgtccagc cgggccgttc    540
cctgcgtctg gattgcaagg cctcgggcat caccttctcg aactccggca tgcactgggt    600
gcgccaggcc ccgggcaagg cctggaatg gtcgccgtg atctggtacg atggctcgaa    660
gcgctactac gccgattccg tgaagggccg cttcaccatc tcgcgcgaca actccaagaa    720
caccctgttc ctgcagatga actccctgcg cgccgaagac accgccgtgt actactgcgc    780
caccaacgat gactactggg gccagggcac cctggtcacc gtgtccagcg gcggcggcgg    840
ctccggcggc ggcggctcgg gcggcggcgg cagcgaaatc gtgctgaccc agtccccggc    900
caccctgtcc ctgtccccgg gcgaacgtgc caccctgtcg tgccgcgcct cccagtcggt    960
gtccagctac ctggcctggt accagcagaa gccgggccag gccccgcgtc tgctgatcta   1020
cgacgcctcc aaccgcgcca ccggcatccc ggcccgcttc tccggctcgg gctccggcac   1080
```

| | |
|---|---|
| cgacttcacc ctgaccatct cgtccctgga accggaggac ttcgccgtct actactgcca | 1140 |
| gcagtcctcg aactggccgc gcaccttcgg ccagggcacc aaggtcgaga tcaagcacca | 1200 |
| tcatcaccac cactgacctt ctgctcgtag cgattacttc gagcattact gacgacaaag | 1260 |
| accccgaccg agatggtcgg ggtctttttg ttgtggtgct gtgacgtgtt gtccaaccgt | 1320 |
| attattccgg tagccggcat tttcgcgata cattccccgg aatgttgcgc aacggggaac | 1380 |
| gcgcaccaca ccgcaaccac agtgcgccac gcccagtccg gccctgtgcg ctataatagg | 1440 |
| tcagttattc gcgcgcgcgt ggcgccctct acacccgag ccgcgaggac acgtggattc | 1500 |
| cggacggcca tgccccacat ggcaaaccga gaacccgcac acctagcatt acaaggagag | 1560 |
| ccattatggt ttataacatt cacatattgc aaacaaggaa aaccggtcgt gtggttgctg | 1620 |
| ctgcggctgc atccgtgctg tgttgcatgg gggctgtatt ccagcgact atcggagtga | 1680 |
| ctgcggcgtc ggccgatcag gtccagctgg tcgaatcggg cggcggcgtc gtccagccgg | 1740 |
| gccgttccct cgtctgtcg tgcgccgcct cgggcttcac cttctccagc tacggcatgc | 1800 |
| actgggtgcg tcaggcccg gcaagggcc tggagtgggt ggccgtcatc tggtacgacg | 1860 |
| gctccaacaa gtactacgcc gattccgtca agggccgctt caccatctcg cgtgacaact | 1920 |
| ccaagaacac cctgtacctg cagatgaact ccctgcgtgc cgaagacacc gccgtgtact | 1980 |
| actgcgcccg cgatccgcgt ggcgccaccc tgtactacta ctactacggc atggatgtct | 2040 |
| ggggccaggg caccaccgtg accgtctcgt ccggcggcgg cggctccggc ggcggcggca | 2100 |
| gcggcggcgg cggctccgac atccagatga cccagtcccc gagctcgctg agcgcctcgg | 2160 |
| tgggcgatcg cgtcaccatc acctgccgtg cctcccagag catcaactcc tacctggact | 2220 |
| ggtaccagca gaagccgggc aaggccccga agctgctgat ctacgccgcc tccagcctgc | 2280 |
| agagcggcgt gccgtcgcgc ttctcgggct ccggcagcgg caccgacttc accctgacca | 2340 |
| tctcgtccct gcagccggag gatttcgcca cctactactg ccagcagtac tactccaccc | 2400 |
| cgttcacctt cggcccgggc accaaggtcg agatcaagga ctacaaggac gacgacgaca | 2460 |
| agtgaccagg catcaaataa aacgaaaggc tcagtcgaaa gactgggcct ttcgttttat | 2520 |
| ctgttgtttg tcggtgaacg ctctctacta gagtcacact ggctcacctt cgggtgggcc | 2580 |
| tttctgcgtt tata | 2594 |

<210> SEQ ID NO 135
<211> LENGTH: 2609
<212> TYPE: DNA
<213> ORGANISM: Artificial
<220> FEATURE:
<223> OTHER INFORMATION: pPC6 scFv expression cassettes sequence

<400> SEQUENCE: 135

| | |
|---|---|
| gtcttcctgc tggcctatgc attgggttcc gcagtgccca ctccaggcgg tctgggcggt | 60 |
| gtggaagcgg cgctgacatt cgcgttcgtg gcggtcggag tgccgcaggg cgtggcgctt | 120 |
| tccgccactt tgctgcaccg cgtggtgttc tactggctgc gcattccgct gggcgcggcg | 180 |
| gccatgaagt ggcttgacaa gcataatctt gtctgattcg tctattttca taccccttc | 240 |
| ggggaaatag atgtgaaaac ccttataaaa cgcgggtttt cgcagaaaca tgcgctagta | 300 |
| tcattgatga caacatggac taagcaaaag tgcttgtccc ctgacccaag aaggatgctt | 360 |
| tatgaattat ttacgacaaa aaatttcggc tagtgctatc gcggtgttgt cgacttgtgg | 420 |
| gttgattttg gcgccaatgc cggtctttgc ggatcaggtc cagctggtcg aatcgggcgg | 480 |
| cggcgtcgtc cagccgggcc gttccctgcg tctggattgc aaggcctcgg gcatcacctt | 540 |

```
ctcgaactcc ggcatgcact gggtgcgcca ggccccgggc aagggcctgg aatgggtcgc    600
cgtgatctgg tacgatggct cgaagcgcta ctacgccgat ccgtgaagg gccgcttcac    660
catctcgcgc gacaactcca agaacaccct gttcctgcag atgaactccc tgcgcgccga    720
agacaccgcc gtgtactact gcgccaccaa cgatgactac tggggccagg gcaccctggt    780
caccgtgtcc agcggcggcg gcggctccgg cggcggcggc tcgggcggcg gcggcagcga    840
aatcgtgctg acccagtccc cggccaccct gtccctgtcc ccgggcgaac gtgccaccct    900
gtcgtgccgc gcctcccagt cggtgtccag ctacctggcc tggtaccagc agaagccggg    960
ccaggccccg cgtctgctga tctacgacgc ctccaaccgc gccaccggca tcccggcccg   1020
cttctccggc tcgggctccg gcaccgactt caccctgacc atctcgtccc tggaaccgga   1080
ggacttcgcc gtctactact gccagcagtc ctcgaactgg ccgcgcacct cggccaggg   1140
caccaaggtc gagatcaagc accatcatca ccaccactga ccttctgctc gtagcgatta   1200
cttcgagcat tactgacgac aaagaccccg accgagatgg tcgggtcttt tttgttgtgg   1260
tgctgtgacg tgttgtccaa ccgtattatt ccggtagccg gcattttcgc gatacattcc   1320
ccggaatgtt gcgcaacggg gaacgcgcac acaccgcaa ccacagtgcg ccacgcccag    1380
tccggccctg tgcgctataa taggtcagtt attcgcgcgc gcgtggcgcc ctctacaccc   1440
cgagccgcga ggacacgtgg attccggacg gccatgcccc acatggcaaa ccgagaaccc   1500
gcacacctag cattacaagg agagccatta tgatcgtggc ctacccgcac acagtgcagt   1560
atgcggggaa acgtaccagg aaaggacgaa tgatgataac gacatggcgg caacggggca   1620
tggccatcgt agcgatgctg accggtctga taataatggt gggagtggtg ttcggctcgg   1680
cgaatacggc gtatgccgcg acgttgacgc cccaggtcca gctggtcgaa tcgggcggcg   1740
gcgtcgtcca gccgggccgt tcctgcgtc tgtcgtgcgc cgcctcgggc ttcaccttct   1800
ccagctacgg catgcactgg gtgcgtcagg ccccgggcaa gggcctggag tgggtggccg   1860
tcatctggta cgacggctcc aacaagtact acgccgattc cgtcaagggc cgcttcacca   1920
tctcgcgtga caactccaag aacaccctgt acctgcagat gaactcctg cgtgccgaag   1980
acaccgccgt gtactactgc gcccgcgatc cgcgtggcgc caccctgtac tactactact   2040
acggcatgga tgtctggggc cagggcacca ccgtgaccgt ctcgtccggc ggcggcggct   2100
ccggcggcgg cggcagcggc ggcggcggct ccgacatcca gatgacccag tccccgagct   2160
cgctgagcgc ctcggtgggc gatcgcgtca ccatcacctg ccgtgcctcc cagagcatca   2220
actcctacct ggactggtac cagcagaagc cgggcaaggc cccgaagctg ctgatctacg   2280
ccgcctccag cctgcagagc ggcgtgccgt cgcgcttctc gggctccggc agcggcaccg   2340
acttcaccct gaccatctcg tccctgcagc cggaggattt cgccacctac tactgccagc   2400
agtactactc cacccccgttc accttcggcc cgggcaccaa ggtcgagatc aaggactaca   2460
aggacgacga cgacaagtga ccaggcatca aataaaacga aaggctcagt cgaaagactg    2520
ggcctttcgt tttatctgtt gtttgtcggt gaacgctctc tactagagtc acactggctc   2580
accttcgggt gggcctttct gcgtttata                                     2609
```

<210> SEQ ID NO 136
<211> LENGTH: 2528
<212> TYPE: DNA
<213> ORGANISM: Artificial
<220> FEATURE:
<223> OTHER INFORMATION: pPC7 scFv expression cassettes sequence

<400> SEQUENCE: 136

```
gtcttcctgc tggcctatgc attgggttcc gcagtgccca ctccaggcgg tctgggcggt      60
gtggaagcgg cgctgacatt cgcgttcgtg gcggtcggag tgccgcaggg cgtggcgctt     120
tccgccactt tgctgcaccg cgtggtgttc tactggctgc gcattccgct gggcgcggcg     180
gccatgaagt ggcttgacaa gcataatctt gtctgattcg tctattttca taccccttc     240
ggggaaatag atgtgaaaac ccttataaaa cgcgggtttt cgcagaaaca tgcgctagta     300
tcattgatga caacatggac taagcaaaag tgcttgtccc ctgacccaag aaggatgctt     360
tatgaattat ttacgacaaa aaatttcggc tagtgctatc gcggtgttgt cgacttgtgg     420
gttgattttg gcgccaatgc cggtctttgc ggatcaggtc cagctggtcg aatcgggcgg     480
cggcgtcgtc cagccgggcc gttccctgcg tctggattgc aaggcctcgg gcatcacctt     540
ctcgaactcc ggcatgcact gggtgcgcca ggccccgggc aagggcctgg aatgggtcgc     600
cgtgatctgg tacgatggct cgaagcgcta ctacgccgat ccgtgaagg gccgcttcac      660
catctcgcgc gacaactcca agaacaccct gttcctgcag atgaactccc tgcgcgccga     720
agacaccgcc gtgtactact gcgccaccaa cgatgactac tggggccagg gcaccctggt     780
caccgtgtcc agcggcggcg gcggctccgg cggcggcggc tcgggcggcg gcggcagcga     840
aatcgtgctg acccagtccc cggccaccct gtccctgtcc ccgggcgaac gtgccaccct     900
gtcgtgccgc gcctcccagt cggtgtccag ctacctggcc tggtaccagc agaagccggg     960
ccaggccccg cgtctgctga tctacgacgc ctccaaccgc gccaccggca tcccggcccg    1020
cttctccggc tcgggctccg gcaccgactt caccctgacc atctcgtccc tggaaccgga    1080
ggacttcgcc gtctactact gccagcagtc ctcgaactgg ccgcgcacct tcggccaggg    1140
caccaaggtc gagatcaagc accatcatca ccaccactga ccttctgctc gtagcgatta    1200
cttcgagcat tactgacgac aaagaccccg accgagatgg tcggggtctt tttgttgtgg    1260
tgctgtgacg tgttgtccaa ccgtattatt ccggtagccg gcattttcgc gatacattcc    1320
ccggaatgtt gcgcaacggg gaacgcgcac cacaccgcaa ccacagtgcg ccacgcccag    1380
tccggccctg tgcgctataa taggtcagtt attcgcgcgc gcgtggcgcc ctctacaccc    1440
cgagccgcga ggacacgtgg attccggacg gccatgcccc acatggcaaa ccgagaaccc    1500
gcacacctag cattacaagg agagccatta tgaagataaa caataagggc aagggcgctc    1560
ttatcgcggc aattaccgcc gcggcaacgc tattgtcatg cgggctggcc gctgcaagtg    1620
ccagtgcgg acaggtccag ctggtcgaat cgggcggcgg cgtcgtccag ccgggccgtt    1680
ccctgcgtct gtcgtgcgcc gcctcgggct tcaccttctc cagctacggc atgcactggg    1740
tgcgtcaggc cccgggcaag ggcctggagt gggtggccgt catctggtac gacggctcca    1800
acaagtacta cgccgattcc gtcaagggcc gcttcaccat ctcgcgtgac aactccaaga    1860
acaccctgta cctgcagatg aactccctgc gtgccgaaga caccgccgtg tactactgcg    1920
cccgcgatcc gcgtggcgcc accctgtact actactacta cggcatggat gtctggggcc    1980
agggcaccac cgtgaccgtc tcgtccggcg gcggcggctc cggcggcggc ggcagcggcg    2040
gcggcggctc cgacatccag atgacccagt ccccgagctc gctgagcgcc tcggtgggcg    2100
atcgcgtcac catcacctgc cgtgcctccc agagcatcaa ctcctacctg gactggtacc    2160
agcagaagcc gggcaaggcc ccgaagctgc tgatctacgc cgcctccagc ctgcagagcg    2220
gcgtgccgtc gcgcttctcg ggctccggca gcggcaccga cttcacctg accatctcgt    2280
ccctgcagcc ggaggatttc gccacctact actgccagca gtactactcc accccgttca    2340
```

```
ccttcggccc gggcaccaag gtcgagatca aggactacaa ggacgacgac gacaagtgac    2400
caggcatcaa ataaaacgaa aggctcagtc gaaagactgg gcctttcgtt ttatctgttg    2460
tttgtcggtg aacgctctct actagagtca cactggctca ccttcgggtg gcctttctg    2520 cgtttata                                                             2528

<210> SEQ ID NO 137
<211> LENGTH: 2558
<212> TYPE: DNA
<213> ORGANISM: Artificial
<220> FEATURE:
<223> OTHER INFORMATION: pPC8 scFv expression cassettes sequence

<400> SEQUENCE: 137
gtcttcctgc tggcctatgc attgggttcc gcagtgccca ctccaggcgg tctgggcggt      60
gtggaagcgg cgctgacatt cgcgttcgtg gcggtcggag tgccgcaggg cgtggcgctt     120
tccgccactt tgctgcaccg cgtggtgttc tactggctgc gcattccgct gggcgcggcg     180
gccatgaagt ggcttgacaa gcataatctt gtctgattcg tctattttca taccccttc     240 ggggaaatag atgtgaaaac ccttataaaa cgcgggtttt cgcagaaaca tgcgctagta     300
tcattgatga caacatggac taagcaaaag tgcttgtccc ctgacccaag aaggatgctt     360
tatgaattat ttacgacaaa aaatttcggc tagtgctatc gcggtgttgt cgacttgtgg     420
gttgattttg gcgccaatgc cggtctttgc ggatcaggtc cagctggtcg aatcgggcgg     480
cggcgtcgtc cagccgggcc gttccctgcg tctggattgc aaggcctcgg gcatcacctt     540
ctcgaactcc ggcatgcact gggtgcgcca ggccccgggc aagggcctgg aatgggtcgc     600
cgtgatctgg tacgatggct cgaagcgcta ctacgccgat ccgtgaagg gccgcttcac     660 catctcgcgc gacaactcca agaacaccct gttcctgcag atgaactccc tgcgcgccga     720
agacaccgcc gtgtactact gcgccaccaa cgatgactac tggggccagg gcaccctggt     780
caccgtgtcc agcggcggcg gcggctccgg cggcggcggc tcgggcggcg gcggcagcga     840
aatcgtgctg acccagtccc cggccaccct gtccctgtcc ccgggcgaac gtgccaccct     900
gtcgtgccgc gcctcccagt cggtgtccag ctacctggcc tggtaccagc agaagccggg     960
ccaggccccg cgtctgctga tctacgacgc ctccaaccgc gccaccggca tcccggcccg    1020
cttctccggc tcgggctccg gcaccgactt caccctgacc atctcgtccc tggaaccgga    1080
ggacttcgcc gtctactact gccagcagtc ctcgaactgg ccgcgcacct tcggccaggg    1140
caccaaggtc gagatcaagc accatcatca ccaccactga ccttctgctc gtagcgatta    1200
cttcgagcat tactgacgac aaagaccccg accgagatgg tcggggtctt tttgttgtgg    1260
tgctgtgacg tgttgtccaa ccgtattatt ccggtagccg gcattttcgc gatacattcc    1320
ccggaatgtt gcgcaacggg gaacgcgcac cacaccgcaa ccacagtgcg ccacgcccag    1380
tccggccctg tgcgctataa taggtcagtt attcgcgcgc gcgtggcgcc ctctacaccc    1440
cgagccgcga ggacacgtgg attccggacg gccatgcccc acatggcaaa ccgagaaccc    1500
gcacacctag cattacaagg agagccatta tggtttataa cattcacata ttgcaaacaa    1560
ggaaaaccgg tcgtgtggtt gctgctgcgg ctgcatccgt gctgtgttgc atggggctg    1620 tatttccagc gactatcgga gtgactgcgg cgtcggccga tcaggtccag ctggtcgaat    1680 cgggcggcg cgtcgtccag ccgggccgtt ccctgcgtct gtcgtgcgcc gcctcgggct    1740
tcaccttctc cagctacggc atgcactggg tgcgtcaggc ccggggcaag ggcctggagt    1800
```

| | |
|---|---|
| gggtggccgt catctggtac gacggctcca acaagtacta cgccgattcc gtcaagggcc | 1860 |
| gcttcaccat ctcgcgtgac aactccaaga acaccctgta cctgcagatg aactccctgc | 1920 |
| gtgccgaaga caccgccgtg tactactgcg cccgcgatcc gcgtggcgcc accctgtact | 1980 |
| actactacta cggcatggat gtctggggcc agggcaccac cgtgaccgtc tcgtccggcg | 2040 |
| gcggcggctc cggcggcggc ggcagcggcg gcggcggctc cgacatccag atgacccagt | 2100 |
| ccccgagctc gctgagcgcc tcggtgggcg atcgcgtcac catcacctgc cgtgcctccc | 2160 |
| agagcatcaa ctcctacctg gactggtacc agcagaagcc gggcaaggcc ccgaagctgc | 2220 |
| tgatctacgc cgcctccagc ctgcagagcg gcgtgccgtc gcgcttctcg gctccggca | 2280 |
| gcggcaccga cttcaccctg accatctcgt ccctgcagcc ggaggatttc gccacctact | 2340 |
| actgccagca gtactactcc accccgttca ccttcggccc gggcaccaag gtcgagatca | 2400 |
| aggactacaa ggacgacgac gacaagtgac caggcatcaa ataaaacgaa aggctcagtc | 2460 |
| gaaagactgg gcctttcgtt ttatctgttg tttgtcggtg aacgctctct actagagtca | 2520 |
| cactggctca ccttcgggtg ggcctttctg cgtttata | 2558 |

<210> SEQ ID NO 138
<211> LENGTH: 2576
<212> TYPE: DNA
<213> ORGANISM: Artificial
<220> FEATURE:
<223> OTHER INFORMATION: pPC2TL scFv expression cassettes sequence

<400> SEQUENCE: 138

| | |
|---|---|
| gtcttcctgc tggcctatgc attgggttcc gcagtgccca ctccaggcgg tctgggcggt | 60 |
| gtggaagcgg cgctgacatt cgcgttcgtg gcggtcggag tgccgcaggg cgtggcgctt | 120 |
| tccgccactt tgctgcaccg cgtggtgttc tactggctgc gcattccgct gggcgcggcg | 180 |
| gccatgaagt ggcttgacaa gcataatctt gtctgattcg tctattttca taccccttc | 240 |
| ggggaaatag atgtgaaaac ccttataaaa cgcgggtttt cgcagaaaca tgcgctagta | 300 |
| tcattgatga caacatggac taagcaaaag tgcttgtccc ctgacccaag aaggatgctt | 360 |
| tatgatcgtg gcctacccgc acacagtgca gtatgcgggg aaacgtacca ggaaaggacg | 420 |
| aatgatgata acgacatggc ggcaacgggg catggccatc gtagcgatgc tgaccggtct | 480 |
| gataataatg gtgggagtgg tgttcggctc ggcgaatacg gcgtatgccg cgacgttgac | 540 |
| gccccaggtc cagctggtcg aatcgggcgg cggcgtcgtc cagccgggcc gttccctgcg | 600 |
| tctggattgc aaggcctcgg gcatcacctt ctcgaactcc ggcatgcact gggtgcgcca | 660 |
| ggccccgggc aagggcctgg aatgggtcgc cgtgatctgg tacgatggct cgaagcgcta | 720 |
| ctacgccgat tccgtgaagg gccgcttcac catctcgcgc gacaactcca gaacacccct | 780 |
| gttcctgcag atgaactccc tgcgcgccga agacaccgcc gtgtactact gcgccaccaa | 840 |
| cgatgactac tggggccagg gcaccctggt caccgtgtcc agcggcggcg gcggctccgg | 900 |
| cggcggcggc tcgggcggcg gcggcagcga aatcgtgctg acccagtccc cggccaccct | 960 |
| gtccctgtcc ccgggcgaac gtgccaccct gtcgtgccgc gcctcccagt cggtgtccag | 1020 |
| ctacctggcc tggtaccagc agaagccggg ccaggcccg cgtctgctga tctacgacgc | 1080 |
| ctccaaccgc gccaccggca tcccggcccg cttctccggc tcgggctccg gcaccgactt | 1140 |
| caccctgacc atctcgtccc tggaaccgga ggacttcgcc gtctactact gccagcagtc | 1200 |
| ctcgaactgg ccgcgcacct tcggccaggg caccaaggtc gagatcaagt gaccttctgc | 1260 |
| tcgtagcgat tacttcgagc attactgacg acaaagaccc cgaccgagat ggtcggggtc | 1320 |

```
tttttgttgt ggtgctgtga cgtgttgtcc aaccgtatta ttccggtagc cggcattttc     1380
gcgatacatt ccccggaatg ttgcgcaacg gggaacgcgc accacaccgc aaccacagtg     1440
cgccacgccc agtccggccc tgtgcgctat aataggtcag ttattcgcgc gcgcgtggcg     1500
ccctctacac cccgagccgc gaggacacgt ggattccgga cggccatgcc ccacatggca     1560
aaccgagaac ccgcacacct agcattacaa ggagagccat tatgaagata acaataagg     1620 gcaagggcgc tcttatcgcg gcaattaccg ccgcggcaac gctattgtca tgcgggctgg     1680
ccgctgcaag tgccagtgcg gcacaggtcc agctggtcga atcgggcggc ggcgtcgtcc     1740
agccgggccg ttccctgcgt ctgtcgtgcg ccgcctcggg cttcaccttc tccagctacg     1800
gcatgcactg ggtgcgtcag gccccgggca agggcctgga gtgggtggcc gtcatctggt     1860
acgacggctc caacaagtac tacgccgatt ccgtcaaggg ccgcttcacc atctcgcgtg     1920
acaactccaa gaacaccctg tacctgcaga tgaactccct gcgtgccgaa gacaccgccg     1980
tgtactactg cgcccgcgat ccgcgtggcc cacccctgta ctactactac tacggcatgg     2040
atgtctgggg ccagggcacc accgtgaccg tctcgtccgg cggcggcggc tccggcggcg     2100
gcggcagcgg cggcggcggc tccgacatcc agatgaccca gtccccgagc tcgctgagcg     2160
cctcggtggg cgatcgcgtc accatcacct gccgtgcctc ccagagcatc aactcctacc     2220
tggactggta ccagcagaag ccgggcaagg ccccgaagct gctgatctac gccgcctcca     2280
gcctgcagag cggcgtgccg tcgcgcttct cgggctccgg cagcggcacc gacttcaccc     2340
tgaccatctc gtccctgcag ccggaggatt tcgccaccta ctactgccag cagtactact     2400
ccaccccgtt caccttcggc ccgggcacca aggtcgagat caagtgacca ggcatcaaat     2460
aaaacgaaag gctcagtcga aagactgggc ctttcgtttt atctgttgtt tgtcggtgaa     2520
cgctctctac tagagtcaca ctggctcacc ttcgggtggg cctttctgcg tttata         2576
```

<210> SEQ ID NO 139
<211> LENGTH: 2606
<212> TYPE: DNA
<213> ORGANISM: Artificial
<220> FEATURE:
<223> OTHER INFORMATION: pPC3TL scFv expression cassettes sequence

<400> SEQUENCE: 139

```
gtcttcctgc tggcctatgc attgggttcc gcagtgccca ctccaggcgg tctgggcggt       60
gtggaagcgg cgctgacatt cgcgttcgtg gcggtcggag tgccgcaggg cgtggcgctt      120
tccgccactt tgctgcaccg cgtggtgttc tactggctgc gcattccgct gggcgcggcg      180
gccatgaagt ggcttgacaa gcataatctt gtctgattcg tctatttca taccccttc       240 ggggaaatag atgtgaaaac ccttataaaa cgcgggtttt cgcagaaaca tgcgctagta      300
tcattgatga caacatggac taagcaaaag tgcttgtccc ctgacccaag aaggatgctt      360
tatgatcgtg gcctacccgc acacagtgca gtatgcgggg aaacgtacca ggaaaggacg      420
aatgatgata acgacatggc ggcaacgggg catggccatc gtagcgatgc tgaccggtct      480
gataataatg gtgggagtgg tgttcggctc ggcgaatacg gcgtatgccg cgacgttgac      540
gccccaggtc cagctggtcg aatcgggcgg cggcgtcgtc cagccgggcc gttccctgcg      600
tctggattgc aaggcctcgg gcatcacctt ctcgaactcc ggcatgcact gggtgcgcca      660
ggccccgggc aagggcctgg aatgggtcgc cgtgatctgg tacgatggct cgaagcgcta      720
ctacgccgat tccgtgaagg gccgcttcac catctcgcgc gacaactcca gaacaccct      780
```

```
gttcctgcag atgaactccc tgcgcgccga agacaccgcc gtgtactact gcgccaccaa      840
cgatgactac tggggccagg gcaccctggt caccgtgtcc agcggcggcg gcggctccgg      900
cggcggcggc tcgggcggcg gcggcagcga aatcgtgctg acccagtccc cggccaccct      960
gtccctgtcc ccgggcgaac gtgccaccct gtcgtgccgc gcctcccagt cggtgtccag     1020
ctacctggcc tggtaccagc agaagccggg ccaggccccg cgtctgctga tctacgacgc     1080
ctccaaccgc gccaccggca tcccggcccg cttctccggc tcgggctccg gcaccgactt     1140
caccctgacc atctcgtccc tggaaccgga ggacttcgcc gtctactact gccagcagtc     1200
ctcgaactgg ccgcgcacct tcggccaggg caccaaggtc gagatcaagt gaccttctgc     1260
tcgtagcgat tacttcgagc attactgacg acaaagaccc cgaccgagat ggtcggggtc     1320
tttttgttgt ggtgctgtga cgtgttgtcc aaccgtatta ttccggtagc cggcattttc     1380
gcgatacatt ccccggaatg ttgcgcaacg gggaacgcgc accacccgc aaccacagtg      1440 cgccacgccc agtccggccc tgtgcgctat aataggtcag ttattcgcgc gcgcgtggcg     1500
ccctctacac cccgagccgc gaggacacgt ggattccgga cggccatgcc ccacatggca     1560
aaccgagaac ccgcacacct agcattacaa ggagagccat tatggtttat aacattcaca     1620
tattgcaaac aaggaaaaac cggtcgtgtg gttgctgctgc ggctgcatcc gtgctgtgtt     1680 gcatggggc tgtatttcca gcgactatcg gagtgactgc ggcgtcggcc gatcaggtcc     1740
agctggtcga atcgggcggc ggcgtcgtcc agccgggccg ttccctgcgt ctgtcgtgcg     1800
ccgcctcggg cttcaccttc tccagctacg gcatgcactg ggtgcgtcag gccccgggca     1860
agggcctgga gtgggtggcc gtcatctggt acgacggctc caacaagtac tacgccgatt     1920
ccgtcaaggg ccgcttcacc atctcgcgtg acaactccaa gaacaccctg tacctgcaga     1980
tgaactccct gcgtgccgaa gacaccgccg tgtactactg cgcccgcgat ccgcgtggcg     2040
ccaccctgta ctactactac tacggcatgg atgtctgggg ccagggcacc accgtgaccg     2100
tctcgtccgg cggcggcggc tccggcggcg gcggcagcgg cggcggcggc tccgacatcc     2160
agatgaccca gtccccgagc tcgctgagcg cctcggtggg cgatcgcgtc accatcacct     2220
gccgtgcctc ccagagcatc aactcctacc tggactggta ccagcagaag ccgggcaagg     2280
ccccgaagct gctgatctac gccgcctcca gcctgcagag cggcgtgccg tcgcgcttct     2340
cgggctccgg cagcggcacc gacttcaccc tgaccatctc gtccctgcag ccggaggatt     2400
tcgccaccta ctactgccag cagtactact ccaccccgtt caccttcggc ccgggcacca     2460
aggtcgagat caagtgacca ggcatcaaat aaaacgaaag gctcagtcga aagactgggc     2520
ctttcgtttt atctgttgtt tgtcggtgaa cgctctctac tagagtcaca ctggctcacc     2580
ttcgggtggg cctttctgcg tttata                                         2606
```

<210> SEQ ID NO 140
<211> LENGTH: 2603
<212> TYPE: DNA
<213> ORGANISM: Artificial
<220> FEATURE:
<223> OTHER INFORMATION: pPC4TL scFv expression cassettes sequence

<400> SEQUENCE: 140

```
gtcttcctgc tggcctatgc attgggttcc gcagtgccca ctccaggcgg tctgggcggt       60
gtggaagcgg cgctgacatt cgcgttcgtg gcggtcggag tgccgcaggg cgtggcgctt      120
tccgccactt tgctgcaccg cgtggtgttc tactggctgc gcattccgct gggcgcggcg      180
gccatgaagt ggcttgacaa gcataatctt gtctgattcg tctattttca tacccccttc      240
```

-continued

```
ggggaaatag atgtgaaaac ccttataaaa cgcgggtttt cgcagaaaca tgcgctagta    300
tcattgatga caacatggac taagcaaaag tgcttgtccc ctgacccaag aaggatgctt    360
tatgaagata acaataagg gcaagggcgc tcttatcgcg gcaattaccg ccgcggcaac     420
gctattgtca tgcgggctgg ccgctgcaag tgccagtgcg gcaggtgtgg attacctgcc    480
taccatcggc caggtccagc tggtcgaatc gggcggcggc gtcgtccagc cgggccgttc    540
cctgcgtctg gattgcaagg cctcgggcat caccttctcg aactccggca tgcactgggt    600
gcgccaggcc ccgggcaagg gcctggaatg ggtcgccgtg atctggtacg atggctcgaa    660
gcgctactac gccgattccg tgaagggccg cttcaccatc tcgcgcgaca actccaagaa    720
caccctgttc ctgcagatga actccctgcg cgccgaagac accgccgtgt actactgcgc    780
caccaacgat gactactggg gccagggcac cctggtcacc gtgtccagcg gcggcggcgg    840
ctccggcggc ggcggctcgg gcggcggcgg cagcgaaatc gtgctgaccc agtccccggc    900
caccctgtcc ctgtccccgg gcgaacgtgc caccctgtcg tgccgcgcct cccagtcggt    960
gtccagctac ctggcctggt accagcagaa gccgggccag ccccgcgtc tgctgatcta   1020 cgacgcctcc aaccgcgcca ccggcatccc ggcccgcttc tccggctcgg gctccggcac   1080
cgacttcacc ctgaccatct cgtccctgga accggaggac ttcgccgtct actactgcca   1140
gcagtcctcg aactggccgc gcaccttcgg ccagggcacc aaggtcgaga tcaagtgacc   1200
ttctgctcgt agcgattact cgagcatta ctgacgacaa agaccccgac cgagatggtc    1260
ggggtctttt tgttgtggtg ctgtgacgtg ttgtccaacc gtattattcc ggtagccggc   1320
attttcgcga tacattcccc ggaatgttgc gcaacgggga acgcgcacca caccgcaacc   1380
acagtgcgcc acgcccagtc cggccctgtg cgctataata ggtcagttat tcgcgcgcgc   1440
gtggcgccct ctacaccccg agccgcgagg acacgtggat tccggacggc catgcccac    1500 atggcaaacc gagaacccgc acacctagca ttacaaggag agccattatg atcgtggcct   1560
acccgcacac agtgcagtat gcggggaaac gtaccaggaa aggacgaatg atgataacga   1620
catggcggca acgggcatg gccatcgtag cgatgctgac cggtctgata ataatggtgg    1680
gagtggtgtt cggctcggcg aatacggcgt atgccgcgac gttgacgccc caggtccagc   1740
tggtcgaatc gggcggcggc gtcgtccagc cgggccgttc cctgcgtctg tcgtgcgccg   1800
cctcgggctt caccttctcc agctacggca tgcactgggt gcgtcaggcc ccgggcaagg   1860
gcctggagtg ggtggccgtc atctggtacg acggctccaa caagtactac gccgattccg   1920
tcaagggccg cttcaccatc tcgcgtgaca actccaagaa caccctgtac ctgcagatga   1980
actccctgcg tgccgaagac accgccgtgt actactgcgc ccgcgatccg cgtggcgcca   2040
ccctgtacta ctactactac ggcatggatg tctgggggcca gggcaccacc gtgaccgtct   2100
cgtccggcgg cggcggctcc ggcggcggcg gcagcggcgg cggcggctcc gacatccaga   2160
tgacccagtc cccgagctcg ctgagcgcct cggtgggcga tcgcgtcacc atcacctgcc   2220
gtgcctccca gagcatcaac tcctacctgg actggtacca gcagaagccg ggcaaggccc   2280
cgaagctgct gatctacgcc gcctccagcc tgcagagcgg cgtgccgtcg cgcttctcgg   2340
gctccggcag cggcaccgac ttcacccctga ccatctcgtc cctgcagccg gaggatttcg   2400
ccacctacta ctgccagcag tactactccca ccccgttcac cttcggcccg ggcaccaagg   2460
tcgagatcaa gtgaccaggc atcaaataaa acgaaaggct cagtcgaaag actgggcctt   2520
tcgttttatc tgttgtttgt cggtgaacgc tctctactag agtcacactg gctcaccttc   2580
```

```
gggtgggcct tctgcgttt ata                                        2603

<210> SEQ ID NO 141
<211> LENGTH: 2552
<212> TYPE: DNA
<213> ORGANISM: Artificial
<220> FEATURE:
<223> OTHER INFORMATION: pPC5TL scFv expression cassettes sequence

<400> SEQUENCE: 141
gtcttcctgc tggcctatgc attgggttcc gcagtgccca ctccaggcgg tctgggcggt    60
gtggaagcgg cgctgacatt cgcgttcgtg gcggtcggag tgccgcaggg cgtggcgctt   120
tccgccactt tgctgcaccg cgtggtgttc tactggctgc gcattccgct gggcgcggcg   180
gccatgaagt ggcttgacaa gcataatctt gtctgattcg tctattttca tacccccttc   240
ggggaaatag atgtgaaaac ccttataaaa cgcgggtttt cgcagaaaca tgcgctagta   300
tcattgatga caacatggac taagcaaaag tgcttgtccc ctgacccaag aaggatgctt   360
tatgaagata acaataagg gcaagggcgc tcttatcgcg gcaattaccg ccgcggcaac   420
gctattgtca tgcgggctgg ccgctgcaag tgccagtgcg gcaggtgtgg attacctgcc   480
taccatcggc caggtccagc tggtcgaatc gggcggcggc gtcgtccagc cgggccgttc   540
cctgcgtctg gattgcaagg cctcgggcat caccttctcg aactccggca tgcactgggt   600
gcgccaggcc ccgggcaagg gcctggaatg ggtcgccgtg atctggtacg atggctcgaa   660
gcgctactac gccgattccg tgaagggccg cttcaccatc tcgcgcgaca actccaagaa   720
caccctgttc ctgcagatga actccctgcg cgccgaagac accgccgtgt actactgcgc   780
caccaacgat gactactggg gccagggcac cctggtcacc gtgtccagcg gcggcggcgg   840
ctccggcggc ggcggctcgg gcggcggcgg cagcgaaatc gtgctgaccc agtcccggc   900 caccctgtcc ctgtccccgg gcgaacgtgc caccctgtcg tgccgcgcct cccagtcggt   960
gtccagctac ctggcctggt accagcagaa gccgggccag gccccgcgtc tgctgatcta  1020
cgacgcctcc aaccgcgcca cggcatccc ggccgcttc tccggctcgg gctccggcac  1080
cgacttcacc ctgaccatct cgtccctgga accggaggac ttcgccgtct actactgcca  1140
gcagtcctcg aactggccgc gcaccttcgg ccagggcacc aaggtcgaga tcaagtgacc  1200
ttctgctcgt agcgattact tcgagcatta ctgacgacaa agaccccgac cgagatggtc  1260 gggggtctttt tgttgtggtg ctgtgacgtg ttgtccaacc gtattattcc ggtagccggc  1320
attttcgcga tacattccc ggaatgttgc gcaacgggga acgcgcacca caccgcaacc  1380
acagtgcgcc acgcccagtc cggccctgtg cgctataata ggtcagttat tcgcgcgcgc  1440
gtggcgccct ctacaccccg agccgcgagg acacgtggat tccggacggc catgccccac  1500
atggcaaacc gagaacccgc acacctagca ttacaaggag agccattatg gtttataaca  1560
ttcacatatt gcaaacaagg aaaaccggtc gtgtggttgc tgctgcggct gcatccgtgc  1620
tgtgttgcat gggggctgta tttccagcga ctatcggagt gactgcggcg tcggccgatc  1680
aggtccagct ggtcgaatcg ggcggcggcg tcgtccagcc gggccgttcc ctgcgtctgt  1740
cgtgcgccgc ctcgggcttc accttctcca gctacggcat gcactgggtg cgtcaggccc  1800
cgggcaaggg cctggagtgg gtggccgtca tctggtacga cggctccaac aagtactacg  1860
ccgattccgt caagggccgc ttcaccatct cgcgtgacaa ctccaagaac accctgtacc  1920
tgcagatgaa ctccctgcgt gccgaagaca ccgccgtgta ctactgcgcc cgcgatccgc  1980
gtggcgccac cctgtactac tactactacg gcatggatgt ctggggccag ggcaccaccg  2040
```

| | |
|---|---|
| tgaccgtctc gtccggcggc ggcggctccg gcggcggcgg cagcggcggc ggcggctccg | 2100 |
| acatccagat gacccagtcc ccgagctcgc tgagcgcctc ggtgggcgat cgcgtcacca | 2160 |
| tcacctgccg tgcctcccag agcatcaact cctacctgga ctggtaccag cagaagccgg | 2220 |
| gcaaggcccc gaagctgctg atctacgccg cctccagcct gcagagcggc gtgccgtcgc | 2280 |
| gcttctcggg ctccggcagc ggcaccgact tcaccctgac catctcgtcc ctgcagccgg | 2340 |
| aggatttcgc cacctactac tgccagcagt actactccac cccgttcacc ttcggcccgg | 2400 |
| gcaccaaggt cgagatcaag tgaccaggca tcaaataaaa cgaaaggctc agtcgaaaga | 2460 |
| ctgggccttt cgttttatct gttgtttgtc ggtgaacgct ctctactaga gtcacactgg | 2520 |
| ctcaccttcg ggtgggcctt tctgcgttta ta | 2552 |

<210> SEQ ID NO 142
<211> LENGTH: 2567
<212> TYPE: DNA
<213> ORGANISM: Artificial
<220> FEATURE:
<223> OTHER INFORMATION: pPC6TL scFv expression cassettes sequence

<400> SEQUENCE: 142

| | |
|---|---|
| gtcttcctgc tggcctatgc attgggttcc gcagtgccca ctccaggcgg tctgggcggt | 60 |
| gtggaagcgg cgctgacatt cgcgttcgtg gcggtcggag tgccgcaggg cgtggcgctt | 120 |
| tccgccactt tgctgcaccg cgtggtgttc tactggctgc gcattccgct gggcgcggcg | 180 |
| gccatgaagt ggcttgacaa gcataatctt gtctgattcg tctattttca taccccttc | 240 |
| ggggaaatag atgtgaaaac ccttataaaa cgcgggtttt cgcagaaaca tgcgctagta | 300 |
| tcattgatga caacatggac taagcaaaag tgcttgtccc ctgacccaag aaggatgctt | 360 |
| tatgaattat ttacgacaaa aaatttcggc tagtgctatc gcggtgttgt cgacttgtgg | 420 |
| gttgattttg gcgccaatgc cggtctttgc ggatcaggtc cagctggtcg aatcgggcgg | 480 |
| cggcgtcgtc cagccgggcc gttccctgcg tctggattgc aaggcctcgg gcatcacctt | 540 |
| ctcgaactcc ggcatgcact gggtgcgcca ggcccggggc aagggcctgg aatgggtcgc | 600 |
| cgtgatctgg tacgatggct cgaagcgcta ctacgccgat tccgtgaagg gccgcttcac | 660 |
| catctcgcgc gacaactcca gaacacccct gttcctgcag atgaactccc tgcgcgccga | 720 |
| agacaccgcc gtgtactact gcgccaccaa cgatgactac tggggccagg gcaccctggt | 780 |
| caccgtgtcc agcggcggcg gcggctccgg cggcggcggc tcgggcggcg gcggcagcga | 840 |
| aatcgtgctg acccagtccc cggccaccct gtccctgtcc ccgggcgaac gtgccaccct | 900 |
| gtcgtgccgc gcctcccagt cggtgtccag ctacctggcc tggtaccagc agaagccggg | 960 |
| ccaggccccc cgtctgctga tctacgacgc ctccaaccgc gccaccggca tcccggcccg | 1020 |
| cttctccggc tcgggctccg gcaccgactt caccctgacc atctcgtccc tggaaccgga | 1080 |
| ggacttcgcc gtctactact gccagcagtc ctcgaactgg ccgcgcacct tcggccaggg | 1140 |
| caccaaggtc gagatcaagt gaccttctgc tcgtagcgat tacttcgagc attactgacg | 1200 |
| acaaagaccc cgaccgagat ggtcgggtc ttttgttgt ggtgctgtga cgtgttgtcc | 1260 |
| aaccgtatta ttccggtagc cggcattttc gcgatacatt ccccggaatg ttgcgcaacg | 1320 |
| gggaacgcgc accacaccgc aaccacagtg cgccacgccc agtccggccc tgtgcgctat | 1380 |
| aataggtcag ttattcgcgc gcgcgtggcg ccctctacac cccgagccgc gaggacacgt | 1440 |
| ggattccgga cggccatgcc ccacatggca aaccgagaac ccgcacacct agcattacaa | 1500 |

```
ggagagccat tatgatcgtg gcctacccgc acacagtgca gtatgcgggg aaacgtacca    1560
ggaaaggacg aatgatgata acgacatggc ggcaacgggg catggccatc gtagcgatgc    1620
tgaccggtct gataataatg gtgggagtgg tgttcggctc ggcgaatacg gcgtatgccg    1680
cgacgttgac gccccaggtc cagctggtcg aatcgggcgg cggcgtcgtc cagccgggcc    1740
gttccctgcg tctgtcgtgc gccgcctcgg gcttcacctt ctccagctac ggcatgcact    1800
gggtgcgtca ggccccgggc aagggcctgg agtgggtggc cgtcatctgg tacgacggct    1860
ccaacaagta ctacgccgat ccgtcaagg gccgcttcac catctcgcgt gacaactcca     1920
agaacaccct gtacctgcag atgaactccc tgcgtgccga agacaccgcc gtgtactact    1980
gcgcccgcga tccgcgtggc gccaccctgt actactacta ctacggcatg gatgtctggg    2040
gccagggcac caccgtgacc gtctcgtccg gcggcggcgg ctccggcggc ggcggcagcg    2100
gcggcggcgg ctccgacatc cagatgaccc agtccccgag ctcgctgagc gcctcggtgg    2160
gcgatcgcgt caccatcacc tgccgtgcct cccagagcat caactcctac ctggactggt    2220
accagcagaa gccgggcaag gccccgaagc tgctgatcta cgccgcctcc agcctgcaga    2280
gcggcgtgcc gtcgcgcttc tcgggctccg gcagcggcac cgacttcacc ctgaccatct    2340
cgtccctgca gccggaggat ttcgccacct actactgcca gcagtactac tccaccccgt    2400
tcaccttcgg cccggggcacc aaggtcgaga tcaagtgacc aggcatcaaa taaaacgaaa    2460
ggctcagtcg aaagactggg cctttcgttt tatctgttgt ttgtcggtga acgctctcta    2520
ctagagtcac actggctcac cttcgggtgg gcctttctgc gtttata                  2567
```

<210> SEQ ID NO 143
<211> LENGTH: 2486
<212> TYPE: DNA
<213> ORGANISM: Artificial
<220> FEATURE:
<223> OTHER INFORMATION: pPC7TL scFv expression cassettes sequence

<400> SEQUENCE: 143

```
gtcttcctgc tggcctatgc attgggttcc gcagtgccca ctccaggcgg tctgggcggt      60
gtggaagcgg cgctgacatt cgcgttcgtg gcggtcggag tgccgcaggg cgtggcgctt     120
tccgccactt tgctgcaccg cgtggtgttc tactggctgc gcattccgct gggcgcggcg     180
gccatgaagt ggcttgacaa gcataatctt gtctgattcg tctattttca tacccccttc     240
ggggaaatag atgtgaaaac ccttataaaa cgcgggtttt cgcagaaaca tgcgctagta     300
tcattgatga caacatggac taagcaaaag tgcttgtccc ctgacccaag aaggatgctt     360
tatgaattat ttacgacaaa aaatttcggc tagtgctatc gcggtgttgt cgacttgtgg    420
gttgattttg gcgccaatgc cggtctttgc ggatcaggtc cagctggtcg aatcgggcgg    480
cggcgtcgtc cagccgggcc gttccctgcg tctggattgc aaggcctcgg gcatcacctt    540
ctcgaactcc ggcatgcact gggtgcgcca ggccccgggc aagggcctgg aatgggtcgc    600
cgtgatctgg tacgatggct cgaagcgcta ctacgccgat ccgtcgaagg gccgcttcac    660
catctcgcgc gacaactcca agaacaccct gttcctgcag atgaactccc tgcgcgccga    720
agacaccgcc gtgtactact cgccaccaa cgatgactac tggggccagg caccctggt     780 caccgtgtcc agcggcggcg cgggctccgg cggcggcggc tcgggcggcg cggcagcga    840 aatcgtgctg acccagtccc cggccaccct gtccctgtcc ccgggcgaac gtgccaccct   900
gtcgtgccgc gcctcccagt cggtgtccag ctacctggcc tggtaccagc agaagccggg   960
ccaggccccg cgtctgctga tctacgacgc ctccaaccgc gccaccggca tcccggcccg   1020
```

```
cttctccggc tcgggctccg gcaccgactt caccctgacc atctcgtccc tggaaccgga    1080
ggacttcgcc gtctactact gccagcagtc ctcgaactgg ccgcgcacct tcggccaggg    1140
caccaaggtc gagatcaagt gaccttctgc tcgtagcgat tacttcgagc attactgacg    1200
acaaagaccc cgaccgagat ggtcgggggtc ttttgttgt ggtgctgtga cgtgttgtcc    1260
aaccgtatta ttccggtagc cggcatttc gcgatacatt ccccggaatg ttgcgcaacg    1320
gggaacgcgc accaccgc aaccacagtg cgccacgccc agtccggccc tgtgcgctat    1380
aataggtcag ttattcgcgc gcgcgtggcg ccctctacac cccgagccgc gaggacacgt    1440
ggattccgga cggccatgcc ccacatggca accgagaac ccgcacacct agcattacaa    1500
ggagagccat tatgaagata acaataagg gcaagggcgc tcttatcgcg gcaattaccg    1560
ccgcggcaac gctattgtca tgcgggctgg ccgctgcaag tgccagtgcg gcacaggtcc    1620
agctggtcga atcgggcggc ggcgtcgtcc agccgggccg ttccctgcgt ctgtcgtgcg    1680
ccgcctcggg cttcaccttc tccagctacg gcatgcactg ggtgcgtcag gccccggggca    1740 agggcctgga gtgggtggcc gtcatctggt acgacggctc caacaagtac tacgccgatt    1800
ccgtcaaggg ccgcttcacc atctcgcgtg acaactccaa gaacaccctg tacctgcaga    1860
tgaactccct gcgtgccgaa gacaccgccg tgtactactg cgcccgcgat ccgcgtggcg    1920
ccaccctgta ctactactac tacggcatgg atgtctgggg ccaggcacc accgtgaccg    1980 tctcgtccgg cggcggcggc tccggcggcg gcggcagcgg cggcggcggc tccgacatcc    2040
agatgaccca gtccccgagc tcgctgagcg cctcggtggg cgatcgcgtc accatcacct    2100
gccgtgcctc ccagagcatc aactcctacc tggactggta ccagcagaag ccgggcaagg    2160
ccccgaagct gctgatctac gccgcctcca gcctgcagag cggcgtgccg tcgcgcttct    2220
cgggctccgg cagcggcacc gacttcaccc tgaccatctc gtccctgcag ccggaggatt    2280
tcgccaccta ctactgccag cagtactact ccaccccgtt cacctcggc ccgggcacca    2340 aggtcgagat caagtgacca ggcatcaaat aaaacgaaag gctcagtcga aagactgggc    2400
ctttcgtttt atctgttgtt tgtcggtgaa cgctctctac tagagtcaca ctggctcacc    2460
ttcgggtggg cctttctgcg tttata                                           2486

<210> SEQ ID NO 144
<211> LENGTH: 2516
<212> TYPE: DNA
<213> ORGANISM: Artificial
<220> FEATURE:
<223> OTHER INFORMATION: pPC8TL scFv expression cassettes sequence

<400> SEQUENCE: 144
gtcttcctgc tggcctatgc attgggttcc gcagtgccca ctccaggcgg tctgggcggt     60
gtggaagcgg cgctgacatt cgcgttcgtg gcggtcggag tgccgcaggg cgtggcgctt    120
tccgccactt tgctgcaccg cgtggtgttc tactggctgc gcattccgct gggcgcggcg    180
gccatgaagt ggcttgacaa gcataatctt gtctgattcg tctattttca tacccccttc    240
ggggaaatag atgtgaaaac ccttataaaa cgcgggtttt cgcagaaaca tgcgctagta    300
tcattgatga caacatggac taagcaaaag tgcttgtccc ctgacccaag aaggatgctt    360
tatgaattat ttacgacaaa aaatttcggc tagtgctatc gcggtgttgt cgacttgtgg    420
gttgattttg gcgccaatgc cggtctttgc ggatcaggtc cagctggtcg aatcgggcgg    480
cggcgtcgtc cagccgggcc gttccctgcg tctggattgc aaggcctcgg gcatcacctt    540
```

```
ctcgaactcc ggcatgcact gggtgcgcca ggccccgggc aagggcctgg aatgggtcgc    600
cgtgatctgg tacgatggct cgaagcgcta ctacgccgat tccgtgaagg gccgcttcac    660
catctcgcgc gacaactcca agaacaccct gttcctgcag atgaactccc tgcgcgccga    720
agacaccgcc gtgtactact gcgccaccaa cgatgactac tggggccagg gcaccctggt    780
caccgtgtcc agcggcggcg gcggctccgg cggcggcggc tcgggcggcg gcggcagcga    840
aatcgtgctg acccagtccc cggccaccct gtccctgtcc ccgggcgaac gtgccaccct    900
gtcgtgccgc gcctcccagt cggtgtccag ctacctggcc tggtaccagc agaagccggg    960
ccaggcgccg cgtctgctga tctacgacgc ctccaaccgc gccaccggca tcccggcccg   1020
cttctccggc tcgggctccg gcaccgactt caccctgacc atctcgtccc tggaaccgga   1080
ggacttcgcc gtctactact gccagcagtc ctcgaactgg ccgcgcacct tcggccaggg   1140
caccaaggtc gagatcaagt gaccttctgc tcgtagcgat tacttcgagc attactgacg   1200
acaaagaccc cgaccgagat ggtcggggtc tttttgttgt ggtgctgtga cgtgttgtcc   1260
aaccgtatta ttccggtagc cggcattttc gcgatacatt ccccggaatg ttgcgcaacg   1320
gggaacgcgc accacaccgc aaccacagtg cgccacgccc agtccggccc tgtgcgctat   1380
aataggtcag ttattcgcgc gcgcgtggcg ccctctacac cccgagccgc gaggacacgt   1440
ggattccgga cggccatgcc ccacatggca aaccgagaac ccgcacacct agcattacaa   1500
ggagagccat tatggtttat aacattcaca tattgcaaac aaggaaaacc ggtcgtgtgg   1560
ttgctgctgc ggctgcatcc gtgctgtgtt gcatgggggc tgtatttcca gcgactatcg   1620
gagtgactgc ggcgtcggcc gatcaggtcc agctggtcga atcgggcggc ggcgtcgtcc   1680
agccgggccg ttccctgcgt ctgtcgtgcg ccgcctcggg cttcaccttc tccagctacg   1740
gcatgcactg ggtgcgtcag gccccgggca agggcctgga gtgggtggcc gtcatctggt   1800
acgacggctc caacaagtac tacgccgatt ccgtcaaggg ccgcttcacc atctcgcgtg   1860
acaactccaa gaacaccctg tacctgcaga tgaactccct gcgtgccgaa gacaccgccg   1920
tgtactactg cgcccgcgat ccgcgtggcg ccaccctgta ctactactac tacggcatgg   1980
atgtctgggg ccagggcacc accgtgaccg tctcgtccgg cggcggcggc tccggcggcg   2040
gcggcagcgg cggcggcggc tccgacatcc agatgaccca gtccccgagc tcgctgagcg   2100
cctcggtggg cgatcgcgtc accatcacct gccgtgcctc ccagagcatc aactcctacc   2160
tggactggta ccagcagaag ccgggcaagg ccccgaagct gctgatctac gccgcctcca   2220
gcctgcagag cggcgtgccg tcgcgcttct cgggctccgg cagcggcacc gacttcaccc   2280
tgaccatctc gtccctgcag ccggaggatt tcgccaccta ctactgccag cagtactact   2340
ccacccccgtt caccttcggc cccgggcacca aggtcgagat caagtgacca ggcatcaaat   2400
aaaacgaaag gctcagtcga aagactgggc ctttcgtttt atctgttgtt tgtcggtgaa   2460
cgctctctac tagagtcaca ctggctcacc ttcgggtggg cctttctgcg tttata         2516
```